United States Patent
Engler et al.

(10) Patent No.: US 8,058,425 B2
(45) Date of Patent: Nov. 15, 2011

(54) PURINE DERIVATIVES AS KINASE INHIBITORS

(75) Inventors: Thomas Albert Engler, Indianapolis, IN (US); Timothy Paul Burkholder, Carmel, IN (US); Joshua Ryan Clayton, Cicero, IN (US); Clive Gideon Diefenbacher, Greenwood, IN (US); Kelly Wayne Furness, Avon, IN (US); James Robert Henry, Indianapolis, IN (US); Yihong Li, Carmel, IN (US); Sushant Malhotra, Indianapolis, IN (US); Angela Lynn Marquart, Greenwood, IN (US); Johnathan Alexander McLean, Indianapolis, IN (US); David Mendel, Indianapolis, IN (US); Jon Kevin Reel, Carmel, IN (US); Brian Raymond Berridge, Greenfield, IN (US); Charles Edward Ruegg, Indianapolis, IN (US); John Morris Sullivan, Greenfield, IN (US)

(73) Assignee: Eli Lilly and Company, Indianapolis, IN (US)

(*) Notice: Subject to any disclaimer, the term of this patent is extended or adjusted under 35 U.S.C. 154(b) by 0 days.

(21) Appl. No.: 13/100,618

(22) Filed: May 4, 2011

(65) Prior Publication Data

US 2011/0207721 A1     Aug. 25, 2011

Related U.S. Application Data

(60) Continuation of application No. 12/333,775, filed on Dec. 12, 2008, which is a division of application No. 10/506,459, filed as application No. PCT/US03/05050 on Mar. 4, 2003, now Pat. No. 7,491,716.

(60) Provisional application No. 60/362,245, filed on Mar. 5, 2002.

(51) Int. Cl.
- *A61P 25/08* (2006.01)
- *A61K 31/55* (2006.01)
- *C07D 487/06* (2006.01)

(52) U.S. Cl. .................................. 540/220; 540/561
(58) Field of Classification Search .................. 514/220; 540/561

See application file for complete search history.

(56) References Cited

U.S. PATENT DOCUMENTS

| 5,057,614 A | 10/1991 | Davis et al. |
| 5,721,245 A | 2/1998 | Davis et al. |

FOREIGN PATENT DOCUMENTS

| WO | WO 98/16528 | 4/1998 |
| WO | WO 00/38675 | 7/2000 |
| WO | WO 01/44235 | 6/2001 |
| WO | WO 01/44247 | 6/2001 |
| WO | WO 02/10158 | 2/2002 |
| WO | WO 02/46183 | 6/2002 |
| WO | WO 02/46197 | 6/2002 |

*Primary Examiner* — Brenda Coleman
(74) *Attorney, Agent, or Firm* — John C. Demeter; Robert D. Titus

(57) ABSTRACT

The present invention provides kinase inhibitors of Formula I.

I.

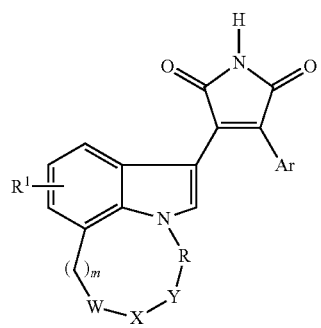

8 Claims, No Drawings

PURINE DERIVATIVES AS KINASE INHIBITORS

This application is a continuation of U.S. Ser. No. 12/333,775, filed Dec. 12, 2008, which is a divisional application of U.S. Ser. No. 10/506,459, filed Dec. 6, 2004, now U.S. Pat. No. 7,491,716 B2, which is a national phase application under 35 U.S.C. Section 371 of PCT/US03/05050, filed Mar. 4, 2003, which claims the benefit under 35 U.S.C. Section 119(e) of U.S. provisional patent application 60/362,245, filed Mar. 5, 2002.

Glycogen synthase kinase-3 (GSK-3) is a serine/threonine protein kinase first discovered as one of a number of kinases capable of phosphorylating and inactivating glycogen synthase, the regulatory enzyme of glycogen synthesis in mammals (Embi, et al., *Eur. J. Biochem.*, 107, 519-527 (1980)). Existing in two isoforms, GSK-3α and GSK-3β, GSK-3 phosphorylates a wide variety of proteins in vitro. The diversity of these proteins suggests a role for GSK-3 in the control of cellular metabolism, growth, and development.

Type I diabetes is characterized by a lack of insulin resulting from the destruction of insulin producing cells in the pancreas. Type II diabetes is characterized by defective insulin secretion and action. The binding of insulin to its receptor initiates a cascade of events resulting in the phosphorylation and inhibition of GSK-3, contributing to the insulin-induced stimulation of glycogen and protein synthesis. Inhibitors of GSK-3 have been shown to mimic the actions of insulin (Coghlan, et al., *Chem. Biol.*, 7, 793-803 (2000)), including the ability to lower blood glucose levels in vivo (Norman, *Drug News Perspect.*, 14, 242-247 (2001)). These recent discoveries suggest that inhibitors of GSK-3 have a potential role in the treatment of diabetes.

Alzheimer's disease is characterized by the micro-tubule-associated protein Tau existing in an abnormally hyperphosphorylated state (Cohen and Frame, *Nature Reviews: Molecular Cell Biology*, 2, 769-776 (October 2001) <www.nature.com/reviews/mol-cellbio>). GSK-3 phosphorylates many of the hyperphosphorylated sites on Tau in vitro, preventing it from binding to microtubules, making it available to undergo the aberrant filament assembly that may underlie the neuronal degeneration observed in Alzheimer's disease and other neurological disorders. Inhibitors of GSK-3, such as insulin and lithium ions, have been shown to induce a partial dephosphorylation of Tau in neuronal cells (Cross, et al., *J. Neurochem.*, 77, 94-102 (2001)). These discoveries suggest that inhibitors of GSK-3 have a potential role in the treatment of degenerative neurological disorders such as Alzheimer's disease.

WO 98/16528 describes purine derivatives, WO 99/65897 describes pyrimidine and pyridine derivatives, WO 00/38675 describes maleimides, and WO 01/56567 describes diaminothiazole derivatives that are taught to be inhibitors of GSK-3. Additional GSK-3 inhibitors are necessary to provide treatments for GSK-3 mediated endocrine and neurological disorders. The present invention provides inhibitors of GSK-3.

The present invention provides compounds of Formula I:

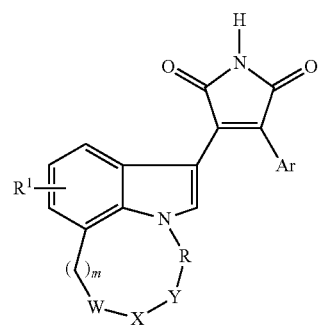

where:
$R^1$ is hydrogen, halo, or $C_1$-$C_4$ alkyl;
m is 0, 1, 2, 3, or 4;
R is —$(CH_2)_n$—, —$CH(CH_3)$—, —$C(CH_3)_2$—, —$CH_2$-$Q^1$-$CH_2$—, or —$CH(OH)$—$CH(OH)$—$CH_2$—;
$Q^1$ is CH(OH) or carbonyl;
n is 0, 1, 2, 3, or 4;
W—X—Y is —$CH_2$—$CH_2$—$CH_2$—, —$CH(R^{3'})$—$N(R^2)$—$CH(R^3)$—, —$N(R^4)$—$C(O)$—$CH_2$—, —$C(O)$-$Q^2$-$CH_2$—, —$CH(R^{3'})$—O—$CH_2$—, or —$CH(R^{3'})$—$N(R^4)$—$C(O)$—;
$Q^2$ is —$N(R^4)$— or —$CH_2$—;
$R^2$ is hydrogen, —($C_1$-$C_4$ alkylene)-$R^5$, $C_5$-$C_7$ cycloalkyl, tetrahydropyran-4-yl, pyridinyl, pyrimidinyl, triazolyl optionally substituted with amino, benzothiazol-2-yl, —C(S)-(morpholin-4-yl or $C_1$-$C_4$ alkoxy), —C(NR$^{16}$)R$^{17}$, —C(O)R$^6$, —CO$_2$R$^7$, —CO(NR$^8$R$^9$), —SO$_2$(NR$^8$R$^9$), —SO$_2$($C_1$-$C_4$ alkyl), or an amino acid residue;
$R^3$ and $R^{3'}$ are independently selected from the group consisting of hydrogen and $C_1$-$C_4$ alkyl provided that only one of $R^3$ and $R^{3'}$ may be $C_1$-$C_4$ alkyl;
$R^4$ is hydrogen or $C_1$-$C_4$ alkyl;
$R^5$ is hydrogen, pentahaloethyl or trihalomethyl, cyano, hydroxy, $C_1$-$C_4$ alkoxy optionally substituted with $C_1$-$C_4$ alkoxy, $C_3$-$C_6$ cycloalkyl, phenyl optionally substituted with up to three substituents independently selected from the group consisting of halo and $C_1$-$C_4$ alkoxy, pyridinyl, imidazolyl optionally substituted on a nitrogen atom with $C_3$-$C_6$ cycloalkyl, morpholin-4-yl, —CO$_2$H, —CO($C_1$-$C_4$ alkoxy), —CO(NR$^8$R$^9$), —NR$^8$R$^9$ or -(morpholin-4-yl)carbonyl;
$R^6$ is hydrogen, $C_1$-$C_{10}$ alkyl optionally substituted with up to three halo substituents, 1-amino-2-methoxyeth-1-yl, $C_3$-$C_6$ cycloalkyl, pyridinyl optionally substituted with $C_1$-$C_4$ alkyl, trifluoromethyl, carboxyl, or ($C_1$-$C_4$ alkoxy)carbonyl, pyridinyl-N-oxide, pyrazinyl, pyrimidinyl, imidazolyl, morpholin-4-yl optionally substituted with up to two $C_1$-$C_4$ alkyl groups, [1,4]oxazepin-4-yl, azetidin-4-yl, tetrahydropyran-4-yl, 3-methyl-6,7-dihydropyrrolo[1,2-a]imidazol-6-yl, piperazin-4-yl optionally substituted in the 4 position with phenyl or $C_1$-$C_4$ alkyl, pyrrolidin-1-yl, piperidin-1-yl optionally substituted in the 4-position with oxo or geminal dimethyl, piperidin-4-yl optionally substituted in the 1-position with ($C_1$-$C_4$ alkoxy)carbonyl or $C_1$-$C_4$ alkyl, or —($C_1$-$C_4$ alkylene)-$R^{10}$;
$R^7$ is $C_1$-$C_6$ alkyl optionally substituted with halo, 2-methoxyeth-1-yl, —($C_1$-$C_2$ alkylene)-(morpholin-4-yl or pyrrolidin-2-on-1-yl), or phenyl optionally substituted with one or two substituents independently selected from the group consisting of halo, $C_1$-$C_4$ alkyl, $C_1$-$C_4$ alkoxy, and trifluoromethyl;

$R^8$ is hydrogen or $C_1$-$C_6$ alkyl optionally substituted with $C_1$-$C_4$ alkoxy;

$R^9$ is hydrogen or $C_1$-$C_6$ alkyl optionally substituted with $C_1$-$C_4$ alkoxy;

$R^{10}$ is —OCH$_2$CH$_2$OCH$_3$, $C_3$-$C_6$ cycloalkyl, morpholin-4-yl, thiomorpholin-4-yl, 1,1-dioxothiomorpholin-4-yl, piperidin-1-yl, pyrrolidin-2-yl optionally substituted at the 1-position with $C_1$-$C_4$ alkyl, or imidazolyl optionally substituted with nitro;

Ar is benzofur-4-yl, benzofur-7-yl, benzothien-4-yl, benzothien-7-yl, 1-($R^{11}$)benzimidazol-4-yl, 1-($R^{11}$)indol-4-yl, indol-7-yl, isoquinolin-5-yl, 2,3-dihydrobenzofur-4-yl, 2,3-dihydrobenzofur-7-yl, 1,3-dihydroisobenzofur-4-yl, 1,3-dihydroisobenzofur-5-yl, benzo[1,3]dioxol-4-yl, benzo[1,3]dioxol-5-yl, 2,3-dihydrobenzo[1,4]dioxin-5-yl, 2,3-dihydrobenzo[1,4]dioxin-6-yl, 2',2'-difluorobenzo[1,3]dioxol-4-yl, or 2',2'-difluorobenzo[1,3]dioxol-5-yl each optionally substituted in the phenyl ring with substituents $R^{12}$ and $R^{13}$, or Ar is a group selected from imidazo[1,2-a]pyridin-3-yl optionally substituted with one or two substituents independently selected from the group consisting of halo, amino, $C_1$-$C_4$ alkyl, $C_1$-$C_4$ alkoxy, benzyloxy, cyano, and trifluoromethyl, 5,6,7,8-tetrahydroimidazo[1,2-a]pyridin-3-yl, imidazo[1,2-a]pyridin-5-yl, imidazo[1,2-a]pyrimidin-3-yl optionally substituted with amino, imidazo[1,2-c]pyrimidin-3-yl, imidazo[1,2-a]pyrazin-3-yl, imidazo[1,2-b]pyridazin-3-yl, imidazo[2,1-b]thiazol-3-yl, thiazolo[3,2-b][1,2,4]triazol-6-yl, furo[3,2-c]pyridin-7-yl optionally substituted with halo or —NR$^{14}$R$^{15}$, thieno[3,2-b]pyridin-7-yl, pyrazolo[2,3-a]pyridin-3-yl, pyrazolo[1,5-a]pyridin-3-yl, or 4,5,6,7-tetrahydropyrazolo[1,5-a]pyridin-3-yl;

$R^{11}$ is hydrogen, $C_1$-$C_4$ alkyl, or —(CH$_2$)$_p$-G;

$R^{12}$ is halo, hydroxy, amino, $C_1$-$C_4$ alkoxy, —NHC(O)($C_1$-$C_4$ alkyl), or —O—(CH$_2$)$_p$-G;

$R^{13}$ is halo;

p is 2, 3, 4, or 5;

G is hydroxy or NR$^{14}$R$^{15}$;

$R^{14}$ and $R^{15}$ are independently selected from the group consisting of hydrogen and $C_1$-$C_5$ alkyl;

$R^{16}$ is hydrogen or cyano, $R^{17}$ is —NR$^8$R$^9$, $C_1$-$C_4$ alkyl, morpholin-4-yl, or piperidin-1-yl; or a pharmaceutically acceptable salt thereof, provided that when n is 0, W—X—Y is not —CH(R$^3$')—N(R$^2$)—C(O)—.

The present invention further provides a method of inhibiting GSK-3 in a mammal comprising administering to a mammal in need of such treatment an effective amount of a compound of Formula I.

The present invention also provides a method of treating diabetes in a mammal comprising administering to a mammal in need of such treatment an effective amount of a compound of Formula I.

The present invention also provides a method of treating Alzheimer's disease in a mammal comprising administering to a mammal in need of such treatment an effective amount of a compound of Formula I.

The present invention further provides a method of stimulating bone deposition in a mammal comprising administering to a mammal in need of such treatment an effective amount of a GSK-3 inhibitor.

The present invention also provides a method of stimulating bone deposition in a mammal comprising administering to a mammal in need of such treatment an effective amount of a compound of Formula I.

The present invention also provides a pharmaceutical formulation comprising a compound of Formula I, in combination with a pharmaceutically acceptable carrier, diluent or excipient.

This invention also provides the use of a compound of Formula I for the manufacture of a medicament for the inhibition of GSK-3. Additionally, this invention provides a pharmaceutical formulation adapted for the treatment of diabetes containing a compound of Formula I. Furthermore, this invention provides the use of a compound of Formula I for the manufacture of a medicament for the treatment of diabetes. This invention also provides the use of a compound of Formula I for the manufacture of a medicament for the treatment of Alzheimer's disease. The present invention also provides a formulation adapted for stimulating bone deposition in mammals containing a compound of Formula. The present invention further provides the use of a compound of Formula I for the manufacture of a medicament for stimulating bone deposition.

The general chemical terms used in the formulae above have their usual meanings. For example, the term "$C_1$-$C_6$ alkyl" includes methyl, ethyl, propyl, isopropyl, butyl, isobutyl, sec-butyl, tert-butyl, neopentyl, and hexyl moieties. The term "$C_1$-$C_4$ alkoxy" is taken to mean a $C_1$-$C_4$ alkyl group linked to the parent molecule through an oxygen atom, and includes the groups methoxy, ethoxy, isopropoxy, and the like. Likewise, the term "$C_1$-$C_4$ alkylthio" is taken to mean a $C_1$-$C_4$ alkyl group linked to the parent molecule through a sulfur atom, and includes methylthio, ethylthio, isobutylthio, and the like. The term "halo" includes fluoro, chloro, bromo, and iodo.

The term "($C_1$-$C_4$ alkylene)-R$^5$" is taken to mean a linear or branched alkylene chain substituted at any carbon atom with the variable $R^5$ and includes, for example, linear or branched alkyl chains, benzyl, and α-methylbenzyl moieties.

Likewise, the term "($C_1$-$C_4$ alkylene)-R$^{10}$" is taken to mean a linear or branched alkylene chain substituted at any carbon atom with the variable $R^{10}$ and includes, for example, linear or branched alkyl chains, benzyl, and α-methylbenzyl moieties.

The term "amino acid residue" is taken to mean an amino acid moiety selected from the group consisting of alanyl, arginyl, asparaginyl, aspartyl, cysteinyl, glutaminyl, glutamyl, glycyl, histidyl, isoleucyl, leucyl, lysyl, methionyl, phenylalanyl, phenylglycyl, prolyl, seryl, threonyl, tryptophanyl, tyrosyl, and valyl bonded through an acid carbonyl.

The term "GSK-3" is taken to mean GSK-3α and/or GSK-3β.

The term "diabetes" is taken to mean Type I and/or Type II diabetes.

The skilled artisan will appreciate that certain compounds of Formula I contain at least one chiral center. The present invention contemplates all individual enantiomers or diastereomers, as well as mixtures of the enantiomers and diastereomers of said compounds including racemates. It is preferred that compounds of Formula I containing at least one chiral center exist as single enantiomers or diastereomers. The single enantiomers or diastereomers may be prepared beginning with chiral reagents or by stereoselective or stereospecific synthetic techniques. Alternatively, the single enantiomers or diastereomers may be isolated from mixtures by standard chiral chromatographic or crystallization techniques.

It will be understood by the skilled reader that most or all of the compounds of the present invention are capable of forming salts. In all cases, the pharmaceutically acceptable salts of all of the compounds are included in the names of them. The compounds of the present invention are amines, and accordingly react with any of a number of inorganic and organic acids to form pharmaceutically acceptable acid addition salts. Preferred pharmaceutically acceptable salts are those formed with hydrochloric acid or methanesulfonic acid.

While all of the compounds of Formula I are useful inhibitors of GSK-3, certain classes of compounds are preferred. The following paragraphs describe such preferred classes:

aa) W—X—Y is —$CH_2$—$CH_2$—$CH_2$—;
ab) W—X—Y is —$CH(R^{3'})$—$N(R^2)$—$CH(R^3)$—;
ac) W—X—Y is —$CH(R^{3'})$—O—$CH_2$—;
ad) R is —$(CH_2)_n$—;
ae) R is —$C(CH_3)_2$—
af) m is 0, 1, or 2;
ag) m is 0;
ah) n is 0, 1, 2, or 3;
ai) n is 1;
aj) n is 3;
ak) $R^1$ is H;
al) $R^1$ is halo;
am) $R^1$ is chloro;
an) $R^1$ is fluoro;
ao) $R^2$ is H;
ap) $R^2$ is —$CO_2R^7$;
aq) $R^7$ is $C_1$-$C_6$ alkyl;
ar) $R^7$ is ethyl;
as) $R^7$ is isopropyl;
at) $R^7$ is isobutyl;
au) $R^7$ is tert-butyl;
av) $R^7$ is 2-methoxyeth-1-yl;
aw) $R^7$ is ($C_1$-$C_2$ alkylene)morpholin-4-yl;
ax) $R^7$ is (morpholin-4-yl)methyl;
ay) $R^7$ is ($C_1$-$C_2$ alkylene)pyrrolidin-2-on-1-yl;
az) $R^7$ is (pyrrolidin-2-on-1-yl)methyl;
ba) $R^2$ is ($C_1$-$C_4$ alkylene)-$R^5$;
bb) $R^5$ is hydrogen;
bc) $R^2$ is methyl;
bd) $R^2$ is isopropyl;
be) $R^5$ is cyano;
bf) $R^2$ is cyanomethyl;
bg) $R^5$ is phenyl optionally substituted with halo;
bh) $R^2$ is benzyl;
bi) $R^2$ is 4-fluorobenzyl;
bj) $R^5$ is pyridinyl;
bk) $R^5$ is pyridin-3-yl;
bl) $R^2$ is (pyridin-3-yl)methyl;
bm) $R^5$ is $C_3$-$C_6$ cycloalkyl;
bn) $R^5$ is cyclopropyl;
bo) $R^2$ is (cyclopropyl)methyl;
bp) $R^5$ is $C_1$-$C_4$ alkoxy;
bq) $R^5$ is methoxy;
br) $R^2$ is 2-(methoxy)eth-1-yl;
bs) $R^5$ is morpholin-4-yl;
bt) $R^2$ is 2-(morpholin-4-yl)eth-1-yl;
bu) $R^5$ is 1-(cyclohexyl)imidazol-5-yl;
by) $R^2$ is (1-(cyclohexyl)imidazol-5-yl)methyl;
bw) $R^2$ is —$C(O)R^6$;
bx) $R^6$ is $C_1$-$C_{10}$ alkyl optionally substituted with up to three halo substituents;
by) $R^6$ is methyl;
bz) $R^6$ is ethyl;
ca) $R^6$ is propyl;
cb) $R^6$ is isopropyl;
cc) $R^6$ is 3-methylbut-1-yl;
cd) $R^6$ is difluoromethyl;
ce) $R^6$ is 3,3,3-trifluoroprop-1-yl;
cf) $R^6$ is heptyl;
cg) $R^6$ is morpholin-4-yl optionally substituted with up to two $C_1$-$C_4$ alkyl substituents;
ch) $R^6$ is morpholin-4-yl;
ci) $R^6$ is cis-2,6-dimethylmorpholin-4-yl;
cj) $R^6$ is piperidin-1-yl;
ck) $R^6$ is piperidin-4-on-1-yl;
cl) $R^6$ is tetrahydropyran-4-yl;
cm) $R^6$ is 4-phenylpiperazin-1-yl;
cn) $R^6$ is [1,4]oxazepin-4-yl;
co) $R^6$ is $C_3$-$C_6$ cycloalkyl;
cp) $R^6$ is cyclopropyl;
cq) $R^6$ is pyridinyl optionally substituted with $C_1$-$C_4$ alkyl or trifluoromethyl;
cr) $R^6$ is pyridin-3-yl;
cs) $R^6$ is 2-trifluoromethylpyridin-4-yl;
ct) $R^6$ is 2-methylpyridin-5-yl;
cu) $R^6$ is ($C_1$-$C_4$ alkylene)-$R^{10}$;
cv) $R^{10}$ is $C_3$-$C_6$ cycloalkyl;
cw) $R^{10}$ is cyclopentyl;
cx) $R^6$ is (cyclopentyl)methyl;
cy) $R^{10}$ is thiomorpholin-4-yl;
cz) $R^6$ is (thiomorpholin-4-yl)methyl;
da) $R^2$ is —$C(O)(NR^8R^9)$;
db) $R^8$ and $R^9$ are both hydrogen;
dc) one of $R^8$ and $R^9$ is hydrogen and the other is methyl;
dd) $R^8$ and $R^9$ are both methyl;
de) $R^8$ and $R^9$ are both ethyl;
df) $R^8$ and $R^9$ are both propyl;
dg) $R^8$ and $R^9$ are both isopropyl;
dh) $R^8$ and $R^9$ are both butyl;
di) $R^8$ and $R^9$ are both isobutyl;
dj) $R^2$ is $C_3$-$C_6$ cycloalkyl;
dk) $R^2$ is cyclopentyl;
dl) $R^2$ is pyrimidin-2-yl;
dm) $R^2$ is pyridin-2-yl;
dn) $R^2$ is tetrahydropyran-4-yl;
do) $R^2$ is —C(S)-(morpholin-4-yl);
dp) $R^3$ is H and $R^{3'}$ is $C_1$-$C_4$ alkyl;
dq) $R^3$ is $C_1$-$C_4$ alkyl and $R^{3'}$ is H;
dr) $R^3$ and $R^{3'}$ are both H;
ds) $R^3$ is methyl;
dt) $R^{3'}$ is methyl;
du) Ar is benzofur-4-yl;
dv) Ar is benzofur-7-yl;
dw) Ar is 2,3-dihydrobenzofur-4-yl;
dx) Ar is 1-($R^{11}$)indol-4-yl;
dy) Ar is 1-($R^{11}$)benzimidazol-4-yl;
dz) Ar is imidazo[1,2-a]pyridin-3-yl optionally substituted with one or two substituents independently selected from the group consisting of halo, $C_1$-$C_4$ alkyl, and $C_1$-$C_4$ alkoxy;
ea) Ar is imidazo[1,2-a]pyridin-3-yl;
eb) Ar is imidazo[1,2-a]pyridin-3-yl substituted with halo;
ec) Ar is imidazo[1,2-a]pyridin-3-yl substituted with fluoro;
ed) Ar is 8-fluoroimidazo[1,2-a]pyridin-3-yl;
ee) Ar is imidazo[1,2-a]pyridin-3-yl substituted with chloro;
ef) Ar is 7-chloroimidazo[1,2-a]pyridin-3-yl;
eg) Ar is 8-chloroimidazo[1,2-c]pyridin-3-yl;
eh) Ar is imidazo[1,2-a]pyridin-3-yl substituted with bromo;
ei) Ar is 6-bromoimidazo[1,2-a]pyridin-3-yl;
ej) Ar is imidazo[1,2-a]pyridin-3-yl substituted with $C_1$-$C_4$ alkyl;
ek) Ar is imidazo[1,2-a]pyridin-3-yl substituted with methyl;
el) Ar is 2-methylimidazo[1,2-a]pyridin-3-yl;

em) Ar is 6-methylimidazo[1,2-a]pyridin-3-yl;
en) Ar is 7-methylimidazo[1,2-a]pyridin-3-yl;
eo) Ar is 8-methylimidazo[1,2-a]pyridin-3-yl;
ep) Ar is 6,8-dimethylimidazo[1,2-a]pyridin-3-yl;
eq) Ar is imidazo[1,2-a]pyridin-3-yl substituted with $C_1$-$C_4$ alkoxy;
er) Ar is imidazo[1,2-a]pyridin-3-yl substituted with methoxy;
es) Ar is 7-methoxyimidazo[1,2-a]pyridin-3-yl;
et) Ar is 8-methoxyimidazo[1,2-a]pyridin-3-yl;
eu) Ar is imidazo[1,2-a]pyridin-7-yl;
ev) Ar is furo[3,2-c]pyridin-3-yl;
ew) Ar is imidazo[1,2-b]pyridazin-3-yl;
ex) Ar is 6-methylimidazo[1,2-b]pyridazin-3-yl;
ey) Ar is pyrazolo[1,5-a]pyridin-3-yl;
ez) Ar is 4,5,6,7-tetrahydropyrazolo[1,5-a]pyridin-3-yl;
fa) $R^{11}$ is hydrogen;
fb) $R^{11}$ is —$(CH_2)_p$-G;
fc) p is 3;
fd) G is hydroxy;
fe) $R^{12}$ is halo;
ff) $R^{12}$ is fluoro;
fg) $R^{12}$ is hydroxy;
fh) $R^{12}$ is $C_1$-$C_4$ alkoxy;
fi) $R^{12}$ is methoxy;
fj) $R^{12}$ is —NHC(O)($C_1$-$C_4$ alkyl);
fk) $R^{12}$ is —NHC(O)$CH_3$;
fl) $R^{13}$ is fluoro;
fm) The compound is a free base;
fn) The compound is a salt;
fo) The compound is the hydrochloride salt.

It will be understood that the above classes may be combined to form additional preferred classes.

The compounds of Formula I are inhibitors of GSK-3. Thus, the present invention also provides a method of inhibiting GSK-3 in a mammal that comprises administering to a mammal in need of said treatment a GSK-3 inhibiting amount of a compound of Formula I. The present compounds are believed to be useful in treating Type I and/or Type II diabetes. Furthermore, the compounds of the present invention are believed to be useful in the treatment of neurological disorders such as dementias, especially dementia of the Alzheimer's type. The compounds of the present invention are also believed to be useful for the treatment of bipolar disorder.

A further embodiment of the present invention is the use of inhibitors of GSK-3 for rapid bone deposition. This ability to stimulate rapid bone deposition provides a new means to treat a variety of disease states and conditions where it would be beneficial to grow new bone. These disease states include osteoporosis and fraility as well as bone loss due to periodontal disease. Compounds exhibiting this activity will also be useful in promoting wound healing and bone fracture repair. It is also contemplated that GSK-3 inhibitor mediated bone deposition will improve patient outcomes in joint replacement surgeries by enhancing the attachment of a joint prosthesis to the patient's bone. The use of the compounds of the present invention for the induction of rapid bone deposition is preferred. It is also preferred that the mammal to be treated by the administration of the compounds of Formula I is human.

The compounds of the present invention can be prepared by a variety of procedures, some of which are illustrated in the Schemes below. It will be recognized by one of skill in the art that the individual steps in the following schemes may be varied to provide the compounds of Formula I. The particular order of steps required to produce the compounds of Formula I is dependent upon the particular compound being synthesized, the starting compound, and the relative lability of the substituted moieties. Some substituents have been eliminated in the following schemes for the sake of clarity and are not intended to limit the teaching of the schemes in any way.

The compounds of Formula I are prepared from an appropriately substituted oxoacetic acid ester and an appropriately substituted acetamide as illustrated in Scheme I essentially as described by Faul, et al., *J. Org. Chem.* 63, 6053-6058 (1998), where the ring designated "A" corresponds to the annulated rings of Formula I.

Scheme I

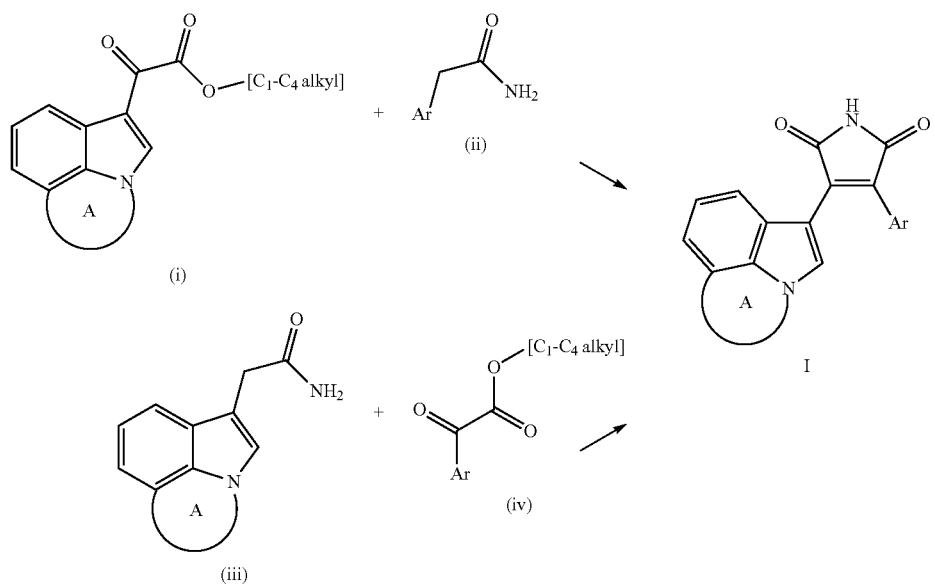

The oxoacetic acid esters of formula (I) or (iv) are reacted with an acetamide of formula (II) or (iii), respectively, in a suitable solvent, such as tetrahydrofuran, in the presence of a suitable base, preferably potassium tert-butoxide. The condensation reaction is conducted at a temperature from about 0° C. to about room temperature, and the reactants are stirred for 1-24 hours. The reaction mixture is treated with a suitable acid, such as hydrochloric acid, after which the mixture is stirred at about ambient temperature for 1-24 hours. The resulting maleimide may be isolated by standard techniques, and purified by crystallization or chromatography as necessary or desired.

The requisite oxoacetic acid esters of formulae (Iv) are prepared from appropriately substituted Ar groups by methods well known to the skilled artisan as illustrated in Scheme II, where X is bromo or iodo.

Scheme II

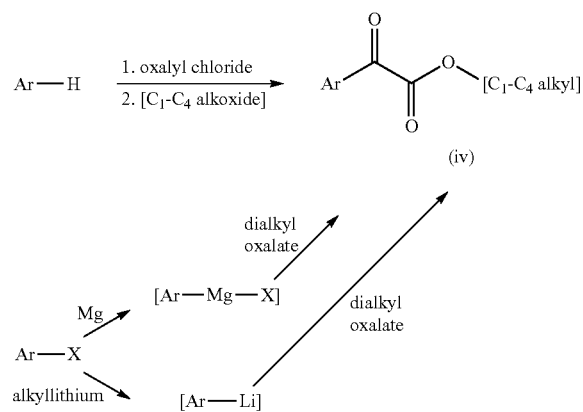

An appropriately substituted Ar is reacted with an oxalyl halide, such as oxalyl chloride, in the presence of an organic base, such as 2,6-lutidine or triethylamine, in an appropriate solvent, such as dichloromethane or diethyl ether, to give the corresponding Ar-oxalyl halide. The reaction is performed at from 0° C. to reflux for from 1-24 hours. The mixture is cooled to about −78° C. and an alkoxide source, such as sodium methoxide, is added in an appropriate solvent, such as methanol. The resulting oxoacetic acid ester may be isolated by standard techniques and purified by crystallization or chromatography as necessary or desired. Alternatively, a compound of Formula Ar—X is subjected to a lithium-halogen exchange, following which the lithium anion is quenched by an appropriate dialkyl oxalate to provide the desired oxoacetic acid ester. Alternatively, the subject oxoacetic acid esters may be prepared by first reacting a compound of Formula Ar—X with magnesium and then quenching the resulting Grignard reagent with a dialkyl oxalate under standard conditions.

The requisite acetamides of formula (II) may be prepared from the corresponding oxoacetic acid ester of formula (Iv) as illustrated in Scheme III.

Scheme III

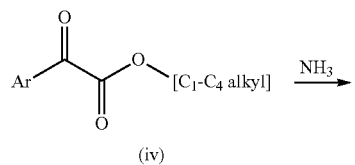

-continued

The oxoacetic acid ester (iv) is reacted with ammonia or ammonium hydroxide in a suitable solvent, such as tetrahydrofuran or diethyl ether. The reaction is conducted at about 0° C. for 1-12 hours, after which the reaction mixture is allowed to warm to about ambient temperature. The resulting ketoamide may be isolated by standard techniques and purified by crystallization or chromatography as necessary or desired. This ketoamide is then reduced by reaction with a metal catalyst, such as palladium, and sodium hypophosphite in a suitable solvent, such as tetrahydrofuran, dioxane, or dimethylformamide. The reaction is conducted under nitrogen at about reflux conditions for 1-12 hours. The resulting acetamide is isolated by standard techniques and may be purified by crystallization or chromatography as necessary or desired.

Alternatively, the requisite acetamides may be prepared from an appropriate Ar—X by standard functional group transformations well known to the skilled artisan as illustrated in Scheme IV (see, Larock, *Comprehensive Organic Transformations*, 2$^{nd}$ Ed., John Wiley & Sons, New York, pg. 1988-1989 (1999)).

Scheme IV

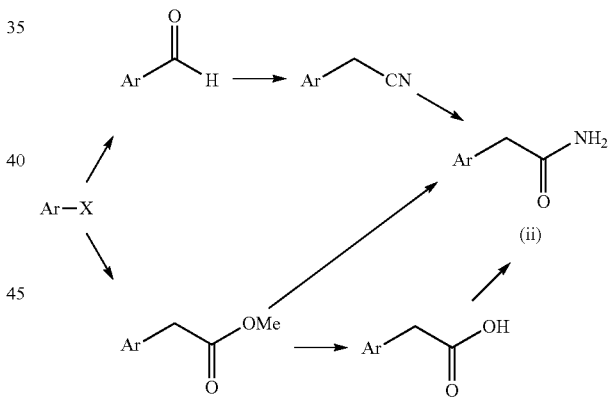

The compounds of formula Ar—X may be converted to the corresponding aldehyde by reaction with an appropriate alkyllithium under standard conditions, and the quenching with N,N'-dimethylformamide. This aldehyde is then converted to the corresponding acetonitrile via a phosphorylated cyanohydrin formed in situ by reaction with diethylcyano-phosphonate and lithium cyanide in a suitable solvent, such as tetrahydrofuran. For similar examples of this conversion see, Yoneda, et al., *Tetrahedron Lett.*, 30, 3681-3684 (1989); Yoneda, et al., *J. Org. Chem.*, 56, 1827-1832 (1991). Base hydrolysis of the acetonitrile provides the desired acetamides (ii). Alternatively, Ar—X may be reacted with 2-ethoxy-2-oxoethylzinc bromide with a palladium catalyst in a suitable solvent, such as tetrahydrofuran, to provide the corresponding arylacetic acid ester. This ester may be reacted with ammonia directly in a sealed tube with a suitable solvent at elevated temperature to provide the requisite acetamide.

Alternatively, the arylacetic acid ester is subjected to base hydrolysis to provide the corresponding aryl acetic acid, and this acid subjected to standard peptide coupling conditions in the presence of a source of ammonia, such as ammonium hydroxide or ammonia gas. Suitable coupling reagents include N,N'-carbonyldiimidazole (CDI), N,N'-dicyclohexylcarbodiimide (DCC), 1-(3-dimethylamino-propyl)-3-ethylcarbodiimide hydrochloride (EDC), and 1-(3-(1-pyrrolidinyl)propyl)-3-ethylcarbodiimide (PEPC). Suitable optional catalysts for the coupling reaction include N,N-[dimethyl]-4-aminopyridine (DMAP). All of the reagents are combined in a suitable solvent, typically dichloromethane, chloroform, tetrahydrofuran, dioxane, or diethyl ether, and are stirred for from 1 to 72 hours at a temperature of from ambient to about the reflux temperature of the solvent. The desired product may be isolated by standard extractive and crystallization techniques, and purified by chromatography or crystallization as necessary or desired.

The annulated-indole oxoacetic acid esters (i) and annulated-indole acetamides (iii) may be similarly prepared from the corresponding annulated-indoles of formula (v):

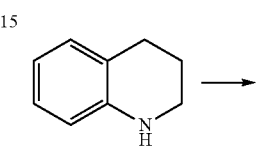

where the ring designated "A" corresponds to the annulated ring in Formula I.

The requisite aryl intermediates for the formation of formula (II) or (iv) are either commercially available or may be prepared by methods well known to the skilled artisan. The requisite benzofurans, for example, may be prepared as described in Scheme V.

Scheme V

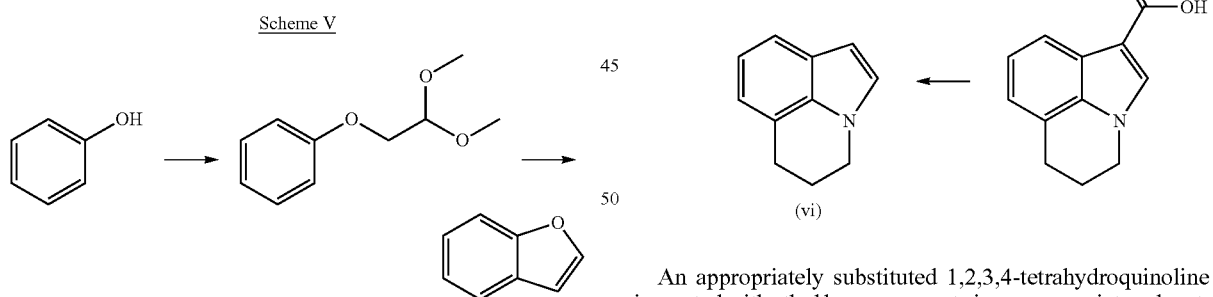

Appropriately substituted phenols are O-alkylated with bromoacetaldehyde dimethyl or diethyl acetal and a suitable base, such as potassium carbonate. Cyclization is accomplished in a suitable solvent, such as chlorobenzene at refluxing temperatures.

The requisite indoles are either commercially available or may be prepared by methods well known in the art. Indole syntheses are described in Robinson, *The Fischer Indole Synthesis*, Wiley, New York (1983); Hamel, et al., *Journal of Organic Chemistry*, 59, 6372 (1994); and Russell, et al., *Organic Preparations and Procedures International*, 17, 391 (1985).

The requisite annulated-indoles are prepared by a variety of methods depending upon the specific structure of the ring system. Synthetic methodologies leading to the various annulated-indoles are illustrated in the following schemes and discussed in the following paragraphs. The preparations and examples further illustrate these basic routes as well as modifications to these routes to prepare certain requisite substituted variants. Substituents have been removed from the structures in the following schemes for the sake of clarity, and are not intended to limit the scope of the invention in any way.

5,6-dihydro-4H-pyrrolo[3,2,1-ij]quinolines

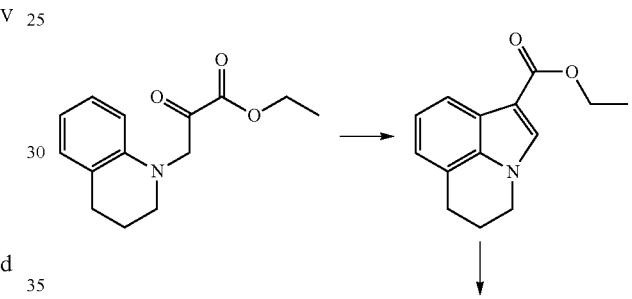

An appropriately substituted 1,2,3,4-tetrahydroquinoline is reacted with ethyl bromopyruvate in an appropriate solvent, such as dimethylformamide or tetrahydrofuran. The reaction mixture is stirred for 1-30 hours. The product from this reaction is isolated by standard techniques and is then reacted with an appropriate magnesium halide, typically magnesium chloride, and an appropriate alcohol such as methoxyethanol in an appropriate cosolvent, such as tetrahydrofuran or dimethylformamide. The skilled artisan will appreciate that the addition must be performed slowly and carefully, after which the resulting reaction mixture is stirred for 1-12 hours at about reflux. The resulting carboxylic acid ester is isolated by standard techniques. This ester is then hydrolyzed and decarboxylated under standard conditions to provide compounds of formula (vi).

6,7-dihydro-6H-[1,4]diazepino[6,7,1-hi]indoles

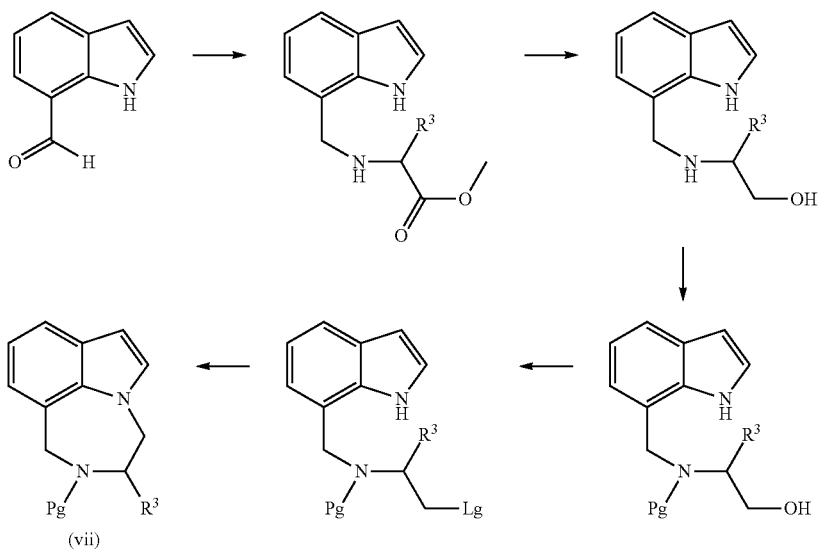

(vii)

An appropriately substituted indole-7-carboxaldehyde in an appropriate solvent, such as 1,2-dichloroethane, is reacted with an appropriately substituted amino acid methyl ester and acetic acid. This reaction is conducted under nitrogen at about ambient temperature in the presence of a mild reducing agent, such as sodium cyanoborohydride or sodium triacetoxyborohydride. The reaction mixture is stirred for about 24 hours, and the resulting amino ester is isolated by standard techniques. The ester moiety is reduced to the corresponding alcohol by treatment with a suitable reducing agent, typically lithium aluminum hydride, in an appropriate solvent, typically tetrahydrofuran or diethyl ether. The secondary amine moiety is now reacted with an appropriate reagent to introduce a suitable amino protecting group "Pg", such as a formyl group, acetyl group, or preferably a tert-butoxycarbonyl moiety. Techniques for the introduction of these groups are well known to the skilled artisan. A solution of this compound in an appropriate solvent, such as dichloromethane or diethyl ether, is reacted with an appropriate reagent to activate the hydroxy moiety, providing a leaving group ("Lg"). The skilled artisan will appreciate that appropriate leaving groups include halides, oxonium ions, alkyl perchlorates, ammonio- alkanesulfonate esters, alkyl fluorosulfonates, nonaflates, tresylates, triflates, and sulfonic esters, preferably the mesylate or tosylate. Techniques for the introduction of these groups are well known to the skilled artisan. (See for example: March, "Advanced Organic Chemistry," John Wiley and Sons, New York, N.Y., 1992, pg. 352-362). The activated compound is then dissolved in an appropriate solvent, such as tetrahydrofuran, diethyl ether or N,N-dimethylformamide and is reacted with a strong base, such as potassium hydride or sodium hydride. The reaction is conducted under nitrogen at about 0° C. and stirred for 30-120 minutes. The compound of formula (vii) is isolated and purified by standard techniques. The skilled artisan will appreciate that the nitrogen-protecting groups may be removed at any convenient point in the synthesis of the compounds of the present invention. Methods of removing an amino-protecting group are well known in the art (for example, see: T. W. Greene, "Protective Groups in Organic Synthesis," John Wiley and Sons, New York, N.Y., 1991, Chapter 7).

5,6,7,8-tetrahydro-6H-[1,4]diazocino[7,8,1-hi]indoles

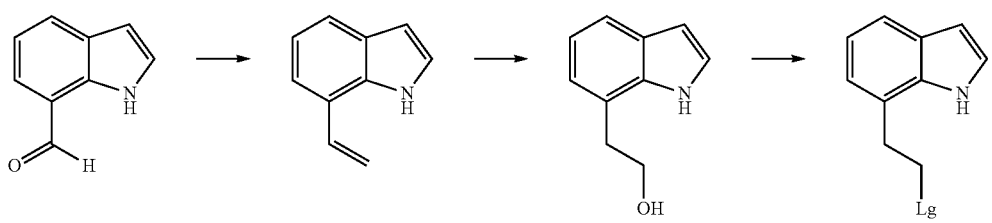

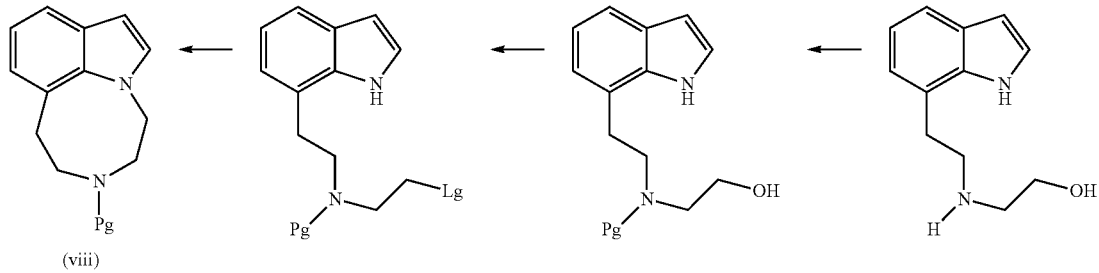

An appropriately substituted indole-7-carboxaldehyde in an appropriate solvent, such as tetrahydrofuran or toluene, is reacted with a suitable methylenating reagent at about ambient temperature. Suitable methylenating reagents include Tebbe reagent (μ-chloro-μ-methylene[bis(cyclopentadienyl)titanium]dimethylaluminum) and appropriate Wittig reagents, such as methyltriphenylphosphonium bromide, in the presence as a suitable base, such as potassium tert-butoxide. The reaction mixture is stirred for 1-6 hours, after which the resultant vinylindole is isolated under standard techniques. This compound is then hydroborated and oxidized under standard conditions to provide the corresponding hydroxyethylindole. This alcohol is then activated as previously described, and reacted with ethanolamine or an appropriate amino acid ester. When aminoethanol is employed, the resulting alcohol is activated and the compound cyclized as previously described. When an amino acid ester is employed, the resulting ester is first reduced, and then activated and the compound cyclized as previously described to provide compounds of formula (xiii). The skilled artisan will appreciate that the nitrogen-protecting groups may be removed at any convenient point in the synthesis of the compounds of the present invention.

Pyrrolo[3,2,1-kl]benzo[b]azacyclooctane

An appropriately substituted 7-vinylindole is alkylated with an appropriate bromoalkene under standard conditions and the resulting diene is reacted with bis(tricyclohexylphosphine)benzylidine ruthenium (IV) dichloride (Grubb's catalyst) at room temperature in a suitable solvent, such as dichloromethane. After about 24 hours the cyclized alkene is isolated by standard techniques. The double bond may then be reduced under standard hydrogenation conditions to provide the compounds of formula (ix).

[1,5]diazaperhydroonino[8,9,1-hi]indoles

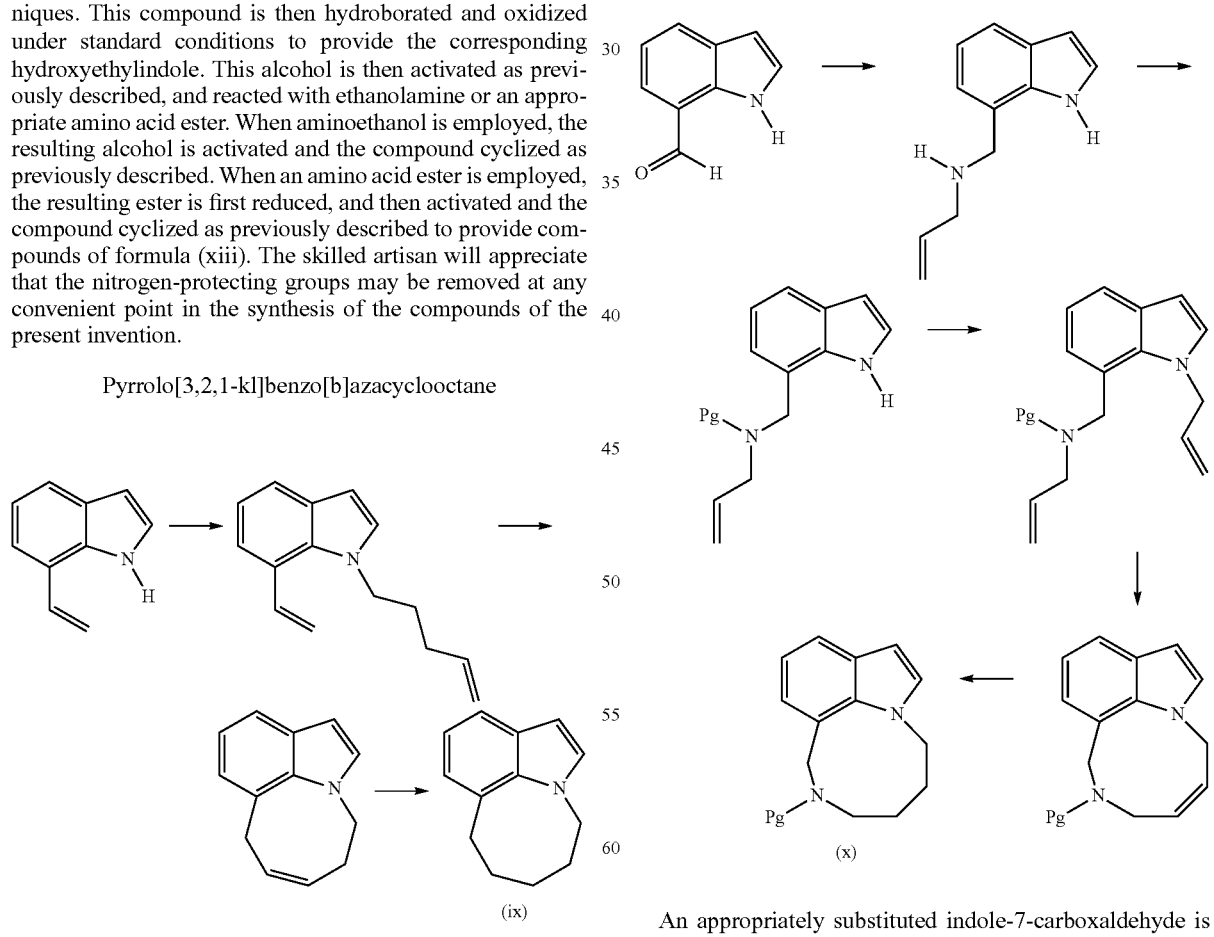

An appropriately substituted indole-7-carboxaldehyde is reductively aminated with allylamine in the presence of a suitable acid, such as acetic acid, and an appropriate reducing agent, such as sodium cyanoborohydride or sodium triacetoxyborohydride in an appropriate solvent, such as 1,2- dichloroethane. The mixture is stirred at room temperature for about 24 hours and the resulting amine is isolated and purified by standard techniques. The amine is then protected as previously described and the indole nitrogen alkylated with allyl bromide under standard conditions. The diene is then cyclized as previously described to provide the cyclic alkene. The double bond may then be reduced under standard hydrogenation conditions to provide the compounds of formula (x). The double bond may also be oxidized to introduce the diol functionality.

The skilled artisan will appreciate that the general synthetic schemes discussed in the preceding paragraphs may be modified by methods well known in the art to provide the remaining annulated indoles necessary to prepare the compounds of the present invention.

Many of the compounds of the present invention are not only inhibitors of GSK-3, but are also useful intermediates for the preparation of additional compounds of the present invention. For example, secondary amines may be acylated, alkylated or coupled with carboxylic acids or amino acids under standard peptide coupling conditions. Furthermore, ester moieties may be reduced to the corresponding alcohols or converted to amides under standard conditions. Alcohols may be activated and displaced by a number of nucleophiles to provide other compounds of the invention. Such leaving groups include but are not limited to halides, oxonium ions, alkyl perchlorates, ammonioalkanesulfonate esters, alkyl fluorosulfonates, nonaflates, tresylates, triflates, and sulfonic esters, preferably the mesylate or tosylate. Techniques for the introduction of these groups are also well known to the skilled artisan; see, for example, March, *Advanced Organic Chemistry*, $5^{th}$ Ed., John Wiley and Sons, New York, pg. 445-449 (2001).

The skilled artisan will also appreciate that not all of the substituents in the compounds of Formula I will tolerate certain reaction conditions employed to synthesize the compounds. These moieties may be introduced at a convenient point in the synthesis, or may be protected and then deprotected as necessary or desired. The skilled artisan will appreciate that the protecting groups may be removed at any convenient point in the synthesis of the compounds of the present invention. Methods for introducing and removing nitrogen and oxygen protecting groups are well known in the art; see, for example, Greene and Wuts, *Protective Groups in Organic Synthesis*, $3^{rd}$ Ed., John Wiley and Sons, New York, Chapter 7 (1999). Furthermore, the skilled artisan will appreciate that in many circumstances, the order in which moieties are introduced is not critical. The particular order of steps required to produce the compounds of Formula I is dependent upon the particular compound being synthesized, the starting compound, and the relative lability of the substituted moieties.

PREPARATION 1

5-fluoro-1,2,3,4-tetrahydroquinoline 5-fluoroquinoline

Add sodium nitrite in portions to a suspension of 5-aminoquinoline (50 g, 347 mmol) in 48% $HBF_4$ (200 mL) at 0° C. Stir for 1 hour and then pour into 1:1 diethyl ether/ethyl acetate (500 mL). Filter the resulting suspension and dry the solid. Add this solid (82.5 g, 338 mmol) in portions to refluxing xylene (1 L), stir for 2 hours, and then cool. Decant the xylene and dissolve the residue in 1N hydrochloric acid (600 mL). Neutralize with sodium carbonate, extract with ethyl acetate (10×500 mL), dry the extracts over sodium sulfate, filter and concentrate under reduced pressure. Subject the residue to silica gel chromatography, eluting with 10-20% diethyl ether in hexanes. Combine fractions containing product and concentrate them under reduced pressure to provide the desired compound (28.1 g, 55%).

MS (EI, m/z) $C_9H_6FN$ (M+1) 148.0

Reduction

Shake a mixture of 5-fluoroquinoline (28.1 g) and 5% palladium on carbon (5.6 g) in methanol over night at 40° C. under 60 psi hydrogen. Filter the mixture through Celite and concentrate under reduced pressure. Subject the residue to silica gel chromatography, eluting with 5-10% ethyl acetate in hexanes. Combine fractions containing product and concentrate them under reduced pressure to provide the title compound (22.5 g, 78%).

MS (EI, m/z) $C_9H_{10}FN$ (M+1) 152.0

PREPARATION 2

6-Fluoro-1,2,3,4-tetrahydroquinoline

Beginning with 6-aminoquinoline, the title compound is prepared essentially as described in Preparation 1.

MS (EI, m/z) $C_9H_{10}FN$ (M+1) 152.0.

PREPARATION 3

5-Chloro-1,2,3,4-tetrahydroquinoline

A mixture of 5-chloroquinoline (10.0 g) and platinum oxide (50 mg) in acetic acid was shaken under a hydrogen atmosphere at room temperature for 4 hours. The mixture was diluted with diethyl ether and filtered through Celite. The volatiles were removed under reduced pressure and the residue was partitioned between saturated aqueous sodium bicarbonate and ethyl acetate (3×300 mL). The organic extracts were dried over sodium sulfate, filtered and concentrated under reduced pressure. The residue was purified over silica gel and the fractions containing product were combined and concentrated under reduced pressure to provide 7.0 g (69%) of the desired compound.

PREPARATION 4

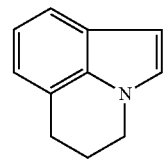

5,6-Dihydro-4H-pyrrolo[3,2,1-ij]quinoline 3-(3,4-Dihydro-2H-quinolin-1-yl)-2-oxopropionic acid ethyl ester Add bromoethyl pyruvate (40 mL, 0.29 mol) to a solution of 1,2,3,4-tetrahydroquinoline (75.5 mL, 0.59 mol) in tetrahydrofuran (300 mL) dropwise over 30 minutes. Stir for 24 hours, filter the reaction mixture, rinse the filter cake well with tetrahydrofuran (100 mL), and concentrate the filtrate under reduced pressure to provide the desired compound as a red oil (79.7 g).

5,6-Dihydro-4H-pyrrolo[3,2,1-ij]quinoline-1-carboxylic acid ethyl ester

Add magnesium chloride (27.7 g, 0.29 mol) to 2-methoxyethanol (400 mL) and heat the mixture to reflux. Add a solution of 3-(3,4-Dihydro-2H-quinolin-1-yl)-2-oxopropionic acid ethyl ester (0.29 mol) in 2-methoxyethanol (100 mL) and tetrahydrofuran (40 mL) slowly to the MgCl$_2$ mixture over 1 hour. Upon completion of addition, stir the mixture for 5 hours at reflux, and then concentrate under reduced pressure. Treat the concentrated crude mixture with 2N hydrochloric acid (500 mL) and extract with dichloromethane (3×400 mL). Combine the organic layers, dry over sodium sulfate, filter, and concentrate under reduced pressure. Subject the residue to silica gel chromatography, eluting with 20% ethyl acetate/hexanes. Combine fractions containing product and concentrate them under reduced pressure to provide the desired compound as an orange solid (31.6 g, 48%).
MS (IS, m/z) $C_{14}H_{15}NO_2$ (M$^+$+1)=230.

5,6-Dihydro-4H-pyrrolo[3,2,1-ij]quinoline-1-carboxylic acid

Add 5 N aqueous sodium hydroxide (60 mL, 0.3 mol) to a solution of 5,6-Dihydro-4H-pyrrolo[3,2,1-ij]quinoline-1-carboxylic acid ethyl ester (31 g, 0.14 mol) in ethanol (200 mL) and water (70 mL) and stir the resulting mixture at reflux for 3 hours. Cool the reaction mixture to 20-24° C., dilute with water (2 L), and wash sequentially with dichloromethane (2×200 mL) and diethyl ether (1×200 mL). Filter the aqueous layer through Celite and treat the filtrate with concentrated hydrochloric acid (25 mL) to precipitate the product. Filter the solid, wash with water (200 mL), and dry under reduced pressure to give the desired compound as a light yellow solid (23.2 g, 85%).
MS (IS, m/z) $C_{12}H_{11}NO_2$ (M$^+$+1)=202.

Decarboxylation

Add copper chromite (1.5 g, 4.8 mmol) to a solution of 5,6-Dihydro-4H-pyrrolo[3,2,1-ij]quinoline-1-carboxylic acid (3.7 g, 18.4 mmol) in 20 mL of quinoline. Stir the resulting mixture at 185° C. for 4 hours and then cool to 20-24° C., dilute with dichloromethane (100 mL), and filter through Celite. Wash the filtrate sequentially with 2 N hydrochloric acid (2×50 mL) and 2 N aqueous sodium hydroxide (25 mL). Concentrate the remaining organic phase under reduced pressure and then subject the residue to silica gel chromatography, eluting with 5% EtOAc/Hexanes. Combine fractions containing product and concentrate them under reduced pressure to provide the title compound as a light tan solid (1.67 g, 58%).
$^1$H-NMR (400 MHz, DMSO-d$_6$): δ 7.31-7.29 (d, 1H, J=7.8 Hz), 7.28-7.27 (d, 1H, J=2.93 Hz), 6.9-6.86 (t, 1H, J=7.6 Hz), 6.82-6.8 (dd, 1H, J=6.8, 1.0 Hz), 6.33-6.32 (d, 1 H, J=2.93 Hz), 4.15-4.12 (t, 2H, J=5.6 Hz), 2.92-2.89 (t, 2H, J=6.1 Hz), 2.15-2.08 (m, 2H).

The compounds of Preparations 5-8 are prepared essentially as described in Preparation 4.

| Prep. | Compound | Data (m/z) |
|---|---|---|
| 5 | 7-fluoro-5,6-dihydro-4H-pyrrolo[3,2,1-ij]quinoline | MS (EI): 176.1 (M + 1) |
| 6 | 8-fluoro-5,6-dihydro-4H-pyrrolo[3,2,1-ij]quinoline | MS (EI): 175.1 (M$^+$) |
| 7 | 7-chloro-5,6-dihydro-4H-pyrrolo[3,2,1-ij]quinoline | MS (EI): 192.1 (M$^+$) |
| 8 | 8-chloro-5,6-dihydro-4H-pyrrolo[3,2,1-ij]quinoline | MS (IS): 191.9 (M$^+$) |

PREPARATION 9

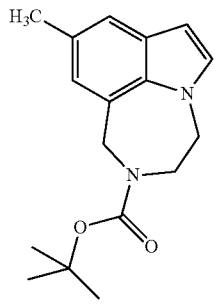

9-methyl-6-(tert-butoxycarbonyl)-6,7-dihydro-6H-[1,4]diazepino[6,7,1-hi]indole

5-Methyl-1H-indole-7-carboxaldehyde

Dissolve 5-methyl-2-nitrobenzaldehyde (7.84 g, 47.52 mmol), 1-butanol (10.55 g, 142.6 mmol) and 4-toluenesulfonic acid monohydrate (0.5 g, 2.6 mmol) in toluene (200 mL). Heat the reaction mixture to reflux with constant water removal (Dean-Stark Trap). Continue to heat the reaction mixture for 3 hours. Add water and extract the aqueous layer with ethyl acetate. Combine the organic layers and dry over sodium sulfate, filter, concentrate under reduced pressure, and purify by flash chromatography (1% v/v triethylamine buffered silica gel, 5% ethyl acetate/hexane) to give the dibutyl acetal derivative as a colorless oil (14 g, 99%).

Dissolve 2-Dibutoxymethyl-4-methyl-1-nitrobenzene (13.957 g, 47.373 mmol) in anhydrous tetrahydrofuran (474 mL) under nitrogen, and cool the solution to −40° C. Add vinylmagnesium bromide (190 mL, 190 mmol, 1.0 M in tetrahydrofuran) at −40° C. with stirring. Stir the reaction mixture for 40 minutes and add saturated aqueous ammonium chloride. Extract the aqueous layer with ethyl acetate. Combine the organic layers, dry over sodium sulfate, filter, and concentrate. Dissolve the residue in tetrahydrofuran (160 mL) and cool to 0° C. Add aqueous 0.5 molar hydrochloric acid (20 mL) and stir the mixture at 0° C. for 1 hour. Add saturated aqueous sodium hydrogen carbonate (200 mL) and extract the aqueous layer with ethyl acetate (3×200 mL). Combine the organic layers, dry over anhydrous sodium sulfate, filter, concentrate under reduced pressure and purify by flash column chromatography (silica gel, 5% ethyl acetate/hexane) to give the title compound as a white solid.
$^1$H-NMR (CDCl$_3$): δ 10.10 (s, 1H), 10.06 (s, 1H), 7.72 (s, 1H), 7.40 (s, 1H), 7.28 (m, 1H), 6.54 (m, 1H), 2.50 (s, 3H).

N-[2-hydroxyeth-1-yl](5-Methyl-1H-indol-7-yl)methylamine

Dissolve 5-Methyl-1H-indole-7-carboxaldehyde (4.036 g, 25.384 mmol) in absolute methanol (200 mL), add 2-aminoethanol (3.1 g, 50.767 mmol) and 10% palladium on carbon (0.4 g). Stir the mixture for 1 hour under nitrogen, then under 1 atmosphere of hydrogen for 3 hours. Filter, concentrate under reduced pressure, and purify by flash column chromatography (silica gel, 90/9/1, dichloromethane/methanol/ammonia) to give the title compound as a colorless oil.

MS (ES, m/z): =203 (M−1)

N-[tert-butoxycarbonyl]N-[2-hydroxyeth-1-yl](5-Methyl-1H-indol-7-yl)methylamine Dissolve N-[2-hydroxyeth-1-yl](5-Methyl-1H-indol-7-yl)methylamine (3.0 g, 14.706 mmol) in tetrahydrofuran (120 mL) and cool the solution to 0° C. Add aqueous potassium carbonate (30 mL, 29.41 mmol, 0.98 M solution) and di-tert-butyl dicarbonate (3.53 g, 16.18 mmol). Stir the reaction mixture for 4 hours at 0° C., add water and extract the aqueous layer with ethyl acetate. Combine the organic layers, dry with anhydrous sodium sulfate, filter, concentrate under reduced pressure and purify by flash column chromatography (silica gel, 20% ethyl acetate/hexane) to give the title compound as a white solid (4.12 g, 92%).

MS (ES, m/z): (M−1)=303.

N-[tert-butoxycarbonyl]N-[2-(methanesulfonyloxy)eth-1-yl](5-Methyl-1H-indol-7-yl)methylamine Dissolve N-[tert-butoxycarbonyl]N-[2-hydroxyeth-1-yl](5-Methyl-1H-indol-7-yl)methylamine (1.15 g, 3.78 mmol) in tetrahydrofuran (22 mL) under nitrogen and cool to 0° C. Add triethylamine (1.91 g, 18.88 mmol) and methanesulfonic anhydride (0.72 g, 4.15 mmol). Stir the reaction mixture for 2 hours at 0° C. Add water to the reaction mixture and extract the aqueous layer with ethyl acetate. Combine the organic layers, dry with anhydrous sodium sulfate, filter, and concentrate under reduced pressure to give the desired compound as colorless oil.

$^1$H-NMR (CDCl$_3$): δ 9.93 (s, 1H), 7.40 (s, 1H), 7.19 (t, 1H), 6.86 (s, 1H), 6.45 (t, 1H), 4.67 (s, 2H), 4.13 (t, 2H), 3.53 (t, 2H), 2.72 (s, 3H), 2.44 (s, 3H, CH$_3$Ar), 1.51 (s, 9H, 3CH$_3$).

Ring Closure

Dissolve N-[tert-butoxycarbonyl]N-[2-(methanesulfonyloxy)eth-1-yl](5-Methyl-1H-indol-7-yl)methylamine (1.22 g, 3.19 mmol) in anhydrous dimethylformamide (32 mL) under nitrogen and cool to 0° C. Add sodium hydride (0.15 g, 3.83 mmol, 60% in oil) and stir the reaction mixture for 1 hour at 0° C. Add water and extract the aqueous layer with ethyl acetate. Combine the organic layers, dry with anhydrous sodium sulfate, filter, concentrate under reduced pressure and purify by flash column chromatography (silica gel, 10% ethyl acetate/hexane) to give the title compound as white solid.
$^1$H-NMR (CDCl$_3$): δ 7.31 (m, 1H), 7.01 (m, 1H), 6.90 and 6.80 (2 singlets, 1H), 6.45 (d, 1H), 4.85 and 4.78 (2 singlets, 2H), 4.22 (m, 2H), 3.93 (m, 2H), 2.43 and 2.41 (2 singlets, 3H, CH$_3$Ar), 1.45 and 1.44 (2 singlets, 9H, 3CH$_3$).

PREPARATION 10

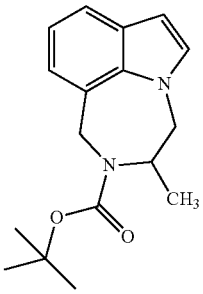

6-(tert-butoxycarbonyl)-5-methyl-6,7-dihydro-6H-[1,4]diazepino[6,7,1-hi]indole

Beginning with indole-7-carboxaldehyde and DL-alanine methyl ester hydrochloride (0.72 g, 5.16 mmol), the title compound is prepared essentially as described in Preparation 9.

MS (ES, m/z) (M+1)=287.0.

PREPARATION 11

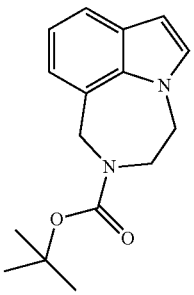

6-(tert-butoxycarbonyl)-6,7-dihydro-6H-[1,4]diazepino[6,7,1-hi]indole

Beginning with indole-7-carboxaldehyde and ethanolamine, the title compound is prepared essentially as described in Preparation 9.

MS (IS, m/z) C$_{16}$H$_{20}$N$_2$O$_2$ (M$^+$+1)=273

PREPARATION 12

9-fluoro-6-(tert-butoxycarbonyl)-6,7-dihydro-6H-[1,4]diazepino[6,7,1-hi]indole

Beginning with 5-fluoroindole-7-carboxaldehyde and ethanolamine, the title compound is prepared essentially as described in Preparation 9.

MS: (ES, m/z) 291 (M+1).

PREPARATION 13

8-fluoro-6-(tert-butoxycarbonyl)-6,7-dihydro-6H-[1,4]diazepino[6,7,1-hi]indole

Beginning with 6-fluoroindole-7-carboxaldehyde and ethanolamine, the title compound is prepared essentially as described in Preparation 9.

PREPARATION 14

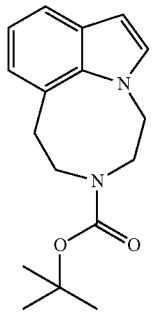

6-(tert-butoxycarbonyl)-5,6,7,8-tetrahydro-6H-[1,4]diazocino[7,8,1-hi]indole 7-vinylindole Add potassium tert-butoxide (1 M in tetrahydrofuran, 14.1 mL, 14.1 mmol) to a solution of methyl triphenylphosphonium bromide (5.05 g, 14.1 mmol) in tetrahydrofuran (80 mL) and stir the reaction mixture for 45 minutes at room temperature. Add a solution of 7-formylindole (1.00 g, 6.89 mmol) in tetrahydrofuran (10 mL) and stirred for 1.5 hours. Dilute the reaction mixture with ethyl acetate (250 mL), wash sequentially with an 8:1 mixture of water and 1 N hydrochloric acid (2×100 mL) and saturated aqueous sodium chloride (100 mL), dry over sodium sulfate, filter, and concentrate the filtrate under reduced pressure. Subject the residue silica gel chromatography. Combine fractions containing product and concentrate them under reduced pressure to provide the desired compound as a brown oil.

MS (IS, m/z) $C_{10}H_9N$ ($M^++1$)=144

Hydroboration/Oxidation

Add 1 M borane-tetrahydrofuran complex in tetrahydrofuran (9.95 mL, 9.95 mmol) to a 0° C. solution of 7-vinylindole (0.95 g, 6.6 mmol) in anhydrous tetrahydrofuran (60 mL) and stir the reaction mixture overnight at room temperature. Add 1 N sodium hydroxide (25 mL) and 30% hydrogen peroxide (35 mL) and stir the mixture at reflux for 1 hour. Cool the reaction mixture to room temperature, dilute with ethyl acetate (100 mL), wash sequentially with water (50 mL) and saturated aqueous sodium chloride (2×50 mL), dry over sodium sulfate, and concentrate under reduced pressure. Subject the residue to silica gel chromatography, eluting with 50% ethyl acetate in hexanes. Combine fractions containing product concentrate them under reduced pressure to provide the desired compound as a yellow oil (0.60 g, 56%).

MS (IS, m/z) $C_{10}H_{11}NO$ ($M^++1$)=162.

Alcohol Activation

Add a solution of methanesulfonyl chloride (0.29 mL, 3.68 mmol) in dichloromethane (5 mL) dropwise over 30 minutes to a solution of 7-(2-hydroxyeth-1-yl)indole (0.54 g, 3.34 mmol) and triethylamine (2.3 mL, 16.7 mmol) in dichloromethane (45 mL). Stir the mixture for an additional 2 hours at room temperature. Dilute the reaction mixture with dichloromethane (50 mL), wash sequentially with water (30 mL) and saturated aqueous sodium chloride (2×30 mL), dry over sodium sulfate, filter, and concentrate under reduced pressure.

Nucleophilic Displacement

Add ethanolamine (5 mL, 82 mmol) to a solution of 7-(2-(methanesulfonyloxy)eth-1-yl)indole (0.79 g, 3.3 mmol) in ethanol (50 mL) and stir the reaction mixture at reflux overnight. Dilute with ethyl acetate (150 mL), wash sequentially with water (3×50 mL) and saturated aqueous sodium chloride (2×50 mL), dry over sodium sulfate, filter, and concentrate under reduced pressure to provide 7-(2-(N-[2-hydroxyeth-1-yl]amino)eth-1-yl)indole as a light-brown solid (0.57 g, 85%).

MS (IS, m/z) $C_{12}H_{16}N_2O$ ($M^++1$)=205

Ring Formation

Beginning with 7-(2-(N-[2-hydroxyeth-1-yl]amino)eth-1-yl)indole, the title compound is prepared essentially as described in Preparation 9.

MS (IS, m/z) $C_{17}H_{22}N_2O_2$ ($M^++1$)=287

PREPARATION 15

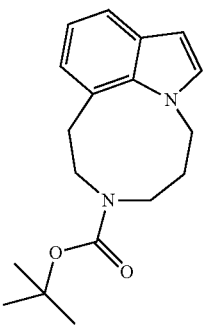

7-(tert-butoxycarbonyl)-[1,6]diazaperhydroonino[8,9,1-hi]indole

Beginning with 7-(2-(N-[3-hydroxyprop-1-yl]amino)eth-1-yl)indole, the title compound is prepared essentially as described in Preparation 9.

MS (ES): m/z=301.2 ($M^++1$)

PREPARATION 16

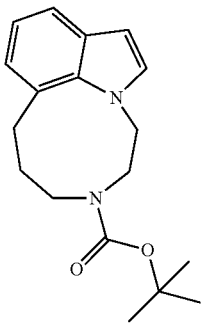

6-(tert-butoxycarbonyl)-[1,7]diazaperhydroonino[8,9,1-hi]indole

Beginning with 7-(3-(N-[2-hydroxyeth-1-yl]amino)prop-1-yl)indole, the title compound is prepared essentially as described in Preparation 9.

PREPARATION 17

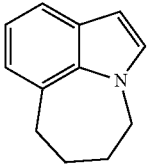

4,5,6,7-Tetrahydroazepino[3,2,1-hi]indole

3,4-Dihydro-2H-naphthalen-1-one oxime

Add hydroxylamine hydrochloride (71.0 g, 1.03 mol) to a solution of α-tetralone (100.0 g, 0.68 mol) in 300 mL of methanol and stir the resulting solution at reflux for 2 hours. Cool the mixture to 20-24° C. and concentrate under reduced pressure. Dilute the residue with 1 L of water and extract with dichloromethane. Wash the organic layer with saturated aqueous sodium chloride, dry over sodium sulfate, filter, and concentrate under reduced pressure. Crystallize the residue from isopropanol to provide the desired compound as an off-white solid (70.0 g, 63%).
MS (FIA, m/z) $C_{10}H_{11}NO$ ($M^+$+1)=162.4.

1,3,4,5-Tetrahydrobenzo[b]azepin-2-one

Charge a 1 L 3-neck round bottom flask equipped with a mechanical stirrer with neat polyphosphoric acid (100 g) and heat the acid heated to 125° C. while stirring under nitrogen. Add 3,4-Dihydro-2H-naphthalen-1-one oxime (15.0 g, 93 mmol) carefully to control exotherm, keeping the temperature below 175° C. After 10 minutes of heating, cool the mixture 20-24° C. and quenched with ice and water. Filter the aqueous suspension and wash the filter cake with water until the filtrate is neutral. Dry the filter cake under vacuum to provide the desired compound as an off-white solid (12.8 g, 85%).
MS (ES, m/z) $C_{10}H_{11}NO$ ($M^+$+1)=161.9

2,3,4,5-Tetrahydro-1H-benzo[b]azepine

Add 80 mL of lithium aluminum hydride (1 M solution in tetrahydrofuran) to a solution of 1,3,4,5-tetrahydrobenzo-[b]azepin-2-one (12.9 g, 80.0 mmol) in 720 mL of tetrahydrofuran. Stir the reaction mixture at reflux for 3 hours and cool to 0° C. Quench the reaction by the sequential addition of 3 mL of water, 3 mL of 15% sodium hydroxide, and 9 mL of water. Filter the resulting suspension through Celite and rinse the filter cake with ethyl acetate. Concentrate the filtrate under reduced pressure to provide the desired compound as an orange solid (10.0 g, 85%).
MS (FIA, m/z) $C_{10}H_{13}N$ ($M^+$+1)=148.2.

2-Oxo-3-(2,3,4,5-tetrahydrobenzo[b]azepin-1-yl) propionic acid ethyl ester

Add 2,3,4,5-tetrahydro-1H-benzo[b]azepine in small portions to a 0° C. suspension of 60% sodium hydride (3.0 g, 0.12 mol) in 300 mL of dimethylformamide. Upon complete addition of the amine, remove the ice bath and stir the reaction at 20-24° C. for 40 minutes. Add ethyl bromopyruvate (22.6 mL, 0.16 mol) and stir the resulting mixture at 20-24° C. for 6 hours. Add an additional 5 mL of ethyl bromopyruvate and stir the mixture for 1 hour. Quench by adding 50 mL of water then dilute with 1.5 L of dichloromethane. Separate the layers, wash the organic layer sequentially with water (2×500 mL) and saturated aqueous sodium chloride (500 mL), dry over sodium sulfate, filter, and concentrate under reduced pressure at 60° C. Dissolve the residue in ethyl acetate (500 mL), wash sequentially with water (3×100 mL) and saturated aqueous sodium chloride, dry over sodium sulfate, filter, and concentrate under reduced pressure. Subject the residue to silica gel chromatography, eluting with 5-10% EtOAc/hexanes to provide the desired compound as an off white solid (7.0 g, 40%).
MS (HD, m/z) $C_{15}H_{19}NO_3$ ($M^+$)=261.13.

4,5,6,7-Tetrahydroazepino[3,2,1-hi]indole-1-carboxylic acid ethyl ester

Add magnesium chloride (2.55 g, 26.8 mmol) to 30 mL of 2-methoxyethanol and heat the mixture to reflux. Add a solution of 2-oxo-3-(2,3,4,5-tetrahydro-benzo[b]azepin-1-yl) propionic acid ethyl ester (7.0 g, 26.8 mmol) in 2-methoxyethanol (20 mL) over 1 hour. Stir the resulting mixture for 6 hours at reflux, cool to 20-24° C., and concentrate under reduced pressure. Dilute the residue with 400 mL of dichloromethane and wash sequentially with 2 N hydrochloric acid (100 mL), saturated aqueous sodium bicarbonate (100 mL) and saturated aqueous sodium chloride (100 mL), dry over sodium sulfate, filter, and concentrate under reduced pressure. Subject the residue to silica gel chromatography, eluting with 20% ethyl acetate in hexane. Combine fractions containing product and concentrate them under reduced pressure to provide the desired compound as a yellow oil (3.1 g, 48%).
MS (FIA, m/z) $C_{15}H_{17}NO_2$ ($M^+$+1)=244.4.

4,5,6,7-Tetrahydroazepino[3,2,1-hi]indole-1-carboxylic acid

Add powdered sodium hydroxide (0.71 g, 17.8 mmol) to a solution of 4,5,6,7-tetrahydroazepino[3,2,1-hi]indole-1-carboxylic acid ethyl ester (2.0 g, 8.22 mmol) in ethanol (13 mL) and water (9 mL) and stir the resulting mixture at reflux for 4 hours. Cool the reaction mixture to room temperature, dilute with water (100 mL) and wash with dichloromethane (2×50 mL). Separate the layers, filter the aqueous layer through Celite and acidify the filtrate with concentrated hydrochloric acid. Filter the suspension, wash the recovered solid with water, and dry under reduced pressure to provide the desired compound as a white solid (1.59 g, 90%).

MS (FIA, m/z) $C_{13}H_{13}NO_2$ (M$^+$+1)=216.3

Decarboxylation

Add copper chromite (0.55 g, 1.77 mmol) to a solution of 4,5,6,7-tetrahydroazepino[3,2,1-hi]indole-1-carboxylic acid (1.4 g, 6.5 mmol) in 7.5 mL of quinoline and stir the resulting mixture at 185° C. for 4 hours. Cool the reaction mixture to room temperature, dilute with dichloromethane and filter through Celite. Wash the filtrate sequentially with 2 N hydrochloric acid (2×25 mL) and 2 N sodium hydroxide (25 mL). Concentrate the organic layer under reduced pressure and subject the residue to silica gel chromatography, eluting with 5% EtOAc/Hexane to provide the title compound as an orange solid (0.85 g, 76%).

MS (EI, m/z) $C_{12}H_{13}N$ (M$^+$)=171.4

PREPARATION 18

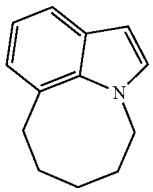

Pyrrolo[3,2,1-kl]benzo[b]azacyclooctane

7-Vinyl-1H-indole

Add tributyl(vinyl)tin (9.8 mL, 33.7 mmol), triphenylphosphine (0.4 g, 1.53 mmol), diphenylpalladium(II) dichloride (1.07 g, 1.53 mmol) and lithium chloride (4.0 g, 94.4 mmol) to 7-bromo-1H-indole (6.0 g, 30.6 mmol) in 150 mL of dimethylformamide and heat the resulting mixture at 100° C. overnight. Cool the reaction mixture to 20-24° C. and poured into a mixture of 150 mL of water and 150 mL of ethyl acetate. Wash the aqueous layer with additional ethyl acetate (3×100 mL), combine the organic layers, wash with saturated aqueous sodium chloride, dry over magnesium sulfate, filter, and concentrate under reduced pressure. Subject the residue to silica gel chromatography, eluting with 5-10% ethyl acetate in hexanes. Combine fractions containing product and concentrate them under reduced pressure to provide the desired compound as a clear oil (3.5 g, 80%).

MS (FIA, m/z) $C_{10}H_9N$ (M$^+$+1)=144.2

1-(Pent-4-en-1-yl)-7-vinyl-1H-indole

Add sodium hydride (60% dispersion in mineral oil) (3.5 g, 87.3 mmol) to a 0° C. solution of 7-vinylindole (5.0 g, 34.9 mmol) in 140 mL of dimethylformamide. Warm the resulting mixture to 20-24° C. and stir an additional 30 minutes. Add 5-bromo-1-pentene (20 mL, 175 mmol) dropwise and stir for 3 hours. Pour the reaction mixture into a mixture of 150 mL of water and 150 mL of ethyl acetate. Wash the aqueous layer with ethyl acetate (3×100 mL). Combine the organic layers, wash with saturated aqueous sodium chloride, dry over sodium sulfate, filter, and concentrate under reduced pressure. Subject the residue to silica gel chromatography, eluting with 5-10% ethyl acetate in hexanes. Combine fractions containing product and concentrate them under reduced pressure to provide the desired compound as a clear oil (5.39 g, 73%).

MS (ES, m/z) $C_{15}H_{17}N$ (M$^+$+1)=212

Ring Closure

Add 1.4 g of bis(tricyclohexylphosphine)benzylidine ruthenium (IV) dichloride (Grubb's catalyst) to a solution of 1-(Pent-4-en-1-yl)-7-vinyl-1H-indole (4.4 g, 20.8 mmol) in anhydrous dichloromethane (3.0 L) and stir the resulting mixture at 20-24° C. for 24 hours. Add an additional 1.0 g of Grubb's catalyst and stir for 4 hours. Concentrate the reaction mixture under reduced pressure and subject the residue to silica gel chromatography, eluting with 2-5% ethyl acetate in hexanes. Combine fractions containing product and concentrate them under reduced pressure to provide 8,9-dehydropyrrolo[3,2,1-kl]benzo[b]azacyclooctane as a brown oil (3.0 g, 79%).

$^1$H-NMR (400 MHz, DMSO-d$_6$): δ 7.41-7.39 (dd, 1H, J=7.81, 0.98 Hz), 7.22-7.21 (d, 1 H, J=3.42 Hz), 6.94-6.9 (d, 1H, J=7.57 Hz), 6.81-6.8 (d, 1H, J=2.93 Hz), 6.79 (s, 1 H), 6.36-6.35 (d, 1H, J=2.93 Hz), 5.69-5.62 (m, 1H), 4.45-4.3 (bs, 2H), 2.19-2.14 (m, 2H), 1.75-1.55 (bs, 2H).

Reduction

Hydrogenate a solution of 8,9-Dehydropyrrolo[3,2,1-kl]benzo[b]azacyclooctane (0.66 g, 3.6 mmol) in ethanol (130 mL) in the presence of platinum oxide (100 mg) under balloon pressure for three hours. Filter the mixture through Celite, wash solid with dichloromethane, and concentrate the filtrate under reduced pressure to provide of the title compound as a light yellow oil (0.65 g, 97%).

MS (ES, m/z) $C_{13}H_{15}N$ (M$^+$+1)=186

PREPARATION 19

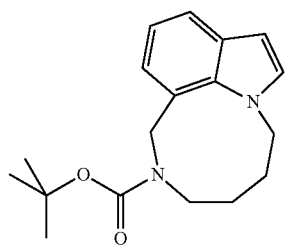

8-(tert-butoxycarbonyl)-[1,5]diazaperhydroonino[8,9,1-hi]indole

N-Allyl N-[(1H-indol-7-yl)methyl]amine

Add allylamine (2.50 mL, 33.1 mmol), acetic acid (3.4 mL), and sodium triacetoxyborohydride (5.85 g, 27.6 mmol) to a solution of indole-7-carboxaldehyde (4.00 g, 27.6 mmol) in 1,2-dichloroethane (120 mL) at 20-24° C. and stir the resulting mixture at 20-24° C. for 5 hours. Add an additional 1.5 g (7.1 mmol) of sodium triacetoxyborohydride and stir the resulting mixture overnight. Dilute the mixture with dichloromethane (300 mL), wash carefully with aqueous sodium bicarbonate (100 mL), and separate the layers. Wash the organic layer sequentially with water (100 mL) and saturated aqueous sodium chloride (100 mL), dry over sodium sulfate, filter, and concentrate under reduced pressure. Subject the residue to silica gel chromatography, eluting with 10-30% ethyl acetate in hexanes. Combine fractions containing product and concentrate them under reduced pressure to provide the desired compound as a light yellow oil (4.21 g, 82%).

N-[tert-butoxycarbonyl]N-allyl N-[(1H-indol-7-yl)methyl]amine

Add a 0° C. solution of di-tert-butyl dicarbonate (4.93 g, 22.6 mmol) in anhydrous tetrahydrofuran (20 mL) to a 0° C. solution of N-allyl N-[(1H-indol-7-yl)methyl]amine (4.21 g, 22.6 mmol) in anhydrous tetrahydrofuran (100 mL) and stir the mixture for two hours as it warms to 20-24° C. Dilute the reaction mixture ethyl acetate (500 mL). Separate the phases and wash the organic layer sequentially with water (2×150 mL) and saturated aqueous sodium chloride (100 mL), dry over sodium sulfate, filter, and concentrate under reduced pressure to provide the desired compound as a light yellow oil (6.5 g, 100%).

MS (ES, m/z) $C_{17}H_{22}N_2O_2$ ($M^+$+1)=287.2

N-[tert-butoxycarbonyl]N-allyl-N-[(1-allyl-1H-indol-7-yl)methyl]amine

Slowly add sodium hydride (60% dispersion in mineral oil, 1.75 g, 43.7 mmol) to a 0° C. solution of N-[tert-butoxycarbonyl]N-allyl N-[(1H-indol-7-yl)methyl]amine (6.6 g, 23 mmol) in anhydrous dimethylformamide. Warm the mixture to 20-24° C., stir for 30 minutes, add allyl bromide (4.0 mL, 46 mmol), and stir the mixture at 20-24° C. overnight. Dilute the reaction mixture with ethyl acetate (450 mL), wash sequentially with water (2×100 mL) and saturated aqueous sodium chloride (150 mL), dry over sodium sulfate, filter, and concentrate under reduced pressure. Subject the residue to silica gel chromatography, eluting with 10% ethyl acetate in hexanes. Combine fractions containing product and concentrate them under reduced pressure to provide the desired compound as a light brown oil (6.8 g, 91%).

MS (ES, m/z) $C_{20}H_{26}N_2O_2$ ($M^+$+Na)=349.2

Ring Closure

Beginning with N-[tert-butoxycarbonyl]N-allyl N-[(1-allyl-1H-indol-7-yl)methyl]amine, the ring closure was performed essentially as described in Preparation 17.

MS (ES, m/z) $C_{18}H_{22}N_2O_2$ ($M^+$+Na)=321.2

Reduction

Beginning with the alkene prepared in the previous paragraph, the double bond was reduced to provide the title compound essentially as described in Preparation 18.

MS (ES, m/z) $C_{18}H_{25}N_2O_2$ ($M^+$)=301.2

PREPARATION 20

7-Bromofuro[3,2-c]pyridine

7-Bromo-5H-furo[3,2-c]pyridin-4-one

Add N-bromosuccinimide (63.16 g, 354.9 mmol) as a solution in anhydrous acetonitrile (480 mL) to a suspension of 5H-furo[3,2-c]pyridin-4-one (36.9 g, 273 mmol) in anhydrous acetonitrile (740 mL) at 0° C. over 1 hour. Warm to room temperature, add anhydrous methyl alcohol (1.5 L) and stir at room temperature for 18 hours. Quench with water (20 ml) and saturated sodium bicarbonate (20 mL), concentrate to a volume of 1.3 liters, and pour into water (1.3 L). Collection of the precipitate by filtration and drying (vacuum oven 2 days 40-60° C.) gives the title compound as an off-white solid.

ESMS: (m/z)=213.9, 215.9 ($M^+$+1).

4,7-Dibromofuro[3,2-c]pyridine

Combine 7-bromo-5H-furo[3,2-c]pyridin-4-one (16.16 g, 75.5 mmol), dichloroethane (160 mL), and phosphorus oxybromide (100 g, 348.8 mmol) and heat at reflux for about 2 hours. Cool to room temperature and pour the reaction mixture into ice water (1 L). Adjust the pH to 8 with 5N NaOH, extract into dichloromethane, wash with brine, dry over magnesium sulfate, filter, and concentrate. Purification by flash chromatography, eluting with hexane:ethyl acetate gives the title compound as a white solid.

HRMS: 274.8581 ($M^+$).

Reduction

Combine 4,7-dibromofuro[3,2-c]pyridine (14.5 g, 52.3 mmol), anhydrous dimethylformamide (250 mL), sodium formate (10.67 g, 156.9 mmol), and tetrakis(triphenyl-phosphine)palladium(0) (3.021 g, 2.61 mmol) under nitrogen. Heat for 3 to 24 hours at 100° C., cool to room temperature, filter through CELITE® and concentrate (high vacuum 0.7 mmHg, 40° C.). Dilute with ethyl acetate (500 mL), wash with water and brine, dry over magnesium sulfate, filter and concentrate. Purification by flash chromatography, eluting with hexane:ethyl acetate gives the title compound as a white solid.

MS: (m/z)=197.9, 199.9 ($M^+$+1).

PREPARATION 21

5-Bromoimidazo[1,2-a]pyridine

Add 2-bromo-1,1-diethoxyethane (3.64 g, 18.48 mmol) to a solution of 6-bromopyridin-2-ylamine (1.0 g, 5.77 mmol) in n-butanol (40 ml). Reflux the reaction overnight, cool. Filtration of the reaction mixture gives 5-bromoimidazo[1,2-a]pyridine hydrobromide as a white solid.

ESMS: (m/z)=198.9 ($M^+$+1).

Add saturated sodium bicarbonate (300 ml) to a suspension of 5-bromoimidazo[1,2-a]pyridine hydrobromide (13.0 g, 46.96 mmol) in ethyl acetate. Separate the organic layer and wash it with saturated sodium bicarbonate, dry over magnesium sulfate, and concentrated under reduced pressure to give the title compound as a white solid.

PREPARATION 22

5-Bromoisoquinoline

Add a solution of sodium nitrite (9.6 g, 139 mmol) in water (50 mL) cautiously to 5-aminoisoquinoline (20 g, 139 mmol) in hydrobromic acid (48%, 100 mL) at 0° C. Transfer this mixture to a vessel containing CuBr (25 g, 174 mmol) in hydrobromic acid (48%, 200 mL) at 75° C. After complete addition, stir the mixture at 75° C. for one hour, cool to room temperature and stir overnight. Place the mixture in an ice bath, add ice to the reaction mixture, and then add sodium hydroxide aqueous solution (20%, 250 mL). Filter the slurry and extract the filtrate with diethyl ether. Combine the solid and the extract sonicate for one hour in chloroform. Filter the suspension through a plug of Celite™, and concentrate the filtrate under reduced pressure. Subject the residue to silica gel chromatography, eluting with chloroform.

MS (ES): m/z=208.0 ($M^+(^{79}Br)$+1), 210.0 ($M^+(^{81}Br)$+1)

PREPARATION 23

(5,6-Dihydro-4H-pyrrolo[3,2,1-ij]quinolin-1-yl)oxoacetic acid methyl ester

Add oxalyl chloride (1.05 mL, 12.08 mmol) dropwise to a solution of 5,6-dihydro-4H-pyrrolo[3,2,1-ij]quinoline (1.67 g, 10.6 mmol) in 150 mL of anhydrous diethyl ether at 0° C. and stir the resulting solution at 0° C. for 40 minutes. Cool the mixture to −78° C. and slowly add sodium methoxide (42 mL, 21 mmol, 0.5 M in methanol). Upon completion of the addition, remove the dry ice bath and allow the reaction to warm to 20-24° C. over 2 hours. Dilute the mixture with ethyl acetate (200 mL), wash with water (100 mL) and separate the layers. Wash the organic layer with saturated aqueous sodium chloride (50 mL), dry over sodium sulfate, filter, and concentrate under reduced pressure. Dissolve the residue in ethyl acetate (100 mL), filter through a 2 inch plug of coarse silica gel, and concentrate under reduced pressure to give the title compound as a yellow solid (2.16 g, 84%).

MS (EI, m/z) $C_{14}H_{13}NO_3$ (M$^+$−59)=184.

The compounds of Preparations 24-35 are prepared essentially as described in Preparation 22.

| Prep.# | Compound | Data |
|---|---|---|
| 24 | (4,5,6,7-tetrahydroazepino[3,2,1-hi]indol-1-yl)oxoacetic acid methyl ester | MS (FIA, m/z) $C_{15}H_{15}NO_3$ (M$^+$ + 1) = 258.2 |
| 25 | (6-(tert-butoxycarbonyl)-5,6-dihydro-6H-[1,4]diazepino[6,7,1-hi]indol-1-yl)oxoacetic acid methyl ester | MS (IS, m/z) $C_{16}H_{20}N_2O_2$ (M$^+$ + 1) = 273 |
| 26 | (Pyrrolo[3,2,1-kl]benzo[b]aza-cyclooct-1-yl)oxoacetic acid methyl ester | $^1$H-NMR (400 MHz, DMSO-$d_6$): δ 8.38 (s, 1 H), 8.05-8.03 (d, 1 H, J = 7.81 Hz), 7.18-7.15 (t, 1 H, J = 7.57 Hz), 7.03-7.01 (d, 1 H, J = 6.84 Hz), 4.65-4.62 (t, 2 H, J = 6.1 Hz), 3.86 (s, 3 H), 3.3-3.15 (bs, 2 H), 1.94-1.91 (t, 2 H, J = 6.1 Hz), 1.82-1.79 (t, 2 H, J = 5.86 Hz), 1.3-1.15 (bs, 2 H) |
| 27 | (8-(tert-butoxycarbonyl)-[1,5]diaza-perhydro-onino[8,9,1-hi]indol-1-yl)oxoacetic acid methyl ester | MS (IS, m/z) $C_{21}H_{26}N_2O_5$ (M$^+$ + 1) = 387. |
| 28 | (6-(tert-butoxycarbonyl)-5,6,7,8-tetrahydro-6H-[1,4]diazocino[7,8,1-hi]indol-1-yl)oxoacetic acid methyl ester | MS (IS, m/z) $C_{20}H_{24}N_2O_5$ (M$^+$ + 1) = 373 |
| 29 | (9-chloro-5,6-dihydro-4H-pyrrolo[3,2,1-ij]quinolin-1-yl)oxoacetic acid methyl ester | MS (IS m/z) $C_{14}H_{12}ClNO_3$ (M + 1) 278 |
| 30 | (8-chloro-5,6-dihydro-4H-pyrrolo-[3,2,1-ij]-quinolin-1-yl)oxoacetic acid methyl ester | MS (IS, m/z) $C_{14}H_{12}ClNO_3$ (M + 1) 277.8 |
| 31 | (7-Fluoro-5,6-dihydro-4H-pyrrolo[3,2,1-ij]-quinolin-1-yl)oxoacetic acid methyl ester | MS (EI, m/z) $C_{14}H_{12}FNO_3$ (M + 1) 262.1 |
| 32 | (8-Fluoro-5,6-dihydro-4H-pyrrolo[3,2,1-ij]-quinolin-1-yl)oxoacetic acid methyl ester | MS (EI, m/z) $C_{14}H_{12}FNO_3$ (M + 1) 262.1 |
| 33 | (6-(tert-butoxycarbonyl)-5-methyl-6,7-dihydro-6H-[1,4]diazepino-[6,7,1-hi]indol-1-yl)oxoacetic acid methyl ester | MS (ES, m/z) (M + 1) = 373.0 |
| 34 | (9-methyl-6-(tert-butoxycarbonyl)-3,4-dihydro-6H-[1,4]diazepino-[6,7,1-hi]indol-1-yl)oxoacetic acid methyl ester | ESMS: m/z = 373 (M + 1) |
| 35 | (9-fluoro-6-(tert-butoxycarbonyl)-3,4-dihydro-6H-[1,4]diazepino-[6,7,1-hi]indol-1-yl)oxoacetic acid methyl ester | $^1$H-NMR (CDCl$_3$): δ 8.36 (s, 1H), 8.02 (d, 1H), 6.92 and 6.84 (2 d, 1H), 4.89 and 4.80 (2 s, 2H), 4.43 (m, 2H), 3.98 (m, 2H), 3.94 (s, 3H), 1.46 and 1.42 (2 s, 9H) |
| 36 | R-6-(tert-butoxycarbonyl)-5-methyl-6,7-dihydro-6H-[1,4]diazepino-[6,7,1-hi]indol-1-yl)oxoacetic acid methyl ester | MS (ES, m/z) (M + 1) = 373.0 |
| 37 | (8-fluoro-6-(tert-butoxycarbonyl)-3,4-dihydro-6H-[1,4]diazepino-[6,7,1-hi]indol-1-yl)oxoacetic acid methyl ester | ESMS: m/z = 377 (M + 1) |

PREPARATION 38

(Imidazo[1,2-a]pyridin-5-yl)oxoacetic acid ethyl ester

Add Mg turnings (0.25 g, 9.95 mmol) to a solution of 5-Bromoimidazo[1,2-a]pyridine (1.5 g, 7.65 mmol) in tetrahydrofuran (20 ml). Heat the reaction to 60° C. and add bromoethane (1.2 ml, 11.1 mmol). Reflux for another 0.5 hours, cool and cannula dropwise into a solution of diethyl oxalate (5 ml) in tetrahydrofuran (5 ml) at −15° C. Stir at −15° C. for 0.5 hours and at room temperature for 0.5 hours. Quench the reaction by adding pH 7 buffer, extract into ethyl acetate, wash with saturated sodium chloride, dry over magnesium sulfate, and concentrate under reduced pressure. Purification by flash chromatography, eluting with ethyl acetate: hexane: methanol gradient gives the title compound as a light brown oil.

The compounds of Preparations 39-47 are prepared essentially as described in Preparation 38.

| Prep. | Compound | Data |
|---|---|---|
| 39 | Methyl (benzofur-7-yl)oxoacetate | MS (ES): m/z = 218.9 (M + 1) |
| 40 | Ethyl (4-methoxybenzofur-7-yl)oxoacetate | MS (ES): m/z = 248.9 (M + 1) |
| 41 | Ethyl (5-methoxybenzofur-7-yl)oxoacetate | MS (ES): m/z = 249.0 (M + 1) |
| 42 | Methyl (6-methoxybenzofur-7-yl)oxoacetate | $^1$H-NMR (400 MHz, CDCl$_3$): δ 1.41 (t, J = 7.31 Hz, 3H), 4.40 (m, 2H), 6.74 (d, J = 1.95 Hz, 1H), 6.94 (d, J = 8.78 Hz, 1H), 7.68 (d, J = 2.44 Hz, 1H), 7.78 (d, J = 8.23 Hz, 1H) |
| 43 | Ethyl (imidazo[1,2-a]pyridin-3-yl)oxoacetate | $^1$H-NMR (400 MHz, DMSO-$d_6$): δ 8.3 (m, 1H), 7.53 (m, 1H), |

-continued

| Prep. | Compound | Data |
|---|---|---|
| 44 | Ethyl (5-fluorobenzofur-7-yl)oxoacetate | 7.46 (s, 1H), 6.9 (m, 1H), 6.42 (m, 1H), 4.1 (q, J = 7 Hz, 2H), 1.15 (t, J = 7 Hz, 3H). ESMS: m/z = 237.0 (M + 1) |
| 45 | Methyl (5-oxo-6-propyl-5,6-dihydro-[1,4]diazepino[6,7,1-hi]indol-7-yl)oxoacetate | $^1$H-NMR (400 MHz, DMSO-$d_6$): δ 8.58 (s, 1 H), 8.05 (m, 1H), 7.24-7.2 (m, 2H), 5.35 (m, 2H), 4.8 (m, 2H), 3.8 (s, 3H), 3.4 (m, 2H), 1.45 (m, 2H), 0.7 (m, 3H). |
| 46 | Ethyl 4-methyl-6-(tert-butoxycarbonyl)-5,6-dihydro[1,4]diazepino[6,7,1-hi]indol-3-yl)-oxoacetate | ESMS: m/z = 237.0 (M + 1) |
| 47 | Ethyl 4,4-dimethyl-6-(2,4-dimethoxybenzyl)-5,6-dihydro[1,4]diazepino[6,7,1-hi]indol-3-yl)oxoacetate | ESMS: m/z = 437.3 (M + 1) |

PREPARATION 48

(Imidazo[1,2-a]pyridin-3-yl)oxoacetic acid methyl ester

Add oxalyl chloride (2.13 g, 1.46 ml, 16.8 mmol) to a solution of imidazo[1,2-a]pyridine (1.0 g, 8.47 mmol) in toluene (75 ml). Heat the mixture at reflux for 15 hours. Cool the reaction and gently add methanol. Concentrate the resulting mixture under reduced pressure and partition between hot ethyl acetate and saturated aqueous sodium bicarbonate. Wash organic phase with saturated aqueous sodium chloride, dry over magnesium sulfate, and concentrate under reduced pressure. Triturate in ethyl acetate to give the title compound as an off-white solid (0.75 gm).

ESMS: m/z=204.9 (M$^+$+1)

The compounds of Preparations 49-54 may be prepared essentially as described in Preparation 48.

| Prep. | Compound | Data |
|---|---|---|
| 49 | Methyl (8-bromo-6-methylimidazo[1,2-a]-pyridin-3-yl)oxoacetate | MS (ES): m/z = 297.0 (M + 1) |
| 50 | Methyl (5,6-dihydropyrrolo[3,2,1-ij]quinolin-6-on-1-yl)oxoacetate | |
| 51 | Methyl (6-methyl-4,5-dihydro-6H-[1,4]diazepino[6,7,1-hi]indol-7-on-1-yl)oxoacetate | |
| 52 | Methyl (7-methyl-4,5-dihydro-7H-[1,4]diazepino[6,7,1-hi]indol-6-on-1-yl)oxoacetate | |
| 53 | Methyl (6-((2-(dimethylamino)eth-1-yl)-4,5-dihydro-6H-[1,4]diazepino[6,7,1-hi]indol-7-on-1-yl)oxoacetate | |
| 54 | Methyl (6-((2-(hydroxy)eth-1-yl)-4,5-dihydro-6H-[1,4]diazepino[6,7,1-hi]indol-7-on-1-yl)oxoacetate | |

PREPARATION 55

(1-[3-(tert-Butyldimethylsilyloxy)prop-1-yl]-1H-indol-4-yl)oxoacetic acid methyl ester Add tert-butyl lithium (88.1 ml, 149.8 mmol, 1.7 M in hexane) to a solution of 4-Bromo-1-[3-(tert-butyldimethylsilyloxy)propyl]-1H-indole (22.0 g, 59.92 mmol) in anhydrous tetrahydrofuran (100 ml) at −78° C. Stir the reaction at −78° C. for 20 min. Transfer the mixture into a solution of dimethyl oxalate (24.8 g, 209.72 mmol) in tetrahydrofuran (400 ml) at −40° C. via a dry-ice cooled cannula. Upon complete addition, stir the reaction at −78° C. for 15 minutes and slowly warm to room temperature. Quench the reaction with saturated aqueous ammonium chloride and extract into ethyl acetate. Combine the organic layers, dry over magnesium sulfate, and concentrate under reduced pressure. Purification by flash chromatography, eluting with ethyl acetate:hexane gradient (100% hexane to 15% ethyl acetate:hexane over 90 minutes) gives the title compound, as a light brown oil.

ESMS: m/z=376.2 (M$^+$+1)

The compounds of Preparations 56-58 may be prepared essentially as described in Preparation 55.

| Prep. | Product | Data |
|---|---|---|
| 56 | Methyl (1-methyl-1H-indol-4-yl)oxoacetate | HRMS: 218.0826 (M + H) |
| 57 | Methyl (benzofur-7-yl)oxoacetate | HRMS: 205.0501 (M + H) |
| 58 | Methyl (isoquinolin-5-yl)oxoacetate | MS (ES): m/z = 216.1 (M$^+$ + 1) |

PREPARATION 59

1-[3-(tert-butyldimethylsilyloxy)prop-1-yl]-1H-indole-4-carboxaldehyde

Add tert-butyl lithium (27.07 ml, 46.03 mmol, 1.7 M in pentane) to a solution of 4-Bromo-1-[3-(tert-butyldimethylsilyloxy)prop-1-yl]-1H-indole (6.76 g, 18.41 mmol) in anhydrous tetrahydrofuran (100 ml) at −78° C. Stir the reaction at −78° C. for 30 min, quench with N,N-dimethylformamide (4.7 ml, 64.45 mmol), warm to 0° C., quench with pH=7 buffer, and extract into ethyl acetate. Combine the organic layers, dry over magnesium sulfate, and concentrate under reduced pressure. Purification by flash chromatography, eluting with ethyl acetate:hexane gradient (100% hexane to 50% ethyl acetate:hexane over 45 minutes) gives the title compound as a clear oil.

ESMS: (m/z)=318.2 (M$^+$+1)

The compounds of Preparations 60-63 may be prepared essentially as described in Preparation 59.

| Prep. | Compound | Data |
|---|---|---|
| 60 | 1-Methyl-1H-indole-4-carboxaldehyde | HRMS: 160.0760 (M + H) |
| 61 | 5-Fluorobenzofuran-7-carboxaldehyde | $^1$H NMR (400 MHz, DMSO-$d_6$): δ10.25 (s, 1H), 8.25 (d, J = 2 Hz, 1H), 7.87 (dd, J = 8, 3 Hz), 7.65 (J = 8, 3 Hz), 7.1 (d, J = 2, 1H) |
| 62 | 5,6-Difluorobenzofuran-7-carboxaldehyde | HRMS: 182.0179 (M$^+$) |
| 63 | 6-Fluorobenzofuran-7-carboxaldehyde | MS (ES): 165.0 (M$^+$) |

PREPARATION 64

Benzo[b]thiophene-7-carboxaldehyde

Dissolve 7-bromothiophene (5.0 g, 23.5 mmol) in anhydrous tetrahydrofuran (15 mL) under nitrogen and add magnesium metal turnings (712 mg, 29.3 mmol). Stir and warm the reaction to 50° C. to initiate the Grignard reagent formation. After the exothermic reaction subsides, reflux for 30 minutes. Dilute the solution with tetrahydrofuran (15 ml) and cool to 25° C. Add the Grignard reagent dropwise via cannula to a stirred solution of N,N-dimethylformamide (10.2 g, 139 mmol) in tetrahydrofuran (25 mL) at −78° C. under nitrogen. Stir the reaction at 0° C. for 1 hour and quench with aqueous saturated ammonium chloride. Dilute with diethyl ether, wash with distilled water, and aqueous saturated sodium chloride. Dry the organic phase over anhydrous magnesium sulfate, filter, and concentrate under reduced pressure. Chromatograph on flash silica using a gradient from neat hexane to 50% ethyl acetate in hexane to obtain the title compound as an off-white solid.

HRMS: 162.0138

The compounds of Preparations 65-71 may be prepared essentially as described in Preparation 64.

| Prep. | Compound | Data |
|---|---|---|
| 65 | 4-Methoxybenzofuran-7-carboxaldehyde | $^1$H NMR (400 MHz, DMSO-$d_6$): δ 10.1 (s, 1H), 8.06 (s, 1H), 7.85 (d, J = 9 Hz, 1H), 7.04 (m, 2H, 4.0 (s, 2H) |
| 66 | 4-Fluorobenzofuran-7-carboxaldehyde | $^1$H NMR (400 MHz, DMSO-$d_6$): δ 10.21 (s, 1H), 8.21 (d, J = 2 Hz, 1H), 7.89 (dd, J = 8, 8 Hz, 1H), 7.28 (dd, J = 8, 8 Hz, 1H), 7.2 (d, J = 2 Hz, 1H) |
| 67 | 4,5-Difluorobenzofuran-7-carboxaldehyde | HRMS: 182.0179 (M$^+$) |
| 68 | Benzo[b]thiophene-7-carboxaldehyde | HRMS: 162.0138 (M$^+$) |
| 69 | Benzo[b]thiophene-4-carboxaldehyde | HRMS: 162.0125 (M$^+$) |
| 70 | 5-(tetrahydropyran-2-yloxy)benzofuran-7-carboxaldehyde | ESMS: (m/z) = 246.9 (M + 1) |
| 71 | 4-(tetrahydropyran-2-yloxy)benzofuran-7-carboxaldehyde | ESMS: (m/z) = 163.0 (M + 1) |

PREPARATION 72

Benzo[b]thiophene-7-acetonitrile

Add Benzo[b]thiophene-7-carboxaldehyde (2.34 g, 14.4 mmol) and lithium cyanide tetrahydrofuran complex (LiCN*1.5 Tetrahydrofuran, 204 mg, 1.44 mmol) to tetrahydrofuran (40 mL) under nitrogen. Add dropwise neat diethyl cyanophosphonate (2.8 mL, 18.4 mmol) to the stirring reaction mixture. Stir at room temp under nitrogen for 60 hours. Add 2-methyl-2-propanol (1.4 mL, 14.6 mmol). Add the reaction mixture via cannula to a stirred 0.1 molar solution of samarium(II) iodide in tetrahydrofuran (360 mL, 36.0 mmol) at 25° C. under nitrogen. If the resulting reaction mixture is not deep blue add additional samarium(II) iodide solution until deep blue color persists. Stir the reaction at 25° C. for 1 hour. Concentrate under reduced pressure, dilute with ethyl acetate, diethyl ether (1:1), wash with aqueous 0.1 M hydrochloric acid, and aqueous saturated sodium chloride. Dry the organic phase over anhydrous magnesium sulfate, filter, and concentrate under reduced pressure. Chromatograph on flash silica using a gradient from neat hexane to 25% ethyl acetate in hexane to obtain the title compound as an off-white solid.

HRMS: 173.0289 (M$^+$)

The compounds of Preparations 73-85 may be prepared essentially as described in Preparation 72.

| Prep. | Compound | Data |
|---|---|---|
| 73 | {1-[3-(tert-butyldimethylsilyloxy)-prop-1-yl]-1H-indol-4-yl}acetonitrile | $^1$H-NMR (400 MHz, DMSO-$d_6$): δ 7.43 (d, J = 8 Hz, 1H), 7.38 (m, 1H), 7.14 (m, 1H), 7.0 (d, J = 8 Hz, 1H), 6.54 (m, 1H), 4.23 (t, J = 7, 2H), 4.18 (s, 3H), 3.5 (t, J = 7 Hz, 2H), 1.9 m, 2H), 0.85 (s, 9H), 0.0 (s, 6H) |
| 74 | (1-Methyl-1H-indol-4-yl)acetonitrile | HRMS: 171.0939 (M + H) |
| 75 | (1H-Indol-7-yl)acetonitrile | HRMS: 156.0687 (M$^+$) |
| 76 | (4-Methoxybenzofur-7-yl)acetonitrile | $^1$H-NMR (400 MHz, DMSO-$d_6$): δ 7.99 (d, J = 2 Hz, 1H), 7.23 (d, J = 8 Hz, 1H), 6.98 (d, J = 2 Hz, 1H) 6.8 (d, J = 8 Hz, 1H), 4.16 (s, 2H), 3.88 (s, 3H) |
| 77 | (5-Methoxybenzofur-7-yl)acetonitrile | $^1$H-NMR (400 MHz, DMSO-$d_6$): δ 8.02 (d, J = 2.2 Hz, 1H), 7.17 (d, J = 2.2 Hz, 1H), 6.9 (m, 2H), 4.24 (s, 3H) |
| 78 | (4-Fluorobenzofur-7-yl)acetonitrile | $^1$H NMR (400 MHz, DMSO-$d_6$): δ 8.15 (d, J = 2.2 Hz, 1H), 7.33 (m, 1H), 7.17-7.1 (m, 2H), 4.26 (s, 2H) |
| 79 | (4,5-Difluorobenzofur-7-yl)acetonitrile | $^1$H NMR (400 MHz, DMSO-$d_6$): δ 8.2 (d, J < 1 Hz, 1H), 7.42 (m, 1H), 7.22 (d, J < 1 Hz, 1H), 4.28 (s, 2H) |
| 80 | (5-Fluorobenzofur-7-yl)acetonitrile | $^1$H NMR (400 MHz, DMSO-$d_6$): δ 8.15 (d, J = 2 Hz, 1H), 7.47 (dd, J = 8, 2 Hz, 1H), 7.18 (dd, J = 8, 2 Hz, 1H), 7.01 (d, J = 2 Hz, 1H), 4.3 (s, 2H) |
| 81 | (5,6-Difluorobenzofur-7-yl)acetonitrile | ESMS (M$^−$ − 1): 192.3 |
| 82 | (6-Fluorobenzofur-7-yl)acetonitrile | $^1$H-NMR (400 MHz, CDCl$_3$): δ 7.62 (d, J = 2.44 Hz, 1H), 7.47 (m, 1H), 7.00 (m, 1H), 6.72 (d, J = 2.44 Hz, 1H), 3.91 (s, 2H) |
| 83 | (Benzo[b]thien-7-yl)acetonitrile | HRMS (M): 173.0289 |
| 84 | (Benzofur-7-yl)acetonitrile | HRMS (M): 157.0524 |
| 85 | (Benzo[b]thien-4-yl)acetonitrile | HRMS (M): 173.0288 |

PREPARATION 86

(Furo[3,2-c]pyridin-7-yl)acetonitrile

Furo[3,2-c]pyridine-7-carbonitrile

Combine 7-bromofuro[3,2-c]pyridine (4.673 g, 23.5 mmol), copper cyanide (4.21 g, 47.1 mmol), copper iodide (8.96 g, 47.1 mmol), and anhydrous dimethylformamide (100 mL) and at 130° C. for 30 hours. Cool to room temperature, dilute with diethyl ether and wash with 15% aqueous ammonium hydroxide. Extract combined aqueous layers with diethyl ether, wash combined organic layers with 15% aqueous ammonium hydroxide, and brine, dry over magnesium sulfate, and concentrate. Purification using flash chromatography, eluting with hexane:ethyl acetate gives the title compound as a white solid.

ESMS: (m/z)=145.1 (M$^+$+1)

Furo[3,2-c]pyridine-7-carboxylic acid

Add furo[3,2-c]pyridine-7-carbonitrile (1.5 g, 10.4 mmol) and 28-30% aqueous ammonium hydroxide (50 mL) to high pressure reactor. Heating at 150° C. for 18 hours, cooling to room temperature and freeze-drying gives the title compound as a white solid.

ESMS: (m/z)=164.0 (M$^+$+1).

(Furo[3,2-c]pyridin-7-yl)methanol

Add Borane (1.0 M in tetrahydrofuran, 0.61 mL, 0.61 mmol) to a solution of furo[3,2-c]pyridine-7-carboxylic acid (0.100 g, 0.61 mmol) in tetrahydrofuran (2 mL) and stir for 1 hour. Add additional borane (0.61 mL) stir for 30 minutes, add additional borane (0.61 ml), quench with 1N HCl (10 mL) and stir for 15 minutes. Add aqueous ammonium hydroxide (28-30%, 3 mL), extract with diethyl ether, dry over magnesium sulfate, filter and concentrate to give the title compound as a white solid.

ESMS: (m/z)=150.1 (M$^+$+1)

Conversion of Alcohol to Nitrile

Combine (furo[3,2-c]pyridin-7-yl)methanol (0.40 g, 2.68 mmol), 1N HCl (1.0 M in diethyl ether, 3 mL). Cool to 0° C. and add thionyl chloride (5 ml). Heat at reflux for 2 hours, cool to room temperature and concentrate to the white solid 7-(chloromethyl)furo[3,2-c]pyridine hydrochloride. Dissolve in ethanol (4.4 mL) and water (1.7 mL) and introduce drop wise a refluxing solution of sodium cyanide (0.656 g, 13.4 mmol) in ethanol (5.4 mL) and water (1 ml) over 40 minutes. Heat for 40 minutes at reflux, cool to room temperature, dilute with water, and extract with ethyl acetate. Combine organic layers, wash with brine, dry over magnesium sulfate, filter and concentrate. Purification by flash chromatography, eluting with hexane:ethyl acetate gives the title compound.

ESMS: (m/z)=159.0 (M$^+$+1)

PREPARATION 87

(2,3-Dihydrobenzo[1,4]dioxin-5-yl)acetonitrile

(2,3-Dihydrobenzo[1,4]dioxin-5-yl)methanol

Dissolve 2,3-Dihydroxybenzaldehyde (25 g, 181 mmol) and 1,2-dibromoethane (34 g, 181 mmol) in N,N-dimethylformamide (500 mL). Add cesium carbonate (118 g, 362 mmol), stir and reflux under nitrogen for 2 hours. Cool the reaction to 20° C., dilute with absolute ethanol (250 mL) and add sodium borohydride (6.8 g, 181 mmol). Stir at 20° C. for 1 hour and concentrate under high vacuum to remove the ethanol and dimethylformamide. Dilute the residue with diethyl ether and wash with distilled water, 0.25 molar aqueous sodium hydroxide, and aqueous saturated sodium chloride. Dry the organic phase over anhydrous magnesium sulfate, filter and concentrate under reduced pressure. Chromatograph on flash silica using a gradient from 75% hexane, 25% ethyl acetate to 25% hexane, 75% ethyl acetate to obtain the title compound as a white solid.

HRMS: 166.0621 (M)

Halogenation/Displacement

Beginning with (2,3-dihydrobenzo[1,4]dioxin-5-yl)methanol (1.8 g, 10.8 mmol), the title compound is prepared essentially as described in Preparation 75.

HRMS: 175.0624 (M$^+$)

PREPARATION 88

(5-hydroxybenzofur-7-yl)acetonitrile

7-bromo-5-(tetrahydropyran-2-yloxy)benzofuran

Combine 7-bromo-5-hydroxybenzofuran (5.0 g, 0.0235 mol) with pyridinium para-toluenesulfonate (0.59 g, 0.1 equivalent) and dissolve in 60 mL dichloromethane under nitrogen. Add via syringe 3,4-dihydro-2H-pyran (3.2 mL, 1.5 equivalents) and stir at 20° C. overnight. Dilute with dichloromethane then extract with 1N sodium hydroxide and wash with brine. Dry over sodium sulfate, filtered, and then concentrate to afford the title compound as a brown oil.

$^1$H NMR (400 MHz, CDCl$_3$): δ 1.70 (m, 6H), 3.57 (m, 1H), 3.86 (m, 1H), 5.31 (t, J=3.17 Hz, 1H), 6.69 (d, J=2.20 Hz, 1H), 7.19 (m, 2H), 7.58 (d, J=2.20 Hz, 1H).

[5-(tetrahydropyran-2-yloxy)benzofur-7-yl]acetonitrile

Combine 5-(tetrahydropyran-2-yloxy)benzofuran-7-carboxaldehyde (3.75 g, 0.015 mol) with lithium cyanide-tetrahydrofuran (1:1.5 complex, 0.215 g, 0.1 equivalent) in tetrahydrofuran (80 mL) under nitrogen. Add diethyl cyanophosphonate (3.0 mL, 1.3 equivalents) and stir at 20° C. for 2 days. Add tert-butanol (1.6 mL, 1.1 equivalents) then SmI$_2$ in tetrahydrofuran (0.1 M solution, approximately 400 mL). Concentrate the solution in vacuo then redissolve in a solution of ethyl acetate:diethyl ether (approximately 3:1, 100 mL). Add saturated aqueous ammonium chloride and stir for 20 min, until the release of hydrogen cyanide is complete. Filter to remove insoluble material, then extract against 1 N hydrochloric acid. Dry over sodium sulfate, then filter and concentrate. Purification by a plug column (4:1 hexanes:ethyl acetate) to provide the title compound as a light yellow oil.

$^1$H NMR (400 MHz, CDCl$_3$): δ 1.70 (m, 6H), 3.54 (m, 1H), 3.88 (m, 1H), 3.91 (s, 2H), 5.34 (t, J=3.17 Hz, 1H), 6.67 (d, J=2.20 Hz, 1H), 7.01 (d, J=1.95 Hz, 1H), 7.20 (d, J=2.44 Hz, 1H), 7.55 (d, J=2.20 Hz, 1H).

Deprotection

Dissolve [5-(tetrahydropyran-2-yloxy)benzofur-7-yl]-acetonitrile (3.89 g, 0.015 mol) in methanol (100 mL) and add para-toluenesulfonic acid monohydrate (0.288 g, 0.1 equivalent). After 20 minutes extract with ethyl acetate against water, then wash with brine. Concentration in vacuo affords the title compound as an off-white solid.

HRMS: Calculated: 173.0465. Found: 173.0477.

PREPARATION 89

(4-Hydroxybenzofur-7-yl)acetonitrile

Beginning with 4-(Tetrahydropyran-2-yloxy)benzofuran-7-carboxaldehyde, the title compound is prepared essentially as described in Preparation 87.

ESMS: m/z=172.0 (M−1)

Benzo[b]thiophene-7-acetamide

Add benzo[b]thiophene-7-acetonitrile (1.9 g, 11.0 mmol) to 2-methyl-2-propanol (20 mL). Heat to reflux under nitrogen and add potassium hydroxide pellets (7.4 g, 132 mmol). Stir and reflux under nitrogen for 30 minutes. Pour solution off of the excess potassium hydroxide and dilute with ethyl acetate. Wash with a 1:1 mixture of aqueous saturated sodium chloride, aqueous saturated sodium hydrogen carbonate. Dry the organic phase over anhydrous magnesium sulfate, filter, and concentrate under reduced pressure. Rinse the solid with cold diethyl ether and dry under vacuum to obtain the title compound as an off-white solid.

HRMS: 192.0483 (M$^+$+H)

The compounds of Preparations 91-106 may be prepared essentially as described in Preparation 90.

| Prep. | Product | Data |
|---|---|---|
| 91 | 2-(1-Methyl-1H-indol-4-yl)acetamide | HRMS: 189.1028 (M + H) |
| 92 | 2-(1H-Indol-7-yl)acetamide | $^1$H-NMR (400 MHz, DMSO-d$_6$) δ 10.9 (bs, 1H), 7.44-7.37 (m, 2H), 7.32 (dd, J = 2, <1), 6.98-6.91 (m 3H), 6.41 (m, 1H), 3.62 (s, 2H) |
| 93 | 2-(4-Methoxybenzofur-7-yl)acetamide | MS (ES): 206.0 (M$^+$ + 1) |
| 94 | 2-(5-Methoxybenzo-fur-7-yl)acetamide | $^1$H-NMR (400 MHz, DMSO-d$_6$) δ 7.91 (d, J = 2 Hz, 1H), 7.5 (bs, 1H), 7.1 (d, J = 2 Hz, 1H), 6.96 (bs, 1H), 6.85 (d, J = 2 HZ, 1H) 6.8 (d, J = 2 Hz, 1H), 3.74 (s, 3H), 3.61 (s, 2H) |
| 95 | 2-(4-Fluorobenzofur-7-yl)acetamide | HRMS: 194.0617 (M$^+$ + 1) |
| 96 | 2-(4,5-Difluoro-benzofur-7-yl)acetamide | $^1$H-NMR (400 MHz, DMSO-d$_6$) δ 8.1 (d, J = 2 Hz, 1H), 7.55 (bs, 1H), 7.27 (m, 2H), 7.14 (d, J = 2 Hz, 1H), 7.01 (bs, 1H), 3.65 (s, 2H) |
| 97 | 2-(5-Fluorobenzofur-7-yl)acetamide | MS (ES): 194.1 (M$^+$ + 1) |
| 98 | 2-(5,6-Difluorobenzo-fur-7-yl)acetamide | $^1$H-NMR (400 MHz, DMSO-d$_6$) δ 8.08 (d, J = 2.2, 1H), 7.63 (bs, 1H), 7.59 (dd, J = 8, 8 Hz, 2H), 7.09 (bs, 1H), 6.9 (d, J = 2.2 Hz, d), 3.75 (s, 3H) |
| 99 | 2-(6-Fluorobenzofur-7-yl)acetamide | MS (ES): m/z = 194.0 (M$^+$ + 1) |
| 100 | 2-(Benzo[b]thien-7-yl)acetamide | HRMS: 192.0483 (M$^+$ + H) |
| 101 | 2-(Benzofur-7-yl)acetamide | HRMS: 176.0717 (M$^+$ + H) |
| 102 | 2-(Benzo[b]thien-4-yl)acetamide | HRMS: 192.0490 (M$^+$ + H) |
| 103 | 2-(Furo[3,2-c]pyridin-7-yl)acetamide | MS (ES): m/z = 177.1 (M$^+$ + 1) |
| 104 | 2-(2,3-Dihydrobenzo[1,4]dioxin-5-yl)-acetamide | HRMS: 194.0810 (M + H) |
| 105 | 2-{4-[3-(tert-Butyldimethyl-silyloxy)-propoxy]benzofur-7-yl}acetamide | MS (ES): m/z = 364.2 (M$^+$ + 1) |
| 106 | 2-(1,3-dihydroisobenzofur-5-yl)acetamide | MS (ES): m/z = 178.1 (M$^+$ + 1) |

PREPARATION 107

(5,6-Dihydro-4H-pyrrolo[3,2,1-ij]quinolin-1-yl)acetamide (5,6-Dihydro-4H-pyrrolo[3,2,1-ij]quinolin-1-yl)oxoacetamide Add concentrated ammonium hydroxide (2 mL) to a solution of (5,6-Dihydro-4H-pyrrolo[3,2,1-ij]quinolin-1-yl) oxoacetic acid methyl ester (0.50 g, 2.06 mmol) in 10 mL of tetrahydrofuran at 0° C. Remove the cooling bath and stir the mixture for 3 hours. Dilute the reaction with 20 mL of water and filter the suspension. Wash the filter cake with 10 mL of water followed by 10 mL of diethyl ether, and dry under reduced pressure to provide the desired compound as a light yellow solid (0.403 g, 86%).

MS (IS, m/z) $C_{13}H_{12}N_2O_2$ (M$^+$+1)=229

Reduction

Add 10% palladium on carbon (0.060 g) followed by the careful addition of NaH$_2$PO$_2$.H$_2$O (0.60 g, 5.67 mmol) to a solution of (5,6-dihydro-4H-pyrrolo[3,2,1-ij]quinolin-1-yl) oxoacetamide (0.30 g, 1.31 mmol) in dioxane (6 mL) and water (2 mL) and reflux the reaction under nitrogen. After 3 hours add 0.60 g of NaH$_2$PO$_2$.H$_2$O and reflux for 6 hours. Cool the mixture, filter through Celite, and wash with ethyl acetate (100 mL). Concentrate the filtrate under reduced pressure and treat the residue with water (20 mL). Filter the resulting suspension and dry the recovered solid dried under reduced pressure to provide the title compound as a white solid (0.27 g, 96%).

MS (IS, m/z) $C_{13}H_{14}N_2O_1$ (M$^+$+1)=215

PREPARATION 108

2-(6-(tert-butoxycarbonyl)-6,7-dihydro-6H-[1,4]diazepino[6,7,1-hi]indol-1-yl)acetamide Beginning with (2-(6-(tert-butoxycarbonyl)-6,7-dihydro-6H-[1,4]diazepino[6,7,1-hi]indol-1-yl)oxoacetic acid methyl ester (5.0 g, 13.95 mmol), the title compound is prepared essentially as described in Preparation 107.

MS (ES, m/z): $C_{18}H_{23}N_3O_3$: 330.3 (M$^+$+1), 328.4 (M$^+$−1)

PREPARATION 109

2-(Benzofur-4-yl)acetamide

Add 1,1'-carbonyldiimidazole (2.3 g, 14.2 mmol) to a solution of 2-(benzofur-4-yl)acetic acid (2.5 g, 14.2 mmol) in anhydrous tetrahydrofuran (12 mL) under nitrogen and stir at 20° C. for 4 hours. Bubble anhydrous ammonia through the solution, dilute with anhydrous tetrahydrofuran (10 mL) and stir at 20° C. for 18 hours. Concentrate under reduced pressure, wash the solid with aqueous sodium hydrogen sulfate, distilled water, and dry under vacuum to obtain the title compound as a pale yellow solid.

ESMS: m/z=176.1 (M$^+$+1)

PREPARATION 109

2-(Imidazo[1,2-a]pyridin-3-yl)acetamide

Add ethyl (E)-oxybutenoate (14.3 g, 111.66 mmol) to 2-aminopyridine (10.0 g, 106.4 mmol) in acetonitrile (270 ml). Heat the reaction at 80° C. for 6 hours. Concentrate the reaction mixture under reduced pressure. Purify the resulting oil by flash chromatography, eluting with a gradient of 100% hexane to 95% ethyl acetate: methanol to provide imidazo[1,2-a]pyridin-3-yl-acetic acid ethyl ester (10.95 g, 50.0%) as a brown solid.

$^1$H-NMR (400 MHz, DMSO-d6): δ 8.3 (m, 1H), 7.53 (m, 1H), 7.46 (s, 1H), 6.9 (m, 1H), 6.42 (m, 1H), 4.1 (q, J=7 Hz, 2H), 1.15 (t, J=7 Hz, 3H)

Bubble ammonia through a solution of (imidazo[1,2-a] pyridin-3-yl)acetic acid ethyl ester (10.0 g, 48.96 mmol) in methanol (30 ml) at 0° C. Heat the reaction mixture in a sealed tube at 100° C. for 2 hours. Concentrate the reaction mixture under reduced pressure. Triturate with ethyl acetate to give the title compound as a white solid.

ESMS: m/z=176.1 (M$^+$+1)

The compounds of Preparations 111-114 may be prepared essentially as described in Preparation 110.

| Prep. | Product | Data |
|---|---|---|
| 111 | 2-(8-fluoroimidazo[1,2-a]pyridin-3-yl)acetamide | MS (ES): m/z = 206.0 (M$^+$ + 1) |
| 112 | 2-(8-(benzyloxy)imidazo[1,2-a]pyridin-3-yl)acetamide | HRMS: m/z = 282.1232 |
| 113 | 2-(7-chloroimidazo[1,2-a]pyridin-3-yl)acetamide | MS (ES): m/z = 210.0 (M$^+$ + 1) |

| Prep. | Product | Data |
|---|---|---|
| 114 | 2-(8-methoxyimidzo[1,2-a]pyridin-3-yl)acetamide | MS (ES): m/z = 206.0 (M+ + 1) |

PREPARATION 115

2-(Imidazo[2,1-b]thiazol-3-yl)acetamide

Beginning with methyl 2-(imidazo[2,1-b]thiazol-3-yl)acetate, the title compound may be prepared essentially as described in Preparation 110.
HRMS: m/z=373.1756 (M+ +1)

PREPARATION 116

2-(Thiazolo[3,2-b][1,2,4]triazol-6-yl)acetamide

Methyl 3-oxo-4-(([1,2,4]triazol-3-yl)sulfanyl)butyrate

Add dropwise potassium tert-butoxide (11.4 g, 101.8 mmol) in 30 ml N,N-dimethylformamide (30 ml) to a solution of [1,2,4]triazole-3-thiol (10.3 gm, 101.8 mmol) in N,N-dimethylformamide (50 ml). Add dropwise methyl 4-chloroacetoacetate (15.3 gm, 101.8 mmol) in N,N-dimethylformamide (15 ml) and stir for 3 hours. Concentrate under reduced pressure, dilute with ethyl acetate (500 ml), filter, and concentrate under reduced pressure. Subject the residue to silica gel chromatography to provide the desired compound (18.3 gm, 83%) as a yellow oil.
HRMS: m/z=216.0443 (M+ +1)
Ring Formation/Amide Formation Heat a mixture of methyl 3-oxo-4-(([1,2,4]triazol-3-yl)sulfanyl)butyrate (16.4 g, 76.2 mmol) and 85% polyphosphoric acid (140 g) at 120° C. for 30 minutes. Pour into a stirring mixture of distilled water (1.4 L) and ethyl acetate (600 ml). Separate the layers. Wash the organic phase with saturated aqueous sodium bicarbonate followed by saturated aqueous sodium chloride, dry over magnesium sulfate, and concentrate under reduced pressure. Subject the residue to silica gel chromatography to provide a yellow oil. Dissolve the oil in 7 M ammonia in methanol. After 72 hours cool the mixture to −10° C. Filter the resulting suspension. Wash the solid with diethyl ether containing 20% methanol then dry under reduced pressure to provide 1.25 g of the desired compound as a white solid.
HRMS: m/z=183.0351 (M+ +1)
Beginning with methyl 2-(imidazo[2,1-b]thiazol-3-yl)acetate, the title compound prepared essentially as described in Preparation 110.
HRMS: m/z=373.1756 (M+ +1)

PREPARATION 117

5-oxo-6-propyl-5,6-dihydro-[1,4]diazepino[6,7,1-hi]indole (1H-Indol-7-ylmethyl)propylamine Add propyl amine (3.66 g, 62.07 mmol) to a solution of indole-7-carboxaldehyde (3.0 g, 20.68 mmol) and acetic acid (2.65 ml, 41.3 mmol) in toluene (100 ml). Heat at reflux constantly removing water with a Dean Stark apparatus. Concentrate the reaction under reduced pressure and re-dissolve in methanol. Gently add sodium borohydride (0.39 g, 10.34 mmol). Stir for 1 hour at room temperature, concentrate, and partition between ethyl acetate and saturated aqueous sodium bicarbonate. Concentrate the organic layers under reduced pressure. Compound carried onto next step without purification.
$^1$H NMR (400 MHz, CDCl$_3$) δ 10.9 (bs, 1H), 7.4 (d, J=8 Hz, 1H), 7.28 (d, J=1.5 Hz, 1H), 7.0 (d, J=7 Hz, 1H), 6.1 (dd, J=8.06, <1 Hz, 1H), 6.4 (d, J=1.5 Hz, 1H), 3.95 (s, 1 H), 2.5 (t, H=7 Hz, 2H), 1.45 (m, 2H), 0.8 (t, J=7 Hz, 3H).
Ring Formation Add chloroacetyl chloride (1.7 ml, 21.71 mmol) and diisopropylethylamine (10.38 ml, 62.04 mmol) to a solution of (1H-Indol-7-ylmethyl)propylamine (3.89 g, 20.68 mmol) in methylene chloride. Stir for 2 hours, quench with saturated aqueous ammonium chloride and extract into ethyl acetate. Wash the organic layers with saturated aqueous sodium chloride, dry over magnesium sulfate, filter, and concentrate under reduced pressure to yield N-(1H-indol-7-yl)methyl N-propyl 2-chloroacetamide (5.47 gm, 20.68 mMol).

Add 5.47 gm (20.68 mMol) N-(1H-indol-7-yl)methyl N-propyl 2-chloroacetamide to a suspension of sodium hydride (10 gm, 60% dispersion in mineral oil) in 350 mL dimethylformamide and stir the reaction at room temperature. Once starting material is consumed concentrate the reaction mixture under reduced pressure. Dissolve the residue in ethyl acetate, wash sequentially with water and saturated aqueous sodium bicarbonate. Subject to silica gel chromatography to provide the title compound (3.15 gm, 69%).
ESMS: 229.1 (M+ +1).

PREPARATION 118

4-Bromo-1-[2-(tert-butyldimethylsilyloxy)eth-1-yl]-1H-indole

Add sodium hydride (4.89 g, 122.4 mmol, 60% dispersion in mineral oil) to a solution of 4-Bromo-1H-indole (12 g, 61.2 mmol) in dimethylformamide (100 ml). Cool the reaction to 0° C. and add (2-bromo-1-(tert-butyldimethylsilyloxy)ethane (17.04 g, 67.32 mmol). Stir the reaction for 1 hour at room temperature, quench with aqueous saturated sodium bicarbonate, and extract into ethyl acetate. Combine the organic layers and wash with saturated aqueous sodium chloride, dry over magnesium sulfate. Concentrate under reduced pressure to obtain the title compound, as a clear oil.
$^1$H-NMR (400 MHz, DMSO-d$_5$): δ 7.48 (d, J=8, 1H), 7.4 (d, J=3 Hz, 1H), 7.22 (d, J=8 Hz, 1H), 7.05 (dd, J=8, 1 Hz, 1H), 6.4 (d, J=3 Hz, 1H), 4.25 (t, J=7 Hz, 2H), 3.49 (t, J=7 Hz, 2H), 1.9 (quintuplet, 2H), 0.82 (s, 9H), 0.0 (s, 6H).
The compounds of Preparations 119-122 may be prepared essentially as described in Preparation 118.

| Prep. | Compound | Data |
|---|---|---|
| 119 | 4-Bromo-1-[3-(tert-butyldimethylsilyloxy)prop-1-yl]-1H-indole | $^1$H-NMR (400 MHz, DMSO-d$_6$): δ 7.48 (d, J = 8, 1H), 7.4 (d, J = 3 Hz, 1H), 7.22 (d, J = 8 Hz, 1H), 7.05 (dd, J = 8, 1 Hz, 1H), 6.4 (d, J = 3 Hz, 1H), 4.25 (t, J = 7 Hz, 2H), 3.49 (t, J = 7 Hz, 2H), 1.9 (quintuplet, 2H), 0.82 (s, 9H), 0.0 (s, 6H) |
| 120 | 4-Bromo-1-methyl-1H-indole | $^1$H-NMR (400 MHz, CDCl$_3$): δ 7.29-7.25 (m, 2H), 7.10 (d, J = 3.2 Hz, 1H), |

-continued

| Prep. | Compound | Data |
|---|---|---|
| 121 | 1-[2-(tert-butyldimethylsilyloxy)-eth-1-yl]-6-methoxy-1H-indole | 7.07 (d, J = 8 Hz, 1H), 6.53 (d, J = 2.4 Hz, 1H), 3.79 (s, 3H) HRMS (M$^+$ + 1): 306.1882 |
| 122 | 7-Bromo-1-(but-3-enyl)-1H-pyrrolo[2,3-c]pyridine | MS (ES+): 251.3 [M($^{79}$Br) + 1]$^+$, 253.3 [M($^{81}$Br) + 1]$^+$ |

PREPARATION 123

(6-Methanesulfonyl-5,6-dihydro-[1,4]diazepino[6,7,1-hi]indol-1-yl)oxoacetic acid methyl ester 6-Methanesulfonyl-5,6-dihydro-[1,4]diazepino[6,7,1-hi]indole Add triethylamine (3.19 g, 31.56 mmol) to a solution of 2-[(1H-Indol-7-ylmethyl)amino]-ethan-1-ol (2.0 g, 10.52 mmol) in tetrahydrofuran (50 ml) at 0° C. Slowly add 1.75 mL (22.09 mMol) methanesulfonyl chloride and allow the reaction to warm to room temperature. Quench the reaction with saturated aqueous sodium bicarbonate and extract into ethyl acetate. Combine the organic layers, wash sequentially with saturated aqueous ammonium chloride, water, and saturated aqueous sodium chloride, dry over magnesium sulfate, and concentrate under reduced pressure. Add sodium hydride (0.8416 g, 21.04 mmol, 60% dispersion in mineral oil) to the resulting oil in dimethylformamide (20 ml). Quench the reaction with saturated aqueous sodium bicarbonate, concentrate to about 10 ml and extract into ethyl acetate. Combine the organic layers, wash sequentially with saturated ammonium chloride, water, and saturated aqueous sodium chloride, dry over magnesium sulfate, and concentrate under reduced pressure. Purification by flash chromatography, eluting with ethyl acetate:hexane gradient gives the title compound as an off-white solid.

Oxoacetic Acid Formation

Beginning with 6-methanesulfonyl-5,6-dihydro[1,4]diazepino[6,7,1-hi]indole (1.47 g, 5.89 mmol), the title compound (1.1 gm, 56%) is prepared essentially as described in Preparation 23

ESMS (M$^+$+1): 337.1

PREPARATION 124

2-(4-(acetylamino)benzofur-7-yl)acetamide 2-(2,2-Dimethoxyethoxy)-1-methyl-4-nitrobenzene Add bromoacetaldehyde dimethylacetal (30.3 g, 179 mmol) to 2-methyl-5-nitrophenol (25 g, 163 mmol) and potassium carbonate (50 g, 362 mmol) in dimethylformamide (200 mL). Stir and reflux under nitrogen for 2.5 hours. Cool to 20° C. temperature and add aqueous sodium hydroxide (200 mL, 1 M). Dilute the mixture with hexane, diethyl ether (1:1), wash with 0.2 M aqueous sodium hydroxide, aqueous saturated sodium chloride, dry the organic phase over anhydrous magnesium sulfate, filter, and concentrate under reduced pressure. Recrystallize the product from hexane to obtain the desired compound, as tan colored solid 30.6 gm (77%).

7-Methyl-4-nitro-benzofuran

Add Amberlyst® 15 ion-exchange resin (36 g) to chlorobenzene (700 mL). Heat the reaction mixture to reflux and azeotrope out water, to dry the resin. Dissolve 2-(2,2-dimethoxyethoxy)-1-methyl-4-nitrobenzene (34.8 g, 144 mmol) in chlorobenzene (125 mL) and add dropwise to the stirring, refluxing reaction mixture under nitrogen over 15 minutes. Continue refluxing for 1.5 hours. Cool to room temperature, filter to remove the resin and concentrate under reduced pressure. Dissolve the residue in hexane, diethyl ether (1:1), wash with 0.5 M aqueous sodium hydroxide, aqueous saturated sodium chloride, dry the organic phase over anhydrous magnesium sulfate, filter, and concentrate under reduced pressure. Chromatograph on flash silica using hexane, ethyl acetate (9:1) and recrystallize from hexane, toluene (1:1) to obtain the desired compound as a yellow solid (9.7 g, 42%).

N,N-[Dimethyl](2-(4-nitrobenzofur-7-yl)vinyl)amine

Add 7-methyl-4-nitro-benzofuran (3.5 g, 19.7 mmol) to tert-butoxy bis(dimethyl-amino)methane (10.3 g, 59.1 mmol). Reflux under nitrogen for 40 minutes. Concentrate under reduced pressure. Dissolve in xylenes (50 mL), concentrate under reduced pressure and dry under vacuum to obtain the desired compound as a deep red-brown solid (4.9 g, 100%).

HRMS: 233.0928 (M+H)

(4-Nitrobenzofur-7-yl)acetonitrile

Add N,N-[dimethyl](2-(4-nitrobenzofur-7-yl)vinyl)amine (4.8 g, 20.6 mmol) and hydroxylamine-O-sulfonic acid (4.6 g, 40.6 mmol) to dimethylformamide (45 mL) and stir the mixture at room temperature for 15 minutes. Heat at 100° C. under nitrogen for 1 hour. Cool to room temperature, dilute with diethyl ether, wash with water, aqueous saturated sodium chloride, dry the organic phase over anhydrous magnesium sulfate, filter, and concentrate under reduced pressure. Chromatograph on flash silica using 85% hexane, 15% ethyl acetate to obtain the desired compound as a light brown solid (2.9 g, 64%).

ESMS: m/z=200.9 (M−1)

N-[7-(Cyanomethyl)benzofur-4-yl]acetamide

Add (4-Nitrobenzofur-7-yl)acetonitrile (600 mg, 2.96 mmol), acetic anhydride (600 mg, 5.88 mmol), and 5% palladium on carbon (300 mg) to tetrahydrofuran (25 mL). Stir under 1 atmosphere of hydrogen for 45 minutes. Dilute with ethyl acetate, filter through a pad of Celite®, concentrate under reduced pressure, and chromatograph on flash silica using 75% ethyl acetate, 25% hexane to obtain the desired compound as an off-white solid (0.43 gm, 67%).

HRMS: 215.0816 (M+H)

Nitrile Hydrolysis

Dissolve N-[7-(Cyanomethyl)benzofur-4-yl]acetamide (300 mg, 1.40 mmol) in 2-methyl-2-propanol (15 mL). Heat to reflux under nitrogen and add potassium hydroxide pellets (1.50 g, 26.7 mmol). Stir and reflux under nitrogen for 30 minutes. Pour solution off of the excess potassium hydroxide and dilute with ethyl acetate. Wash with aqueous saturated sodium chloride, aqueous saturated sodium hydrogen carbonate (3:1), dry the organic phase over anhydrous magnesium sulfate, filter, and concentrate under reduced pressure. Rinse the solid with cold ethyl acetate, cold methanol and dry under vacuum to obtain the title compound as a tan solid (160 mg, 49%).

HRMS: 255.0733 (M+H)

PREPARATION 125

2-(thieno[3,2-b]pyridin-7-yl)acetamide

7-Bromo-thieno[3,2-b]pyridine

Heat phosphorus oxybromide (145.00 g, 0.50 moles) to 60° C. to form a melt. Add thieno[3,2-b]-7-pyridinol (14.73 g, 97.43 mmol) while stirring and increase heat to 100° C. for 2 hours. Pour the reaction contents over ice (1.0 kg). Dilute the slurry with ice and water to about 3 L. Extract the aqueous solution with chloroform (4×500 mL). Make the aqueous solution basic (pH 10-11) with 2 N sodium hydroxide and reextract with chloroform (3×400 mL). Treat the organic layers with magnesium sulfate, filter and concentrate. Redissolve the crude solid in dichloromethane (100 mL) and load the solution onto silica (300 g). Elute with 2 L of 30% ethyl acetate/dichloromethane. Concentrate the eluent to yield the desired compound as a crystalline solid (18.68 g, 89.5%).

2-Thieno[3,2-b]pyridin-7-yl-malonic acid diethyl ester

Charge a flask containing sodium hydride (17.45 g, 0.44 moles) with anhydrous dioxane (500 ml) while cooling at 0° C. Add diethyl malonate (69.88 g, 0.44 moles) dropwise over one hour. Upon reaching ambient temperature, add copper (I) bromide (62.59 g, 0.44 moles). Add 7-bromothieno[3,2-b] pyridine (18.68 g, 87.26 mmol) as a solution in dioxane (50 mL). Heat the reaction to reflux for 18 hours. Concentrate the reaction solution to ~175 mL. Pour the concentrate into concentrated ammonium hydroxide (2.5 L). Extract the aqueous phase with ethyl acetate (6×300 mL). Wash the organic layers exhaustively with 2 N sodium hydroxide until the blue color dissipates. Treat the organic layers with magnesium sulfate, filter and concentrate. Purification on silica utilizing a solution of 1:1:3 of ether, ethyl acetate and hexane as eluent yields the desired compound (14.6 gm, 57%).

(Thieno[3,2-b]pyridin-7-yl)acetic acid ethyl ester

Dissolve 2-(thieno[3,2-b]pyridin-7-yl)malonic acid diethyl ester (12.90 g, 44.0 mmol) in dimethyl sulfoxide (295 mL). Add water (0.79 mL) and lithium chloride (3.73 g, 87.9). Heat the solution to 110° C. for 3 hours. Quench the reaction with saturated brine (3 L) and extract with ethyl acetate (3×1 L). Rewash the organic layers with saturated brine (1 L). Treat the organic layers with magnesium sulfate, filter and concentrate. The residue was purified on silica using 25% ethyl acetate/hexanes to yield the desired compound (5.25 g, 54%).

2-(Thieno[3,2-b]pyridin-7-yl)acetamide

In a high pressure flask, dissolve (thieno[3,2-b]pyridin-7-yl)acetic acid (3.02 g, 13.65 mmol) in absolute ethanol (100 mL). Add ammonium chloride (1.09 g, 20.38 mmol) to the solution. Cool the solution to −78° C. Condense ammonia gas into the solution by bubbling (15 minutes at 10 psi). Seal the flask and slowly bring to ambient temperature. Stir the reaction at room temperature for 4 days. Cool the reaction vessel to −78° C. Open the flask and allow it to slowly return to ambient pressure. Filter the contents and wash with water (10 mL) to obtain the title compound as a white solid (1.46 g). Concentrate the filtrate and triturate the residue with diethyl ether. Filter and wash with water (5 mL) to obtain additional pure product (0.46 g).

PREPARATION 126

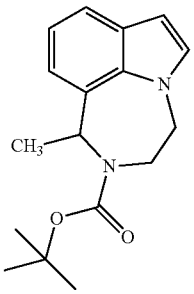

6-(tert-butoxycarbonyl)-7-methyl-6,7-dihydro-6H-[1,4]diazepino[6,7,1-hi]indole

N-[tert-butoxycarbonyl]-N-[2-hydroxyeth-1-yl]7-(1-aminoeth-1-yl)indole

Dissolve 7-formylindole (2.5 g, 17.2 mmol), 2-aminoethanol (1.31 g, 21.4 mmol), and glacial acetic acid (1.29 g, 21.4 mmol) in toluene (250 mL). Reflux for 30 minutes and remove the water using a Dean-Stark trap. Distill some of the toluene (200 mL) from the reaction mixture and cool the reaction to 0° C. To the stirring reaction at 0° C. add dropwise 1.5 molar methyllithium-lithium bromide complex in diethyl ether (57 mL, 85.5 mmol) under nitrogen. Stir the reaction at 0° C. for 15 minutes and quench by adding saturated aqueous sodium hydrogen carbonate (125 mL). Add a solution of di-tert-butyl dicarbonate (7.52 g, 34.4 mmol) in tetrahydrofuran (50 mL) and stir at 20° C. for 18 hours. Add aqueous ammonia (29%, 15 mL), dilute the reaction with ethyl acetate, wash the organic layer sequentially with distilled water and saturated aqueous sodium chloride. Dry the organic layer over anhydrous magnesium sulfate, filter, concentrate under reduced pressure and chromatograph on flash silica using ethyl acetate in hexane to obtain 2.5 g (47%) of the desired compound as a colorless oil.

HRMS: m/z=327.1677 (M+Na)

Ring Formation

Add N-[tert-butoxycarbonyl]-N-[2-hydroxyeth-1-yl]7-(1-aminoeth-1-yl)indole (2.5 g, 8.21 mmol) to a solution of triethylamine (2.5 g, 24.7 mmol) and anhydrous dimethylformamide (40 mL) and cool to 0° C. under nitrogen. Add a solution of methanesulfonic anhydride (1.80 g, 10.3 mmol) in dimethylformamide (10 mL) dropwise and stir at 0° C. for 30 minutes. Dilute the reaction mixture with cold (0° C.) anhydrous dimethylformamide (200 mL) and hexane (50 mL). Add sodium hydride 60% dispersion in mineral oil (1.97 g, 49.2 mmol), to the stirring reaction mixture under nitrogen, and allow the reaction to slowly warm to 20° C. Stir at 20° C. for 18 hours. Quench the excess sodium hydride by adding 50% aqueous acetic acid (20 mL) and concentrate under reduced pressure. Dilute the residue with diethyl ether, ethyl acetate (1:1), wash with distilled water, 0.5 molar aqueous sodium hydrogen carbonate and aqueous saturated sodium chloride. Dry the organic phase over anhydrous magnesium sulfate, filter, and concentrate under reduced pressure. Chromatograph on flash silica using ethyl acetate in hexane to obtain 2.2 g (94%) of the title compound as a white solid.
HRMS: m/z=309.1579 (M+Na)

PREPARATION 127

6-(tert-butoxycarbonyl)-7-methyl-6,7-dihydro-6H-[1,4]diazepino[6,7,1-hi]indol-1-yl)oxoacetic acid methyl ester Beginning with 6-(tert-butoxycarbonyl)-7-methyl-6,7-dihydro-6H-[1,4]diazepino-[6,7,1-hi]indole, the title compound was prepared essentially as described in Preparation 23.
HRMS: m/z=373.1749 (M+H)
Subject the racemic material to chiral chromatography on a ChiralPak® AD 4.6×250 mm column, eluting with methanol at a flow rate of 1.0 ml/min.
The first eluting isomer (5.1 minutes) is (+)-6-(tert-butoxycarbonyl)-7-methyl-6,7-dihydro-6H-[1,4]diazepino[6,7,1-hi]indol-1-yl)oxoacetic acid methyl ester.
$[\alpha]_{589}$ (DMSO, c=10 mg/ml)=+98°
HRMS: m/z=373.1766 (M+H)
The second eluting isomer (7.2 minutes) is (−)-6-(tert-butoxycarbonyl)-7-methyl-6,7-dihydro-6H-[1,4]diazepino[6,7,1-hi]indol-1-yl)oxoacetic acid methyl ester.
$[\alpha]_{589}$ (DMSO, c=10 mg/ml)=−94.9°
HRMS: m/z=373.1756 (M+H)

PREPARATION 128

1-iodo-2-oxo-2-(morpholin-4-yl)ethane

Dissolve 1-chloro-2-oxo-2-(morpholin-4-yl)ethane (7.0 g, 42.8 mmol) and sodium iodide (8.0 g, 53.4 mmol) in 2-butanone (150 mL) and reflux for 3 hours under nitrogen. Dilute with ethyl acetate (200 mL), filter, concentrate under reduced pressure and chromatograph on flash silica using neat ethyl acetate to obtain 9.4 g (86%) of the title compound as a yellow oil.
HRMS: m/z=255.9837 (M+H)

PREPARATION 129

2-(2,3-Dihydrobenzo[1,4]dioxin-5-yl)acetamide (2,3-Dihydrobenzo[1,4]dioxin-5-yl)methanol Dissolve 2,3-dihydroxybenzaldehyde (25 g, 181 mmol) and 1,2-dibromoethane (34 g, 181 mmol) in N,N-dimethylformamide (500 mL). Add cesium carbonate (118 g, 362 mmol), stir and reflux under nitrogen for 2 hours. Cool the reaction to 20° C., dilute with absolute ethanol (250 mL) and add sodium borohydride (6.8 g, 181 mmol). Stir at 20° C. for 1 hour and concentrate under high vacuum to remove the ethanol and dimethylformamide. Dilute the residue with diethyl ether and wash with distilled water, 0.25 molar aqueous sodium hydroxide, and aqueous saturated sodium chloride. Dry the organic phase over anhydrous magnesium sulfate, filter and concentrate under reduced pressure. Chromatograph on flash silica using a gradient from 75% hexane, 25% ethyl acetate to 25% hexane, 75% ethyl acetate to obtain 8.1 g (27%) of the desired compound as a white solid.
HRMS: m/z=166.0621 (M)

(2,3-Dihydrobenzo[1,4]dioxin-5-yl)-chloromethane

Dissolve (2,3-Dihydrobenzo[1,4]dioxin-5-yl)methanol (1.8 g, 10.8 mmol) in dichloromethane (15 mL). Add neat thionyl chloride (2 mL, 27.4 mmol) dropwise to the stirring reaction mixture at 25° C. under nitrogen. Stir the reaction for 15 minutes and concentrate under reduced pressure to obtain 2.0 g (100%) of the desired compound as a yellow oil.
HRMS: m/z=184.0290 (M)

(2,3-Dihydrobenzo[1,4]dioxin-5-yl)acetonitrile

Add (2,3-Dihydrobenzo[1,4]dioxin-5-yl)-chloromethane (1.9 g, 10.2 mmol) and sodium cyanide (655 mgs, 13.3 mmol) to dimethylsulfoxide (20 mL). Stir under nitrogen at 65° C. for 18 hours. Dilute the reaction with ethyl acetate, wash with 0.1 molar aqueous sodium carbonate and aqueous saturated sodium chloride. Dry the organic phase over anhydrous magnesium sulfate, filter and concentrate under reduced pressure. Chromatograph on flash silica using a gradient from neat hexane to 50% ethyl acetate in hexane to obtain 1.23 g (68%) of the desired compound as a white solid.
HRMS: m/z=175.0624 (M)

Nitrile Hydrolysis

Beginning with (2,3-Dihydrobenzo[1,4]dioxin-5-yl)acetonitrile (1.1 g, 6.2 mmol), 850 mg (70%) of the title compound is prepared as a white solid essentially as described in Preparation 79.
HRMS: m/z=194.0810 (M+H)

PREPARATION 130

5-Fluoro-1H-indole-7-carboxaldehyde (5-Fluoro-2-nitrophenyl)methanol

Dissolve 5-fluoro-2-nitrobenzoic acid (15 g, 81.08 mmol) in anhydrous tetrahydrofuran (200 mL) and add dropwise with stirring at 20° C. a 1 molar solution of borane in tetrahydrofuran (243 ml, 243 mmol). Stir the mixture at 20° C. for 72 hours then add methanol (200 ml). Concentrate under reduced pressure and purify the residue by flash column chromatography (silica gel, 10-30% ethyl acetate/hexane) to obtain 13.92 g (100%) of the title compound as a white solid.
$^1$H-NMR (CDCl$_3$): δ 8.14 (dd, 1H), 7.48 (dd, 1H), 7.06 (ddd, 1H), 4.98 (s, 3H), 2.04 (s, 1H)

5-Fluoro-2-nitrobenzaldehyde

Dissolve (5-fluoro-2-nitrophenyl)methanol (13.92 g, 81.08 mmol) in dichloromethane (284 mL). Add 4 Å molecular sieves (73 g) and pyridinium dichromate (36.58 g, 97.3 mmol). Stir the mixture at 20° C. for 6 hours. Filter the crude reaction mixture through a short silica gel column. Remove the solvent under reduced pressure and purify the residue by flash chromatography (silica gel, 10-20% ethyl acetate/hexane) to obtain 9.43 g (69%) of title compound as colorless oil.
$^1$H-NMR (CDCl$_3$): δ 10.44 (d, 1H), 8.22 (dd, 1H), 7.62 (dd, 1H), 7.41 (ddd, 1H)

2-Dibutoxymethyl-4-fluoro-1-nitrobenzene

Dissolve 5-fluoro-2-nitrobenzaldehyde (9.43 g, 55.81 mmol), 1-butanol (12.41 g, 167.4 mmol) and 4-toluenesulfonic acid monohydrate (0.9 g, 4.7 mmol) in toluene (84 mL). Heat the reaction mixture to reflux, and remove the water using a Dean-Stark apparatus. Continue to heat the reaction mixture for 3 hours. Add water and extract the aqueous layer with ethyl acetate. Combine the organic layers and dry over anhydrous sodium sulfate. Filter, concentrate under reduced pressure and purify by flash column chromatography (1% v/v triethylamine buffered silica gel, 5% ethyl acetate/hexane) to obtain 15.8 g (95%) of the title compound as colorless oil.

$^1$H-NMR (CDCl$_3$): δ 7.90 (dd, 1H), 7.53 (dd, 1H), 7.12 (ddd, 1H), 6.04 (s, 1H), 3.64 (t, 1H), 3.62 (t, 1H), 3.54 (t, 1H), 3.52 (t, 1H), 1.59 (m, 4H), 1.38 (s, 4H), 0.92 (t, 6H).

Ring Formation/Deprotection

Dissolve 2-dibutoxymethyl-4-fluoro-1-nitrobenzene (15.8 g, 52.84 mmol) in tetrahydrofuran (528 mL) under nitrogen and cool the solution to −40° C. Add with stirring a 1 molar solution of vinylmagnesium bromide in tetrahydrofuran (211 mL, 211 mmol), maintaining a temperature of −40° C. Stir the reaction mixture at −40° C. for 40 minutes, then add aqueous saturated ammonium chloride. Extract the aqueous layer with ethyl acetate. Combine the organic layers, dry over anhydrous sodium sulfate, filter, and concentrate under reduced pressure. Dissolve the residue in tetrahydrofuran (160 mL) and cool to 0° C. Add 0.5 N aqueous hydrochloric acid (20 mL) and stir the mixture at 0° C. for 1 hour. Add aqueous saturated sodium hydrogen carbonate (200 mL) and extract the aqueous layer with ethyl acetate. Combine the organic layers, dry over anhydrous sodium sulfate, filter, concentrate under reduced pressure and purify by flash column chromatography (silica gel, 5% ethyl acetate/hexane) to obtain 4.76 g (55%) of the title compound as a white solid.

$^1$H-NMR (CDCl$_3$): δ 10.07 (s, 2H), 7.62 (dd, 1H), 7.40 (m, 1H), 6.60 (t, 1H)

PREPARATION 131

2-(5,6,7,8-tetrahydroimidazo[1,2-a]pyridin-3-yl)acetamide

Hydrogenate a mixture 2-(imidazo[1,2-a]pyridin-3-yl)acetamide (0.64 gm) and 0.158 gm platinum oxide in 200 mL ethanol saturated with hydrogen chloride at 60 p.s.i. for 2 hours at room temperature. Filter the reaction mixture and concentrate the filtrate under reduced pressure to provide 0.58 gm ethyl 2-(5,6,7,8-tetrahydroimidazo[1,2-a]pyridin-3-yl)acetate. Heat a solution of this ester in 40 mL 2 M ammonia in methanol in a sealed tube at 100° C. for 2 hours. Cool the reaction mixture to room temperature and concentrate under reduced pressure to a volume of about 5 mL. Dilute with ethyl acetate and filter the resulting solid to provide the title compound.

MS (ES): m/z=180.1 (M$^+$+1)

PREPARATION 132

2-(pyrazolo[2,3-a]pyridin-3-yl)acetamide

Beginning with 2-(pyrazolo[2,3-a]pyridin-3-yl)acetonitrile, the title compound is prepared essentially as described in Preparation 90.

PREPARATION 133

2-(4-Chlorofuro[3,2-c]pyridin-7-yl)acetamide 7-(Hydroxymethyl)furo[3,2-c]pyran-4-one Add lithium diisopropylamine (0.454 mole) as a solution in tetrahydrofuran (100) mL to a solution of 3-furoic acid (23.36 g, 0.208 mole) at −78° C. over 30 minutes and stir for 1 hour at −78° C. To the resulting di-anion add 1,3-Bis-triisopropyl-silanyloxy-propan-2-one as a solution in tetrahydrofuran (250 mL) over 30 minutes and stir at −78° C. for 1 hour and allow to warm to room temperature overnight. Quench the reaction with saturated aqueous ammonium chloride, pour into ethylacetate (1 L), add 1N HCL (1 L) and separate the two layers. Wash the organic layer with 1N HCl, water, and brine, dry over magnesium sulfate, filter and concentrate to an oil. Dissolve the crude oil in 50% tetrahydrofuran and 50% 3N HCl (1 L) and heat a reflux over night. Distill off tetrahydrofuran, concentrate under reduced pressure and, add acetonitrile remove it under reduced pressure to azeotrope off the remaining water. Dissolve the resulting crude oil in acetonitrile (250 mL) and add the solution to a solution of toluene containing a catalytic amount of p-toluenesulfonic acid at reflux that is fitted with a Dean Stark trap over 30 minutes. Toluene was added to replace the acetonitrile and water removed by distillation and azetroping (500 mL). Heat the solution at reflux until it appears no further water is being removed. The hot solution was poured into an erlenmeyer flask and allowed to cool. Triturate the brown remaining residue with ethylacetate and methanol and combine it with the toluene solution and concentrate. Dilute with ethylacetate and wash with saturated aqueous sodium bicarbonate and brine, dry over magnesium sulfate and concentrate to an off white solid. Purification by flash chromatography eluting with hexane:ethylacetate gives 13.27 g (42%) of the title compound as a white solid.

MS (ES): m/e=167.0 (M$^+$+1).

Methyl (4-oxo-4,5-dihydrofuro[3,2-c]pyridin-7-yl)acetate

Combine 7-(hydroxymethyl)furo[3,2-c]pyran-4-one (8.28 g, 49.8 mmol), ammonium acetate (76.8 g, 996 mmol), and glacial acetic acid and heat at reflux for 3.5 hours. Cooling to room temperature, pouring into ethylacetate, washing with water saturated aqueous sodium bicarbonate, and brine, drying over magnesium sulfate, filtering and concentrating gives 4.42 g (42%) of the title compound.

$^1$H-NMR (DMSO$_{d6}$): δ 11.5 (s, 1H), 7.91 (d, J=2 Hz), 7.41 (s, 1H), 6.94 (d, J=1.6 Hz, 1H), 5.06 (s, 2H), 2.00 (s, 3H).

(4-Oxo-4,5-dihydrofuro pyridin-7-yl)acetonitrile

Combine methyl (4-oxo-4,5-dihydrofuro[3,2-c]pyridin-7-yl)acetate (4.42 g, 21.3 mmol), sodium cyanide (5.22 g, 106 mmol), and dimethylsulfoxide (44 mL) and heat at 80° C. for 1 hour. Cool to room temperature, pour into ethyl acetate, wash sequentially with water, saturated aqueous sodium bicarbonate, and saturated aqueous sodium chloride, dry over magnesium sulfate, filter, and concentrate under reduced pressure to provide the desired compound (3.63 g, 63%).

MS (ES): m/z=173.1 (M$^-$−1)

Chlorination

Add phosphorus oxychloride (150 mL) to (4-oxo-4,5-dihydrofuro[3,2-c]pyridin-7-yl)acetonitrile (2.363 g, 13.5 mmol) and heat at reflux. Concentrate under reduced pressure, dissolve the residue in tert-butanol (35 mL), and heat to reflux. Add KOH (85%) pellets and heat at reflux for 15 minutes. Cool the reaction and pour into ethyl acetate. Wash the organic solution with water and saturated aqueous sodium chloride, dry over sodium sulfate, and filter. Subject residue to flash chromatography, eluting with ethyl acetate:methanol to provide the title compound (858 mg, 31%) as an off white solid.

MS (ES): m/e=210.9 (M$^+$).

PREPARATION 134

2-(4-Dimethylaminofuro[3,2-c]pyridin-7-yl)acetamide

Combine 2-(4-chlorofuro[3,2-c]pyridin-7-yl)acetamide (850 mg, 4.21 mmol), dimethylformamide (5 mL) and ethanolamine (0.76 mL, 12.63 mmol). Heat the reaction at 130° C. overnight. Add additional ethanolamine (0.25 ml) and heat at 130° C. overnight. Cool to room temperature, concentrate, and dilute with ethyl acetate. Wash with saturated aqueous sodium bicarbonate and concentrate. Subject to flash chromatography, eluting with ethylacetate:methanol to provide the title compound as a white solid (400 mg, 43%).
MS (ES): m/e=220.1 (M$^+$+1)

PREPARATION 135

2-(7-cyanoimidazo[1,2-a]pyridin-3-yl)acetamide

Add 100 mL ammonium hydroxide to a sealed tube containing 12.5 gm (90.21 mMol) 2-chloro-3-cyanopyridine. Seal the tube and heat the suspension at 120° C. for 6 hours. Cool the reaction mixture to room temperature and partition between ethyl acetate and saturated aqueous sodium bicarbonate. Extract the aqueous phase with ethyl acetate (3×100 mL) followed by 70:30 ethyl acetate:n-butanol (2×100 mL). Combine organic phases and concentrate under reduced pressure to provide 2-amino-3-cyanopyridine.
MS (ES): m/z=120 (M$^+$+1)
2-amino-3-cyanopyridine is reacted as described in Preparation 110 to provide the title compound.
MS (ES): m/e=230 (M$^+$+1)

PREPARATION 136

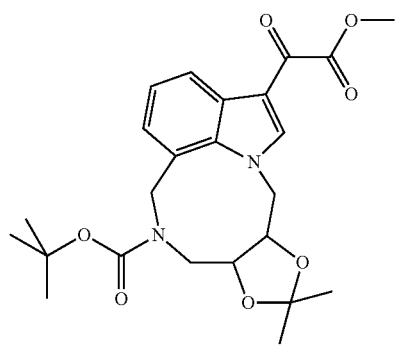

Methyl (5,6-(2,2-dimethyl-[1,3]-dioxolanyl)-8-(tert-butoxycarbonyl)-[1,5]diazaperhydroonino[8,9,1-hi]indol-1-yl)oxoacetate Oxidation
Add osmium tetraoxide (9 mg, 0.035 mmol) in butanol (1.5 mL) to a solution of the alkene prepared in Preparation 18 (0.5 g, 1.75 mmol) in 9:1 tetrahydrofuran:water. Stir the mixture for 1 hour at room temperature. Quench with NaHSO$_3$, dilute with ethyl acetate, and filter. Wash the organic layer sequentially with water and saturated aqueous sodium chloride, dry over sodium sulfate and concentrate under reduced pressure. Subject to silica gel chromatography, eluting with a gradient of 3:1-0:1 hexane:ethyl acetate to provide the desired diol.

Diol Protection
Dissolve the diol (0.22 g, 0.66 mmol) and p-toluenesulfonic acid (25 mg) in 5 mL acetone and stir the mixture for 1 hour at room temperature. Concentrate under reduced pressure and subject the residue to silica gel chromatography, eluting with a gradient of hexane containing from 0-33% ethyl acetate to provide the protected diol (150 mg, 61%).
Oxoacetic Acid Ester Formation
Beginning with the protected diol, the title compound is prepared as a yellow solid essentially as described in Preparation 23 (60 mg).
MS (ES): m/z=459 (M$^+$+H)

PREPARATION 137

3-(8-tert-butoxycarbonyl-[1,5]diazoperhydroonino[8,9,1-hi]indol-1-yl)-4-(benzofur-7-yl)-2,5-dioxopyrrole Add potassium tert-butoxide (2.19 ml, 2.19 mmol, 1M solution in tetrahydrofuran) to a suspension of 2-(benzofur-7-yl)acetamide (0.13 g, 0.73 mmol) and (8-tert-butoxy-carbonyl-[1,5]diazoperhydroonino[8,9,1-hi]indol-1-yl)oxoacetic acid methyl ester (0.283 g, 0.73 mmol) in dimethylformamide (5 ml). Stir the reaction for 2 hours, quench with 1N HCl, and extract into ethyl acetate. Wash the organic extracts sequentially with saturated aqueous sodium bicarbonate and saturated aqueous sodium chloride, dry over magnesium sulfate, filter, and concentrate under reduced pressure. Chromatograph on flash silica, eluting with a gradient from neat hexane to 100% ethyl acetate to obtain the title compound as an orange solid (0.19 g, 51%).
MS (ES): m/z=512.1 (M$^+$+1)

The compounds of Preparations 138-150 are prepared essentially as described in Preparation 137.

| Prep. | Compound | Data |
|---|---|---|
| 138 | 3-(8-tert-butoxycarbonyl-[1,5]diazoperhydroonino-[8,9,1-hi]indol-1-yl)-4-(5-Fluoro-4-methoxybenzofur-7-yl)-2,5-dioxopyrrole | MS (ES): m/z = 560.8 (M$^+$ + 1) |
| 139 | 3-(8-tert-butoxycarbonyl-[1,5]diazoperhydroonino-[8,9,1-hi]indol-1-yl)-4-(furo[3,2-c]pyridin-7-yl)-2,5-dioxopyrrole | MS (ES): m/z = 513.2 (M$^+$ + 1) |
| 140 | 3-(6-tert-butoxycarbonyl-[1,8]diazoperhydroonino-[8,9,1-hi]indol-1-yl)-4-(furo[3,2-c]pyridin-7-yl)-2,5-dioxopyrrole | MS (ES): m/z = 513.2 (M$^+$ + 1) |
| 141 | 3-(6-tert-butoxycarbonyl-6,7-dihydro-6H-[1,4]diazepino[6,7,1-hi]indol-1-yl)-4-(furo[3,2-c]pyridin-7-yl)-2,5-dioxopyrrole | HRMS: m/z = 485.1832 |
| 142 | 3-(6-tert-butoxycarbonyl-6,7-dihydro-6H-[1,4]diazepino[6,7,1-hi]indol-1-yl)-4-(isoquinolin-5-yl)-2,5-dioxopyrrole | MS (ES): m/z = 495.1 (M$^+$ + 1) |
| 143 | 3-(8-tert-butoxycarbonyl-[1,5]diazoperhydroonino-[8,9,1-hi]indol-1-yl)-4-(imidazo[1,2-a]pyridin-3-yl)-2,5-dioxopyrrole | MS (ES): m/z = 512.2 (M$^+$ + 1) |
| 144 | 3-(6-(2,4-dimethoxybenzyl)-6,7-dihydro-6H-[1,4]diazepino[6,7,1-hi]indol-1-yl)-4-(imidazo[1,2-a]-pyridin-3-yl)-2,5-dioxopyrrole | MS (ES): m/z = 564.2 (M$^+$ + 1) |
| 145 | 3-(8-fluoro-6-(tert-butoxycarbonyl)-6,7-dihydro-6H-[1,4]diazepino[6,7,1-hi]indol-1-yl)-4-(imidazo[1,2-a]-pyridin-3-yl)-2,5-dioxopyrrole | MS (ES): m/z = 502.0 (M$^+$ + 1) |
| 146 | 3-(6-(tert-butoxycarbonyl)-6,7-dihydro-6H-[1,4]diazepino[6,7,1-hi]indol-1-yl)-4-(7-chloroimidazo[1,2-a]-pyridin-3-yl)-2,5-dioxopyrrole | MS (ES): m/z = 518.1 (M$^+$ + 1) |

-continued

| Prep. | Compound | Data |
|---|---|---|
| 147 | 3-(9-fluoro-6-(tert-butoxycarbonyl)-6,7-dihydro-6H-[1,4]diazepino[6,7,1-hi]indol-1-yl)-4-(7-chloro-imidazo[1,2-a]pyridin-3-yl)-2,5-dioxopyrrole | MS (ES): m/z = 535.9 ($M^+$ + 1) |
| 148 | 3-(6-(tert-butoxycarbonyl)-6,7-dihydro-6H-[1,4]diazepino[6,7,1-hi]indol-1-yl)-4-(8-methoxyimidazo[1,2-a]-pyridin-3-yl)-2,5-dioxopyrrole | MS (ES): m/z = 513.9 ($M^+$ + 1) |
| 149 | 3-(6-(tert-butoxycarbonyl)-6,7-dihydro-6H-[1,4]diazepino[6,7,1-hi]indol-1-yl)-4-(6-chloroimidazo[1,2-a]-pyridin-3-yl)-2,5-dioxopyrrole | MS (ES): m/z = 518 ($M^+$ + 1) |
| 150 | 3-(6-(tert-butoxycarbonyl)-6,7-dihydro-6H-[1,4]diazepino[6,7,1-hi]indol-1-yl)-4-(imidazo[1,2-a]-pyridimin-3-yl)-2,5-dioxopyrrole | MS (ES): m/z = 485.1 ($M^+$ + 1) |

PREPARATION 151

6-methyl-8-bromoimidazo[1,2-a]pyridine

Add chloroacetaldehyde (2.51 g, 32.08 mmol) to a solution of 2-amino-3-bromo-5-methylpyridine (2.0 g, 10.69 mmol) in acetonitrile (200 ml). Reflux the reaction for 4 hours and then cool. Filter the reaction mixture and partition the white solid between saturated aqueous sodium bicarbonate (300 ml) and ethyl acetate. Separate the organic layer, wash with saturated aqueous sodium bicarbonate, dry over magnesium sulfate, and concentrated under reduced pressure to give the title compound as a tan solid.
MS (ES) m/z=211.0 ($M^+$+1)

PREPARATION 152

6,8-dimethylimidazo[1,2-a]pyridine

Microwave a mixture of 6-methyl-8-bromoimidazo[1,2-a]pyridine (1.0 g, 4.76 mmol), tetramethyl tin (2.0 g, 11.2 mmol), and palladium tetrakis(triphenylphosphine) (0.28 g, 0.024 mmol) at 120° C. for 10 minutes at 300 watts. Subject the reaction mixture to flash silica gel chromatography to provide a quantitative yield of the title compound as a tan oil.

PREPARATION 153

R-6-(tert-butoxycarbonyl)-5-methyl-6,7-dihydro-6H-[1,4]diazepino[6,7,1-hi]indole N-[(1H-indol-7-1 methyl]-R-2-aminopropan-1-ol Add D-alaninol (2.9 ml, 37.39 mmol), sodium triacetoxy borohydride (8.7 g, 41.09 mmol), and acetic acid (0.8 ml, 13.7 mmol) to a solution of 1H-indole-7-carboxaldehyde (2.0 g, 13.7 mmol) in dichloroethane (100 ml). Stir the reaction mixture at room temperature for one day and then at 60° C. for 1 day. Quench with saturated aqueous sodium bicarbonate, wash with saturated aqueous sodium chloride, dry over magnesium sulfate, and concentrate under reduced pressure to provide the title compound (0.87 g, 31%) as a yellow oil.
MS (ES): m/z=205 ($M^+$+1)

N-[tert-butoxycarbonyl]-N-[1H-indol-7-yl)methyl]-R-2-aminopropan-1-ol

Reflux N-[(1H-indol-7-yl)methyl]-R-2-aminopropan-1-ol (0.500 g, 2.45 mmol) and di-tert-butyl dicarbonate (0.640 g, 2.94 mmol) in tetrahydrofuran (25 ml) under nitrogen for 1.5 hr. Cool to room temperature and concentrate under reduced pressure. Subject the residue to silica gel chromatography, eluting with 1:1 ethyl acetate:hexane to provide the title compound (0.680 g, 96%) as a clear oil.
MS (ES): m/z=305.0 (M+1)

N-[tert-butoxycarbonyl]-N-[(1H-indol-7-yl)methyl]-R-2-amino-1-methanesulfonyloxypropane Add a solution of methanesulfonyl chloride (0.237 g, 0.16 ml, 2.07 mmol) in dichloromethane (5 ml) dropwise to a solution of N-[tert-butoxycarbonyl]-N-[(1H-indol-7-yl)methyl]-R-2-aminopropan-1-ol (0.600 g, 2.07 mmol) and triethylamine (1.44 ml, 1.045 g, 10.33 mmol) in dichloromethane (20 ml) at 0° C. under nitrogen for 1 hour. Dilute the reaction mixture with ice water and extract with dichloromethane. Wash the organic phase with concentrated aqueous sodium chloride, dry over magnesium sulfate and concentrate under reduced pressure to provide the title compound.
$^1$H NMR (400 MHz, $CDCl_3$): δ 10.20 (s, br, 1H), 7.61 (m, 1H), 7.22 (m, 1H), 7.04 (m, 2H), 6.53 (d, J=2.44 Hz, 1H), 4.91 (m, 1H), 4.59 (m, 1H), 4.24 (m, 1H), 4.12 (m, 1H), 3.90 (m, 1H), 3.45 (m, 2H), 2.31 (s, 3H).

Ring Closure

Add sodium hydride (0.124 g, 3.11 mmol, 60% suspension in oil) to a solution of N-[tert-butoxycarbonyl]-N-[(1H-indol-7-yl)methyl]-R-2-amino-1-methanesulfonyloxy-propane in dimethylformamide at 0° C. under nitrogen. Stir the reaction for 1 hour and then partition between ethyl acetate and saturated aqueous ammonium chloride. Wash the organic phase with saturated aqueous sodium chloride, dry over magnesium sulfate, and concentrate under reduced pressure. Subject the residue to silica gel chromatography, eluting with 1:1 hexane:ethyl acetate to provide the title compound (0.367 g, 66%) as a white solid.
MS (ES): m/z=287.0 (M+1)

PREPARATION 154

6-(tert-butoxycarbonyl)-4-methyl-6,7-dihydro-6H-[1,4]diazepino[6,7,1-hi]indole (Indol-7-yl)methylamine Add hydroxylamine hydrochloride (2.87 g, 41.37 mmol) and ammonium acetate (4.78 g, 62.06 mmol) to a solution of indole-7-carboxaldehyde (3.0 g, 20.68 mmol) in ethanol:$H_2O$ (3:1) (120 ml). Stir at room temperature for 2 hours. Add ammonium hydroxide (25 ml, 0.72 mmol) and zinc (11.0 g, 8.1 mmol) in portions. Filter the reaction mixture, dilute with ethyl acetate, and wash with water. Extract the organic layer with 1N HCl. Make the aqueous layer basic by adding 1N NaOH and extract with ethyl acetate. Wash the organic layer with water followed by saturated aqueous sodium chloride, dry over magnesium sulfate, and concentrate under reduced pressure to provide the desired compound (2.69 g, 89%) as a white solid.
MS (ES): m/z=147 ($M^+$+1)

N-[(Indol-7-yl)methyl]-2-bromopropionamide

Add 2-bromopropionyl chloride to a solution of (indol-7-yl)methylamine and triethylamine (0.49 g, 47.6 mmol) in tetrahydrofuran (20 ml) at 0° C. Stir for 1 hour at room temperature and quench with saturated aqueous sodium bicarbonate. Extract with ethyl acetate, concentrate under reduced pressure and subject the residue to silica gel chromatography to provide the desired compound (0.62 g, 46%) as a yellow solid.

MS (ES): m/z=281.0 (M$^+$+1)

4-methyl-6,7-dihydro-6H-[1,4]diazepino[6,7,1-hi]indol-3-one

Add sodium hydride (0.03 g, 1.59 mmol, 60% dispersion in mineral oil) to a solution of N-[(indol-7-yl)methyl]-2-bromopropionamide (0.6 g, 2.12 mmol) in dimethyl-formamide (20 ml). Stir the reaction at room temperature for 1 hour, quench with saturated aqueous saturated sodium bicarbonate. Extract with ethyl acetate, concentrate under reduced pressure and subject the residue to silica gel chromatography, eluting with 1:1 ethyl acetate:hexanes to provide the desired compound (0.3 g, 94%).

MS (ES): m/z=201.1 (M$^+$+1)

Reduction

Add 4-methyl-6,7-dihydro-6H-[1,4]diazepino[6,7,1-hi]indol-3-one (1.0 g, 4.99 mmol) to a suspension of lithium aluminum hydride (0.194 g, 4.99 mmol) in tetrahydro-furan (100 ml) at 0° C. and stir for 1 hour. Add sequentially water, aqueous sodium hydroxide, and water with vigorous stirring. Add di-tert-butyl dicarbonate (1.30 g, 5.99 mmol) and stir at room temperature to give the title compound (0.62 g, 44%) as a white solid.

$^1$H-NMR (400 MHz, DMSO-d$_6$): δ7.4 (m, 2H), 6.85 (m, 2H), 6.5 (d, 1H), 5.1-3.6 (m, 5H), 1.4-1.2 (m, 12H).

PREPARATION 155

6-(2,4-dimethoxybenzyl)-4,4-dimethyl-6,7-dihydro-6H-[1,4]diazepino[6,7,1-hi]indole N-[(indol-7-yl)methyl]-2,4-dimethoxybenzylamine Add 2,4-dimethoxybenzylamine (27.64 g, 165.3 mmol) to a solution of indole-7-carboxaldehyde (20.0 g, 137.7 mmol) and acetic acid (8.26 ml, 137.7 mmol) in toluene (250 ml). Reflux and collect water using a Dean-Stark trap while replacing with fresh anhydrous toluene. Concentrate under reduced pressure, dissolve the residue in methanol and add sodium borohydride in portions. Dilute with ethyl acetate and wash sequentially with saturated aqueous sodium bicarbonate followed by saturated aqueous sodium chloride, dry over magnesium sulfate, and concentrate under reduced pressure to provide the desired compound as a brown oil.

N-[2,4-dimethoxybenzyl]-N-[indol-7-ylmethyl]-2-bromopropionamide

Add 2-bromopropionyl chloride (3.25 g, 18.96 mmol) to a solution of N-[(indol-7-yl)methyl]-2,4-dimethoxybenzylamine (5.0 g, 17.24 mmol) and triethylamine (3.49 g, 64.48 mmol) in tetrahydrofuran (100 ml). Stir for 1 hour at room temperature and quench with saturated aqueous sodium bicarbonate. Extract with ethyl acetate, concentrate under reduced pressure, and subject the residue to silica gel chromatography eluting with 1:1 ethyl acetate:hexanes to provide the desired compound (4.72 g, 63%).

$^1$H-NMR (400 MHz, DMSO-d$_6$): δ11.2 and 10.7 (bs, 1H, rotamers), 7.5-6.5 (m, 8H), 5.2-4.0 (m, 6H), 3.7 (d, 3H, rotamers), 1.8-1.5 (m, 2H, rotamers).

6-(2,4-dimethoxybenzyl)-4-methyl-6,7-dihydro-6H-[1,4]diazepino[6,7,1-hi]indol-3-one Add sodium hydride (0.08 g, 3.47 mmol, 60% dispersion in mineral oil) to a solution of N-[2,4-dimethoxybenzyl]-N-[indol-7-ylmethyl]-2-bromopropionamide (1.0 g, 2.32 mmol) in dimethylformamide (10 ml). Stir at room temperature for 1 hour, quench with saturated aqueous sodium bicarbonate, extract with ethyl acetate, concentrate under reduced pressure, and subject the residue to silica gel chromatography to provide the desired compound (0.74 g, 91%).

MS (ES): m/z=350.7 (M$^+$+1)

6-(2,4-dimethoxybenzyl)-4,4-dimethyl-6,7-dihydro-6H-[1,4]diazepino[6,7,1-hi]indol-3-one Add n-butyllithium (15.9 ml, 1.6 M in hexane) to a solution of diisopropylamine (2.74, 27.16 mmol) in tetrahydrofuran (200 ml) at −15° C. and stir for 30 minutes. Cool to −78° C. and add 6-(2,4-dimethoxybenzyl)-4-methyl-6,7-dihydro-6H-[1,4]diazepino[6,7,1-hi]indol-3-one (5.95 g, 16.97 mmol). Stir for 30 minutes, quench with methyl iodide (6.5 g, 23.1 mmol), and gently warm to room temperature. Quench with saturated aqueous sodium bicarbonate, extract with ethyl acetate, and concentrate under reduced pressure. Subject the residue to silica gel chromatography to provide the desired compound (0.844 g, 75%).

$^1$H-NMR (400 MHz, DMSO-d$_6$): δ7.51 (d, 1H), 7.48 (dd, 1H), 6.95-6.82 (m, 3H), 6.5-6.35 (m, 3H), 4.85 (bs, 2H), 4.55 (bs, 2H), 3.65 (s, 3H), 3.64 (s, 3H), 1.83 (s, 6H).

Reduction

Add borane (1M in tetrahydrofuran, excess) to a solution of 6-(2,4-dimethoxy-benzyl)-4,4-dimethyl-6,7-dihydro-6H-[1,4]diazepino[6,7,1-hi]indol-3-one in tetrahydrofuran (60 ml). Reflux for 30 hours and dilute with ethyl acetate. Quench with saturated aqueous sodium bicarbonate. Extract with ethyl acetate and concentrate under reduced pressure. Subject the residue to silica gel chromatography to provide the title compound.

$^1$H-NMR (400 MHz, DMSO-d$_6$): δ7.49 (d, 1H), 7.35 (d, 1H), 7.29 (d, 1H), 7.0 (dd, 1H), 6.9 (d, 1H), 6.9 (d, 1H), 6.57 (d, 1H), 6.48-6.44 (m, 2H).

PREPARATION 156

Alternate Synthesis of 2-(imidazo[1,2-a]pyridin-3-yl)acetamide

Ethyl 4,4-dimethoxy-but-2-enoate

Dissolve dimethoxyacetaldehyde (97 g, 0.635 mol, 60% in water) and triethylphosphonoacetate (142 g, 0.633 mmol) in 7:1 tetrahydrofuran:water. Add potassium carbonate (100 g, 0.723 mole) and stir for 4 hours at room temperature. Pour the reaction into ethyl acetate (500 ml) and wash with saturated aqueous sodium bicarbonate and saturated aqueous sodium chloride. Concentrate under reduced pressure to provide the desired compound as a clear oil.

$^1$H-NMR (400 MHz, DMSO-d$_6$): δ 6.6 (dd, 1H), 6.1 (d, 1H), 4.95 (dd, 1H), 4.13 (q, 2H), 1.2 (t, 3H).

Ethyl 2-(imidazo[1,2-a]pyridin-3-yl)acetate

Add ethyl 4,4-dimethoxybut-2-enoate (2.0 g, 11.48 mmol) and p-toluenesulfonic acid (catalytic) to 4:1 acetonitrile:water. Reflux for 1 hour and add 2-aminopyridine (1.08 g, 11.48 mmol). Reflux for 1 hour, dilute with ethyl acetate, and wash saturated aqueous sodium bicarbonate followed by saturated aqueous sodium chloride. Concentrate under reduced pressure to provide the desired compound as a brown oil.

$^1$H-NMR (400 MHz, DMSO-d$_6$): δ 8.3 (m, 1H), 7.53 (m, 1H), 7.46 (s, 1H), 6.9 (m, 1H), 6.42 (m, 1H), 4.1 (q, J=7 Hz, 2H), 1.15 (t, J=7 Hz, 3H)

Amide Formation

Bubble ammonia through a solution of ethyl 2-(imidazo[1,2-a]pyridin-3-yl)acetate (10.0 g, 48.96 mmol) in methanol (30 ml) at 0° C. Heat the reaction mixture in a sealed tube at 100° C. for 2 hours. Concentrate the reaction mixture under reduced pressure. Add ethyl acetate to the residue to provide the title compound as a white solid.

ESMS: m/z=176.1 (M$^+$+1)

Beginning with the appropriately substituted aminopyridine, aminopyrimidine, aminopyrazine, or aminopyridazine, the compounds of Preparations 157 to 171 may be prepared essentially as described in Preparation 156.

| Preparation | Compound | Data |
|---|---|---|
| 157 | 2-(6-fluoroimidazo[1,2-a]pyridin-3-yl)acetamide | MS (ES): m/z = 194.0 (M$^+$ + 1) |
| 158 | 2-(6-trifluoromethylimidazo[1,2-a]pyridin-3-yl)acetamide | MS (ES): m/z = 244.1 (M$^+$ + 1) |
| 159 | 2-(8-cyanoimidazo[1,2-a]pyridin-3-yl)acetamide | MS (ES): m/z = 201.1 (M$^+$ + 1) |
| 160 | 2-(imidazo[1,2-a]pyrazin-3-yl)acetamide | MS (ES): m/z = 177.0 (M$^+$ + 1) |
| 161 | 2-(N-[tert-butoxycarbonyl]-8-amino-imidazo[1,2-a]pyridin-3-yl)acetamide | MS (ES): m/z = 235.0 (M$^+$ + 1) |
| 162 | 2-(imidazo[1,2-b]pyridazin-3-yl)acetamide | MS (ES): m/z = 177.0 (M$^+$ + 1) |
| 163 | 2-(6-methylimidazo[1,2-b]pyridazin-3-yl)acetamide | MS (ES): m/z = 190.9 (M$^+$ + 1) |
| 164 | 2-(7-methoxyimidazo[1,2-a]pyridin-3-yl)acetamide | MS (ES): m/z = 206 (M$^+$ + 1) |
| 165 | 2-(6-methoxyimidazo[1,2-a]pyridin-3-yl)acetamide | MS (ES): m/z = 206 (M$^+$ + 1) |
| 166 | 2-(7-methylimidazo[1,2-a]pyridin-3-yl)acetamide | MS (ES): m/z = 204 (M$^+$ + 1) |
| 167 | 2-(6-chloroimidazo[1,2-a]pyridin-3-yl)acetamide | MS (ES): m/z = 210 (M$^+$ + 1) |
| 168 | 2-(imidazo[1,2-c]pyrimidin-3-yl)acetamide | MS (ES): m/z = 177 (M$^+$ + 1) |
| 169 | 2-(6-isopropylimidazo[1,2-a]pyridin-3-yl)acetamide | |
| 170 | 2-(imidazo[1,2-a]pyrimidin-3-yl)acetamide | |
| 171 | 2-(7-aminoimidazo[1,2-a]pyrimidin-3-yl)acetamide | |

PREPARATION 172

6-Fluoroindole-7-carboxaldehyde 2,3-dihydro-6-fluoro-indole

Add sodium cyanoborohydride (5.57 g, 88.78 mmol) to a solution of 6-fluoro-indole (10 g, 73.99 mmol) in acetic acid (100 ml). Stir at room temperature for 30 minutes. Pour the reaction mixture into 5N sodium hydroxide and extract with ethyl acetate. Wash the combined organic phases with saturated aqueous sodium bicarbonate followed by saturated aqueous sodium chloride. Concentrated under reduced pressure and subject the residue to silica gel chromatography to provide the desired compound as a colorless oil (7.69 g, 76%).

MS (ES): m/z=138.1 (M$^+$+1)

1-(tert-butoxycarbonyl)-2,3-dihydro-6-fluoro-indole

Add di-tert-butyl dicarbonate (12.35 g, 56.62 mmol) to a solution of 2,3-dihydro-6-fluoroindole (7.67 g, 56.06 mmol) in tetrahydrofuran (100 ml) and stir at room temperature overnight. Concentrate the reaction mixture under reduced pressure to provide the desired compound as a white solid (13.2 g, 55.6 mmol).

$^1$H-NMR (400 MHz, DMSO-d$_6$): δ7.4 (bs, 1H), 7.15 (dd, 1H), 6.7 (m, 1H), 3.92 (t, 2H), 3.0 (t, 2H), 1.45 (s, 9H).

2,3-dihydro-6-fluoroindole-7-carboxaldehyde

Add tert-butyllithium (21.13 ml, 35.93 mmol, 1.7 M solution in heptane) to a solution of 1-(tert-butoxycarbonyl)-2,3-dihydro-6-fluoroindole (3.28 g, 13.82 mmol) in anhydrous tetrahydrofuran (100 ml) at −78 C. Stir for 20 minutes, quench with excess dimethylformamide, and stir for 1 hour at −78 C. Warm to room temperature, add saturated aqueous ammonium chloride, and extract with ethyl acetate. Concentrate the combined organic phases under reduced pressure and subject the residue to silica gel chromatography to provide the desired compound as a bright yellow solid (0.91 g, 42%).

$^1$H-NMR (400 MHz, DMSO-d$_6$): δ10.1 (s, 1H), 7.1 (dd, 1H), 6.15 (m, 1H), 3.75 (t, 2H), 2.98 (t, 2H) (dd, 1H), 6.7 (m, 1H), 3.92 (t, 2H), 3.0 (t, 2H), 1.45 (s, 9H).

Oxidation

Add manganese(IV) oxide (3.0 grams) to a solution of 2,3-dihydro-6-fluoroindole-7-carboxaldehyde (350 mg, 2.11 mmol) in dichloromethane and reflux for 2 hours. Cool to room temperature and filter through celite. Concentrate the filtrate under reduced pressure to provide the title compound as an off-white solid (240 mg, 68%).

$^1$H-NMR (400 MHz, DMSO-d$_6$): δ9.7 (s, 1H), 7.1 (dd, 1H), 6.55 (d, 1H), 6.15 (m, 1H), 5.75 (s, 1H).

PREPARATION 173

3-(6,7-dihydro-6H-[1,4]diazepino[6,7,1-hi]indol-1-yl)-4-(imidazo[1,2-a]pyridin-3-yl)-2,5-dioxopyrrole Add pyridine hydrochloride (1 g, 8.36) to a test tube containing 3-(6-(2,4-dimethoxybenzyl)-6,7-dihydro-6H-[1,4]diazepino[6,7,1-hi]indol-1-yl)-4-(imidazo[1,2-a]-pyridin-3-yl)-2,5-dioxopyrrole (0.25 g, 0.445 mmol). Heat at 150° C. for 1 hour. Pour into water, add solid sodium bicarbonate, and extract into ethyl acetate. Concentrate under reduced pressure subject the residue to silica gel chromatography to provide the title compound (0.143 g, 0.347 mmol).

PREPARATION 174

2-amino-3-fluoropyridine trifluoroacetate

Lithium 3-fluoropyridine-2-carboxylate

Add n-butyllithium (1.6 M in hexane, 200 mL) to a mixture of diethyl ether (1.5 L) and 1,4-diazabicyclo[2.2.2]octane (34.26 g, 305 mmol) at −78° C. under nitrogen. Add a solution of 3-fluoropyridine (29.6 g, 305 mmol) in diethyl ether (150 mL) dropwise over 30 minutes. Warm the reaction to −70 to −68° C. and stir for 45 minutes. Bubble dry carbon dioxide gas into the mixture for ~1 hour then warm to room temperature. Filter the suspension, wash the solid with diethyl ether, and dry under reduced pressure at 40° C. overnight to provide the desired compound (43.3 g) as a white solid.

N-[tert-butoxycarbonyl]-2-amino-3-fluoropyridine

Combine lithium 3-fluoropyridine-2-carboxylate (1 g, 6.88 mmol), diphenylphos-phorylazide (3.72 mL, 17.5 mmol), and 2-methyl-2-propanol (3.72 mL). Heat at reflux for 3 hours. Cool and concentrate under reduced pressure. Subject the residue to silica gel chromatography to provide the desired compound (0.714 g) as a white solid.
Deprotection
Stir a mixture of N-[tert-butoxycarbonyl]-2-amino-3-fluoropyridine (0.714 g) and trifluoroacetic acid (7 mL) for 30 minutes. Concentrate under reduced pressure and dry the residue at 40° C. under reduced pressure to provide the title compound as an off-white solid.
$^1$H-NMR (DMSO-$d_6$): δ7.80-7.75 (m, 2H), 6.78-6.73 (m, 1H).

PREPARATION 175

1-methyl-3-((4-(tert-butoxycarbonyl)piperazin-1-yl)carbonyl)imidazol-1-ium iodide 3-((4-(tert-butoxycarbonyl)piperazin-1-yl)carbonyl)imidazole Add N-[tert-butoxycarbonyl]piperazine (1.14 g, 6.15 mmol) in dichloromethane (15 ml) to a solution of N,N'-carbonyldiimidazole (1.0 g, 6.15 mmol) in dichloromethane (10 ml) and stir at room temperature for 48 hours. Concentrate under reduced pressure and subject the residue to silica gel chromatography, eluting with ethyl acetate to provide the title compound (1.35 g, 78%) as a white solid.
HRMS: m/z=281.1606 (M$^+$+1)
Alkylation
Add iodomethane (1.2 ml, 18.5 mmol) to a solution of 3-((4-(tert-butoxycarbonyl)-piperazin-1-yl)carbonyl)imidazole (1.3 g, 4.6 mmol) in acetonitrile (25 ml) and stir at room temperature for 72 hours. Concentrate under reduced pressure, rinse residue with hexane, dry under reduced pressure to provide the title compound (1.84 g, 93%) as a white solid.
$^1$H-NMR (DMSO-$d_6$): δ9.53 (s, 1H), 7.99 (dd, 1H), 7.84 (dd, 1H), 3.89 (s, 3H), 3.48 (m, 4H), 3.45 (m, 4H), 1.40 (s, 9H).

PREPARATION 176

7-methyl-6-oxa-4,5-dihydro-3-azabenzo[cd]azulene

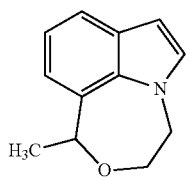

1-(indol-7-yl)ethan-1-ol

Add 7-formylindole (1.0 g, 6.89 mmol) in anhydrous tetrahydrofuran (15 ml) dropwise to a solution of 1.4M methyllithium in diethyl ether (12.2 ml, 17.1 mmol) at −78° C. After 15 minutes add saturated aqueous sodium bicarbonate (15 ml). Dilute with 1:1 ethyl acetate:diethyl ether, wash with saturated aqueous sodium bicarbonate followed by saturated aqueous sodium chloride, dry over magnesium sulfate, and concentrate under reduced pressure to provide desired compound (1.05 g, 94%) as a white solid.
MS (ES): m/z=160.4 (M$^+$−1)

7-(1-(tert-butyldimethylsilyloxy)eth-1-yl)indole

Add tert-butyldimethylsilyl chloride (16.4 g, 108 mmol) in anhydrous tetrahydro-furan (100 ml) to 1-(indol-7-yl)ethan-1-ol (10.7 g, 66.4 mmol) and imidazole (11.8 g, 173 mmol) in anhydrous tetrahydrofuran (100 ml). Stir at 20° C. for 2 hours. Dilute with hexanes (400 ml). Wash with 0.25 M aqueous sodium bicarbonate followed by saturated aqueous sodium chloride. Dry over magnesium sulfate and concentrate under reduced pressure. Subject the residue to silica gel chromatography, eluting with hexane containing 10-25% ethyl acetate to provide the desired compound (16 g, 87%) as a colorless oil.
HRMS: m/z=275.1701 (M$^+$)

1-(2-(tert-butyldimethylsilyloxy)eth-1-yl)-7-(1-(tert-butyldimethylsilyloxy)eth-1-yl)indole Add sodium hydride (2.75 g, 24 mmol, 35% in mineral oil) to 1-(tert-butyldimethylsilyloxy)eth-1-yl)indole (5.5 g, 20 mmol) in N,N-dimethylformamide (50 ml) and stir for 15 minutes at 20° C. Add (2-bromoethoxy)-tert-butyldimethylsilane and stir at 20° C. for 4 hours. Dilute with hexanes. Wash with 0.25 M aqueous sodium bicarbonate followed by saturated aqueous sodium chloride. Dry over magnesium sulfate and concentrate under reduced pressure. Subject the residue to silica gel chromatography, eluting with hexane containing 30% ethyl acetate to provide the desired compound (8.0 g, 89%) as a colorless oil.
MS (ES): m/z=433.36 (M$^+$)
Ring Formation
Add a mixture of tetrahydrofuran (100 ml) and 1M hydrochloric acid (100 ml) to a stirring solution of 1-(2-(tert-butyldimethylsilyloxy)eth-1-yl)-7-(1-(tert-butyldimethyl-silyloxy)eth-1-yl)indole (8.0 g, 17.9 mmol) in tetrahydrofuran (150 ml) at 15° C. Stir at 20° C. for 3 hours. Add 37% aqueous ammonia and solid sodium chloride. Separate the layers and extract the aqueous layer with ethyl acetate. Combine all organic phases, dry over magnesium sulfate and concentrate under reduced pressure. Subject the residue to silica gel chromatography, eluting with hexane containing 10-50% ethyl acetate to provide the title compound (0.65 g, 19%) as an oil.
HRMS: m/z=188.1078 (M$^+$+H)

PREPARATION 177

2-amino-5-methoxypyridine

Add 2-amino-5-bromopyridine (5.0 g, 29 mmol) to a freshly prepared solution of sodium methoxide (1.3 g, 58 mmol) in methanol (50 mL) and then add copper powder (1.8 g, 2.9 mmol). Heat and stir the mixture in a sealed tube at 160° C. for 3 days. Cool, filter through celite and concentrate under reduced pressure. Dissolve the residue in dichloromethane, then wash with water and saturated aqueous sodium chloride. Dry over magnesium sulfate, concentrate under reduced pressure, and subject the residue to silica gel chromatography, eluting with hexane/ethyl acetate; 3:1 to 0:1 to provide the title compound (1.5 g)
MS (ES): m/z=125 (M$^+$+H). .

PREPARATION 178

2-(6-ethylimidazo[1,2-a]pyridin-3-yl)acetamide

Ethyl 2-(6-vinylimidazopyridin[1,2-a]pyridin-3-yl)acetate

Bubble nitrogen into a mixture of ethyl 2-(6-bromoimidazo[1,2-a]pyridin-3-yl)-acetate (2.0 g, 7.0 mmol), vinyltributyltin (3.3 g, 11 mmol) and tetrakis(triphenyl-phosphine) Pd (0) (0.25 mg) in a resealable tube in toluene for 3 minutes. Heat and stir at 110° C. for 16 hours. Cool and concentrate under reduced pressure. Subject the residue to silica gel chromatography, eluting with hexane/ethyl acetate; 1:1 to 0:1 provide the desired compound (0.90 g, 55%).
MS (ES): m/z=231 (M$^+$+H).

Ethyl 2-(6-ethylimidazopyridin[1,2-a]pyridin-3-yl)acetate

Hydrogenate a mixture of ethyl 2-(6-vinylimidazo[1,2-a]pyridin-3-yl)acetate (0.89 g, 3.9 mmol) and 5% palladium on active carbon (80 mg) in ethyl acetate (50 mL) at ambient temperature and 1 atmosphere for 16 hours. Filter and concentrate the filtrate under reduced pressure to provide 0.80 g of the desired compound.
MS (ES): m/z=233 (M$^+$+H).
Amide Formation
Heat ethyl 2-(6-ethylimidazo[1,2-a]pyridin-3-yl)acetate (0.8 g) in 7.0 N ammonia in methanol in a sealed tube at 95° C. for 16 hours. Cool and concentrate under reduced pressure. Recrystallize the residue from methanol and diethyl ether to provide the title compound (0.25 g, 35%).
MS (ES): m/z=204 (M$^+$+H).

PREPARATION 179

2-amino-5-isopropylpyridine

N-[benzyl]-2-amino-5-isopropylpyridine

Dissolve 2-chloro-5-isopropylpyridine (5 g, 0.032 mol), benzylamine (6.8 g, 0.064 mol), Biphenyl-2-yl-dicyclohexyl-phosphine (0.46 g, 1.3 mmol), Pd(OAc)$_2$ (0.14 g, 0.64 mmol), and sodium tert-butoxide (4.3 g, 0.045 mol) in 60 mL of toluene. Deoxygenate three times. Heat at 100° C. for 18 hours. Cool and concentrate under reduced pressure. Subject the residue to silica gel chromatography, eluting with 1:1 hexanes:ethyl acetate to provide 5.5 g of the desired compound.
Debenzylation
Stir N-[benzyl]-2-amino-5-isopropylpyridine (5 g, 0.022 mol) and 95% sulfuric acid at room temperature for 18 hours. Pour into ice, make basic with 15% aqueous sodium hydroxide, and extract with dichloromethane (3×100 mL). Concentrate combined organic phases under reduced pressure to provide 2.5 g of the title compound

PREPARATION 180

5,6-dihydropyrrolo[3,2,1-ij]quinolin-6-one 1,2,5,6-tetrahydropyrrolo[3,2,1-ij]quinolin-6-one Add trifluoromethanesulfonic anhydride (10.5 mL, 63 mmol) in dichloroethane (30 mL) to N,N-dimethylacrylamide (6.4 mL, 63 mmol) in dichloroethane (100 mL) at 0° C. dropwise with vigorous stirring over 5 minutes. Add indoline (5.6 mL, 50 mmol) in dichloroethane (30 mL) dropwise over 5 minutes. Remove from cooling bath and heat at reflux for 3.5 hours. Cool to room temperature. Dilute with diethyl ether (600 mL). Wash with aqueous potassium carbonate (400 mL), dilute aqueous sodium bicarbonate (2×300 mL) and saturated aqueous sodium chloride (300 mL). Dry over sodium sulfate and concentrate under reduced pressure. Subject the residue to chromatography (pre-packed silica gel), eluting with 19:1 dichloromethane/ethyl acetate to provide the desired compound (2.65 g, 31%).
Oxidation
Add DDQ (5.9 g, 26.0 mmol) to 1,2,5,6-tetrahydropyrrolo[3,2,1-ij]quinolin-6-one (1.8 g, 10.4 mmol) in dioxane (40 mL) and stir at room temperature for 3 hours. Partition the reaction mixture between ethyl acetate (200 mL) and 1N sodium hydroxide (100 mL) with ice. Wash the organic phase with water (100 mL) and saturated aqueous sodium chloride. Dry over sodium sulfate and concentrate under reduced pressure. Subject the residue to chromatography, eluting with ethyl acetate/hexanes (1:1) to provide the title compound (460 mg, 25.8%) as a pale yellow solid.

PREPARATION 181

6-methyl-4,5-dihydro-6H-[1,4]diazepino[6,7,1-hi]indol-7-one and 7-methyl-4,5-dihydro-7H-[1,4]diazepino[3,2,1-hi]indol-6-one 1,2,4,5-tetrahydro-6H-[1,4]diazepino[6,7,1-hi]indol-7-one and 1,2,4,5-tetrahydro-7H-[1,4]diazepino[3,2,1-hi]indol-6-one Add 1,2,5,6-tetrahydropyrrolo[3,2,1-ij]quinolin-6-one (15.49 g, 89.43 mmol) to polyphosphoric acid (512 g) at 67-70° C. and stir vigorously. Add three portions of sodium azide (2.43 g (37.4 mmol), 2.42 g (37.2 mmol) and 2.42 g (37.2 mmol)) at 20 minute intervals then heat to 90° C. and stir for 3.5 hours. Pour into ice (511.6 g). Add, with cooling, 50% aqueous sodium hydroxide (500 mL) 40 minutes. Extract with chloroform (3×500 mL). Wash the combined organic phases with water (500 mL) and saturated aqueous sodium chloride (500 mL). Dry over sodium sulfate and concentrate under reduced pressure. Subject the residue to chromatography (pre-packed silica gel), eluting with a gradient: 98:2-97:3-96:4 chloroform/methanol to provide 1,2,4,5-tetrahydro-7H-[1,4]diazepino[3,2,1-hi]indol-6-one (2.95 g, 18%) and 1,2,4,5-tetrahydro-6H-[1,4]diazepino[6,7,1-hi]indol-7-one (11.51 g, 68%) as beige solids.

6-methyl-1,2,4,5-tetrahydro-6H-[1,4]diazepino[6,7,1-hi]indol-7-one

Add sodium hydride (0.78 g, 1.9 mmol, 60% in mineral oil) to 1,2,4,5-tetrahydro-6H-[1,4]diazepino[6,7,1-hi]indol-7-one (3.05 g, 1.62 mmol) in dry dimethylformamide (77 mL). Stir for 30 minutes at room temperature and then add iodomethane (2.0 mL, 3.2 mmol). Stir at room temperature for 134 minutes. Partition between ethyl acetate (1 L) and water (500 mL). Wash the organic phase with saturated aqueous sodium chloride, dry over sodium sulfate, and concentrate under reduced pressure. Subject the residue to chromatography (pre-packed silica gel), eluting with a gradient: 1:0-9:1 ethyl acetate/methanol to provide the desired compound (2.42 g, 74%) as an off-white solid.

Oxidation

Add DDQ (2.29 g, 1.01 mmol) to 6-methyl-1,2,4,5-tetrahydro-6H-[1,4]diazepino[6,7,1-hi]indol-7-one (2.04 g, 1.01 mmol) in dioxane (19 mL) at 11° C. Stir at room temperature for 3 hours and 51 minutes. Partition between ethyl acetate (1000 mL) and 2N aqueous sodium hydroxide (500 mL) with ice. Wash the organic phase with water (500 mL) and saturated aqueous sodium chloride (500 mL). Dry over sodium sulfate and concentrate under reduced pressure. Subject the residue to silica gel chromatography (pre-packed silica gel), eluting with ethyl acetate to provide 6-methyl-4,5-dihydro-6H-[1,4]diazepino[6,7,1-hi]indol-7-one (1.67 g, 84.7%) as an off-white solid.

Beginning with 1,2,4,5-tetrahydro-7H-[1,4]diazepino[3,2,1-hi]indol-6-one, 7-methyl-4,5-dihydro-7H-[1,4]diazepino[3,2,1-hi]indol-6-one may be prepared essentially as described above.

The compounds of Preparations 182-183 may be prepared essentially as described in Preparation 181.

| Preparation | Compound | Data |
|---|---|---|
| 182 | 6-((2-(dimethylamino)eth-1-yl)-4,5-dihydro-6H-[1,4]diazepino[6,7,1-hi]indol-7-one | |
| 183 | 6-((2-(hydroxy)eth-1-yl)-4,5-dihydro-6H-[1,4]diazepino[6,7,1-hi]indol-7-one | |

The compounds of Examples 1-63 may be prepared essentially as described in Preparation 137.

| Example | Compound | Data |
|---|---|---|
| 1 | 3-(6,7-dihydro-6H-[1,4]diazepino[6,7,1-hi]indol-1-yl)-4-(1-methyl-1H-indol-4-yl)-2,5-dioxo-2,5-dihydropyrrole hydrochloride | MS (ES): m/z = 431.0 (M$^-$ − 1) |
| 2 | 3-(6-(tert-butoxycarbonyl)-5,6-dihydro-6H-[1,4]diazepino[6,7,1-hi]indol-1-yl)-(4-(1-(3-hydroxyprop-1-yl)-1H-indol-4-yl)-2,5-dioxopyrrole | MS (ES): m/z = 541.3 (M$^+$ + 1) |
| 3 | 3-(5,6-dihydro-4H-pyrrolo[3,2,1-ij]quinolin-1-yl)-4-(1-(3-hydroxyprop-1-yl)-1H-indol-4-yl)-2,5-dioxopyrrole | MS (ES): m/z = 426.1 (M$^+$ + 1) |
| 4 | 3-(8-tert-butoxycarbonyl-[1,5]diazoperhydroonino-[8,9,1-hi]indol-1-yl)-4-(benzofur-7-yl)-2,5-dioxopyrrole | MS (ES): m/z = 512.2 (M$^+$ + 1) |
| 5 | 3-(6-(tert-butoxycarbonyl)-6,7-dihydro-6H-[1,4]diazepino[6,7,1-hi]indol-1-yl)-4-(4-methoxybenzofur-7-yl)-2,5-dioxopyrrole | MS (ES): m/z = 514.1 |
| 6 | 3-(5,6-dihydro-4H-pyrrolo[3,2,1-ij]quinolin-1-yl)-4-(benzofur-7-yl)-2,5-dioxopyrrole | MS (ES): m/z = 369.1 (M$^+$ + 1) |
| 7 | 3-(6-methanesulfonyl-5,6-dihydro-[1,4]diazepino-[6,7,1-hi]indol-1-yl)-4-(benzofur-7-yl)-2,5-dioxopyrrole | MS (ES): m/z = 462.09 (M$^+$ + 1) |
| 8 | 3-(6-(tert-butoxycarbonyl)-5,6-dihydro-6H-[1,4]diazepino[6,7,1-hi]indol-1-yl)-(4-(5-methoxybenzofur-7-yl)-2,5-dioxopyrrole | MS (ES): m/z = 514.1 (M$^+$ + 1) |
| 9 | 3-(8-tert-butoxycarbonyl)-[1,5]diazoperhydroonino-[8,9,1-hi]indol-1-yl)-4-(5-methoxybenzofur-7-yl)-2,5-dioxopyrrole | MS (ES): m/z = 542.1 (M$^+$ + 1) |
| 10 | 3-(8-tert-butoxycarbonyl)-[1,5]diazoperhydroonino-[8,9,1-hi]indol-1-yl)-4-(4-methoxybenzofur-7-yl)-2,5-dioxopyrrole | MS (ES): m/z = 542.1 (M$^+$ + 1) |
| 11 | 3-(6,7-dihydro-6H-[1,4]diazepino-[6,7,1-hi]indol-1-yl)-4-(5-fluorobenzofur-4-yl)-2,5-dioxopyrrole hydrochloride | MS (ES): m/z = 401.9 (M$^+$ + 1) |
| 12 | 3-([1,5]diazoperhydroonino[8,9,1-hi]indol-1-yl)-4-(isoquinolin-5-yl)-2,5-dioxopyrrole hydrochloride | MS (ES): m/z = 401.9 (M$^+$ + 1) |
| 13 | 3-(8-tert-butoxycarbonyl-[1,5]diazoperhydroonino-[8,9,1-hi]indol-1-yl)-4-(benzofur-4-yl)-2,5-dioxopyrrole | MS (ES): m/z = 512.1 (M$^+$ + 1) |
| 14 | 3-(6-(tert-butoxycarbonyl)-5,6-dihydro-6H-[1,4]diazepino[6,7,1-hi]indol-1-yl)-(4-(5-fluorobenzofur-7-yl)-2,5-dioxopyrrole | MS (ES): m/z = 502.1 (M$^+$ + 1) |
| 15 | 3-(8-tert-butoxycarbonyl-[1,5]diazoperhydroonino-[8,9,1-hi]indol-1-yl)-4-(5-fluorobenzofur-7-yl)-2,5-dioxopyrrole | MS (ES): m/z = 528.7 (M$^-$ − 1) |
| 16 | 3-(5,6-Dihydro-4H-pyrrolo[3,2,1-ij]quinolin-1-yl)-4-(imidazo[1,2-a]pyridin-3-yl)-2,5-dioxopyrrole | MS (ES): m/z = 369.2 (M$^+$ + 1) |
| 17 | 3-(5,6-Dihydro-4H-pyrrolo[3,2,1-ij]quinolin-1-yl)-4-(imidazo[1,2-a]pyridin-5-yl)-2,5-dioxopyrrole hydrochloride | MS (ES): m/z = 369.1 (M$^+$ + 1) |
| 18 | 3-(5-oxo-6-propyl-5,6-dihydro-[1,4]diazepino[6,7,1-hi]indol-7-yl) 3-(benzofur-7-yl)-2,5-dioxopyrrole | MS (ES): m/z = 440.2 (M$^+$ + 1) |
| 19 | 3-([1,5]diazoperhydroonino[8,9,1-hi]indol-1-yl)-4-(5-fluoro-4-methoxybenzofur-7-yl)-2,5-dioxopyrrole hydrochloride | MS (ES): m/z = 460 (M$^+$ + 1) |
| 20 | 3-([1,5]diazoperhydroonino[8,9,1-hi]indol-1-yl)-4-(4,5-difluorobenzofur-7-yl)-2,5-dioxopyrrole hydrochloride | MS (ES): m/z = 448.2 (M$^+$ + 1) |
| 21 | 3-([1,5]diazoperhydroonino[8,9,1-hi]indol-1-yl)-4-(4-fluorobenzofur-7-yl)-2,5-dioxopyrrole hydrochloride | MS (ES): m/z = 430.2 (M$^+$ + 1) |
| 22 | 3-([1,5]diazoperhydroonino[8,9,1-hi]indol-1-yl)-4-(5,6-difluorobenzofur-7-yl)-2,5-dioxopyrrole hydrochloride | MS (ES): m/z = 448.2 (M$^+$ + 1) |
| 23 | 3-(5,6-Dihydro-4H-pyrrolo[3,2,1-ij]quinolin-1-yl)-4-(6-fluorobenzofur-7-yl)-2,5-dioxopyrrole hydrochloride | MS (ES): m/z = 402.1 (M$^+$ + 1) |
| 24 | 3-([1,5]diazoperhydroonino[8,9,1-hi]indol-1-yl)-4-(6-fluorobenzofur-7-yl)-2,5-dioxopyrrole hydrochloride | MS (ES): m/z = 430.2 (M$^+$ + 1) |
| 25 | 3-(6-(tert-butoxycarbonyl)-5,6,7,8-tetrahydro-6H-[1,4]diazocino[7,8,1-hi]indol-1-yl)-4-(Furo[3,2-c]pyridin-7-yl)-2,5-dioxopyrrole | MS (ES): m/z = 499.2 (M$^+$ + 1) |
| 26 | 3-(4,5,6,7-tetrahydroazepino[3,2,1-hi]indol-1-yl)-4-(furo[3,2-c]pyridin-7-yl)-2,5-dioxopyrrole hydrochloride | MS (ES): m/z = 384.1 (M$^+$ + 1) |
| 27 | 3-(6-(tert-butoxycarbonyl)-6,7-dihydro-6H-[1,4]diazepino[6,7,1-hi]indol-1-yl)-4-(benzofur-4-yl)-2,5-dioxopyrrole | HRMS: 484.1856 (M + H) |
| 28 | 3-(6-(tert-butoxycarbonyl)-6,7-dihydro-6H-[1,4]diazepino[6,7,1-hi]indol-1-yl)-4-(benzo[1,3]dioxol-5-yl)-2,5-dioxopyrrole | HRMS: 488.1813 (M + H) |
| 29 | 3-(6-(tert-butoxycarbonyl)-6,7-dihydro-6H-[1,4]diazepino[6,7,1-hi]indol-1-yl)-4-(2,3-dihydrobenzo-[1,4]dioxin-6-yl)-2,5-dioxopyrrole | HRMS: 502.1960 (M + H) |
| 30 | 3-(6-(tert-butoxycarbonyl)-6,7-dihydro-6H-[1,4]diazepino[6,7,1-hi]indol-1-yl)-4-(benzothien-4-yl)-2,5-dioxopyrrole | HRMS: 500.1634 (M + H) |
| 31 | 3-(6-(tert-butoxycarbonyl)-6,7-dihydro-6H-[1,4]diazepino[6,7,1-hi]indol-1-yl)-4-(2,3-dihydrobenzofur-7-yl)-2,5-dioxopyrrole | HRMS: 486.2051 (M + H) |
| 32 | 3-(6-(tert-butoxycarbonyl)-5,6-dihydro-6H-[1,4]diazepino[6,7,1-hi]indol-1-yl)-4-(2,3-dihydrobenzofur-4-yl)-2,5-dioxopyrrole | MS (ES): m/z = 486.1 (M$^+$ + 1) |
| 33 | 3-(8-tert-butoxycarbonyl)-[1,5]diazoperhydroonino-[8,9,1-hi]indol-1-yl)-4-(benzo[1,3]dioxol-4-yl)-2,5-dioxopyrrole | HRMS: 538.1940 (M + Na) |

| Example | Compound | Data |
|---|---|---|
| 34 | 3-(8-tert-butoxycarbonyl)-[1,5]diazoperhydroonino-[8,9,1-hi]indol-1-yl)-4-(2,3-dihydrobenzofur-7-yl)-2,5-dioxopyrrole | HRMS: 514.2341 (M + H) |
| 35 | 3-(9-methyl-6-(tert-butoxycarbonyl)-6,7-dihydro-6H-[1,4]diazepino[6,7,1-hi]indol-1-yl)-4-(benzofur-7-yl)-2,5-dioxopyrrole | MS (ES): m/z = 496.3 ($M^+ - 1$) |
| 36 | 3-(5,6-Dihydro-4H-pyrrolo[3,2,1-ij]quinolin-1-yl)-4-(4-methoxybenzofur-7-yl)-2,5-dioxopyrrole | HRMS: 399.1355 (M + H) |
| 37 | 3-(5,6-Dihydro-4H-pyrrolo[3,2,1-ij]quinolin-1-yl)-4-(5-methoxybenzofur-7-yl)-2,5-dioxopyrrole | HRMS: 399.1347 (M + H) |
| 38 | 3-(5,6-Dihydro-4H-pyrrolo[3,2,1-ij]quinolin-1-yl)-4-((3-hydroxypropoxy)benzofur-7-yl)-2,5-dioxopyrrole | MS (ES): m/z = 443.2 ($M^+ + 1$) |
| 39 | 3-(6-(tert-butoxycarbonyl)-6,7-dihydro-6H-[1,4]diazepino[6,7,1-hi]indol-1-yl)-4-(6-methoxy-benzofur-7-yl)-2,5-dioxopyrrole | MS (ES): m/z = 514.2 ($M^+ + 1$) |
| 40 | 3-(6-(tert-butoxycarbonyl)-6,7-dihydro-6H-[1,4]diazepino[6,7,1-hi]indol-1-yl)-4-(2,2-difluoro-benzo[1,3]dioxol-4-yl)-2,5-dioxopyrrole | MS (ES): m/z = 373.6 ($M^+ + 1$) |
| 41 | 3-(6-(tert-butoxycarbonyl)-6,7-dihydro-6H-[1,4]diazepino[6,7,1-hi]indol-1-yl)-4-(thieno[3,2-b]pyridin-7-yl)-2,5-dioxopyrrole | MS (ES): m/z = 501.2 ($M^+ + 1$) |
| 42 | 3-(8-tert-butoxycarbonyl)-[1,5]diazoperhydroonino-[8,9,1-hi]indol-1-yl)-4-(thieno[3,2-b]pyridin-7-yl)-2,5-dioxopyrrole | MS (ES): m/z = 529.2 ($M^+ + 1$) |
| 43 | 3-(4,5,6,7-tetrahydroazepino[3,2,1-hi]indol-1-yl)-4-(2,3-dihydrobenzo[1,4]dioxin-6-yl)-2,5-dioxopyrrole | MS (ES): m/z = 401.1 ($M^+ + 1$) |
| 44 | 3-(4,5,6,7-tetrahydroazepino[3,2,1-hi]indol-1-yl)-4-(benzo[1,3]dioxol-5-yl)-2,5-dioxopyrrole | MS (ES): m/z = 387.2 ($M^+ + 1$) |
| 45 | 3-(4,5,6,7-tetrahydroazepino[3,2,1-hi]indol-1-yl)-4-(benzo[1,3]dioxol-4-yl)-2,5-dioxopyrrole | MS (ES): m/z = 387.2 ($M^+ + 1$) |
| 46 | 3-(4,5,6,7-tetrahydroazepino[3,2,1-hi]indol-1-yl)-4-(benzofur-4-yl)-2,5-dioxopyrrole | MS (ES): m/z = 383.1 ($M^+ + 1$) |
| 47 | 3-(4,5,6,7-tetrahydroazepino[3,2,1-hi]indol-1-yl)-4-(benzofur-7-yl)-2,5-dioxopyrrole | MS (ES): m/z = 383.1 ($M^+ + 1$) |
| 48 | 3-(4,5,6,7-tetrahydroazepino[3,2,1-hi]indol-1-yl)-4-(1,3-dihydroisobenzofur-5-yl)-2,5-dioxopyrrole | MS (ES): m/z = 385.1 ($M^+ + 1$) |
| 49 | 3-(6-(tert-butoxycarbonyl)-6,7-dihydro-6H-[1,4]diazepino[6,7,1-hi]indol-1-yl)-4-(1,3-dihydro-isobenzofur-5-yl)-2,5-dioxopyrrole | MS (ES): m/z = 431 ($M^+ + 1 - (t-Bu)$) |
| 50 | 3-(6-(tert-butoxycarbonyl)-6,7-dihydro-6H-[1,4]diazepino[6,7,1-hi]indol-1-yl)-4-(benzimidazol-4-yl)-2,5-dioxopyrrole | MS (ES): m/z = 482.1 ($M^+ + 1$) |
| 51 | 3-(6,7-dihydro-6H-[1,4]diazepino[6,7,1-hi]indol-1-yl)-4-(pyrazolo[2,3-a]pyridin-3-yl)-2,5-dioxopyrrole hydrochloride | MS (ES): m/z = 384.2 ($M^+ + 1$) |
| 52 | 3-(6-(tert-butoxycarbonyl)-6,7-dihydro-6H-[1,4]diazepino[6,7,1-hi]indol-1-yl)-4-(2,3-dihydrobenzo-[1,4]dioxin-5-yl)-2,5-dioxopyrrole | HRMS: m/z = 502.1983 (M + H) |
| 53 | 3-(6-(tert-butoxycarbonyl)-9-fluoro-6,7-dihydro-6H-[1,4]diazepino[6,7,1-hi]indol-1-yl)-4-(benzofur-7-yl)-2,5-dioxopyrrole | MS (ES): m/z = 502.2 ($M^+ + 1$) |
| 54 | 3-(6-(tert-butoxycarbonyl)-7-methyl-6,7-dihydro-6H-[1,4]diazepino[6,7,1-hi]indol-1-yl)-4-(benzo-[1,3]dioxol-4-yl)-2,5-dioxopyrrole | HRMS: m/z = 502.1983 (M + H) |
| 55 | 3-(5,6,7,8-tetrahydro-6H-[1,4]diazocino[7,8,1-hi]in-dol-1-yl)-4-(4-(dimethylamino)furo[3,2-c]pyridin-7-yl)-2,5-dioxopyrrole dihydrochloride | MS (ES): m/z = 442.2 ($M^+ + 1$) |
| 56 | 3-(7-methyl-6,7-dihydro-6H-[1,4]diazepino[6,7,1-hi]indol-1-yl)-4-(furo[3,2-c]pyridin-7-yl)-2,5-dioxopyrrole dihydrochloride | MS (ES): m/z = 399.1 ($M^+ + 1$) |
| 57 | 3-(6-methanesulfonyl-6,7-dihydro-6H-[1,4]diazepino[6,7,1-hi]indol-1-yl)-4-(imidazo[1,2-b]pyridin-3-yl)-2,5-dioxopyrrole | HRMS: m/z = 462.1245 (M + H) |
| 58 | 3-(7-methyl-6-oxa-4,5-dihydro-3-azabenzo[cd]azulen-1-yl)-4-(imidazo[1,2-a]pyridin-3-yl)-2,5-dioxopyrrole | HRMS: m/z = 399.1431 (M + H) |
| 59 | 3-(1-oxo-2-methyl-6,7-dihydro-6H-[1,4]diazepino-[6,7,1-hi]indol-1-yl)-4-(pyrazolo[1,5-a]pyridin-3-yl)-2,5-dioxopyrrole hydrochloride | HRMS: m/z = 412.1431 (M + H) |
| 60 | 3-(6-oxo-7-methyl-6,7-dihydro-7H-[1,5]diazepino-[6,7,1-hi]indol-1-yl)-4-(imidazo[1,2-a]pyridin-3-yl)-2,5-dioxopyrrole hydrochloride | HRMS: m/z = 412.1434 (M + H) |
| 61 | 3-(1-oxo-2-(2-hydroxyeth-1-yl)-6,7-dihydro-6H-[1,4]diazepino[6,7,1-hi]indol-1-yl)-4-(imidazo[1,2-a]pyridin-3-yl)-2,5-dioxopyrrole hydrochloride | HRMS: m/z = 442.1509 (M + H) |
| 62 | 3-(1-oxo-2-(2-(dimethylamino)eth-1-yl)-6,7-dihydro-6H-[1,4]diazepino[6,7,1-hi]indol-1-yl)-4-(imidazo[1,2-a]pyridin-3-yl)-2,5-dioxopyrrole hydrochloride | HRMS: m/z = 469.1993 (M + H) |
| 63 | 3-(6-oxo-5,6-dihydro-4H-pyrrolo[3,2,1-ij]quinolin-1-yl)-4-(imidazo[1,2-a]pyridin-3-yl)-2,5-dioxopyrrole | HRMS: m/z = 383.1144 (M + H) |

EXAMPLE 64

3-([1,5]diazoperhydroonino[8,9,1-hi]indol-1-yl)-4-(imidazo[1,2-a]pyridin-3-yl)-2,5-dioxopyrrole dihydrochloride Add ethanethiol (1.0 g, 31.2 mmol) to a flask containing 3-(8-tert-butoxycarbonyl-[1,5]diazoperhydroonino[8,9,1-hi]indol-1-yl)-4-(imidazo[1,2-a]pyridin-3-yl)-2,5-dioxo-pyrrole (0.95 g, 1.86 mmol). Add 4N HCl in dioxane (10 ml, 40 mmol) to the flask and stir for 12 hours. Filter the resulting solid and wash with an appropriate solvent (appropriate solvents include ethyl acetate, diethyl ether, and dioxane). Dry the solid under high vacuum at 45° C. to give the title compound as a bright orange solid (0.83 g, 92%).

MS (ES): m/z=412.2 ($M^+$+1)

The hydrochloride salt may be converted to the free base by dissolving the salt in methanol, passing the solution through a Varian® BondElut™ SCX column, eluting the column with 2 molar ammonia in methanol and concentrating under reduced pressure.

The compounds of EXAMPLES 65-146 are prepared essentially as described in EXAMPLE 64.

| Example | Compound | Data |
|---|---|---|
| 65 | 3-(6,7-dihydro-6H-[1,4]diazepino[6,7,1-hi]indol-1-yl)-4-(1-(3-hydroxyprop-1-yl)-1H-indol-4-yl)-2,5-dioxopyrrole | $^1$H-NMR* |

| Example | Compound | Data |
|---|---|---|
| 66 | 3-([1,5]diazoperhydroonino[8,9,1-hi]indol-1-yl)-4-(benzofur-7-yl)-2,5-dioxopyrrole hydrochloride | MS (ES): m/z = 412.1 (M$^+$ + 1) |
| 67 | 3-(6,7-dihydro-6H-[1,4]diazepino[6,7,1-hi]indol-1-yl)-4-((4-methoxybenzofur-7-yl)-2,5-dioxopyrrole | MS (ES): m/z = 414.2 (M$^+$ + 1) |
| 68 | 3-(6,7-dihydro-6H-[1,4]diazepino[6,7,1-hi]indol-1-yl)-4-(benzofur-7-yl)-2,5-dioxopyrrole hydrochloride | MS (ES): m/z = 383.9 (M$^+$ + 1) |
| 69 | 3-(6,7-dihydro-6H-[1,4]diazepino[6,7,1-hi]indol-1-yl)-4-(5-methoxybenzofur-7-yl)-2,5-dioxopyrrole hydrochloride | MS (ES): m/z = 413.9 (M$^+$ + 1) |
| 70 | 3-([1,5]diazoperhydroonino[8,9,1-hi]indol-1-yl)-4-(5-methoxybenzofur-7-yl)-2,5-dioxopyrrole hydrochloride | MS (ES): m/z = 442.0 (M$^+$ + 1) |
| 71 | 3-([1,5]diazoperhydroonino[8,9,1-hi]indol-1-yl)-4-(4-methoxybenzofur-7-yl)-2,5-dioxopyrrole hydrochloride | MS (ES): m/z = 442.0 (M$^+$ + 1) |
| 72 | 3-([1,5]diazoperhydroonino[8,9,1-hi]indol-1-yl)-4-(benzofur-4-yl)-2,5-dioxopyrrole hydrochloride | MS (ES): m/z = 412.1 (M$^+$ + 1) |
| 73 | 3-(6,7-dihydro-6H-[1,4]diazepino-[6,7,1-hi]indol-1-yl)-4-(4-fluorobenzofur-7-yl)-2,5-dioxopyrrole hydrochloride | MS (ES): m/z = 402.1 (M$^+$ + 1) |
| 74 | 3-(6,7-dihydro-6H-[1,4]diazepino-[6,7,1-hi]indol-1-yl)-4-(4,5-difluorobenzofur-7-yl)-2,5-dioxopyrrole | MS (ES): m/z = 420.1 (M$^+$ + 1) |
| 75 | 3-([1,5]diazoperhydroonino[8,9,1-hi]indol-1-yl)-4-(1-(3-hydroxypropyl)-1H-indol-4-yl)-2,5-dioxopyrrole hydrochloride | MS (ES): m/z = 469.3 (M$^+$ + 1) |
| 76 | 3-(6,7-dihydro-6H-[1,4]diazepino-[6,7,1-hi]indol-1-yl)-4-(4-fluoro-5-methoxybenzofur-7-yl)-2,5-dioxopyrrole hydrochloride | MS (ES): m/z = 432.2 (M$^+$ + 1) |
| 77 | 3-([1,5]diazoperhydroonino[8,9,1-hi]indol-1-yl)-4-(5-fluorobenzofur-7-yl)-2,5-dioxopyrrole hydrochloride | MS (ES): m/z = 430.2 (M$^+$ + 1) |
| 78 | 3-(6,7-dihydro-6H-[1,4]diazepino-[6,7,1-hi]indol-1-yl)-4-(imidazo[1,2-a]pyridin-3-yl)-2,5-dioxopyrrole dihydrochloride | MS (ES): m/z = 384.2 (M$^+$ + 1) |
| 79 | 3-([1,5]diazoperhydroonino[8,9,1-hi]indol-1-yl)-4-(1-methyl-1H-indol-4-yl)-2,5-dioxopyrrole hydrochloride | MS (ES): m/z = 425.3 (M$^+$ + 1) |
| 80 | 3-([1,5]diazoperhydroonino[8,9,1-hi]indol-1-yl)-4-(5,6-difluorobenzofur-7-yl)-2,5-dioxopyrrole hydrochloride | MS (ES): m/z = 420.2 (M$^+$ + 1) |
| 81 | 3-(6,7-dihydro-6H-[1,4]diazepino[6,7,1-hi]indol-1-yl)-4-(3-furo[3,2-c]pyridin-7-yl)-2,5-dioxopyrrole dihydrochloride | MS (ES): m/z = 385.1 (M$^+$ + 1) |
| 82 | 3-([1,5]diazoperhydroonino[8,9,1-hi]indol-1-yl)-4-(furo[3,2-c]pyridin-7-yl)-2,5-dioxopyrrole dihydrochloride | MS (ES): m/z = 413.2 (M$^+$ + 1) |
| 83 | 3-([1,7]diazoperhydroonino[8,9,1-hi]indol-1-yl)-4-(furo[3,2-c]pyridin-7-yl)-2,5-dioxopyrrole dihydrochloride | MS (ES): m/z = 413.2 (M$^+$ + 1) |
| 84 | 3-(6,7-dihydro-6H-[1,4]diazepino[6,7,1-hi]indol-1-yl)-4-(benzofur-7-yl)-2,5-dioxopyrrole | HRMS: 384.1348 (M + H) |
| 85 | 3-(6,7-dihydro-6H-[1,4]diazepino[6,7,1-hi]indol-1-yl)-4-(benzofur-4-yl)-2,5-dioxopyrrole | HRMS: 384.1344 (M + H) |
| 86 | 3-(6,7-dihydro-6H-[1,4]diazepino[6,7,1-hi]indol-1-yl)-4-(benzo[1,3]dioxol-5-yl)-2,5-dioxopyrrole | HRMS: 388.1294 (M + H) |
| 87 | 3-(6,7-dihydro-6H-[1,4]diazepino[6,7,1-hi]indol-1-yl)-4-(2,3-dihydro-benzo[1,4]dioxin-6-yl)-2,5-dioxopyrrole | HRMS: 402.1447 (M + H) |
| 88 | 3-(6,7-dihydro-6H-[1,4]diazepino[6,7,1-hi]indol-1-yl)-4-(benzothien-7-yl)-2,5-dioxopyrrole | HRMS: 400.1118 (M + H) |
| 89 | 3-(6,7-dihydro-6H-[1,4]diazepino[6,7,1-hi]indol-1-yl)-4-(benzo[1,3]dioxol-4-yl)-2,5-dioxopyrrole | HRMS: 388.1298 (M + H) |
| 90 | 3-(6,7-dihydro-6H-[1,4]diazepino[6,7,1-hi]indol-1-yl)-4-(benzothien-4-yl)-2,5-dioxopyrrole | HRMS: 400.1142 (M + H) |
| 91 | 3-(6,7-dihydro-6H-[1,4]diazepino[6,7,1-hi]indol-1-yl)-4-(2,3-dihydrobenzofur-7-yl)-2,5-dioxopyrrole | HRMS: 386.1497 (M + H) |
| 92 | 3-(6,7-dihydro-6H-[1,4]diazepino[6,7,1-hi]indol-1-yl)-4-(2,3-dihydrobenzofur-4-yl)-2,5-dioxopyrrole | HRMS: 386.1519 (M + H) |
| 93 | 3-([1,5]diazoperhydroonino[8,9,1-hi]indol-1-yl)-4-(benzo[1,3]dioxol-4-yl)-2,5-dioxopyrrole | HRMS: 416.1602 (M + H) |
| 94 | 3-([1,5]diazoperhydroonino[8,9,1-hi]indol-1-yl)-4-(2,3-dihydrobenzofur-7-yl)-2,5-dioxopyrrole | HRMS: 414.1823 (M + H) |
| 95 | 3-(5,6,7,8-tetrahydro-6H-[1,4]diazocino[7,8,1-hi]indol-1-yl)-4-(benzofur-7-yl)-2,5-dioxopyrrole | HRMS: 398.1500 (M + H) |
| 96 | 3-(5,6,7,8-tetrahydro-6H-[1,4]diazocino[7,8,1-hi]indol-1-yl)-4-(benzo[1,3]dioxol-4-yl)-2,5-dioxopyrrole | HRMS: 402.1454 (M + H) |
| 97 | 3-(5,6,7,8-tetrahydro-6H-[1,4]diazocino[7,8,1-hi]indol-1-yl)-4-(5-fluorobenzofur-7-yl)-2,5-dioxopyrrole | HRMS: 416.1408 (M + H) |
| 98 | 3-(5,6,7,8-tetrahydro-6H-[1,4]diazocino[7,8,1-hi]indol-1-yl)-4-(2,3-dihydrobenzofur-7-yl)-2,5-dioxopyrrole | HRMS: 400.1675 (M + H) |
| 99 | 3-(9-methyl-6,7-dihydro-6H-[1,4]diazepino[6,7,1-hi]indol-1-yl)-4-(benzofur-7-yl)-2,5-dioxopyrrole | MS (ES): m/z = 398.3 (M$^+$ + 1) |
| 100 | 3-(6,7-dihydro-6H-[1,4]diazepino[6,7,1-hi]indol-1-yl)-4-(4-(3-(diethyl-amino)propoxy)benzofur-7-yl)-2,5-dioxopyrrole | MS (ES): m/z = 513.3 (M$^+$ + 1) |
| 101 | 3-([1,7]diazoperhydroonino[8,9,1-hi]indol-1-yl)-4-(benzofur-7-yl)-2,5-dioxopyrrole | MS (ES): m/z = 412.2 (M$^+$ + 1) |
| 102 | 3-([1,7]diazoperhydroonino[8,9,1-hi]indol-1-yl)-4-(5,6-difluorobenzofur-7-yl)-2,5-dioxopyrrole hydrochloride | HRMS: m/z = 448.1493 |
| 103 | 3-([1,7]diazoperhydroonino[8,9,1-hi]indol-1-yl)-4-(5-fluorobenzofur-7-yl)-2,5-dioxopyrrole hydrochloride | HRMS: 430.1582 |
| 104 | 3-([1,7]diazoperhydroonino[8,9,1-hi]indol-1-yl)-4-(6-fluorobenzofur-7-yl)-2,5-dioxopyrrole hydrochloride | MS (ES): m/z = 430.2 |
| 105 | 3-(6,7-dihydro-6H-[1,4]diazepino-[6,7,1-hi]indol-1-yl)-4-(isoquinolin-5-yl)-2,5-dioxopyrrole dihydrochloride | MS (ES): m/z = 395.2 (M$^+$ + 1) |
| 106 | 3-([1,7]diazoperhydroonino[8,9,1-hi]indol-1-yl)-4-(imidazo[1,2-a]pyridin-3-yl)-2,5-dioxopyrrole hydrochloride | MS (ES): m/z = 412.2 (M$^+$ + 1) |
| 107 | 3-([1,6]diazoperhydroonino[8,9,1-hi]indol-1-yl)-4-(imidazo[1,2-a]pyridin-3-yl)-2,5-dioxopyrrole | MS (ES): m/z = 412.2 (M$^+$ + 1) |
| 108 | 3-(6,7-dihydro-6H-[1,4]diazepino[6,7,1-hi]indol-1-yl)-4-(2,2-difluoro-benzo[1,3]dioxol-4-yl)-2,5-dioxopyrrole | MS (ES): m/z = 424.1 (M$^+$ + 1) |
| 109 | 3-([1,5]diazoperhydroonino[8,9,1-hi]indol-1-yl)-4-(thieno[3,2-b]pyridin-7-yl)-2,5-dioxopyrrole hydrochloride | MS (ES): m/z = 429.1 (M$^+$ + 1) |
| 110 | 3-(6,7-dihydro-6H-[1,4]diazepino[6,7,1-hi]indol-1-yl)-4-(1,3-dihydroisobenzofur-5-yl)-2,5-dioxopyrrole | MS (ES): m/z = 386.7 (M$^+$ + 1) |
| 111 | 3-(6,7-dihydro-6H-[1,4]diazepino[6,7,1-hi]indol-1-yl)-4-(benzimidazol-4-yl)-2,5-dioxopyrrole | MS (ES): m/z = 384.0 (M$^+$ + 1) |
| 112 | 3-(5-methyl-6,7-dihydro-6H-[1,4]diazepino[6,7,1-hi]indol-1-yl)-4-(benzofur-7-yl)-2,5-dioxopyrrole hydrochloride | MS (ES): m/z = 398.2 (M$^+$ + 1) |
| 113 | 3-(6,7-dihydro-6H-[1,4]diazepino[6,7,1-hi]indol-1-yl)-4-(5,6,7,8-tetrahydro-imidazo[1,2-a]pyridin-3-yl)-2,5-dioxopyrrole dihydrochloride | MS (ES): m/z = 388.2 (M$^+$ + 1) |
| 114 | 3-(5,6,7,8-tetrahydro-6H-[1,4]diazocino[7,8,1-hi]indol-1-yl)-4-(imidazo[1,2-a]pyridin-3-yl)-2,5-dioxopyrrole dihydrochloride | MS (ES): m/z = 398.2 (M$^+$ + 1) |

-continued

| Example | Compound | Data |
|---|---|---|
| 115 | 3-(6,7-dihydro-6H-[1,4]diazepino[6,7,1-hi]indol-1-yl)-4-(2,3-dihydro-benzo[1,4]dioxin-5-yl)-2,5-dioxopyrrole hydrochloride | HRMS: m/z = 402.1438 (M⁺ + H) |
| 116 | 3-(9-fluoro-6,7-dihydro-6H-[1,4]diazepino[6,7,1-hi]indol-1-yl)-4-(benzofur-7-yl)-2,5-dioxopyrrole | MS (ES): m/z = 402.1 (M⁺ + 1) |
| 117 | 3-(5,6,7,8-tetrahydro-6H-[1,4]diazocino[7,8,1-hi]indol-1-yl)-4-(furo[3,2-c]pyridin-7-yl)-2,5-dioxopyrrole dihydrochloride | MS (ES): m/z = 510.2 (M⁺ + 1) |
| 118 | 3-(7-methyl-6,7-dihydro-6H-[1,4]diazepino[6,7,1-hi]indol-1-yl)-4-(benzo[1,3]dioxol-4-yl)-2,5-dioxopyrrole | HRMS: m/z = 402.1460 (M⁺ + H) |
| 119 | 3-(7-methyl-6,7-dihydro-6H-[1,4]diazepino[6,7,1-hi]indol-1-yl)-4-(imidazo[1,2-a]pyridin-3-yl)-2,5-dioxopyrrole | HRMS: m/z = 398.1605 (M⁺ + H) |
| 120 | 3-([1,5]diazaperhydroonino[8,9,1-hi]indol-1-yl)-4-(thieno[3,2-b]pyridin-7-yl)-2,5-dioxopyrrole | MS (ES): m/z = 429.1 (M⁺ + 1) |
| 121 | 3-(6,7-dihydro-6H-[1,4]diazepino[6,7,1-hi]indol-1-yl)-4-(5-fluorobenzofur-7-yl)-2,5-dioxopyrrole hydrochloride | MS (ES): m/z = 402.2 (M⁺ + 1) |
| 122 | 3-(5,6,7,8-tetrahydro-6H-[1,4]diazocino[7,8,1-hi]indol-1-yl)-4-(furo[3,2-c]pyridin-7-yl)-2,5-dioxopyrrole dihydrochloride | MS (ES): m/z = 399.1 (M⁺ + 1) |
| 123 | 3-(7-((piperidin-4-yl)carbonyl)-6,7-dihydro-6H-[1,4]diazepino[6,7,1-hi]indol-1-yl)-4-(furo[3,2-c]pyridin-7-yl)-2,5-dioxopyrrole dihydrochloride | MS (ES): m/z = 496.2 (M⁺ + 1) |
| 124 | 3-(6,7-dihydro-6H-[1,4]diazepino[6,7,1-hi]indol-1-yl)-4-(6-fluoroimidazo[1,2-a]pyridin-3-yl)-2,5-dioxopyrrole dihydrochloride | MS (ES): m/z = 402.1 (M⁺ + 1) |
| 125 | 3-(6,7-dihydro-6H-[1,4]diazepino[6,7,1-hi]indol-1-yl)-4-(8-aminoimidazo[1,2-a]pyridin-3-yl)-2,5-dioxopyrrole dihydrochloride | MS (ES): m/z = 398.4 (M⁺ + 1) |
| 126 | 3-(6,7-dihydro-6H-[1,4]diazepino[6,7,1-hi]indol-1-yl)-4-(6-trifluoromethyl-imidazo[1,2-a]pyridin-3-yl)-2,5-dioxopyrrole dihydrochloride | MS (ES): m/z = 451.9 (M⁺ + 1) |
| 127 | 3-(6,7-dihydro-6H-[1,4]diazepino[6,7,1-hi]indol-1-yl)-4-(6-methyl-8-bromoimidazo[1,2-a]pyridin-3-yl)-2,5-dioxopyrrole dihydrochloride | MS (ES): m/z = 476.0 (M⁺ + 1) |
| 128 | 3-(6,7-dihydro-6H-[1,4]diazepino[6,7,1-hi]indol-1-yl)-4-(imidazo[1,2-a]pyrazin-3-yl)-2,5-dioxopyrrole dihydrochloride | MS (ES): m/z = 385.1 (M⁺ + 1) |
| 129 | 3-(6,7-dihydro-6H-[1,4]diazepino[6,7,1-hi]indol-1-yl)-4-(imidazo[1,2-b]pyridazin-3-yl)-2,5-dioxopyrrole dihydrochloride | MS (ES): m/z = 385.1 (M⁺ + 1) |
| 130 | 3-(9-fluoro-6,7-dihydro-6H-[1,4]diazepino[6,7,1-hi]indol-1-yl)-4-(imidazo[1,2-a]pyridin-3-yl)-2,5-dioxo-pyrrole hydrochloride | MS (ES): m/z = 402.1 (M⁺ + 1) |
| 131 | 3-(9-fluoro-6,7-dihydro-6H-[1,4]diazepino[6,7,1-hi]indol-1-yl)-4-(6-fluoroimidazo[1,2-a]pyridin-3-yl)-2,5-dioxo-pyrrole hydrochloride | MS (ES): m/z = 420.0 (M⁺ + 1) |
| 132 | 3-(6,7-dihydro-6H-[1,4]diazepino[6,7,1-hi]indol-1-yl)-4-(8-fluoroimidazo[1,2-a]pyridin-3-yl)-2,5-dioxo-pyrrole | MS (ES): m/z = 402.1 (M⁺ + 1) |
| 133 | 3-(6,7-dihydro-6H-[1,4]diazepino[6,7,1-hi]indol-1-yl)-4-(7-chloroimidazo[1,2-a]pyridin-3-yl)-2,5-dioxo-pyrrole | MS (ES): m/z = 417.9 (M⁺ + 1) |
| 134 | 3-(9-fluoro-6,7-dihydro-6H-[1,4]diazepino[6,7,1-hi]indol-1-yl)-4-(7-chloroimidazo[1,2-a]pyridin-3-yl)-2,5-dioxopyrrole | MS (ES): m/z = 436.1 (M⁺ + 1) |
| 135 | 3-(9-fluoro-6,7-dihydro-6H-[1,4]diazepino[6,7,1-hi]indol-1-yl)-4-(7-chloroimidazo[1,2-a]pyridin-3-yl)-2,5-dioxopyrrole dihydrochloride | MS (ES): m/z = 435.9 (M⁺ + 1) |
| 136 | 3-(6,7-dihydro-6H-[1,4]diazepino[6,7,1-hi]indol-1-yl)-4-(8-methoxyimidazo[1,2-a]pyridin-3-yl)-2,5-dioxo-pyrrole dihydrochloride | MS (ES): m/z = 414.0 (M⁺ + 1) |
| 137 | (−)-3-(7-methyl-6,7-dihydro-6H-[1,4]diazepino[6,7,1-hi]indol-1-yl)-4-(imidazo[1,2-a]pyridin-3-yl)-2,5-dioxopyrrole | HRMS: m/z = 398.1622 (M⁺ + 1) |
| 138 | (+)-3-(7-methyl-6,7-dihydro-6H-[1,4]diazepino[6,7,1-hi]indol-1-yl)-4-(imidazo[1,2-a]pyridin-3-yl)-2,5-dioxopyrrole | HRMS: m/z = 398.1637 (M⁺ + 1) |
| 139 | (−)-3-(7-methyl-6,7-dihydro-6H-[1,4]diazepino[6,7,1-hi]indol-1-yl)-4-(7-chloroimidazo[1,2-a]pyridin-3-yl)-2,5-dioxopyrrole | HRMS: m/z = 432.1218 (M⁺ + 1) |
| 140 | (+)-3-(7-methyl-6,7-dihydro-6H-[1,4]diazepino[6,7,1-hi]indol-1-yl)-4-(7-chloroimidazo[1,2-a]pyridin-3-yl)-2,5-dioxopyrrole | HRMS: m/z = 432.1209 (M⁺ + 1) |
| 141 | (−)-3-(7-methyl-6,7-dihydro-6H-[1,4]diazepino[6,7,1-hi]indol-1-yl)-4-(6-methylimidazo[1,2-a]pyridin-3-yl)-2,5-dioxopyrrole | HRMS: m/z = 412.1782 (M⁺ + 1) |
| 142 | 3-(6,7-dihydro-6H-[1,4]diazepino[6,7,1-hi]indol-1-yl)-4-(imidazo[1,2-a]pyrimidin-3-yl)-2,5-dioxopyrrole hydrochloride | MS (ES): m/z = 385.1 (M⁺ + 1) |
| 143 | 3-(6,7-dihydro-6H-[1,4]diazepino[6,7,1-hi]indol-1-yl)-4-(6-methoxyimidazo[1,2-a]pyrimidin-3-yl)-2,5-dioxopyrrole hydrochloride | MS (ES): m/z = 414 (M⁺ + 1) |
| 144 | 3-(6,7-dihydro-6H-[1,4]diazepino[6,7,1-hi]indol-1-yl)-4-(7-ethylimidazo[1,2-a]pyrimidin-3-yl)-2,5-dioxopyrrole hydrochloride | MS (ES): m/z = 412 (M⁺ + 1) |
| 145 | 3-(6,7-dihydro-6H-[1,4]diazepino[6,7,1-hi]indol-1-yl)-4-(4,5,6,7-tetrahydro-pyrazolo[1,5-a]pyridin-3-yl)-2,5-dioxopyrrole hydrochloride | HRMS: m/z = 388.1773 (M⁺ + 1) |
| 146 | 3-(6,7-dihydro-6H-[1,4]diazepino[6,7,1-hi]indol-1-yl)-4-(8-chloroimidazo[1,2-a]pyridin-3-yl)-2,5-dioxopyrrole dihydrochloride | HRMS: m/z = 418.1071 (M⁺ + 1) |

*¹H-NMR (DMSO-d₆): δ 11.05 (bs, 1H), 7.93 (s, 1H), 7.5 (d, J = 8 Hz, 1H), 7.1-7.18 (m, 2H), 7.04 (d, J = 7 Hz, 1H), 6.8 (d, J = 7 Hz, 1H), 6.3 (dd, J = 7, <1 Hz, 1H), 6.0 (m, 2H), 4.5 (t, J = 1 Hz, 1H), 4.27 (m, 2H), 4.17 (t, J = 7 Hz, 2H), 4.05 (m, 2H), 3.25 (m, 2H), 3.18 (m, 2H), 1.78 (m, 2H)

The compounds of EXAMPLES 147-152 may be prepared essentially as described in EXAMPLE 64 except that the addition of ethanethiol is omitted.

| Example | Compound | Data |
|---|---|---|
| 147 | 3-(6-(3-(amino)propionyl)-6,7-dihydro-6H-[1,4]diazepino[6,7,1-hi]indol-1-yl)-4-(imidazo[1,2-a]pyridin-3-yl)-2,5-dioxopyrrole dihydrochloride | MS (ES): m/z = 455 (M⁺ + 1) |
| 148 | 3-(6-(2-(amino)-2-(methyl)propionyl)-6,7-dihydro-6H-[1,4]diazepino[6,7,1-hi]indol-1-yl)-4-(imidazo[1,2-a]-pyridin-3-yl)-2,5-dioxopyrrole dihydrochloride | MS (ES): m/z = 469 (M⁺ + 1) |
| 149 | R-3-(6-(2-(amino)-3-(methoxy)propionyl)-6,7-dihydro-6H-[1,4]diazepino[6,7,1-hi]indol-1-yl)-4-(imidazo[1,2-a]-pyridin-3-yl)-2,5-dioxopyrrole dihydrochloride | MS (ES): m/z = 485 (M⁺ + 1) |

| Example | Compound | Data |
|---|---|---|
| 150 | 3-(9-fluoro-6,7-dihydro-6H-[1,4]diazepino[6,7,1-hi]-indol-1-yl)-4-(6-methylimidazo[1,2-a]pyridin-3-yl)-2,5-dioxopyrrole hydrochloride | MS (ES): m/z = ($M^+$ + 1) |
| 151 | 3-(9-fluoro-6,7-dihydro-6H-[1,4]diazepino[6,7,1-hi]-indol-1-yl)-4-(7-methoxyimidazo[1,2-a]pyridin-3-yl)-2,5-dioxopyrrole hydrochloride | MS (ES): m/z = ($M^+$ + 1) |
| 152 | 3-(6,7-dihydro-6H-[1,4]diazepino[6,7,1-hi]-indol-1-yl)-4-(7-methoxyimidazo[1,2-a]pyridin-3-yl)-2,5-dioxopyrrole hydrochloride | MS (ES): m/z = ($M^+$ + 1) |

EXAMPLE 153

3-(5,6-dihydro-1H-pyrrolo[3,2,1-ij]quinazolin-1-yl)-4-(isoquinolin-5-yl)-2,5-dioxo-2,5-dihydro-1H-indole Add trifluoroacetic acid (250 μL) to 3-(5-(tert-butoxycarbonyl)-5,6-dihydro-1H-pyrrolo-[3,2,1-ij]quinazolin-1-yl)-4-(isoquinolin-5-yl)-2,5-dioxo-2,5-dihydro-1H-indole (0.400 g, 0.830 mmol) in dichloromethane (5 mL) and stir the reaction mixture at room temperature for 4 hours. Dilute the reaction with 300 mL dichloromethane and carefully quench with saturated sodium bicarbonate solution (200 mL). Separate the phases and wash the organic phase sequentially with water (1×75 mL) and saturated aqueous sodium chloride (1×75 mL), dry over anhydrous magnesium sulfate, and concentrate under reduced pressure to provide the title compound.

MS (ES): m/z=383.1 ($M^+$+1)

The compound of Example 154 may be prepared essentially as described in Example 153.

| Example | Compound | Data |
|---|---|---|
| 154 | 3-(6,7-dihydro-6H-[1,4]diazepino[6,7,1-hi]indol-1-yl)-4-(6-chloroimidazo[1,2-a]pyridin-3-yl)-2,5-dioxopyrrole | MS (ES): m/z = 418 ($M^+$ + 1) |

EXAMPLE 155

3-(5,6-dihydroxy-[1,5]diazaperhydroonino[8,9,1-hi]indol-1-yl)-4-(benzofur-7-yl)-2,5-dioxopyrrole Beginning with methyl (5,6-(2,2-dimethyl-[1,3]dioxolanyl)-8-(tert-butoxy-carbonyl)-[1,5]diazaperhydroonino[8,9,1-hi]indol-1-yl)oxoacetate and 2-(benzofur-7-yl)acetamide, 3-(5,6-(2,2-dimethyl-[1,3]dioxolanyl)-8-(tert-butoxy-carbonyl)-[1,5]diazaperhydroonino[8,9,1-hi]indol-1-yl)-4-(benzofur-7-yl)-2,5-dioxopyrrole is prepared essentially as described in Preparation 120. This material is treated with trifluoroacetic acid as described in EXAMPLE 117 to provide the title compound.

MS (ES): m/z=444 ($M^+$+H)

EXAMPLE 156

3-(6,7-dihydro-6H-[1,4]diazepino[6,7,1-hi]indol-1-yl)-4-(indol-7-yl)-2,5-dioxopyrrole Add aluminum chloride (0.014 g, 0.1 mmol) to a flask containing 3-(6-(tert-butoxycarbonyl)-6,7-dihydro-6H-[1,4]diazepino-[6,7,1-hi]indol-1-yl)-4-(indol-7-yl)-2,5-dioxopyrrole (0.05, 0.1 mmol) in methylene chloride (25 ml). Quench the reaction with saturated aqueous sodium bicarbonate, extract into ethyl acetate, wash combined organic layers with saturated aqueous sodium chloride, dry over magnesium sulfate, and concentrate under reduced pressure. Chromatograph on flash silica using a gradient from neat ethyl acetate to 10% methanol: ethyl acetate to obtain the title compound as an orange solid (10 mg, 26%).

MS (ES): m/z=383.0 ($M^+$+1)

EXAMPLE 157

3-(6-methyl-5,6,7,8-tetrahydro-6H-[1,4]diazocino[7,8,1-hi]-indol-1-yl)-4-(benzofur-7-yl)-2,5-dioxopyrrole Add 3-(5,6,7,8-tetrahydro-6H-[1,4]diazocino[7,8,1-hi]indol-1-yl)-4-(benzofur-7-yl)-2,5-dioxopyrrole (140 mg, 0.35 mmol), paraformaldehyde (264 mg, 8.8 mmol), potassium acetate (104 mg, 1.0 mmol), sodium cyanoborohydride (220 mg, 3.5 mmol), and glacial acetic acid (1.5 mL) to 2-methoxyethanol (13.5 mL). Stir and slowly heat to reflux under nitrogen. After 30 minutes dilute with 1:1 diethyl ether:ethyl acetate. Wash sequentially with aqueous 0.5 molar sodium hydrogen carbonate and distilled water, and pass the organic phase through a Varian® BondElut™ SCX column. Rinse the column with absolute methanol. Elute with 2M ammonia in methanol, concentrate under reduced pressure, filter, rinse the solid with cold methanol and dry under reduced pressure to provide the title compound as an orange solid (115 mg, 79%).

HRMS: 412.1663 (M+H).

The compounds of EXAMPLES 158-237 may be prepared essentially as described in EXAMPLE 157.

| Example | Compound | Data |
|---|---|---|
| 158 | 3-(6-methyl-6,7-dihydro-6H-[1,4]diazepino[6,7,1-hi]indol-1-yl)-4-(benzofur-7-yl)-2,5-dioxopyrrole | MS (ES): m/z = 398.1 ($M^+$ + 1) |
| 159 | 3-(8-methyl-[1,5]diazaperhydroonino[8,9,1-hi]indol-1-yl)-4-(imidazo[1,2-a]pyridin-3-yl)-2,5-dioxopyrrole | MS (ES): m/z = 426.2 ($M^+$ + 1) |
| 160 | 3-(8-methyl-[1,5]diazaperhydroonino[8,9,1-hi]indol-1-yl)-4-(benzofur-7-yl)-2,5-dioxopyrrole hydrochloride | MS (ES): m/z = 426.2 ($M^+$ + 1) |
| 161 | 3-(6-methyl-6,7-dihydro-6H-[1,4]diazepino[6,7,1-hi]-indol-1-yl)-4-(imidazo[1,2-a]pyridin-3-yl)-2,5-dioxopyrrole | MS (ES): m/z = 398.2 ($M^+$ + 1) |
| 162 | 3-(6-methyl-6,7-dihydro-6H-[1,4]diazepino[6,7,1-hi]-indol-1-yl)-4-(5-fluorobenzofur-7-yl)-2,5-dioxopyrrole | MS (ES): m/z = 416.1 ($M^+$ + 1) |
| 163 | 3-(6,7-dihydro-6H-[1,4]diazepino[6,7,1-hi]indol-7-yl)-4-(benzofur-7-yl)-2,5-dioxopyrrole hydrochloride | MS (ES): m/z = 444.6 ($M^+$ + 1) |
| 164 | 3-(6-methyl-6,7-dihydro-6H-[1,4]diazepino[6,7,1-hi]-indol-1-yl)-4-(furo[3,2-c]pyridin-7-yl)-2,5-dioxopyrrole dihydrochloride | MS (ES): m/z = 399.1 ($M^+$ + 1) |
| 165 | 3-(6-methyl-6,7-dihydro-6H-[1,4]diazepino[6,7,1-hi]-indol-1-yl)-4-(benzothien-7-yl)-2,5-dioxopyrrole | HRMS: 414.1300 (M + H) |
| 166 | 3-(6-methyl-6,7-dihydro-6H-[1,4]diazepino[6,7,1-hi]-indol-1-yl)-4-(benzo[1,3]dioxol-4-yl)-2,5-dioxopyrrole | HRMS: 402.1461 (M + H) |
| 167 | 3-(6-isopropyl-6,7-dihydro-6H-[1,4]diazepino[6,7,1-hi]-indol-1-yl)-4-(5-fluorobenzofur-7-yl)-2,5-dioxopyrrole | MS (ES): m/z = 444.6 ($M^+$ + 1) |
| 168 | 3-(6-cyclohexyl-6,7-dihydro-6H-[1,4]diazepino[6,7,1-hi]indol-1-yl)-4-(5- | MS (ES): m/z = 484.2 ($M^+$ + 1) |

-continued

| Example | Compound | Data |
|---|---|---|
| | fluorobenzofur-7-yl)-2,5-dioxopyrrole hydrochloride | |
| 169 | 3-(6-(tetrahydropyran-4-yl)-6,7-dihydro-6H-[1,4]diazepino[6,7,1-hi]indol-1-yl)-4-(benzofur-7-yl)-2,5-dioxopyrrole hydrochloride | MS (ES): m/z = 468.2 (M$^+$ + 1) |
| 170 | 3-(6-(α-methylbenzyl)-6,7-dihydro-6H-[1,4]diazepino-[6,7,1-hi]indol-1-yl)-4-(benzofur-7-yl)-2,5-dioxopyrrole hydrochloride | MS (ES): m/z = 488.2 (M$^+$ + 1) |
| 171 | 3-(6-((imidazol-2-yl)methyl)-6,7-dihydro-6H-[1,4]diazepino[6,7,1-hi]indol-1-yl)-4-(benzofur-7-yl)-2,5-dioxopyrrole hydrochloride | MS (ES): m/z = 464.2 (M$^+$ + 1) |
| 172 | 3-(6-(isopropyl)-5,6,7,8-tetrahydro-6H-[1,4]diazocino[7,8,1-hi]indol-1-yl)-4-(imidazo[1,2-a]pyridin-3-yl)-2,5-dioxopyrrole hydrochloride | MS (ES): m/z = 440.2 (M$^+$ + 1) |
| 173 | 3-(6-(isopropyl)-6,7-dihydro-6H-[1,4]diazepino-[6,7,1-hi]indol-1-yl)-4-(benz[1,3]dioxol-4-yl)-2,5-dioxopyrrole | HRMS: m/z = 430.1781 (M$^+$ + H) |
| 174 | 3-(6-(isopropyl)-6,7-dihydro-6H-[1,4]diazepino-[6,7,1-hi]indol-1-yl)-4-(2,3-dihydrobenzofur-7-yl)-2,5-dioxopyrrole | HRMS: m/z = 428.1986 (M$^+$ + H) |
| 175 | 3-(6-(methyl)-6,7-dihydro-6H-[1,4]diazepino[6,7,1-hi]indol-1-yl)-4-(2,3-dihydrobenzo[1,4]dioxin-5-yl)-2,5-dioxopyrrole | HRMS: m/z = 416.1610 (M$^+$ + H) |
| 176 | 3-(6-(isopropyl)-5,6,7,8-tetrahydro-6H-[1,4]diazo-cino[7,8,1-hi]indol-1-yl)-4-(benzofur-7-yl)-2,5-dioxopyrrole hydrochloride | HRMS: m/z = 440.1970 (M$^+$ + H) |
| 177 | 3-(6-(tetrahydropyran-4-yl)-5,6,7,8-tetrahydro-6H-[1,4]diazocino[7,8,1-hi]indol-1-yl)-4-(benzofur-7-yl)-2,5-dioxopyrrole hydrochloride | HRMS: m/z = 482.2046 (M$^+$ + H) |
| 178 | 3-(6-(α-methylbenzyl)-5,6,7,8-tetrahydro-6H-[1,4]diazocino[7,8,1-hi]indol-1-yl)-4-(benzofur-7-yl)-2,5-dioxopyrrole hydrochloride | HRMS: m/z = 502.2138 (M$^+$ + H) |
| 179 | 3-(6-(methyl)-5,6,7,8-tetrahydro-6H-[1,4]diazocino-[7,8,1-hi]indol-1-yl)-4-(benzofur-7-yl)-2,5-dioxopyrrole hydrochloride | HRMS: m/z = 416.1595 (M$^+$ + H) |
| 180 | 3-(6-(ethyl)-6,7-dihydro-6H-[1,4]diazepino[6,7,1-hi]-indol-1-yl)-4-(benzofur-7-yl)-2,5-dioxopyrrole | HRMS: m/z = 416.1600 (M$^+$ + H) |
| 181 | 3-(6-(methyl)-5,6,7,8-tetrahydro-6H-[1,4]diazocino-[7,8,1-hi]indol-1-yl)-4-(furo[3,2-c]pyridin-7-yl)-2,5-dioxopyrrole dihydrochloride | MS (ES): m/z = 413.1 (M$^+$ + 1) |
| 182 | 3-(6-(isopropyl)-5,6,7,8-tetrahydro-6H-[1,4]diazocino[7,8,1-hi]indol-1-yl)-4-(furo[3,2-c]pyridin-7-yl)-2,5-dioxopyrrole dihydrochloride | MS (ES): m/z = 441.2 (M$^+$ + 1) |
| 183 | 3-(6-(isopropyl)-6,7-dihydro-6H-[1,4]diazepino[6,7,1-hi]indol-1-yl)-4-(benzofur-7-yl)-2,5-dioxopyrrole hydrochloride | MS (ES): m/z = 426.2 (M$^+$ + 1) |
| 184 | 3-(6-(1-phenyleth-1-yl)-6,7-dihydro-6H-[1,4]diazepino[6,7,1-hi]indol-1-yl)-4-(benzofur-7-yl)-2,5-dioxopyrrole hydrochloride | MS (ES): m/z = 488.2 (M$^+$ + 1) |
| 185 | 3-(6-(tetrahydropyran-2-yl)-6,7-dihydro-6H-[1,4]diazepino[6,7,1-hi]indol-1-yl)-4-(benzofur-7-yl)-2,5-dioxopyrrole hydrochloride | MS (ES): m/z = 468.2 (M$^+$ + 1) |
| 186 | 3-(6-(methyl)-6,7-dihydro-6H-[1,4]diazepino[6,7,1-hi]indol-1-yl)-4-(5-fluorobenzofur-7-yl)-2,5-dioxopyrrole | MS (ES): m/z = 416.1 (M$^+$ + 1) |
| 187 | 3-(6-(methyl)-6,7-dihydro-6H-[1,4]diazepino[6,7,1-hi]indol-1-yl)-4-(5-fluorobenzofur-7-yl)-2,5-dioxopyrrole hydrochloride | MS (ES): m/z = 416.2 (M$^+$ + 1) |
| 188 | 3-(6-(isopropyl)-6,7-dihydro-6H-[1,4]diazepino[6,7,1-hi]indol-1-yl)-4-(5-fluorobenzofur-7-yl)-2,5-dioxopyrrole | MS (ES): m/z = 444.1 (M$^+$ + 1) |
| 189 | 3-(6-(isopropyl)-6,7-dihydro-6H-[1,4]diazepino[6,7,1-hi]indol-1-yl)-4-(5-fluorobenzofur-7-yl)-2,5-dioxopyrrole hydrochloride | MS (ES): m/z = 416.2 (M$^+$ + 1) |
| 190 | 3-(6-(isopropyl)-6,7-dihydro-6H-[1,4]diazepino[6,7,1-hi]indol-1-yl)-4-(imidazo[1,2-a]pyridin-3-yl)-2,5-dioxopyrrole | MS (ES): m/z = 426.2 (M$^+$ + 1) |
| 191 | 3-(6-(2-methoxyeth-1-yl)-6,7-dihydro-6H-[1,4]diazepino[6,7,1-hi]indol-1-yl)-4-(imidazo[1,2-b]pyridazin-3-yl)-2,5-dioxopyrrole | MS (ES): m/z = 442.9 (M$^+$ + 1) |
| 192 | 3-(6-(isopropyl)-6,7-dihydro-6H-[1,4]diazepino[6,7,1-hi]indol-1-yl)-4-(5,6,7,8-tetrahydroimidazo[1,2-a]-pyridin-3-yl)-2,5-dioxopyrrole hydrochloride | MS (ES): m/z = 426.2 (M$^+$ + 1) |
| 193 | 3-(6-(cyclopentyl)-6,7-dihydro-6H-[1,4]diazepino-[6,7,1-hi]indol-1-yl)-4-(imidazo[1,2-a]pyridin-3-yl)-2,5-dioxopyrrole hydrochloride | MS (ES): m/z = 470.2 (M$^+$ + 1) |
| 194 | 3-(9-fluoro-6-isopropyl-6,7-dihydro-6H-[1,4]diazepino[6,7,1-hi]indol-1-yl)-4-(imidazo[1,2-a]pyridin-3-yl)-2,5-dioxopyrrole hydrochloride | MS (ES): m/z = 444.1 (M$^+$ + 1) |
| 195 | 3-(6-isopropyl-6,7-dihydro-6H-[1,4]diazepino[6,7,1-hi]indol-1-yl)-4-(6-fluoroimidazo[1,2-a]pyridin-3-yl)-2,5-dioxopyrrole hydrochloride | MS (ES): m/z = 444.2 (M$^+$ + 1) |
| 196 | 3-(9-fluoro-6-isopropyl-6,7-dihydro-6H-[1,4]diazepino[6,7,1-hi]indol-1-yl)-4-(6-fluoroimidazo[1,2-a]pyridin-3-yl)-2,5-dioxopyrrole hydrochloride | MS (ES): m/z = 462.1 (M$^+$ + 1) |
| 197 | 3-(9-fluoro-6-isopropyl-6,7-dihydro-6H-[1,4]diazepino[6,7,1-hi]indol-1-yl)-4-(8-fluoroimidazo[1,2-a]pyridin-3-yl)-2,5-dioxopyrrole hydrochloride | MS (ES): m/z = 462.2 (M$^+$ + 1) |
| 198 | 3-(9-fluoro-6-isopropyl-6,7-dihydro-6H-[1,4]diazepino[6,7,1-hi]indol-1-yl)-4-(imidazo[1,2-a]pyrimidin-3-yl)-2,5-dioxopyrrole hydrochloride | MS (ES): m/z = 445.0 (M$^+$ + 1) |
| 199 | 3-(6-(2-methoxyeth-1-yl)-6,7-dihydro-6H-[1,4]diazepino[6,7,1-hi]indol-1-yl)-4-(8-fluoroimidazo[1,2-a]pyridin-3-yl)-2,5-dioxopyrrole | MS (ES): m/z = 460.0 (M$^+$ + 1) |
| 200 | 3-(6-(2-methoxyeth-1-yl)-6,7-dihydro-6H-[1,4]diazepino[6,7,1-hi]indol-1-yl)-4-(imidazo[1,2-a]pyridin-3-yl)-2,5-dioxopyrrole | MS (ES): m/z = 442 (M$^+$ + 1) |
| 201 | 3-(6-(2-(methoxyethoxy)eth-1-yl)-6,7-dihydro-6H-[1,4]diazepino[6,7,1-hi]indol-1-yl)-4-(imidazo[1,2-a]pyridin-3-yl)-2,5-dioxopyrrole | MS (ES): m/z = 486 (M$^+$ + 1) |
| 202 | 3-(6-(2-(morpholin-4-yl)eth-1-yl)-6,7-dihydro-6H-[1,4]diazepino[6,7,1-hi]indol-1-yl)-4-(imidazo[1,2-a]pyridin-3-yl)-2,5-dioxopyrrole | MS (ES): m/z = 497 (M$^+$ + 1) |
| 203 | 3-(6-(2-fluorobenzyl)-6,7-dihydro-6H-[1,4]diazepino[6,7,1-hi]indol-1-yl)-4-(imidazo[1,2-a]pyridin-3-yl)-2,5-dioxopyrrole | MS (ES): m/z = 492 (M$^+$ + 1) |
| 204 | 3-(6-(4-fluorobenzyl)-6,7-dihydro-6H-[1,4]diazepino[6,7,1-hi]indol-1-yl)-4-(imidazo[1,2-a]pyridin-3-yl)-2,5-dioxopyrrole | MS (ES): m/z = 492 (M$^+$ + 1) |
| 205 | 3-(6-(2,4-difluorobenzyl)-6,7-dihydro-6H-[1,4]diazepino[6,7,1-hi]indol-1-yl)-4-(imidazo[1,2-a]pyridin-3-yl)-2,5-dioxopyrrole | MS (ES): m/z = 510 (M$^+$ + 1) |
| 206 | 3-(6-(2,4,6-trifluorobenzyl)-6,7-dihydro-6H-[1,4]diazepino[6,7,1-hi]indol-1-yl)-4-(imidazo[1,2-a]-pyridin-3-yl)-2,5-dioxopyrrole | MS (ES): m/z = 528 (M$^+$ + 1) |
| 207 | 3-(6-((1-cyclohexylimidazol-5-yl)methyl)-6,7-dihydro-6H-[1,4]diazepino[6,7,1-hi]indol-1-yl)-4-(imidazo[1,2-a]-pyridin-3-yl)-2,5-dioxopyrrole | MS (ES): m/z = 546 (M$^+$ + 1) |
| 208 | 3-(6-(2-methoxyeth-1-yl)-6,7-dihydro-6H-[1,4]diazepino[6,7,1-hi]indol-1-yl)-4-(6-methylimidazo[1,2-a]pyridin-3-yl)-2,5-dioxopyrrole | MS (ES): m/z = 456 (M$^+$ + 1) |
| 209 | 3-(6-(2-(pyrrolidin-1-yl)eth-1-yl)-6,7-dihydro-6H-[1,4]diazepino[6,7,1-hi]indol-1-yl)-4- | MS (ES): m/z = 481 (M$^+$ + 1) |

| Example | Compound | Data |
|---|---|---|
| | (imidazo[1,2-a]-pyridin-3-yl)-2,5-dioxopyrrole | |
| 210 | 3-(6-(2-(morpholin-4-yl)eth-1-yl)-6,7-dihydro-6H-[1,4]diazepino[6,7,1-hi]indol-1-yl)-4-(6-methyl-imidazo[1,2-a]-pyridin-3-yl)-2,5-dioxopyrrole | MS (ES): m/z = 511 (M$^+$ + 1) |
| 211 | 3-(9-fluoro-6-(2-(morpholin-4-yl)eth-1-yl)-6,7-dihydro-6H-[1,4]diazepino[6,7,1-hi]indol-1-yl)-4-(6-methylimidazo[1,2-a]-pyridin-3-yl)-2,5-dioxopyrrole | MS (ES): m/z = 529 (M$^+$ + 1) |
| 212 | 3-(9-fluoro-6-(2-(morpholin-4-yl)eth-1-yl)-6,7-dihydro-6H-[1,4]diazepino[6,7,1-hi]indol-1-yl)-4-(7-methoxyimidazo[1,2-a]-pyridin-3-yl)-2,5-dioxopyrrole | MS (ES): m/z = 545 (M$^+$ + 1) |
| 213 | 3-(6-(2-(morpholin-4-yl)eth-1-yl)-6,7-dihydro-6H-[1,4]diazepino[6,7,1-hi]indol-1-yl)-4-(7-methoxy-imidazo[1,2-a]-pyridin-3-yl)-2,5-dioxopyrrole | MS (ES): m/z = 527 (M$^+$ + 1) |
| 214 | 3-(6-(2-methoxyeth-1-yl)-6,7-dihydro-6H-[1,4]diazepino[6,7,1-hi]indol-1-yl)-4-(7-methoxyimidazo[1,2-a]-pyridin-3-yl)-2,5-dioxopyrrole | MS (ES): m/z = 472 (M$^+$ + 1) |
| 215 | 3-(6-(isopropyl)-6,7-dihydro-6H-[1,4]diazepino[6,7,1-hi]indol-1-yl)-4-(7-chloroimidazo[1,2-a]pyridin-3-yl)-2,5-dioxopyrrole methanesulfonate | MS (ES): m/z = 460.2 (M$^+$ + 1) |
| 216 | 3-(6-(isopropyl)-6,7-dihydro-6H-[1,4]diazepino[6,7,1-hi]indol-1-yl)-4-(8-fluoroimidazo[1,2-a]pyridin-3-yl)-2,5-dioxopyrrole methanesulfonate | MS (ES): m/z = 444.2 (M$^+$ + 1) |
| 217 | 3-(6-(2-methoxyeth-yl)-6,7-dihydro-6H-[1,4]diazepino[6,7,1-hi]indol-1-yl)-4-(8-methoxyimidazo[1,2-a]-pyridin-3-yl)-2,5-dioxopyrrole | MS (ES): m/z = 472.0 (M$^+$ + 1) |
| 218 | 3-(9-fluoro-6-(2-methoxyeth-1-yl)-6,7-dihydro-6H-[1,4]diazepino[6,7,1-hi]indol-1-yl)-4-(7-chloro-imidazo[1,2-a]pyridin-3-yl)-2,5-dioxopyrrole | MS (ES): m/z = 493.8 (M$^+$ + 1) |
| 219 | 3-(6-(tetrahydropyran-4-yl)-6,7-dihydro-6H-[1,4]diazepino[6,7,1-hi]indol-1-yl)-4-(imidazo[1,2-a]pyridin-3-yl)-2,5-dioxopyrrole | HRMS: m/z = 468.2036 |
| 220 | (−)-3-(7-methyl-6-isopropyl-6,7-dihydro-6H-[1,4]diazepino[6,7,1-hi]indol-1-yl)-4-(imidazo[1,2-a]pyridin-3-yl)-2,5-dioxopyrrole | HRMS: m/z = 440.2076 |
| 221 | (+)-3-(7-methyl-6-isopropyl-6,7-dihydro-6H-[1,4]diazepino[6,7,1-hi]indol-1-yl)-4-(imidazo[1,2-a]pyridin-3-yl)-2,5-dioxopyrrole | HRMS: m/z = 440.2086 |
| 222 | 3-(6-(2-methoxyeth-yl)-6,7-dihydro-6H-[1,4]diazepino[6,7,1-hi]indol-1-yl)-4-(7-chloro-imidazo[1,2-a]pyridin-3-yl)-2,5-dioxopyrrole | HRMS: m/z = 476.1494 |
| 223 | 3-(6-(isopropyl)-6,7-dihydro-6H-[1,4]diazepino[6,7,1-hi]indol-1-yl)-4-(imidazo[2,1-b]thiazol-3-yl)-2,5-dioxopyrrole | HRMS: m/z = 432.1495 |
| 224 | 3-(6-(2-methoxyeth-1-yl)-6,7-dihydro-6H-[1,4]diazepino[6,7,1-hi]indol-1-yl)-4-(6-methoxy-imidazo[1,2-a]pyridin-3-yl)-2,5-dioxopyrrole | MS (ES): m/z = 472 (M$^+$ + 1) |
| 225 | 3-(6-(2-methoxyeth-1-yl)-6,7-dihydro-6H-[1,4]diazepino[6,7,1-hi]indol-1-yl)-4-(7-ethyl-imidazo[1,2-a]pyridin-3-yl)-2,5-dioxopyrrole | MS (ES): m/z = 470 (M$^+$ + 1) |
| 226 | 3-(6-(isopropyl)-6,7-dihydro-6H-[1,4]diazepino[6,7,1-hi]indol-1-yl)-4-(imidazo[1,2-a]pyridin-3-yl)-2,5-dioxopyrrole methanesulfonate | MS (ES): m/z = 427.2 (M$^+$ + 1) |
| 227 | 3-(6-(cyclopentyl)-6,7-dihydro-6H-[1,4]diazepino-[6,7,1-hi]indol-1-yl)-4-(imidazo[1,2-a]pyridin-3-yl)-2,5-dioxopyrrole | MS (ES): m/z = 427.2 (M$^+$ + 1) |
| 228 | 3-(6-(isopropyl)-6,7-dihydro-6H-[1,4]diazepino[6,7,1-hi]indol-1-yl)-4-(6-chloroimidazo[1,2-a]pyridin-3-yl)-2,5-dioxopyrrole | MS (ES): m/z = 460 (M$^+$ + 1) |
| 229 | 3-(6-(2-fluorobenzyl)-6,7-dihydro-6H-[1,4]diazepino-[6,7,1-hi]indol-1-yl)-4-(imidazo[1,2-a]pyrimidin-3-yl)-2,5-dioxopyrrole | MS (ES): m/z = 493 (M$^+$ + 1) |
| 230 | 3-(6-((pyridin-3-yl)methyl)-6,7-dihydro-6H-[1,4]diazepino-[6,7,1-hi]indol-1-yl)-4-(imidazo[1,2-a]pyrimidin-3-yl)-2,5-dioxopyrrole | MS (ES): m/z = 476 (M$^+$ + 1) |
| 231 | 3-(6-((pyridin-2-yl)methyl)-6,7-dihydro-6H-[1,4]diazepino-[6,7,1-hi]indol-1-yl)-4-(imidazo[1,2-a]pyrimidin-3-yl)-2,5-dioxopyrrole | MS (ES): m/z = 476 (M$^+$ + 1) |
| 232 | 3-(6-(isopropyl)-6,7-dihydro-6H-[1,4]diazepino-[6,7,1-hi]indol-1-yl)-4-(pyrazolo[1,5-a]pyrimidin-3-yl)-2,5-dioxopyrrole hydrochloride | HRMS: m/z = 426.1937 (M$^+$ + 1) |
| 233 | 3-(6-(methyl)-6,7-dihydro-6H-[1,4]diazepino-[6,7,1-hi]indol-1-yl)-4-(pyrazolo[1,5-a]pyrimidin-3-yl)-2,5-dioxopyrrole hydrochloride | HRMS: m/z = 398.1617 (M$^+$ + 1) |
| 234 | 3-(6-(methyl)-6,7-dihydro-6H-[1,4]diazepino-[6,7,1-hi]indol-1-yl)-4-(4,5,6,7-tetrahydropyrazolo[1,5-a]pyrimidin-3-yl)-2,5-dioxopyrrole hydrochloride | HRMS: m/z = 402.1930 (M$^+$ + 1) |
| 235 | 3-(6-(isopropyl)-6,7-dihydro-6H-[1,4]diazepino[6,7,1-hi]indol-1-yl)-4-(4,5,6,7-tetrahydropyrazolo-[1,5-a]pyrimidin-3-yl)-2,5-dioxopyrrole hydrochloride | HRMS: m/z = 430.2243 (M$^+$ + 1) |
| 236 | 3-(6-(2-methoxyeth-1-yl)-6,7-dihydro-6H-[1,4]diazepino[6,7,1-hi]indol-1-yl)-4-(8-chloroimidazo[1,2-a]pyrimidin-3-yl)-2,5-dioxopyrrole | HRMS: m/z = 476.1489 (M$^+$ + 1) |

EXAMPLE 237

3-(5-methyl-5,6-dihydro-1H-pyrrolo[3,2,1-ij]quinazolin-1-yl)-4-(isoquinolin-5-yl)-2,5-dioxopyrrole Add a solution of 3-(5,6-dihydro-1H-pyrrolo[3,2,1-ij]quinazolin-1-yl)-4-(isoquinolin-5-yl)-2,5-dioxopyrrole (0.300 g, 0.7853 mmol) in anhydrous dimethylformamide (1.5 mL) to formalin (37% solution in water, 0.750 ml) in 2 ml glacial acetic acid and stir at 65° C. for 2 hours. Pour into ice water and neutralize with 5.0N sodium hydroxide. Extract with 200 mL ethyl acetate, wash sequentially with water (1×75 mL), and saturated aqueous sodium chloride (1×75 mL), dry over anhydrous magnesium sulfate, and concentration under reduced pressure. Dissolve the residue in 150 ml 2.0 M ammonia in methanol stir at room temperature for 2 hours, concentrate and purify by column chromatography to give the title compound as an orange solid.
MS (ES): m/z=395.2 (M$^+$+1)

EXAMPLE 238

3-(6-formyl-6,7-dihydro-6H-[1,4]diazepino indol-1-yl)-4-(benzofur-7-yl)-2,5-dioxopyrrole Add 3-(6,7-dihydro-6H-[1,4]diazepino[6,7,1-hi]indol-1-yl)-4-(benzofur-7-yl)-2,5-dioxopyrrole (312 mg, 0.74 mmol) and sodium formate (130 mg, 1.91 mmol) to formamide (12 mL) and stir under nitrogen at 140° C. for 30 minutes. Dilute with ethyl acetate:diethyl ether (1:1), wash sequentially with aqueous 0.25 M hydrochloric acid, aqueous 0.5 M sodium hydrogen carbonate, and aqueous saturated sodium chloride, dry over anhydrous magnesium sulfate, filter, and concentrate under reduced pressure. Recrystallize the residue from methanol and dry under reduced pressure to provide the title compound as an orange solid (285 mg, 93%).
HRMS: 412.1324 (M+1)

EXAMPLE 239

3-(6-(phenoxycarbonyl)-6,7-dihydro-6H-[1,4]diazepino[6,7,1-hi]indol-1-yl)-4-(benzofur-7-yl)-2,5-dioxopyrrole Cool a solution of 0.17 gm (0.44 mMol) 3-(6,7-dihydro-6H-[1,4]diazepino-[6,7,1-hi]indol-1-yl)-4-(benzofur-7-yl)-2,5-dioxopyrrole in 5 mL methanol containing 0.12 mL (0.88 mMol) triethylamine. Add 0.10 gm (0.66 mMol) phenyl chloroformate. Stir the reaction mixture for 3 hours. Quench the reaction with water and extract with ethyl acetate. Subject the organic phase to flash silica gel chromatography, eluting with a gradient of hexane containing from 50% to 0% ethyl acetate. Combine fractions containing desired product and concentrate them under reduced pressure to provide 0.096 gm of the title compound.

MS (ES): m/z=504.2 (M$^+$+1)

The compounds of EXAMPLES 240-447 may be prepared essentially as described in EXAMPLE 239.

| Example | Compound | Data |
|---|---|---|
| 240 | 3-(6-(3-trifluoromethylphenoxycarbonyl)-6,7-dihydro-6H-[1,4]diazepino[6,7,1-hi]indol-1-yl)-4-(benzofur-7-yl)-2,5-dioxopyrrole | MS (ES): m/z = 572 (M$^+$ + 1) |
| 241 | 3-(6-(4-methoxyphenoxycarbonyl)-6,7-dihydro-6H-[1,4]diazepino[6,7,1-hi]indol-1-yl)-4-(benzofur-7-yl)-2,5-dioxopyrrole | MS (ES): m/z = 534 (M$^+$ + 1) |
| 242 | 3-(6-(phenoxycarbonyl)-5,6,7,8-tetrahydro-6H-[1,4]diazocino[7,8,1-hi]indol-1-yl)-4-(benzofur-7-yl)-2,5-dioxopyrrole | HRMS: m/z = 518.1737 (M$^+$ + H) |
| 243 | 3-(6-(methoxycarbonyl)-6,7-dihydro-6H-[1,4]diazepino[6,7,1-hi]indol-1-yl)-4-(benzo[1,3]dioxol-4-yl)-2,5-dioxopyrrole | HRMS: m/z = 446.1352 (M$^+$ + H) |
| 244 | 3-(6-(ethoxycarbonyl)-6,7-dihydro-6H-[1,4]diazepino-[6,7,1-hi]indol-1-yl)-4-(benzofur-7-yl)-2,5-dioxopyrrole | MS (ES): m/z = 456.2 (M$^+$ + 1) |
| 245 | 3-(6-(isopropoxycarbonyl)-6,7-dihydro-6H-[1,4]diazepino[6,7,1-hi]indol-1-yl)-4-(benzofur-7-yl)-2,5-dioxopyrrole | MS (ES): m/z = 470 (M$^+$ + 1) |
| 246 | 3-(8-(isopropoxycarbonyl)-[1,5]diazaperhydroonino-[8,9,1-hi]indol-1-yl)-4-(benzofur-7-yl)-2,5-dioxopyrrole | MS (ES): m/z = 444 (M$^+$ + 1) |
| 247 | 3-(6-(butoxycarbonyl)-6,7-dihydro-6H-[1,4]diazepino-[6,7,1-hi]indol-1-yl)-4-(benzofur-7-yl)-2,5-dioxopyrrole | MS (ES): m/z = 484 (M$^+$ + 1) |
| 248 | 3-(6-(2-(methoxy)ethoxycarbonyl)-6,7-dihydro-6H-[1,4]diazepino[6,7,1-hi]indol-1-yl)-4-(benzofur-7-yl)-2,5-dioxopyrrole | MS (ES): m/z = 486.2 (M$^+$ + 1) |
| 249 | 3-(6-(2-(morpholin-4-yl)ethoxycarbonyl)-5,6,7,8-tetrahydro-6H-[1,4]diazocino[7,8,1-hi]indol-1-yl)-4-(benzofur-7-yl)-2,5-dioxopyrrole | HRMS: m/z = 555.2245 (M + H) |
| 250 | 3-(6-((1-methylpiperazin-4-yl)carbonyl)-6,7-dihydro-6H-[1,4]diazepino[6,7,1-hi]indol-1-yl)-4-(benzo[1,3]dioxol-4-yl)-2,5-dioxopyrrole | HRMS: m/z = 514.2090 (M + H) |
| 251 | 3-(6-((morpholin-4-yl)carbonyl)-6,7-dihydro-6H-[1,4]diazepino[6,7,1-hi]indol-1-yl)-4-(benzofur-7-yl)-2,5-dioxopyrrole | MS (ES): m/z = 497.2 (M$^+$ + 1) |
| 252 | 3-(6-((morpholin-4-yl)carbonyl)-6,7-dihydro-6H-[1,4]diazepino[6,7,1-hi]indol-1-yl)-4-(imidazo[1,2-a]pyridin-3-yl)-2,5-dioxopyrrole | MS (ES): m/z = 497.2 (M$^+$ + 1) |
| 253 | 3-(6-((morpholin-4-yl)carbonyl)-6,7-dihydro-6H-[1,4]diazepino[6,7,1-hi]indol-1-yl)-4-(7-cyanoimidazo[1,2-a]pyridin-3-yl)-2,5-dioxopyrrole | MS (ES): m/z = 522.1 (M$^+$ + 1) |
| 254 | 3-(6-((morpholin-4-yl)carbonyl)-5,6,7,8-tetrahydro-6H-[1,4]diazocino[7,8,1-hi]indol-1-yl)-4-(benzofur-7-yl)-2,5-dioxopyrrole | HRMS: m/z = 511.1978 (M + H) |
| 255 | 3-(6-((pyrrolidin-1-yl)carbonyl)-6,7-dihydro-6H-[1,4]diazepino[6,7,1-hi]indol-1-yl)-4-(imidazo[1,2-a]pyridin-3-yl)-2,5-dioxopyrrole | MS (ES): m/z = 497.2 (M$^+$ + 1) |
| 256 | 3-(6-((piperidin-1-yl)carbonyl)-6,7-dihydro-6H-[1,4]diazepino[6,7,1-hi]indol-1-yl)-4-(imidazo[1,2-a]pyridin-3-yl)-2,5-dioxopyrrole | MS (ES): m/z = 497.2 (M$^+$ + 1) |
| 257 | 3-(6-(trimethylacetyl)-6,7-dihydro-6H-[1,4]diazepino[6,7,1-hi]indol-1-yl)-4-(benzofur-7-yl)-2,5-dioxopyrrole | MS (ES): m/z = 468.2 (M$^+$ + 1) |
| 258 | 3-(6-(N,N-[dimethyl]aminocarbonyl)-[1,7]diazoper-hydroonino[8,9,1-hi]indol-1-yl)-4-(imidazo[1,2-a]-pyridin-3-yl)-2,5-dioxopyrrole | MS (ES): m/z = 483.2 (M$^+$ + 1) |
| 259 | 3-(7-(N,N-[dimethyl]aminocarbonyl)-[1,6]diazoper-hydroonino[8,9,1-hi]indol-1-yl)-4-(imidazo[1,2-a]pyridin-3-yl)-2,5-dioxopyrrole | MS (ES): m/z = 483.2 (M$^+$ + 1) |
| 260 | 3-(8-(N,N-[dimethyl]aminocarbonyl)-[1,5]diazoper-hydroonino[8,9,1-hi]indol-1-yl)-4-(imidazo[1,2-a]pyridin-3-yl)-2,5-dioxopyrrole | MS (ES): m/z = 483.2 (M$^+$ + 1) |
| 261 | 3-(8-(N,N-[dimethyl]aminocarbonyl)-[1,5]diazoper-hydroonino[8,9,1-hi]indol-1-yl)-4-(benzo[1,3]dioxol-4-yl)-2,5-dioxopyrrole | HRMS: 487.1973 (M + H) |
| 262 | 3-(6-(N,N-[dimethyl]aminocarbonyl)-6,7-dihydro-6H-[1,4]diazepino[6,7,1-hi]indol-1-yl)-4-(benzofur-7-yl)-2,5-dioxopyrrole | MS (ES): m/z = 455.2 (M$^+$ + 1) |
| 263 | 3-(6-(N,N-[dimethyl]aminocarbonyl)-6,7-dihydro-6H-[1,4]diazepino[6,7,1-hi]indol-1-yl)-4-(5-fluorobenzo-fur-7-yl)-2,5-dioxopyrrole | MS (ES): m/z = 473.2 (M$^+$ + 1) |
| 264 | 3-(6-(N,N-[dimethyl]aminocarbonyl)-6,7-dihydro-6H-[1,4]diazepino[6,7,1-hi]indol-1-yl)-4-(imidazo[1,2-a]pyridin-3-yl)-2,5-dioxopyrrole | MS (ES): m/z = 455.2 (M$^+$ + 1) |
| 265 | 3-(6-(N,N-[dimethyl]aminocarbonyl)-5,6,7,8-tetrahydro-6H-[1,4]diazocino[7,8,1-hi]indol-1-yl)-4-(imidazo[1,2-a]pyridin-3-yl)-2,5-dioxopyrrole | MS (ES): m/z = 469.6 (M$^+$ + 1) |
| 266 | 3-(6-(N,N-[dimethyl]aminocarbonyl)-6,7-dihydro-6H-[1,4]diazepino[6,7,1-hi]indol-1-yl)-4-(2,3-dihydro-benzo[1,4]dioxin-5-yl)-2,5-dioxopyrrole | HRMS: m/z = 473.1822 (M$^+$ + H) |
| 267 | 3-(6-(N,N-[dimethyl]aminocarbonyl)-6,7-dihydro-6H-[1,4]diazepino[6,7,1-hi]indol-1-yl)-4-(benzo[1,3]-dioxol-4-yl)-2,5-dioxopyrrole | HRMS: m/z = 459.1690 (M$^+$ + H) |
| 268 | 3-(6-(N,N-[dimethyl]aminocarbonyl)-[1,7]diazaperhydroonino[8,9,1-hi]indol-1-yl)-4-(imidazo[1,2-a]pyridin-3-yl)-2,5-dioxopyrrole | MS (ES): m/z = 483.2 (M$^+$ + 1) |
| 269 | 3-(7-(N,N-[dimethyl]aminocarbonyl)-[1,6]diazaperhydroonino[8,9,1-hi]indol-1-yl)-4-(imidazo[1,2-a]pyridin-3-yl)-2,5-dioxopyrrole | MS (ES): m/z = 483.2 (M$^+$ + 1) |
| 270 | 3-(6-(N,N-[dimethyl]aminocarbonyl)-5,6,7,8-tetra-hydro-6H-[1,4]diazocino[7,8,1-hi]indol-1-yl)-4-(benzofur-7-yl)-2,5-dioxopyrrole | HRMS: m/z = 469.1889 (M$^+$ + H) |
| 271 | 3-(6-(N,N-[dimethyl]aminocarbonyl)-7-methyl-6,7-dihydro-6H-[1,4]diazepino[6,7,1-hi]indol-1-yl)-4-(benzo[1,3]-dioxol-4-yl)-2,5-dioxopyrrole | HRMS: m/z = 473.1826 (M$^+$ + H) |
| 272 | 3-(6-(N,N-[dimethyl]aminocarbonyl)-7-methyl-6,7-dihydro-6H-[1,4]diazepino[6,7,1-hi]indol-1-yl)-4-(imidazo[1,2-a]pyridin-3-yl)-2,5-dioxopyrrole hydrochloride | HRMS: m/z = 469.2000 (M$^+$ + H) |
| 273 | 3-(6-(N,N-[dimethyl]aminocarbonyl)-5,6,7,8-tetrahydro-6H-[1,4]diazocino[7,8,1-hi]indol-1-yl)-4-(benzo[1,3]dioxol-4-yl)-2,5-dioxopyrrole | HRMS: 473.1841 (M$^+$ + H) |
| 274 | 3-(8-propionyl-[1,5]diazaperhydroonino[8,9,1-hi]indol-1-yl)-4-(2,3-dihydrobenzofur-7-yl)-2,5-dioxopyrrole | HRMS: m/z = 470.2086 (M + H) |

| Example | Compound | Data |
|---|---|---|
| 275 | 3-(6-propionyl-6,7-dihydro-6H-[1,4]diazepino[6,7,1-hi]indol-1-yl)-4-(imidazo[1,2-a]pyridin-3-yl)-2,5-dioxopyrrole | MS (ES): m/z = 440.2 (M⁺ + 1) |
| 276 | 3-(6-acetyl-5,6,7,8-tetrahydro-6H-[1,4]diazocino[7,8,1-hi]indol-1-yl)-4-(furo[3,2-c]pyridin-7-yl)-2,5-dioxopyrrole hydrochloride | MS (ES): m/z = 441.1 (M⁺ + 1) |
| 277 | 3-(8-propionyl-[1,5]diazoperhydroonino[8,9,1-hi]indol-1-yl)-4-(imidazo[1,2-a]pyridin-3-yl)-2,5-dioxopyrrole | MS (ES): m/z = 468.2 (M⁺ + 1) |
| 278 | 3-(6-propionyl-6,7-dihydro-6H-[1,4]diazepino[6,7,1-hi]indol-1-yl)-4-(benzofur-7-yl)-2,5-dioxopyrrole | MS (ES): m/z = 440.1 (M⁺ + 1) |
| 279 | 3-(8-acetyl-[1,5]diazoperhydroonino[8,9,1-hi]indol-1-yl)-4-(benzofur-7-yl)-2,5-dioxopyrrole | MS (ES): m/z = 454.2 (M⁺ + 1) |
| 280 | 3-(8-propionyl-[1,5]diazoperhydroonino[8,9,1-hi]indol-1-yl)-4-benzofur-7-yl)-2,5-dioxopyrrole | MS (ES): m/z = 468.2 (M⁺ + 1) |
| 281 | 3-(6-acetyl-6,7-dihydro-6H-[1,4]diazepino[6,7,1-hi]in-dol-1-yl)-4-(imidazo[1,2-a]pyridin-3-yl)-2,5-dioxopyrrole | MS (ES): m/z = 426.2 (M⁺ + 1) |
| 282 | 3-(8-acetyl-[1,5]diazoperhydroonino[8,9,1-hi]indol-1-yl)-4-(imidazo[1,2-a]pyridin-3-yl)-2,5-dioxopyrrole | MS (ES): m/z = 454.2 (M⁺ + 1) |
| 283 | 3-(6-acetyl-6,7-dihydro-6H-[1,4]diazepino[6,7,1-hi]-indol-1-yl)-4-(5-fluorobenzofur-7-yl)-2,5-dioxopyrrole | MS (ES): m/z = 444.1 (M⁺ + 1) |
| 284 | 3-(6-butyryl-6,7-dihydro-6H-[1,4]diazepino[6,7,1-hi]indol-1-yl)-4-(imidazo[1,2-a]pyridin-3-yl)-2,5-dioxopyrrole | MS (ES): m/z = 454.2 (M⁺ + 1) |
| 285 | 3-(6-isobutyryl-6,7-dihydro-6H-[1,4]diazepino[6,7,1-hi]indol-1-yl)-4-(imidazo[1,2-a]pyridin-3-yl)-2,5-dioxopyrrole | MS (ES): m/z = 454.2 (M⁺ + 1) |
| 286 | 3-(8-propionyl-[1,5]diazoperhydroonino[8,9,1-hi]indol-1-yl)-4-(furo-[3,2-c]pyridin-3-yl)-2,5-dioxopyrrole hydrochloride | MS (ES): m/z = 469.2 (M⁺ + 1) |
| 287 | 3-(8-acetyl-[1,5]diazoperhydroonino[8,9,1-hi]indol-1-yl)-4-(furo-[3,2-c]pyridin-3-yl)-2,5-dioxopyrrole hydrochloride | MS (ES): m/z = 455.1 (M⁺ + 1) |
| 288 | 3-(6-propionyl-5,6,7,8-tetrahydro-6H-[1,4]diazocino[7,8,1-hi]indol-1-yl)-4-(furo[3,2-c]pyridin-7-yl)-2,5-dioxopyrrole hydrochloride | MS (ES): m/z = 455.2 (M⁺ + 1) |
| 289 | 3-(6-propionyl-6,7-dihydro-6H-[1,4]diazepino[6,7,1-hi]indol-1-yl)-4-(furo[3,2-c]pyridin-7-yl)-2,5-dioxopyrrole hydrochloride | MS (ES): m/z = 441.2 (M⁺ + 1) |
| 290 | 3-(6-acetyl-6,7-dihydro-6H-[1,4]diazepino[6,7,1-hi]indol-1-yl)-4-(furo[3,2-c]pyridin-7-yl)-2,5-dioxopyrrole hydrochloride | MS (ES): m/z = 427.1 (M⁺ + 1) |
| 291 | 3-(6-acetyl-6,7-dihydro-6H-[1,4]diazepino[6,7,1-hi]indol-1-yl)-4-(benzo[1,3]dioxol-4-yl)-2,5-dioxopyrrole | HRMS: 430.1422 (M + H) |
| 292 | 3-(6-acetyl-6,7-dihydro-6H-[1,4]diazepino[6,7,1-hi]indol-1-yl)-4-(benzo[b]thien-7-yl)-2,5-dioxopyrrole | HRMS: 442.1251 (M + H) |
| 293 | 3-(6-propionyl-6,7-dihydro-6H-[1,4]diazepino[6,7,1-hi]indol-1-yl)-4-(benzo[1,3]dioxol-4-yl)-2,5-dioxopyrrole | HRMS: 444.1552 (M + H) |
| 294 | 3-(6-acetyl-6,7-dihydro-6H-[1,4]diazepino[6,7,1-hi]indol-1-yl)-4-(2,3-dihydrobenzofur-7-yl)-2,5-dioxopyrrole | HRMS: 428.1599 (M + H) |
| 295 | 3-(6-propionyl-6,7-dihydro-6H-[1,4]diazepino[6,7,1-hi]indol-1-yl)-4-(2,3-dihydrobenzofur-7-yl)-2,5-dioxopyrrole | HRMS: 442.1796 (M + H) |
| 296 | 3-(6-butyryl-6,7-dihydro-6H-[1,4]diazepino[6,7,1-hi]indol-1-yl)-4-(2,3-dihydrobenzofur-7-yl)-2,5-dioxopyrrole | HRMS: 456.1911 (M + H) |
| 297 | 3-(8-acetyl-[1,5]diazoperhydroonino[8,9,1-hi]indol-1-yl)-4-(2,3-dihydrobenzofur-7-yl)-2,5-dioxopyrrole | HRMS: 456.1921 (M + H) |
| 298 | 3-(8-propionyl-[1,5]diazoperhydroonino[8,9,1-hi]-indol-1-yl)-4-(benzo[1,3]dioxol-4-yl)-2,5-dioxopyrrole | HRMS: 472.1864 (M + H) |
| 299 | 3-(6-isobutyryl-[1,7]diazoperhydroonino[8,9,1-hi]indol-1-yl)-4-(imidazo[1,2-a]pyridin-3-yl)-2,5-dioxopyrrole | MS (ES): m/z = 480.3 (M + 1) |
| 300 | 3-(6-acetyl-5,6,7,8-tetrahydro-6H-[1,4]diazocino-[7,8,1-hi]indol-1-yl)-4-(furo[3,2-c]pyridin-7-yl)-2,5-dioxopyrrole hydrochloride | MS (ES): m/z = 441.1 (M⁺ + 1) |
| 301 | 3-(8-propionyl-[1,5]diazoperhydroonino[8,9,1-hi]indol-1-yl)-4-(benzo[1,3]dioxol-4-yl)-2,5-dioxopyrrole | HRMS: m/z = 469.1885 (M + H) |
| 302 | 3-(6-propionyl-5,6,7,8-tetrahydro-6H-[1,4]diazocino[7,8,1-hi]indol-1-yl)-4-(benzofur-7-yl)-2,5-dioxopyrrole | MS (ES): m/z = 454.2 (M⁺ + 1) |
| 303 | 3-(6-(N,N-dimethylaminocarbonyl)-6,7-dihydro-6H-[1,4]diazepino[6,7,1-hi]indol-1-yl)-4-(furo[3,2-c]pyridin-7-yl)-2,5-dioxopyrrole hydrochloride | MS (ES): m/z = 456.2 (M⁺ + 1) |
| 304 | 3-(6-((morpholin-4-yl)carbonyl)-6,7-dihydro-6H-[1,4]diazepino[6,7,1-hi]indol-1-yl)-4-(furo[3,2-c]pyridin-7-yl)-2,5-dioxopyrrole hydrochloride | MS (ES): m/z = 498.1 (M⁺ + 1) |
| 305 | 3-(6-((4-methylpiperazin-1-yl)carbonyl)-6,7-dihydro-6H-[1,4]diazepino[6,7,1-hi]indol-1-yl)-4-(furo[3,2-c]pyridin-7-yl)-2,5-dioxopyrrole dihydrochloride | MS (ES): m/z = 511.2 (M⁺ + 1) |
| 306 | 3-(6-((pyrrolidin-1-yl)carbonyl)-6,7-dihydro-6H-[1,4]diazepino[6,7,1-hi]indol-1-yl)-4-(furo[3,2-c]pyridin-7-yl)-2,5-dioxopyrrole hydrochloride | MS (ES): m/z = 482.2 (M⁺ + 1) |
| 307 | 3-(6-((pyrrolidin-1-yl)carbonyl)-5,6,7,8-tetrahydro-6H-[1,4]diazocino[7,8,1-hi]indol-1-yl)-4-(furo[3,2-c]pyridin-7-yl)-2,5-dioxopyrrole hydrochloride | MS (ES): m/z = 399.1 (M⁺ + 1) |
| 308 | 3-(6-((morpholin-4-yl)carbonyl)-5,6,7,8-tetrahydro-6H-[1,4]diazocino[7,8,1-hi]indol-1-yl)-4-(furo[3,2-c]pyridin-7-yl)-2,5-dioxopyrrole hydrochloride | MS (ES): m/z = 512.2 (M⁺ + 1) |
| 309 | 3-(6-((4-methylpiperazin-1-yl)carbonyl)-5,6,7,8-tetra-hydro-6H-[1,4]diazocino[7,8,1-hi]indol-1-yl)-4-(furo-[3,2-c]pyridin-7-yl)-2,5-dioxopyrrole dihydrochloride | MS (ES): m/z = 525.2 (M⁺ + 1) |
| 310 | 3-(6-((methoxy)carbonyl)-5,6,7,8-tetrahydro-6H-[1,4]diazocino[7,8,1-hi]indol-1-yl)-4-(furo[3,2-c]pyridin-7-yl)-2,5-dioxopyrrole hydrochloride | MS (ES): m/z = 457.1 (M⁺ + 1) |
| 311 | 3-(6-((ethoxy)carbonyl-5,6,7,8-tetrahydro-6H-[1,4]diazocino[7,8,1-hi]indol-1-yl)-4-(furo[3,2-c]pyridin-7-yl)-2,5-dioxopyrrole hydrochloride | MS (ES): m/z = 471.1 (M⁺ + 1) |
| 312 | 3-(6-((N,N-dimethylamino)carbonyl-5,6,7,8-tetrahydro-6H-[1,4]diazocino[7,8,1-hi]indol-1-yl)-4-(furo-[3,2-c]pyridin-7-yl)-2,5-dioxopyrrole hydrochloride | MS (ES): m/z = 470.2 (M⁺ + 1) |
| 313 | 3-(6-((piperidin-1-yl)carbonyl)-6,7-dihydro-6H-[1,4]diazepino[6,7,1-hi]indol-1-yl)-4-(furo[3,2-c]pyridin-7-yl)-2,5-dioxopyrrole hydrochloride | MS (ES): m/z = 496.2 (M⁺ + 1) |
| 314 | 3-(6-((piperidin-1-yl)carbonyl)-5,6,7,8-tetrahydro-6H-[1,4]diazocino[7,8,1-hi]indol-1-yl)-4-(furo[3,2-c]pyridin-7-yl)-2,5-dioxopyrrole hydrochloride | MS (ES): m/z = 510.2 (M⁺ + 1) |
| 315 | 3-(6-(octanoyl)-6,7-dihydro-6H-[1,4]diazepino[6,7,1-hi]indol-1-yl)-4-(furo[3,2-c]pyridin-7-yl)-2,5-dioxopyrrole hydrochloride | MS (ES): m/z = 511.2 (M⁺ + 1) |
| 316 | 3-(6-(octanoyl)-5,6,7,8-tetrahydro-6H-[1,4]diazocino-[7,8,1-hi]indol-1-yl)-4-(furo[3,2-c]pyridin-7-yl)-2,5-dioxopyrrole hydrochloride | MS (ES): m/z = 525.2 (M⁺ + 1) |
| 317 | 3-(7-methyl-6-((morpholin-4-yl)carbonyl)-6,7-dihydro-6H-[1,4]diazepino[6,7,1-hi]indol-1-yl)-4-(furo[3,2-c]pyridin-7-yl)-2,5-dioxopyrrole dihydrochloride | MS (ES): m/z = 512.2 (M⁺ + 1) |

-continued

| Example | Compound | Data |
|---|---|---|
| 318 | 3-(6-(isobutyryl)-5,6,7,8-tetrahydro-6H-[1,4]diazo-cino[7,8,1-hi]indol-1-yl)-4-(4-(dimethylamino)furo-[3,2-c]pyridin-7-yl)-2,5-dioxopyrrole | MS (ES): m/z = 512.2 (M$^+$ + 1) |
| 319 | 3-(6-(N,N-dimethylamino)carbonyl)-5,6,7,8-tetrahydro-6H-[1,4]diazocino[7,8,1-hi]indol-1-yl)-4-(4-(dimethylamino)furo-[3,2-c]pyridin-7-yl)-2,5-dioxopyrrole | MS (ES): m/z = 513.2 (M$^+$ + 1) |
| 320 | 3-(6-(ethoxycarbonyl)-6,7-dihydro-6H-[1,4]diazepino[6,7,1-hi]indol-1-yl)-4-(imidazo[1,2-a]pyridin-3-yl)-2,5-dioxopyrrole | MS (ES): m/z = 456 (M$^+$ + 1) |
| 321 | 3-(6-(isopropoxycarbonyl)-6,7-dihydro-6H-[1,4]diazepino[6,7,1-hi]indol-1-yl)-4-(imidazo[1,2-a]pyridin-3-yl)-2,5-dioxopyrrole | MS (ES): m/z = 470 (M$^+$ + 1) |
| 322 | 3-(6-(butyryl)-6,7-dihydro-6H-[1,4]diazepino[6,7,1-hi]indol-1-yl)-4-(benzofur-7-yl)-2,5-dioxopyrrole | MS (ES): m/z = 452.3 (M$^+$ + 1) |
| 323 | 3-(6-(2-methylpropionyl)-6,7-dihydro-6H-[1,4]diazepino[6,7,1-hi]indol-1-yl)-4-(benzofur-7-yl)-2,5-dioxopyrrole | MS (ES): m/z = 454.2 (M$^+$ + 1) |
| 324 | 3-(6-(propionyl)-6,7-dihydro-6H-[1,4]diazepino-[6,7,1-hi]indol-1-yl)-4-(5-fluorobenzofur-7-yl)-2,5-dioxopyrrole | MS (ES): m/z = 457.9 (M$^+$ + 1) |
| 325 | 3-(6-(butyryl)-6,7-dihydro-6H-[1,4]diazepino[6,7,1-hi]indol-1-yl)-4-(5-fluorobenzofur-7-yl)-2,5-dioxopyrrole | MS (ES): m/z = 471.9 (M$^+$ + 1) |
| 326 | 3-(6-(2-methylpropionyl)-6,7-dihydro-6H-[1,4]di-azepino[6,7,1-hi]indol-1-yl)-4-(5-fluorobenzofur-7-yl)-2,5-dioxopyrrole | MS (ES): m/z = 471.9 (M$^+$ + 1) |
| 327 | 3-(6-(N-methylamino(carbonyl))-6,7-dihydro-6H-[1,4]diazepino[6,7,1-hi]indol-1-yl)-4-(5-fluorobenzo-fur-7-yl)-2,5-dioxopyrrole | MS (ES): m/z = 458.8 (M$^+$ + 1) |
| 328 | 3-(6-(N,N-dimethylamino(carbonyl))-6,7-dihydro-6H-[1,4]diazepino[6,7,1-hi]indol-1-yl)-4-(5-fluorobenzo-fur-7-yl)-2,5-dioxopyrrole | MS (ES): m/z = 473.1 (M$^+$ + 1) |
| 329 | 3-((6-(morpholin-4-yl)carbonyl)-6,7-dihydro-6H-[1,4]diazepino[6,7,1-hi]indol-1-yl)-4-(5-fluorobenzo-fur-7-yl)-2,5-dioxopyrrole | MS (ES): m/z = 515.1 (M$^+$ + 1) |
| 330 | 3-(8-(butyryl)-[1,5]diazoperhydroonino-[8,9,1-hi]-indol-1-yl)-4-(imidazo[1,2-a]pyridin-3-yl)-2,5-dioxopyrrole | MS (ES): m/z = 482.3 (M$^+$ + 1) |
| 331 | 3-(8-(isobutyryl)-[1,5]diazoperhydroonino-[8,9,1-hi]-indol-1-yl)-4-(imidazo[1,2-a]pyridin-3-yl)-2,5-dioxopyrrole | MS (ES): m/z = 482.3 (M$^+$ + 1) |
| 332 | 3-(6-(N-[methyl]aminocarbonyl)-6,7-dihydro-6H-[1,4]diazepino[6,7,1-hi]indol-1-yl)-4-(benzofur-7-yl)-2,5-dioxopyrrole | MS (ES): m/z = 441.1 (M$^+$ + 1) |
| 333 | 3-(6-(butyryl)-5,6,7,8-tetrahydro-6H-[1,4]diazo-cino[7,8,1-hi]indol-1-yl)-4-(imidazo[1,2-a]pyridin-3-yl)-2,5-dioxopyrrole | MS (ES): m/z = 468.6 (M$^+$ + 1) |
| 334 | 3-((6-(piperidin-1-yl)carbonyl)-6,7-dihydro-6H-[1,4]diazepino[6,7,1-hi]indol-1-yl)-4-(imidazo[1,2-a]pyridin-3-yl)-2,5-dioxopyrrole | MS (ES): m/z = 495.1 (M$^+$ + 1) |
| 335 | 3-((6-(pyrrolidin-1-yl)carbonyl)-6,7-dihydro-6H-[1,4]diazepino[6,7,1-hi]indol-1-yl)-4-(imidazo[1,2-a]pyridin-3-yl)-2,5-dioxopyrrole | MS (ES): m/z = 481.1 (M$^+$ + 1) |
| 336 | 3-((5-methyl-6-(morpholin-4-yl)carbonyl)-6,7-dihydro-6H-[1,4]diazepino[6,7,1-hi]indol-1-yl)-4-(imidazo[1,2-a]pyridin-3-yl)-2,5-dioxopyrrole | MS (ES): m/z = 511.1 (M$^+$ + 1) |
| 337 | 3-((4-methyl-6-(morpholin-4-yl)carbonyl)-6,7-dihydro-6H-[1,4]diazepino[6,7,1-hi]indol-1-yl)-4-(imidazo[1,2-a]pyridin-3-yl)-2,5-dioxopyrrole | MS (ES): m/z = 511.2 (M$^+$ + 1) |
| 338 | 3-((6-octanoyl)-6,7-dihydro-6H-[1,4]diazepino[6,7,1-hi]indol-1-yl)-4-(imidazo[1,2-a]pyridin-3-yl)-2,5-dioxopyrrole | MS (ES): m/z = 510.2 (M$^+$ + 1) |
| 339 | 3-((4,4-dimethyl-6-(morpholin-4-yl)carbonyl)-6,7-dihydro-6H-[1,4]diazepino[6,7,1-hi]indol-1-yl)-4-(imidazo[1,2-a]pyridin-3-yl)-2,5-dioxopyrrole | MS (ES): m/z = 525.0 (M$^+$ + 1) |
| 340 | 3-((8-fluoro-6-(morpholin-4-yl)carbonyl)-6,7-dihydro-6H-[1,4]diazepino[6,7,1-hi]indol-1-yl)-4-(imidazo[1,2-a]pyridin-3-yl)-2,5-dioxopyrrole | MS (ES): m/z = 513.0 (M$^+$ + 1) |
| 341 | 3-((6-N,N-[dimethyl]aminocarbonyl)-6,7-dihydro-6H-[1,4]diazepino[6,7,1-hi]indol-1-yl)-4-(6-fluoroimidazo[1,2-a]pyridin-3-yl)-2,5-dioxopyrrole | MS (ES): m/z = 473.1 (M$^+$ + 1) |
| 342 | 3-(6-(isobutyryl)-6,7-dihydro-6H-[1,4]diazepino[6,7,1-hi]indol-1-yl)-4-(6-fluoroimidazo[1,2-a]pyridin-3-yl)-2,5-dioxopyrrole | MS (ES): m/z = 472.1 (M$^+$ + 1) |
| 343 | 3-((6-(morpholin-4-yl)carbonyl)-6,7-dihydro-6H-[1,4]diazepino[6,7,1-hi]indol-1-yl)-4-(8-cyanoimidazo[1,2-a]pyridin-3-yl)-2,5-dioxopyrrole | MS (ES): m/z = 522.1 (M$^+$ + 1) |
| 344 | 3-((6-(piperidin-1-yl)carbonyl)-6,7-dihydro-6H-[1,4]diazepino[6,7,1-hi]indol-1-yl)-4-(8-cyanoimidazo[1,2-a]pyridin-3-yl)-2,5-dioxopyrrole | MS (ES): m/z = 520.0 (M$^+$ + 1) |
| 345 | 3-((6-(morpholin-4-yl)carbonyl)-6,7-dihydro-6H-[1,4]diazepino[6,7,1-hi]indol-1-yl)-4-(8-aminoimidazo[1,2-a]pyridin-3-yl)-2,5-dioxopyrrole | MS (ES): m/z = 512.2 (M$^+$ + 1) |
| 346 | 3-((8-(morpholin-4-yl)carbonyl)-[1,5]diazaperhydro-onino[8,9,1-hi]indol-1-yl)-4-(6-methyl-imidazo[1,2-a]pyridin-3-yl)-2,5-dioxopyrrole | MS (ES): m/z = 586.9 (M$^+$ + 1) |
| 347 | 3-((6-(morpholin-4-yl)carbonyl)-6,7-dihydro-6H-[1,4]diazepino[6,7,1-hi]indol-1-yl)-4-(6,8-dimethyl-imidazo[1,2-a]pyridin-3-yl)-2,5-dioxopyrrole | MS (ES): m/z = 523.0 (M$^+$ + 1) |
| 348 | 3-((6-(morpholin-4-yl)carbonyl)-6,7-dihydro-6H-[1,4]diazepino[6,7,1-hi]indol-1-yl)-4-(6-methyl-8-bromoimidazo[1,2-a]pyridin-3-yl)-2,5-dioxopyrrole | MS (ES): m/z = 586.9 (M$^+$ + 1) |
| 349 | 3-((6-(morpholin-4-yl)carbonyl)-6,7-dihydro-6H-[1,4]diazepino[6,7,1-hi]indol-1-yl)-4-(imidazo[1,2-a]pyrazin-3-yl)-2,5-dioxopyrrole | MS (ES): m/z = 498.2 (M$^+$ + 1) |
| 350 | 3-((6-(piperidin-1-yl)carbonyl)-6,7-dihydro-6H-[1,4]diazepino[6,7,1-hi]indol-1-yl)-4-(imidazo[1,2-a]pyrazin-3-yl)-2,5-dioxopyrrole | MS (ES): m/z = 496.2 (M$^+$ + 1) |
| 351 | 3-((6-(piperidin-1-yl)carbonyl)-6,7-dihydro-6H-[1,4]diazepino[6,7,1-hi]indol-1-yl)-4-(imidazo[1,2-b]pyridazin-3-yl)-2,5-dioxopyrrole | MS (ES): m/z = 496.1 (M$^+$ + 1) |
| 352 | 3-((6-(isopropoxy)carbonyl)-6,7-dihydro-6H-[1,4]diazepino[6,7,1-hi]indol-1-yl)-4-(imidazo[1,2-b]pyridazin-3-yl)-2,5-dioxopyrrole | MS (ES): m/z = 502.0 (M$^+$ + 1) |
| 353 | 3-((6-(piperidin-1-yl)carbonyl)-6,7-dihydro-6H-[1,4]diazepino[6,7,1-hi]indol-1-yl)-4-(6-methyl-imidazo[1,2-b]pyridazin-3-yl)-2,5-dioxopyrrole | MS (ES): m/z = 510.1 (M$^+$ + 1) |
| 354 | 3-(6-(isopropyl)-6,7-dihydro-6H-[1,4]diazepino-[6,7,1-hi]indol-1-yl)-4-(5,6,7,8-tetrahydroimidazo[1,2-b]pyridin-3-yl)-2,5-dioxopyrrole | MS (ES): m/z = 458.2 (M$^+$ + 1) |
| 355 | 3-((6-(N,N-dimethylaminocarbonyl)-6,7-dihydro-6H-[1,4]diazepino-[6,7,1-hi]indol-1-yl)-4-(5,6,7,8-tetrahydroimidazo[1,2-b]pyridin-3-yl)-2,5-dioxopyrrole hydrochloride | MS (ES): m/z = 459.2 (M$^+$ + 1) |
| 356 | 3-((isopropoxy)carbonyl)-6,7-dihydro-6H-[1,4]diazepino[6,7,1-hi]indol-1-yl)-4-(6-methyl-imidazo[1,2-a]pyridin-3-yl)-2,5-dioxopyrrole | MS (ES): m/z = 483.9 (M$^+$ + 1) |
| 357 | 3-(6-((isopropoxy)carbonyl)-6,7-dihydro-6H-[1,4]diazepino[6,7,1-hi]indol-1-yl)-4-(7-methyl-imidazo[1,2-a]pyridin-3-yl)-2,5-dioxopyrrole | MS (ES): m/z = 484.0 (M$^+$ + 1) |
| 358 | 3-((isopropoxy)carbonyl)-6,7-dihydro-6H-[1,4]diazepino[6,7,1-hi]indol-1-yl)-4-(8-methyl-imidazo[1,2-a]pyridin-3-yl)-2,5-dioxopyrrole | MS (ES): m/z = 484.0 (M$^+$ + 1) |
| 359 | 3-((6-(morpholin-4-yl)carbonyl)-6,7-dihydro-6H-[1,4]diazepino[6,7,1-hi]indol-1-yl)-4-(2-methyl-imidazo[1,2-a]pyridin-3-yl)-2,5-dioxopyrrole | MS (ES): m/z = 509.0 (M$^+$ + 1) |
| 360 | 3-((6-(morpholin-4-yl)carbonyl)-6,7-dihydro-6H-[1,4]diazepino[6,7,1-hi]indol-1-yl)-4-(6- | MS (ES): m/z = 508.9 (M$^+$ + 1) |

| Example | Compound | Data |
|---|---|---|
| | methyl-imidazo[1,2-a]pyridin-3-yl)-2,5-dioxopyrrole | |
| 361 | 3-(9-fluoro-6-((morpholin-4-yl)carbonyl)-6,7-dihydro-6H-[1,4]diazepino[6,7,1-hi]indol-1-yl)-4-(6-methyl-imidazo[1,2-a]pyridin-3-yl)-2,5-dioxopyrrole | MS (ES): m/z = 527.0 (M$^+$ + 1) |
| 362 | 3-(6-((morpholin-4-yl)carbonyl)-6,7-dihydro-6H-[1,4]diazepino[6,7,1-hi]indol-1-yl)-4-(5-methyl-imidazo[1,2-a]pyridin-3-yl)-2,5-dioxopyrrole | MS (ES): m/z = 509.0 (M$^+$ + 1) |
| 363 | 3-(9-fluoro-6-((isopropoxy)carbonyl)-6,7-dihydro-6H-[1,4]diazepino[6,7,1-hi]indol-1-yl)-4-(8-methyl-imidazo[1,2-a]pyridin-3-yl)-2,5-dioxopyrrole | MS (ES): m/z = 488.1 (M$^+$ + 1) |
| 364 | 3-(6-((isopropoxy)carbonyl)-6,7-dihydro-6H-[1,4]diazepino[6,7,1-hi]indol-1-yl)-4-(8-fluoroimidazo[1,2-a]pyridin-3-yl)-2,5-dioxopyrrole | MS (ES): m/z = 488.2 (M$^+$ + 1) |
| 365 | 3-(9-fluoro-6-((piperidin-1-yl)carbonyl)-6,7-dihydro-6H-[1,4]diazepino[6,7,1-hi]indol-1-yl)-4-(imidazo[1,2-a]pyridin-3-yl)-2,5-dioxopyrrole | MS (ES): m/z = 513.2 (M$^+$ + 1) |
| 366 | 3-(6-((morpholin-4-yl)carbonyl)-6,7-dihydro-6H-[1,4]diazepino[6,7,1-hi]indol-1-yl)-4-(6-fluoroimidazo[1,2-a]pyridin-3-yl)-2,5-dioxopyrrole | MS (ES): m/z = 515.1 (M$^+$ + 1) |
| 367 | 3-(6-((piperidin-1-yl)carbonyl)-6,7-dihydro-6H-[1,4]diazepino[6,7,1-hi]indol-1-yl)-4-(8-fluoroimidazo[1,2-a]pyridin-3-yl)-2,5-dioxopyrrole | MS (ES): m/z = 513.0 (M$^+$ + 1) |
| 368 | 3-(6-(butyryl)-6,7-dihydro-6H-[1,4]diazepino[6,7,1-hi]indol-1-yl)-4-(6-methylimidazo[1,2-a]pyridin-3-yl)-2,5-dioxopyrrole | MS (ES): m/z = 468 (M$^+$ + 1) |
| 369 | 3-(6-(butyryl)-6,7-dihydro-6H-[1,4]diazepino[6,7,1-hi]indol-1-yl)-4-(7-methoxyimidazo[1,2-a]pyridin-3-yl)-2,5-dioxopyrrole | MS (ES): m/z = 484 (M$^+$ + 1) |
| 370 | 3-(6-(isopropoxycarbonyl)-6,7-dihydro-6H-[1,4]diaze-pino[6,7,1-hi]indol-1-yl)-4-(7-methoxyimidazo[1,2-a]pyridin-3-yl)-2,5-dioxopyrrole | MS (ES): m/z = 500 (M$^+$ + 1) |
| 371 | 3-(6-((piperidin-1-yl)carbonyl)-6,7-dihydro-6H-[1,4]diazepino[6,7,1-hi]indol-1-yl)-4-(7-methoxyimidazo-[1,2-a]pyridin-3-yl)-2,5-dioxopyrrole | MS (ES): m/z = 525 (M$^+$ + 1) |
| 372 | 3-(6-((morpholin-4-yl)carbonyl)-6,7-dihydro-6H-[1,4]diazepino[6,7,1-hi]indol-1-yl)-4-(8-fluoroimidazo[1,2-a]pyridin-3-yl)-2,5-dioxopyrrole | HRMS (ES): m/z = 515.1849 |
| 373 | 3-(6-((morpholin-4-yl)carbonyl)-6,7-dihydro-6H-[1,4]-diazepino[6,7,1-hi]indol-1-yl)-4-(8-methoxy-imidazo[1,2-a]pyridin-3-yl)-2,5-dioxopyrrole | MS (ES): m/z = 527.2 (M$^+$ + 1) |
| 374 | 3-(6-((morpholin-4-yl)carbonyl)-6,7-dihydro-6H-[1,4]-diazepino[6,7,1-hi]indol-1-yl)-4-(8-benzyloxy-imidazo[1,2-a]pyridin-3-yl)-2,5-dioxopyrrole | MS (ES): m/z = 603.2 (M$^+$ + 1) |
| 375 | 3-(6-((morpholin-4-yl)carbonyl)-6,7-dihydro-6H-[1,4]-diazepino[6,7,1-hi]indol-1-yl)-4-(7-chloroimidazo[1,2-a]pyridin-3-yl)-2,5-dioxopyrrole | MS (ES): m/z = 530.9 (M$^+$ + 1) |
| 376 | 3-(6-((piperidin-1-yl)carbonyl)-6,7-dihydro-6H-[1,4]diazepino[6,7,1-hi]indol-1-yl)-4-(8-methoxy-imidazo[1,2-a]pyridin-3-yl)-2,5-dioxopyrrole | MS (ES): m/z = 525.0 (M$^+$ + 1) |
| 377 | 3-(6-((isopropoxy)carbonyl)-6,7-dihydro-6H-[1,4]-diazepino[6,7,1-hi]indol-1-yl)-4-(8-methoxy-imidazo[1,2-a]pyridin-3-yl)-2,5-dioxopyrrole | MS (ES): m/z = 499.9 (M$^+$ + 1) |
| 378 | 3-(6-((piperidin-1-yl)carbonyl)-6,7-dihydro-6H-[1,4]diazepino[6,7,1-hi]indol-1-yl)-4-(7-chloroimidazo[1,2-a]pyridin-3-yl)-2,5-dioxopyrrole | MS (ES): m/z = 546.9 (M$^+$ + 1) |
| 379 | (+/−)-3-(7-methyl-6-isobutyryl-6,7-dihydro-6H-[1,4]diazepino[6,7,1-hi]indol-1-yl)-4-(imidazo[1,2-a]-pyridin-3-yl)-2,5-dioxopyrrole | HRMS: m/z = 468.2031 |
| 380 | (−)-3-(7-methyl-6-isobutyryl-6,7-dihydro-6H-[1,4]diazepino[6,7,1-hi]indol-1-yl)-4-(imidazo[1,2-a]-pyridin-3-yl)-2,5-dioxopyrrole | HRMS: m/z = 468.2006 |
| 381 | (+)-3-(7-methyl-6-isobutyryl-6,7-dihydro-6H-[1,4]diazepino[6,7,1-hi]indol-1-yl)-4-(imidazo[1,2-a]-pyridin-3-yl)-2,5-dioxopyrrole | HRMS: m/z = 468.2040 |
| 382 | (+)-3-(7-methyl-6-(N,N-[dimethyl]aminocarbonyl)-6,7-dihydro-6H-[1,4]diazepino[6,7,1-hi]indol-1-yl)-4-(imidazo[1,2-a]-pyridin-3-yl)-2,5-dioxopyrrole | HRMS: m/z = 469.1981 (M$^+$ + 1) |
| 383 | (+)-3-(7-methyl-6-(N,N-[dimethyl]aminocarbonyl)-6,7-dihydro-6H-[1,4]diazepino[6,7,1-hi]indol-1-yl)-4-(imidazo[1,2-a]-pyridin-3-yl)-2,5-dioxopyrrole hydrochloride | MS (ES): m/z = 496.1 (M$^+$ + 1) |
| 384 | (−)-3-(7-methyl-6-(N,N-[dimethyl]aminocarbonyl)-6,7-dihydro-6H-[1,4]diazepino[6,7,1-hi]indol-1-yl)-4-(imidazo[1,2-a]-pyridin-3-yl)-2,5-dioxopyrrole | HRMS: m/z = 496.1990 |
| 385 | (−)-3-(7-methyl-6-(N,N-[dimethyl]aminocarbonyl)-6,7-dihydro-6H-[1,4]diazepino[6,7,1-hi]indol-1-yl)-4-(imidazo[1,2-a]-pyridin-3-yl)-2,5-dioxopyrrole hydrochloride | MS (ES): m/z = 496.1 (M$^+$ + 1) |
| 386 | (+/−)-3-(7-methyl-6-((morpholin-4-yl)carbonyl)-6,7-dihydro-6H-[1,4]diazepino[6,7,1-hi]indol-1-yl)-4-(imidazo[1,2-a]-pyridin-3-yl)-2,5-dioxopyrrole | HRMS: m/z = 511.2085 |
| 387 | (+)-3-(7-methyl-6-((morpholin-4-yl)carbonyl)-6,7-dihydro-6H-[1,4]diazepino[6,7,1-hi]indol-1-yl)-4-(imidazo[1,2-a]-pyridin-3-yl)-2,5-dioxopyrrole | MS (ES): m/z = 511.1 (M$^+$ + 1) |
| 388 | (−)-3-(7-methyl-6-((morpholin-4-yl)carbonyl)-6,7-dihydro-6H-[1,4]diazepino[6,7,1-hi]indol-1-yl)-4-(imidazo[1,2-a]-pyridin-3-yl)-2,5-dioxopyrrole | MS (ES): m/z = 511.1 (M$^+$ + 1) |
| 389 | 3-(6-((piperidin-1-yl)carbonyl)-6,7-dihydro-6H-[1,4]diazepino[6,7,1-hi]indol-1-yl)-4-(7-chloro-imidazo[1,2-a]pyridin-3-yl)-2,5-dioxopyrrole | HRMS: m/z = 529.1170 |
| 390 | (+)-3-(7-methyl-6-((piperidin-1-yl)carbonyl)-6,7-dihydro-6H-[1,4]diazepino[6,7,1-hi]indol-1-yl)-4-(7-chloroimidazo[1,2-a]pyridin-3-yl)-2,5-dioxopyrrole | HRMS: m/z = 543.1915 |
| 391 | (−)-3-(7-methyl-6-((piperidin-1-yl)carbonyl)-6,7-dihydro-6H-[1,4]diazepino[6,7,1-hi]indol-1-yl)-4-(6-methylimidazo[1,2-a]pyridin-3-yl)-2,5-dioxopyrrole | HRMS: m/z = 523.2465 |
| 392 | 3-(6-((isopropoxy)carbonyl)-6,7-dihydro-6H-[1,4]diazepino[6,7,1-hi]indol-1-yl)-4-(7-chloro-imidazo[1,2-a]pyridin-3-yl)-2,5-dioxopyrrole | HRMS: m/z = 504.1440 |
| 393 | 3-(6-((cyclopropyl)carbonyl)-6,7-dihydro-6H-[1,4]diazepino[6,7,1-hi]indol-1-yl)-4-(imidazo[1,2-a]pyridin-3-yl)-2,5-dioxopyrrole | HRMS: m/z = 452.1706 |
| 394 | 3-(6-(isobutyryl)-6,7-dihydro-6H-[1,4]diazepino-[6,7,1-hi]indol-1-yl)-4-(imidazo[2,1-b]thiazol-3-yl)-2,5-dioxopyrrole | HRMS: m/z = 460.1443 |
| 395 | 3-(6-((morpholin-4-yl)carbonyl)-6,7-dihydro-6H-[1,4]diazepino[6,7,1-hi]indol-1-yl)-4-(imidazo[2,1-b]thiazol-3-yl)-2,5-dioxopyrrole | HRMS: m/z = 503.1494 |
| 396 | 3-(6-(piperidin-1-yl)carbonyl)-6,7-dihydro-6H-[1,4]diazepino[6,7,1-hi]indol-1-yl)-4-(thiazolo[3,2-b][1,2,4]triazol-6-yl)-2,5-dioxopyrrole | HRMS: m/z = 502.1675 |
| 397 | 3-(8-((2-methoxyeth-1-oxy)carbonyl)-[1,5]diazaper-hydroonino[8,9,1-hi]indol-1-yl)-4-(benzofur-7-yl)-2,5-dioxopyrrole | MS (ES): m/z = 514 (M$^+$ + 1) |

-continued

| Example | Compound | Data |
|---|---|---|
| 398 | 3-(6-((isobutoxy)carbonyl)-6,7-dihydro-6H-[1,4]diazepino[6,7,1-hi]indol-1-yl)-4-(imidazo[1,2-a]pyridin-3-yl)-2,5-dioxopyrrole | MS (ES): m/z = 484 (M$^+$ + 1) |
| 399 | 3-(6-((propoxy)carbonyl)-6,7-dihydro-6H-[1,4]diazepino[6,7,1-hi]indol-1-yl)-4-(imidazo[1,2-a]pyridin-3-yl)-2,5-dioxopyrrole | MS (ES): m/z = 470 (M$^+$ + 1) |
| 400 | 3-(6-((neopentoxy)carbonyl)-6,7-dihydro-6H-[1,4]diazepino[6,7,1-hi]indol-1-yl)-4-(imidazo[1,2-a]pyridin-3-yl)-2,5-dioxopyrrole | MS (ES): m/z = 498 (M$^+$ + 1) |
| 401 | 3-(6-((2-fluoroeth-1-oxy)carbonyl)-6,7-dihydro-6H-[1,4]diazepino[6,7,1-hi]indol-1-yl)-4-(imidazo[1,2-a]pyridin-3-yl)-2,5-dioxopyrrole | MS (ES): m/z = 474 (M$^+$ + 1) |
| 402 | 3-(6-((phenoxy)carbonyl)-6,7-dihydro-6H-[1,4]diazepino[6,7,1-hi]indol-1-yl)-4-(imidazo[1,2-a]pyridin-3-yl)-2,5-dioxopyrrole | MS (ES): m/z = 504 (M$^+$ + 1) |
| 403 | 3-(6-((isopropoxy)carbonyl)-6,7-dihydro-6H-[1,4]diazepino[6,7,1-hi]indol-1-yl)-4-(6-methoxy-imidazo[1,2-a]pyridin-3-yl)-2,5-dioxopyrrole | MS (ES): m/z = 500 (M$^+$ + 1) |
| 404 | 3-(6-((piperidin-1-yl)carbonyl)-6,7-dihydro-6H-[1,4]diazepino[6,7,1-hi]indol-1-yl)-4-(6-methoxy-imidazo[1,2-a]pyridin-3-yl)-2,5-dioxopyrrole | MS (ES): m/z = 525 (M$^+$ + 1) |
| 405 | 3-(6-((isobutoxy)carbonyl)-6,7-dihydro-6H-[1,4]diazepino[6,7,1-hi]indol-1-yl)-4-(6-chloro-imidazo[1,2-a]pyridin-3-yl)-2,5-dioxopyrrole | MS (ES): m/z = 518 (M$^+$ + 1) |
| 406 | 3-(6-((piperidin-1-yl)carbonyl)-6,7-dihydro-6H-[1,4]diazepino[6,7,1-hi]indol-1-yl)-4-(6-chloro-imidazo[1,2-a]pyridin-3-yl)-2,5-dioxopyrrole | MS (ES): m/z = 529 (M$^+$ + 1) |
| 407 | 3-(6-((piperidin-1-yl)carbonyl)-6,7-dihydro-6H-[1,4]diazepino[6,7,1-hi]indol-1-yl)-4-(6-bromo-imidazo[1,2-a]pyridin-3-yl)-2,5-dioxopyrrole | MS (ES): m/z = 574 (M$^+$ + 1) |
| 408 | 3-(6-((isopropoxy)carbonyl)-6,7-dihydro-6H-[1,4]diazepino[6,7,1-hi]indol-1-yl)-4-(7-ethyl-imidazo[1,2-a]pyridin-3-yl)-2,5-dioxopyrrole | MS (ES): m/z = 498 (M$^+$ + 1) |
| 409 | 3-(6-((piperidin-1-yl)carbonyl)-6,7-dihydro-6H-[1,4]diazepino[6,7,1-hi]indol-1-yl)-4-(7-ethyl-imidazo[1,2-a]pyridin-3-yl)-2,5-dioxopyrrole | MS (ES): m/z = 523 (M$^+$ + 1) |
| 410 | 3-(6-((2-methoxyeth-1-oxy)carbonyl)-6,7-dihydro-6H-[1,4]diazepino[6,7,1-hi]indol-1-yl)-4-(imidazo[1,2-a]pyridin-3-yl)-2,5-dioxopyrrole | MS (ES): m/z = 486 (M$^+$ + 1) |
| 411 | 3-(6-((piperidin-1-yl)carbonyl)-6,7-dihydro-6H-[1,4]diazepino[6,7,1-hi]indol-1-yl)-4-(6-isopropyl-imidazo[1,2-a]pyridin-3-yl)-2,5-dioxopyrrole | MS (ES): m/z = 537.4 (M$^+$ + 1) |
| 412 | 3-(6-((isopropoxy)carbonyl)-6,7-dihydro-6H-[1,4]diazepino[6,7,1-hi]indol-1-yl)-4-(6-isopropyl-imidazo[1,2-a]pyridin-3-yl)-2,5-dioxopyrrole | MS (ES): m/z = 512.4 (M$^+$ + 1) |
| 413 | 3-(6-((morpholin-4-yl)carbonyl)-6,7-dihydro-6H-[1,4]diazepino[6,7,1-hi]indol-1-yl)-4-(imidazo[1,2-a]pyrimidin-3-yl)-2,5-dioxopyrrole | MS (ES): m/z = 496.1 (M$^+$ + 1) |
| 414 | 3-(6-((piperidin-1-yl)carbonyl)-6,7-dihydro-6H-[1,4]diazepino[6,7,1-hi]indol-1-yl)-4-(imidazo[1,2-a]pyrimidin-3-yl)-2,5-dioxopyrrole | MS (ES): m/z = 496.1 (M$^+$ + 1) |
| 415 | 3-(6-((isopropoxy)carbonyl)-6,7-dihydro-6H-[1,4]diazepino[6,7,1-hi]indol-1-yl)-4-(imidazo[1,2-a]pyrimidin-3-yl)-2,5-dioxopyrrole | MS (ES): m/z = 471.1 (M$^+$ + 1) |
| 416 | 3-(6-((morpholin-4-yl)carbonyl)-6,7-dihydro-6H-[1,4]diazepino[6,7,1-hi]indol-1-yl)-4-(7-amino-imidazo[1,2-a]pyrimidin-3-yl)-2,5-dioxopyrrole | MS (ES): m/z = 513 (M$^+$ + 1) |
| 417 | 3-(6-((morpholin-4-yl)carbonyl)-6,7-dihydro-6H-[1,4]diazepino[6,7,1-hi]indol-1-yl)-4-(imidazo[1,2-c]pyrimidin-3-yl)-2,5-dioxopyrrole | MS (ES): m/z = 498 (M$^+$ + 1) |
| 418 | 3-(6-((piperidin-1-yl)carbonyl)-6H-[1,4]diazepino[6,7,1-hi]indol-1-yl)-4-(7-amino-imidazo[1,2-a]pyrimidin-3-yl)-2,5-dioxopyrrole | MS (ES): m/z = 511.3 (M$^+$ + 1) |
| 419 | 3-(6-((piperidin-1-yl)carbonyl)-6,7-dihydro-6H-[1,4]diazepino[6,7,1-hi]indol-1-yl)-4-(6-ethyl-imidazo[1,2-a]pyrimidin-3-yl)-2,5-dioxopyrrole | MS (ES): m/z = 523 (M$^+$ + 1) |
| 420 | 3-(6-((dipropylamino)carbonyl)-6,7-dihydro-6H-[1,4]diazepino[6,7,1-hi]indol-1-yl)-4-(4,5,6,7-tetrahydro-pyrazolo[1,5-a]pyridin-3-yl)-2,5-dioxopyrrole | HRMS: m/z = 515.2756 (M$^+$ + 1) |
| 421 | 3-(6-((dipropylamino)carbonyl)-6,7-dihydro-6H-[1,4]diazepino[6,7,1-hi]indol-1-yl)-4-(pyrazolo[1,5-a]-pyridin-3-yl)-2,5-dioxopyrrole | HRMS: m/z = 511.2440 (M$^+$ + 1) |
| 422 | 3-(6-((dibutylamino)carbonyl)-6,7-dihydro-6H-[1,4]diazepino[6,7,1-hi]indol-1-yl)-4-(imidazo[1,2-a]-pyridin-3-yl)-2,5-dioxopyrrole | HRMS: m/z = 539.2751 (M$^+$ + 1) |
| 423 | 3-(6-(isobutyryl)-6,7-dihydro-6H-[1,4]diazepino-[6,7,1-hi]indol-1-yl)-4-(pyrazolo[1,5-a]pyridin-3-yl)-2,5-dioxopyrrole | HRMS: m/z = 454.1879 (M$^+$ + 1) |
| 424 | 3-(6-((dimethylamino)carbonyl)-6,7-dihydro-6H-[1,4]diazepino[6,7,1-hi]indol-1-yl)-4-(pyrazolo[1,5-a]-pyridin-3-yl)-2,5-dioxopyrrole | HRMS: m/z = 455.1832 (M$^+$ + 1) |
| 425 | 3-(6-(isobutyryl)-6,7-dihydro-6H-[1,4]diazepino-[6,7,1-hi]indol-1-yl)-4-(4,5,6,7-tetrahydropyrazolo-[1,5-a]pyridin-3-yl)-2,5-dioxopyrrole | HRMS: m/z = 458.2192 (M$^+$ + 1) |
| 426 | 3-(6-((dimethylamino)carbonyl)-6,7-dihydro-6H-[1,4]diazepino[6,7,1-hi]indol-1-yl)-4-(4,5,6,7-tetrahydro-pyrazolo[1,5-a]-pyridin-3-yl)-2,5-dioxopyrrole | HRMS: m/z = 459.2145 (M$^+$ + 1) |
| 427 | 3-(6-((morpholin-4-yl)carbonyl)-6,7-dihydro-6H-[1,4]diazepino[6,7,1-hi]indol-1-yl)-4-(4,5,6,7-tetrahydro-pyrazolo[1,5-a]-pyridin-3-yl)-2,5-dioxopyrrole | HRMS: m/z = 501.2250 (M$^+$ + 1) |
| 428 | 3-(6-((dipropylamino)carbonyl)-6,7-dihydro-6H-[1,4]diazepino[6,7,1-hi]indol-1-yl)-4-(imidazo[1,2-a]-pyridin-3-yl)-2,5-dioxopyrrole | HRMS: m/z = 511.2458 (M$^+$ + 1) |
| 429 | 3-(6-((morpholin-4-yl)carbonyl)-6,7-dihydro-6H-[1,4]diazepino[6,7,1-hi]indol-1-yl)-4-(pyrazolo[1,5-a]-pyridin-3-yl)-2,5-dioxopyrrole | HRMS: m/z = 497.1937 (M$^+$ + 1) |
| 430 | 3-(6-((morpholin-4-yl)carbonyl)-6,7-dihydro-6H-[1,4]diazepino[6,7,1-hi]indol-1-yl)-4-(5,6,7,8-tetrahydro-imidazo[1,2-a]pyridin-3-yl)-2,5-dioxopyrrole | HRMS: m/z = 501.2250 (M$^+$ + 1) |
| 431 | 3-(6-((dipropylamino)carbonyl)-6,7-dihydro-6H-[1,4]diazepino[6,7,1-hi]indol-1-yl)-4-(5,6,7,8-tetrahydro-imidazo[1,2-a]pyridin-3-yl)-2,5-dioxopyrrole | HRMS: m/z = 515.2771 (M$^+$ + 1) |
| 432 | 3-(9-chloro-6,7-dihydro-6H-[1,4]diazepino[6,7,1-hi]-indol-1-yl)-4-(imidazo[1,2-a]pyridin-3-yl)-2,5-dioxopyrrole | HRMS: m/z = 418.1071 (M$^+$ + 1) |
| 433 | 3-(9-chloro-6-((morpholin-4-yl)carbonyl)-6,7-dihydro-6H-[1,4]diazepino[6,7,1-hi]indol-1-yl)-4-(imidazo[1,2-a]pyridin-3-yl)-2,5-dioxopyrrole | HRMS: m/z = 531.1548 (M$^+$ + 1) |
| 434 | 3-(9-chloro-6-((dipropylamino)carbonyl)-6,7-dihydro-6H-[1,4]diazepino[6,7,1-hi]indol-1-yl)-4-(imidazo[1,2-a]pyridin-3-yl)-2,5-dioxopyrrole | HRMS: m/z = 545.2068 (M$^+$ + 1) |
| 435 | 3-(6-((diethylamino)carbonyl)-6,7-dihydro-6H-[1,4]diazepino[6,7,1-hi]indol-1-yl)-4-(imidazo[1,2-a]pyridin-3-yl)-2,5-dioxopyrrole | HRMS: m/z = 483.2145 (M$^+$ + 1) |
| 436 | 3-(6-((4-phenylpyrazin-1-yl)carbonyl)-6,7-dihydro-6H-[1,4]diazepino[6,7,1-hi]indol-1-yl)-4-(imidazo[1,2-a]pyridin-3-yl)-2,5-dioxopyrrole | HRMS: m/z = 572.2410 (M$^+$ + 1) |
| 437 | 3-(6-((cis-2,6-dimethylmorpholin-4-yl)carbonyl)-6,7-dihydro-6H-[1,4]diazepino[6,7,1-hi]indol-1-yl)-4-(imidazo[1,2-a]pyridin-3-yl)-2,5-dioxopyrrole | HRMS: m/z = 525.2250 (M$^+$ + 1) |

| Example | Compound | Data |
|---|---|---|
| 438 | 3-(6-((4,4-dimethylpiperidin-1-yl)carbonyl)-6,7-dihydro-6H-[1,4]diazepino[6,7,1-hi]indol-1-yl)-4-(imidazo[1,2-a]pyridin-3-yl)-2,5-dioxopyrrole | HRMS: m/z = 523.2458 (M$^+$ + 1) |
| 439 | 3-(6-((imidazol-1-yl)carbonyl)-6,7-dihydro-6H-[1,4]diazepino[6,7,1-hi]indol-1-yl)-4-(imidazo[1,2-a]pyridin-3-yl)-2,5-dioxopyrrole | HRMS: m/z = 478.1628 (M$^+$ + 1) |
| 440 | 3-(6-((cis-2,6-dimethylmorpholin-4-yl)carbonyl)-6,7-dihydro-6H-[1,4]diazepino[6,7,1-hi]indol-1-yl)-4-(5,6,7,8-tetrahydroimidazo[1,2-a]pyridin-3-yl)-2,5-dioxopyrrole | MS (ES): m/z = 529.3 (M$^+$ + 1) |
| 441 | 3-(6-((cis-2,6-dimethylmorpholin-4-yl)carbonyl)-6,7-dihydro-6H-[1,4]diazepino[6,7,1-hi]indol-1-yl)-4-(pyrazolo[1,5-a]pyridin-3-yl)-2,5-dioxopyrrole | HRMS: m/z = 525.2250 (M$^+$ + 1) |
| 442 | 3-(6-((cis-2,6-dimethylmorpholin-4-yl)carbonyl)-6,7-dihydro-6H-[1,4]diazepino[6,7,1-hi]indol-1-yl)-4-(4,5,6,7-tetrahydropyrazolo[1,5-a]pyridin-3-yl)-2,5-dioxopyrrole | HRMS: m/z = 529.2563 (M$^+$ + 1) |
| 443 | 3-(6-((4-methylpiperazin-1-yl)carbonyl)-6,7-dihydro-6H-[1,4]diazepino[6,7,1-hi]indol-1-yl)-4-(imidazo[1,2-a]pyridin-3-yl)-2,5-dioxopyrrole | HRMS: m/z = 510.2254 (M$^+$ + 1) |
| 444 | 3-(9-chloro-6-((piperidin-1-yl)carbonyl)-6,7-dihydro-6H-[1,4]diazepino[6,7,1-hi]indol-1-yl)-4-(imidazo[1,2-a]pyridin-3-yl)-2,5-dioxopyrrole | HRMS: m/z = 529.1775 (M$^+$ + 1) |
| 445 | 3-(6-(butyryl)-6,7-dihydro-6H-[1,4]diazepino[6,7,1-hi]indol-1-yl)-4-(8-chloroimidazo[1,2-a]pyridin-3-yl)-2,5-dioxopyrrole | HRMS: m/z = 488.1489 (M$^+$ + 1) |
| 446 | 3-(6-((piperidin-1-yl)carbonyl)-6,7-dihydro-6H-[1,4]diazepino[6,7,1-hi]indol-1-yl)-4-(8-chloro-imidazo[1,2-a]pyridin-3-yl)-2,5-dioxopyrrole | HRMS: m/z = 529.1775 (M$^+$ + 1) |
| 447 | 3-(6-((isopropoxy)carbonyl)-6,7-dihydro-6H-[1,4]diazepino[6,7,1-hi]indol-1-yl)-4-(8-chloro-imidazo[1,2-a]pyridin-3-yl)-2,5-dioxopyrrole | HRMS: m/z = 504.1339 (M$^+$ + 1) |

EXAMPLE 448

3-(6-glycyl-[1,7]diazoperhydroonino[8,9,1-hi]indol-1-yl)-4-(benzofur-7-yl)-2,5-dioxopyrrole trifluoroacetate Combine 3-([1,7]diazoperhydroonino[8,9,1-hi]indol-1-yl)-4-(benzofur-7-yl)-2,5-dioxopyrrole (90 mg, 0.22 mmol), N-[tert-butoxycarbonyl]glycine (40 mg, 0.22 mmol), 4-N,N-dimethylaminopyridine (10 mg), triethylamine (0.091 ml, 0.66 mmol) and 1-(3-dimethylaminopropyl)-3-ethylcarbodiimide hydrochloride (63 mg, 0.33 mmol) in dichloromethane (5 ml) and stir at room temperature overnight. Load the reaction mixture directly onto a 10 gram SCX™ Varian column, wash sequentially with methanol and 2.0 M ammonia in methanol. Combine fractions and concentrate under reduced pressure. Slurry the residue in dichloromethane (5 ml), add trifluoroacetic acid (1 ml), and stir for 1 hour. Concentrate under reduced pressure, treat the residue with diethyl ether, and filter the suspension to provide the title compound as a yellow solid.

HRMS: 469.1891.

The compounds or EXAMPLES 449-482 may be prepared essentially as described in EXAMPLE 448.

| Example | Compound | Data |
|---|---|---|
| 449 | 3-(6-(propionyl)-5,6,7,8-tetrahydro-6H-[1,4]diazo-cino[7,8,1-hi]indol-1-yl)-4-(imidazo[1,2-a]pyridin-3-yl)-2,5-dioxopyrrole | MS (ES): m/z = 454.5 (M$^+$ + 1) |
| 450 | 3-(6-(butyryl)-5,6,7,8-tetrahydro-6H-[1,4]diazocino-[7,8,1-hi]indol-1-yl)-4-(imidazo[1,2-a]pyridin-3-yl)-2,5-dioxopyrrole | MS (ES): m/z = 468.6 (M$^+$ + 1) |
| 451 | 3-(6-(isobutyryl)-5,6,7,8-tetrahydro-6H-[1,4]diazo-cino[7,8,1-hi]indol-1-yl)-4-(imidazo[1,2-a]pyridin-3-yl)-2,5-dioxopyrrole | MS (ES): m/z = 468.6 (M$^+$ + 1) |
| 452 | 3-(6-(isobutyryl)-5,6,7,8-tetrahydro-6H-[1,4]diazo-cino[7,8,1-hi]indol-1-yl)-4-(furo[3,2-c]pyridin-7-yl)-2,5-dioxopyrrole hydrochloride | MS (ES): m/z = 469.2 (M$^+$ + 1) |
| 453 | 3-(6-(methoxyethoxyacetyl)-5,6,7,8-tetrahydro-6H-[1,4]diazocino[7,8,1-hi]indol-1-yl)-4-(benzofur-7-yl)-2,5-dioxopyrrole | MS (ES): m/z = 514.2 (M$^+$ + 1) |
| 454 | 3-(6-(methoxyethoxyacetyl)-5,6,7,8-tetrahydro-6H-[1,4]diazocino[7,8,1-hi]indol-1-yl)-4-(benzo-[1,3]dioxol-4-yl)-2,5-dioxopyrrole | MS (ES): m/z = 518.2 (M$^+$ + 1) |
| 455 | 3-(6-((1-(tert-butoxycarbonyl)piperidin-4-yl)carbonyl)-5,6,7,8-tetrahydro-6H-[1,4]diazocino[7,8,1-hi]indol-1-yl)-4-(furo[3,2-c]pyridin-7-yl)-2,5-dioxopyrrole | MS (ES): m/z = 610.2 (M$^+$ + 1) |
| 456 | 3-(6-(pyrazin-2-ylcarbonyl)-5,6,7,8-tetrahydro-6H-[1,4]diazocino[7,8,1-hi]indol-1-yl)-4-(benzofur-7-yl)-2,5-dioxopyrrole | HRMS: m/z = 504.1678 (M$^+$ + H) |
| 457 | 3-(6-(propionyl)-6,7-dihydro-6H-[1,4]diazepino[6,7,1-hi]indol-1-yl)-4-(2,3-dihydrobenzo[1,4]dioxin-4-yl)-2,5-dioxopyrrole | HRMS: m/z = 458.1729 (M$^+$ + H) |
| 458 | 3-(6-(methoxyethoxyacetyl)-6,7-dihydro-6H-[1,4]diazepino[6,7,1-hi]indol-1-yl)-4-(benzofur-7-yl)-2,5-dioxopyrrole | MS (ES): m/z = 500 (M$^+$ + 1) |
| 459 | 3-(6-(N,N-dimethylglycyl)-6,7-dihydro-6H-[1,4]diazepino[6,7,1-hi]indol-1-yl)-4-(benzofur-7-yl)-2,5-dioxopyrrole | MS (ES): m/z = 469 (M$^+$ + 1) |
| 460 | 3-(6-((pyridin-3-yl)carbonyl)-6,7-dihydro-6H-[1,4]diazepino[6,7,1-hi]indol-1-yl)-4-(benzofur-7-yl)-2,5-dioxopyrrole | MS (ES): m/z = 489 (M$^+$ + 1) |
| 461 | 3-(6-(pyrazin-2-ylcarbonyl)-6,7-dihydro-6H-[1,4]diazepino[6,7,1-hi]indol-1-yl)-4-(benzofur-7-yl)-2,5-dioxopyrrole | MS (ES): m/z = 490.2 (M$^+$ + 1) |
| 462 | 3-(8-(isobutyryl)-[1,5]diazoperhydroonino[8,9,1-hi]indol-1-yl)-4-(benzo[1,3]dioxol-5-yl)-2,5-dioxopyrrole | HRMS: m/z = 486.2029 (M$^+$ + H) |
| 463 | 3-(8-(N,N-dimethylglycyl)-[1,5]diazoperhydroonino-[8,9,1-hi]-indol-1-yl)-4-(benzofur-7-yl)-2,5-dioxopyrrole | MS (ES): m/z = 497 (M$^+$ + 1) |
| 464 | 3-(8-((pyrazin-2-yl)carbonyl)-[1,5]diazoperhydro-onino-[8,9,1-hi]indol-1-yl)-4-(benzofur-7-yl)-2,5-dioxopyrrole | MS (ES): m/z = 518 (M$^+$ + 1) |
| 465 | 3-(6-(oxoacetyl)-6,7-dihydro-6H-[1,4]diazepino[6,7,1-hi]indol-1-yl)-4-(furo[3,2-c]pyridin-7-yl)-2,5-dioxopyrrole | MS (ES): m/z = 456.2 (M$^+$ + 1) |
| 466 | 3-(6-((pyridin-3-yl)carbonyl)-6,7-dihydro-6H-[1,4]diazepino[6,7,1-hi]indol-1-yl)-4-(6-methylimidazo[1,2-a]pyridin-3-yl)-2,5-dioxopyrrole | MS (ES): m/z = 503.0 (M$^+$ + 1) |
| 467 | 3-(9-fluoro-6-(3-(morpholin-4-yl)propionyl)-6,7-dihydro-6H-[1,4]diazepino[6,7,1-hi]indol-1-yl)-4-(imidazo[1,2-a]pyridin-3-yl)-2,5-dioxopyrrole hydrochloride | MS (ES): m/z = 543.0 (M$^+$ + 1) |
| 468 | 3-(6-(2,2-difluoroacetyl)-6,7-dihydro-6H-[1,4]diazepino[6,7,1-hi]indol-1-yl)-4-(imidazo[1,2-a]-pyridin-3-yl)-2,5-dioxopyrrole | MS (ES): m/z = 462.1 (M$^+$ + 1) |
| 469 | 3-(6-((3-(morpholin-4-yl)propionyl)-6,7-dihydro-6H-[1,4]diazepino[6,7,1-hi]indol-1-yl)-4-(8-fluoro-imidazo[1,2-a]-pyridin-3-yl)-2,5-dioxopyrrole | MS (ES): m/z = 543.2 (M$^+$ + 1) |
| 470 | 3-(6-((3-(morpholin-4-yl)propionyl)-6,7-dihydro-6H-[1,4]diazepino[6,7,1-hi]indol-1-yl)-4-(8-benzyloxy-imidazo[1,2-a]-pyridin-3-yl)-2,5-dioxopyrrole | MS (ES): m/z = 631.2 (M$^+$ + 1) |

| Example | Compound | Data |
|---|---|---|
| 471 | 3-(6-((tetrahydropyran-4-yl)carbonyl)-6,7-dihydro-6H-[1,4]diazepino[6,7,1-hi]indol-1-yl)-4-(imidazo[1,2-a]pyridin-3-yl)-2,5-dioxopyrrole | HRMS: m/z = 496.1975 |
| 472 | 3-(6-((pyridin-3-yl)carbonyl)-6,7-dihydro-6H-[1,4]diazepino[6,7,1-hi]indol-1-yl)-4-(imidazo[1,2-a]pyridin-3-yl)-2,5-dioxopyrrole | MS (ES): m/z = 489 ($M^+ + 1$) |
| 473 | 3-(6-((6-methylpyridin-3-yl)carbonyl)-6,7-dihydro-6H-[1,4]diazepino[6,7,1-hi]indol-1-yl)-4-(imidazo[1,2-a]pyridin-3-yl)-2,5-dioxopyrrole | MS (ES): m/z = 503 ($M^+ + 1$) |
| 474 | 3-(6-((pyridin-2-yl)carbonyl)-6,7-dihydro-6H-[1,4]diazepino[6,7,1-hi]indol-1-yl)-4-(6-chloro-imidazo[1,2-a]pyridin-3-yl)-2,5-dioxopyrrole | MS (ES): m/z = 523 ($M^+ + 1$) |
| 475 | 3-(6-((pyridin-3-yl-N-oxide)carbonyl)-6,7-dihydro-6H-[1,4]diazepino[6,7,1-hi]indol-1-yl)-4-(imidazo[1,2-a]pyridin-3-yl)-2,5-dioxopyrrole | MS (ES): m/z = 505 ($M^+ + 1$) |
| 476 | 3-(6-((2-trifluoromethylpyridin-4-yl)carbonyl)-6,7-dihydro-6H-[1,4]diazepino[6,7,1-hi]indol-1-yl)-4-(imidazo[1,2-a]pyridin-3-yl)-2,5-dioxopyrrole | MS (ES): m/z = 557 ($M^+ + 1$) |
| 477 | 3-(6-((6-(2-(pyrrolidin-1-yl)eth-1-yl)pyridin-3-yl)carbonyl)-6,7-dihydro-6H-[1,4]diazepino[6,7,1-hi]indol-1-yl)-4-(imidazo[1,2-a]pyridin-3-yl)-2,5-dioxopyrrole | MS (ES): m/z = 586 ($M^+ + 1$) |
| 478 | 3-(6-((5-(methoxycarbonyl)pyridin-2-yl)carbonyl)-6,7-dihydro-6H-[1,4]diazepino[6,7,1-hi]indol-1-yl)-4-(imidazo[1,2-a]pyridin-3-yl)-2,5-dioxopyrrole | MS (ES): m/z = 547 ($M^+ + 1$) |
| 479 | 3-(6-((4-(carboxy)pyridin-2-yl)carbonyl)-6,7-dihydro-6H-[1,4]diazepino[6,7,1-hi]indol-1-yl)-4-(imidazo[1,2-a]pyridin-3-yl)-2,5-dioxopyrrole | MS (ES): m/z = 533 ($M^+ + 1$) |
| 480 | 3-(6-((pyrazin-2-yl)carbonyl)-6,7-dihydro-6H-[1,4]diazepino[6,7,1-hi]indol-1-yl)-4-(imidazo[1,2-a]pyridin-3-yl)-2,5-dioxopyrrole | MS (ES): m/z = 490 ($M^+ + 1$) |
| 481 | 3-(6-((pyridin-2-yl)carbonyl)-6,7-dihydro-6H-[1,4]diazepino[6,7,1-hi]indol-1-yl)-4-(imidazo[1,2-a]pyridin-3-yl)-2,5-dioxopyrrole | MS (ES): m/z = 489 ($M^+ + 1$) |
| 482 | 3-(6-((pyrimidin-5-yl)carbonyl)-6,7-dihydro-6H-[1,4]diazepino[6,7,1-hi]indol-1-yl)-4-(imidazo[1,2-a]pyridin-3-yl)-2,5-dioxopyrrole | MS (ES): m/z = 490 ($M^+ + 1$) |
| 484 | 3-(6-(3-(imidazol-4-yl)propionyl)-6,7-dihydro-6H-[1,4]diazepino[6,7,1-hi]indol-1-yl)-4-(imidazo[1,2-a]pyridin-3-yl)-2,5-dioxopyrrole | MS (ES): m/z = 506 ($M^+ + 1$) |
| 485 | 3-(6-((1-methylpiperidin-4-yl)carbonyl)-6,7-dihydro-6H-[1,4]diazepino[6,7,1-hi]indol-1-yl)-4-(imidazo[1,2-a]pyridin-3-yl)-2,5-dioxopyrrole | MS (ES): m/z = 509 ($M^+ + 1$) |
| 486 | 3-(6-(3-(morpholin-4-yl)propionyl)-6,7-dihydro-6H-[1,4]diazepino[6,7,1-hi]indol-1-yl)-4-(imidazo[1,2-a]pyridin-3-yl)-2,5-dioxopyrrole | MS (ES): m/z = 525 ($M^+ + 1$) |
| 487 | 3-(6-(imidazol-4-yl)carbonyl)-6,7-dihydro-6H-[1,4]diazepino[6,7,1-hi]indol-1-yl)-4-(imidazo[1,2-a]pyridin-3-yl)-2,5-dioxopyrrole | MS (ES): m/z = 478 ($M^+ + 1$) |
| 488 | 3-(6-(2-(1,1-dioxothiomorpholin-4-yl)acetyl)-6,7-dihydro-6H-[1,4]diazepino[6,7,1-hi]indol-1-yl)-4-(imidazo[1,2-a]pyridin-3-yl)-2,5-dioxopyrrole | MS (ES): m/z = 559 ($M^+ + 1$) |
| 489 | 3-(6-(imidazol-2-yl)carbonyl)-6,7-dihydro-6H-[1,4]diazepino[6,7,1-hi]indol-1-yl)-4-(imidazo[1,2-a]pyridin-3-yl)-2,5-dioxopyrrole | MS (ES): m/z = 478 ($M^+ + 1$) |
| 490 | 3-(6-(3-(4-nitroimidazol-1-yl)propionyl)-6,7-dihydro-6H-[1,4]diazepino[6,7,1-hi]indol-1-yl)-4-(imidazo[1,2-a]pyridin-3-yl)-2,5-dioxopyrrole | MS (ES): m/z = 551 ($M^+ + 1$) |
| 491 | 3-(6-(3-methyl-6,7-dihydropyrrolo[1,2-a]imidazol-6-yl)carbonyl)-6,7-dihydro-6H-[1,4]diazepino[6,7,1-hi]indol-1-yl)-4-(imidazo[1,2-a]pyridin-3-yl)-2,5-dioxopyrrole | MS (ES): m/z = 532 ($M^+ + 1$) |
| 492 | 3-(6-(4-(4-nitroimidazol-1-yl)butyryl)-6,7-dihydro-6H-[1,4]diazepino[6,7,1-hi]indol-1-yl)-4-(imidazo[1,2-a]pyridin-3-yl)-2,5-dioxopyrrole | MS (ES): m/z = 565 ($M^+ + 1$) |
| 493 | 3-(6-((azetidin-3-yl)carbonyl)-6,7-dihydro-6H-[1,4]diazepino[6,7,1-hi]indol-1-yl)-4-(imidazo[1,2-a]pyridin-3-yl)-2,5-dioxopyrrole | HRMS: m/z = 491.1502 ($M^+ + H$) |

EXAMPLE 483

R-3-(6-((1-methylpyrrolidin-1-yl)carbonyl)-6,7-dihydro-6H-[1,4]diazepino[6,7,1-hi]indol-1-yl)-4-(imidazo[1,2-a]pyridin-3-yl)-2,5-dioxopyrrole Combine 3-(6,7-dihydro-6H-[1,4]diazepino[6,7,1-hi]indol-1-yl)-4-(imidazo[1,2-a]pyridin-3-yl)-2,5-dioxopyrrole dihydrochloride (175 mg, 0.38 mmol), N-[methyl]-L-proline (242 mg, 1.92 mmol), 1-hydroxybenzotriazole (259 mg, 1.92 mmol), N,N-diisopropylethylamine (496 mg, 3.84 mmol) and 1-(3-dimethylaminopropyl)-3-ethyl-carbodiimide hydrochloride (386 mg, 1.92 mmol) in dimethylformamide (7 ml) and stir at room temperature for 3 hours. Pour the reaction mixture into saturated aqueous sodium bicarbonate (110 ml) and extract with dichloromethane (3×100 ml). Dry the organic extracts with magnesium sulfate and concentrate under reduced pressure. Subject the residue to silica gel chromatography, eluting with dichloromethane containing 2-15% methanol to provide the title compound.

MS (ES): m/z=495 ($M^+$+1)

The compounds of EXAMPLES 484-493 may be prepared essentially as described in EXAMPLE 483.

EXAMPLE 494

3-(6-((2-(morpholin-4-yl)eth-1-yl)oxy)carbonyl)-6,7-dihydro-6H-[1,4]diazepino[6,7,1-hi]indol-1-yl)-4-(imidazo[1,2-a]pyrrolin-3-yl)-2,5-dioxopyrrole Combine 4-(2-hydroxyethyl)morpholine (79 mg, 0.60 mmol), dihydroxysuccinimid-yl carbonate (228 mg, 0.90 mmol) and triethylamine (182 mg, 1.80 mmol) in acetonitrile (4 ml) and stir at room temperature under nitrogen for 40 minutes. Add triethylamine (1 ml) and 3-(6,7-dihydro-6H-[1,4]diazepino[6,7,1-hi]indol-1-yl)-4-(imidazo[1,2-a]pyridin-3-yl)-2,5-dioxopyrrole (274 mg, 0.60 mmol) and stir for 30 minutes. Pour into saturated aqueous sodium bicarbonate (110 ml) and extract with dichloromethane (3×100 ml). Combine organic phases and wash with saturated aqueous sodium chloride (250 ml), dry over magnesium sulfate, and concentrate under reduced pressure. Subject the residue to silica gel chromatography, eluting with dichloromethane containing 1-10% methanol to provide the title compound.

MS (ES): m/z=541 ($M^+$+1)

The compound in the following table may be prepared essentially as described in EXAMPLE 494.

| Example | Compound | Data |
|---|---|---|
| 495 | 3-(6-((2-(pyrrolidin-2-on-1-yl)eth-1-yl)oxy)carbonyl)-6,7-dihydro-6H-[1,4]diazepino[6,7,1-hi]indol-1-yl)- | MS (ES): m/z = 540 ($M^+ + 1$) |

-continued

| Example | Compound | Data |
|---|---|---|
| | (imidazo[1,2-a]pyridin-3-yl)-2,5-dioxopyrrole | |

EXAMPLE 496

3-(6-((piperazin-1-yl)carbonyl)-6,7-dihydro-6H-[1,4]diazepino[6,7,1-hi]indol-1-yl)-4-(imidazo[1,2-a]pyridin-3-yl)-2,5-dioxopyrrole Add 1-methyl-3-((4-(tert-butoxycarbonyl)piperazin-1-yl)carbonyl)imidazol-1-ium iodide (0.925 g, 0.218 mmol) to 3-(6,7-dihydro-6H-[1,4]diazepino[6,7,1-hi]indol-1-yl)-4-(imidazo[1,2-a]-pyridin-3-yl)-2,5-dioxopyrrole dihydrochloride (0.50 g, 1.09 mmol) and triethylamine (0.66 g, 6.58 mmol) in N,N-dimethylformamide. Stir at 20° C. for 6 hours. Add 2 M ammonia in methanol (50 ml) and concentrate under reduced pressure. Subject the residue to silica gel chromatography, eluting with ethyl acetate to provide an orange solid. Dissolve the solid in ethyl acetate (20 ml) and add ethanethiol (0.5 ml) followed by 4 M hydrogen chloride p-dioxane (20 ml). Stir 1 hour at 20° C. Concentrate under reduced pressure and subject the residue to preparative reverse phase high pressure liquid chromatography (Kromasil KR100-10C18-250P2), eluting with 5-65% acetonitrile in 0.03% hydrochloric acid to provide the title compound as an orange solid.

HRMS: m/z=496.2097 (M$^+$+H)

The compounds of EXAMPLES 497-501 may be prepared essentially as described in EXAMPLE 496.

| Example | Compound | Data |
|---|---|---|
| 497 | 3-(6-((N,N-[di-(2-methoxyeth-1-yl)]amino)carbonyl)-6,7-dihydro-6H-[1,4]diazepino[6,7,1-hi]indol-1-yl)-4-(imidazo[1,2-a]pyridin-3-yl)-2,5-dioxopyrrole | HRMS: m/z = 543.2353 (M$^+$ + 1) |
| 498 | 3-(6-((N,N-[di-(isobutyryl)]amino)carbonyl)-6,7-dihydro-6H-[1,4]diazepino[6,7,1-hi]indol-1-yl)-4-(imidazo[1,2-a]pyridin-3-yl)-2,5-dioxopyrrole | HRMS: m/z = 539.2768 (M$^+$ + 1) |
| 499 | 3-(6-(([1,4]oxazepin-4-yl)carbonyl)-6,7-dihydro-6H-[1,4]diazepino[6,7,1-hi]indol-1-yl)-4-(imidazo[1,2-a]pyridin-3-yl)-2,5-dioxopyrrole | HRMS: m/z = 511.2103 (M$^+$ + 1) |
| 500 | 3-(6-((N,N-[di-(isopropyl)]amino)carbonyl)-6,7-dihydro-6H-[1,4]diazepino[6,7,1-hi]indol-1-yl)-4-(imidazo[1,2-a]pyridin-3-yl)-2,5-dioxopyrrole | HRMS: m/z = 511.2458 (M$^+$ + 1) |
| 501 | 3-(6-((piperidin-4-on-1-yl)carbonyl)-6,7-dihydro-6H-[1,4]diazepino[6,7,1-hi]indol-1-yl)-4-(imidazo[1,2-a]pyridin-3-yl)-2,5-dioxopyrrole | HRMS: m/z = 509.1937 (M$^+$ + 1) |

EXAMPLE 502

3-(6-(aminosulfonyl)-6,7-dihydro-6H-[1,4]diazepino[6,7,1-hi]indol-1-yl)-4-(benzofur-7-yl)-2,5-dioxopyrrole Add 3-(6,7-dihydro-6H-[1,4]diazepino[6,7,1-hi]indol-1-yl)-4-(benzofur-7-yl)-2,5-dioxopyrrole hydrochloride (300 mg, 0.714 mmol) and sulfamide (1.0 g, 10.4 mmol) to pyridine (20 mL). Reflux and stir under nitrogen for 20 minutes, concentrate under reduced pressure. Dilute the residue with ethyl acetate, wash sequentially with 0.25 M hydrochloric acid and aqueous saturated sodium chloride. Dry the organic phase over anhydrous magnesium sulfate, filter, and concentrate under reduced pressure. Precipitate the residue from ethyl acetate to obtain the title compound as an orange solid (125 mg, 37%).

MS (ES): m/z=463.1 (M+1).

The compounds of EXAMPLES 503-506 may be prepared essentially as described in EXAMPLE 502.

| Example | Compound | Data |
|---|---|---|
| 503 | 3-(6-(aminosulfonyl)-5,6,7,8-tetrahydro-6H-[1,4]-diazocino[7,8,1-hi]indol-1-yl)-4-(furo[3,2-c]pyridin-7-yl)-2,5-dioxopyrrole hydrochloride | MS (ES): m/z = 478.1 (M$^+$ + 1) |
| 504 | 3-(6-(aminosulfonyl)-6,7-dihydro-6H-[1,4]diazepino-[6,7,1-hi]indol-1-yl)-4-(furo[3,2-c]pyridin-7-yl)-2,5-dioxopyrrole hydrochloride | MS (ES): m/z = 464.0 (M$^+$ + 1) |
| 505 | 3-(6-(aminosulfonyl)-6,7-dihydro-6H-[1,4]diazepino-[6,7,1-hi]indol-1-yl)-4-(5-fluorobenzofur-7-yl)-2,5-dioxopyrrole | MS (ES): m/z = 481.0 (M$^+$ + 1) |
| 506 | 3-(6-(aminosulfonyl)-6,7-dihydro-6H-[1,4]diazepino-[6,7,1-hi]indol-1-yl)-4-(imidazo[1,2-a]pyridin-3-yl)-2,5-dioxopyrrole | HRMS: m/z = 463.1165 |

EXAMPLE 507

3-(6-((1-methylimidazol-4-yl)sulfonyl)-6,7-dihydro-6H-[1,4]diazepino[6,7,1-hi]indol-1-yl)-4-(imidazo[1,2-a]pyridin-3-yl)-2,5-dioxopyrrole Combine 3-(6,7-dihydro-6H-[1,4]diazepino[6,7,1-hi]indol-1-yl)-4-(imidazo[1,2-a]-pyridin-3-yl)-2,5-dioxopyrrole dihydrochloride (300 mg, 0.714 mmol), triethylamine (263 mg, 2.63 mmol) and (1-methylimidazol-4-yl)sulfonyl chloride in methanol (15 mL). Stir in a sealed vial at room temperature for 2 hours. Filter the reaction mixture, wash the recovered solid with methanol, and dry under reduced pressure to provide the title compound (242 mg, 70%) as an orange solid.

MS (ES): m/z=528 (M+1).

EXAMPLE 508

3-(6-(N,N-[dimethyl]amino)sulfonyl)-6,7-dihydro-6H-[1,4]diazepino[6,7,1-hi]indol-1-yl)-4-(imidazo[1,2-a]pyridin-3-yl)-2,5-dioxopyrrole Add dimethylaminosulfonyl chloride (0.181 g, 1.26 mmol) to 3-(6,7-dihydro-6H-[1,4]diazepino[6,7,1-hi]indol-1-yl)-4-(imidazo[1,2-a]pyridin-3-yl)-2,5-dioxopyrrole dihydrochloride (0.577 g, 1.26 mmol) and triethylamine (0.8 ml) in N,N-dimethylformamide (5 ml) and dichloromethane (10 ml). Stir at 20° C. for 18 hours. Concentrate under reduced pressure and subject the residue to preparative reverse phase high performance chromatography (Kromasil KR100-10C18-250P2), eluting with 5-70% acetonitrile in 0.03% hydrochloric acid followed by chromatography on a Varian® Bond-Elut™ SCX column, eluting with 2 M ammonia in methanol to provide the title compound (370 mg, 59%) as an orange solid.

HRMS: m/z=491.1502 (M$^+$+H)

EXAMPLE 509

3-(6-(N-[methyl]aminocarbonyl)-5,6,7,8-tetrahydro-6H-[1,4]diazocino[7,8,1-hi]indol-1-yl)-4-(furo[3,2-c]pyridin-7-yl)-2,5-dioxopyrrole hydrochloride Add 1,3-dimethylurea (3 g) to 3-(5,6,7,8-tetrahydro-6H-[1,4]diazocino[7,8,1-hi]indol-1-yl)-4-(furo[3,2-c]pyridin-7-yl)-2,5-dioxopyrrole dihydrochloride (50 mg, 0.1 mmol) and heat at 140° C. for 20 minutes. Remove for heat and dilute with water (10 mL) and 1 N HCl (2 mL). Subject residue to reverse phase high performance chromatography and freeze dry fractions to provide the title compound as an orange solid (31 mg, 63%).

MS (ES): m/z=455.48 ($M^+$+1)

The compounds of EXAMPLES 510-520 may be prepared essentially as described in EXAMPLE 509.

| Example | Compound | Data |
|---|---|---|
| 510 | 3-(8-(N-[methyl]aminocarbonyl)-[1,5]-diazoperhydroonino-[8,9,1-hi]indol-1-yl)-4-(furo-[3,2-c]pyridin-3-yl)-2,5-dioxopyrrole hydrochloride | MS (ES): m/z = 470.2 ($M^+$ + 1) |
| 511 | 3-(6-(aminocarbonyl)-6,7-dihydro-6H-[1,4]diazepino[6,7,1-hi]indol-1-yl)-4-(benzofur-7-yl)-2,5-dioxopyrrole | HRMS: 427.1405 (M + H) |
| 512 | 3-(6-(N-[methyl]aminocarbonyl)-6,7-dihydro-6H-[1,4]diazepino[6,7,1-hi]indol-1-yl)-4-(benzo[1,3]-dioxol-4-yl)-2,5-dioxopyrrole | HRMS: 445.1523 (M + H) |
| 513 | 3-(8-(aminocarbonyl)-[1,5]diazoperhydroonino[8,9,1-hi]indol-1-yl)-4-(2,3-dihydrobenzofur-7-yl)-2,5-dioxopyrrole | HRMS: 457.1903 (M + H) |
| 514 | 3-(6-(aminocarbonyl)-6,7-dihydro-6H-[1,4]diazepino[6,7,1-hi]indol-1-yl)-4-(2,3-dihydrobenzofur-7-yl)-2,5-dioxopyrrole | HRMS: 429.1563 (M + H) |
| 515 | 3-(6-(aminocarbonyl)-6,7-dihydro-6H-[1,4]diazepino[6,7,1-hi]indol-1-yl)-4-(benzo[1,3]dioxol-4-yl)-2,5-dioxopyrrole | HRMS: 431.1346 (M + H) |
| 516 | 3-(6-(N-[methyl]aminocarbonyl)-6,7-dihydro-6H-[1,4]diazepino[6,7,1-hi]indol-1-yl)-4-(furo[3,2-c]pyridin-7-yl)-2,5-dioxopyrrole hydrochloride | MS (ES): m/z = 399.1 ($M^+$ + 1) |
| 517 | 3-(6-(N-[methyl]aminocarbonyl)-6,7-dihydro-6H-[1,4]-diazepino[6,7,1-hi]indol-1-yl)-4-(imidazo[1,2-a]pyridin-3-yl)-2,5-dioxopyrrole | MS (ES): m/z = 441.1 ($M^+$ + 1) |
| 518 | 3-(6-(N-[methyl]aminocarbonyl)-6,7-dihydro-6H-[1,4]diazepino[6,7,1-hi]indol-1-yl)-4-(benzofur-7-yl)-2,5-dioxopyrrole | MS (ES): m/z = 498.3 ($M^+$ + 1) |
| 519 | 3-(8-(N-[methyl]aminocarbonyl)-[1,5]diazoperhydroonino-[8,9,1-hi]indol-1-yl)-4-(benzofur-7-yl)-2,5-dioxopyrrole | MS (ES): m/z = 469.2 ($M^+$ + 1) |
| 520 | 3-(6-(aminocarbonyl)-6,7-dihydro-6H-[1,4]diazepino-[6,7,1-hi]indol-1-yl)-4-(imidazo[1,2-a]pyridin-3-yl)-2,5-dioxopyrrole hydrochloride | MS (ES): m/z = 427.1 ($M^+$ + 1) |

EXAMPLE 521

3-(6-(2-(methoxy)ethoxycarbonyl)-5,6,7,8-tetrahydro-6H-[1,4]diazocino[7,8,1-hi]indol-1-yl)-4-(benzofur-7-yl)-2,5-dioxopyrrole Stir 3-(5,6,7,8-tetrahydro-6H-[1,4]diazocino[7,8,1-hi]indol-1-yl)-4-(benzofur-7-yl)-2,5-dioxopyrrole (150 mgs, 0.38 mmol) and triethylamine (250 mgs, 2.4 mmol) in absolute methanol (20 mL). Add a solution of 2-bromoethylchloroformate (141 mgs, 0.75 mmol) in tetrahydrofuran (5 mL) slowly dropwise, then stir at 20° C. for 1 hour. Add morpholine (2 mL, 22.9 mmol), reflux under nitrogen for 2 hours and concentrate under reduced pressure. Purify the product by preparative reverse phase high performance chromatography, followed by chromatography on a Varian® BondElut™ SCX column, eluting with ammonia in methanol to obtain 115 mg (55%) of the title compound as an orange solid.

HRMS: m/z=555.2245 (M+H)

EXAMPLE 522

3-(6-(2-(morpholin-4-yl)acetyl)-5,6,7,8-tetrahydro-6H-[1,4]diazocino[7,8,1-hi]indol-1-yl)-4-(benzofur-7-yl)-2,5-dioxopyrrole hydrochloride Add a solution of bromoacetyl chloride (0.185 gm, 1.17 mMol) in tetrahydrofuran (10 mL) slowly to a solution of 3-(5,6,7,8-tetrahydro-6H-[1,4]diazocino[7,8,1-hi]indol-1-yl)-4-(benzofur-7-yl)-2,5-dioxopyrrole (0.15 gm, 0.38 mMol) and triethylamine (0.23 gm, 2.27 mMol) in absolute methanol (25 mL). Stir the resulting mixture for 1 hour at room temperature and then add morpholine (2 mL, 22.9 mMol). Heat at reflux for 2 hours, concentrate under reduced pressure, and subject to Varian® BondElut™ SCX chromatography, eluting with ammonia in methanol. Dissolve the desired product in 1 M hydrochloric acid and subject to preparative HPLC to provide the title compound as an orange solid (0.13 gm, 61%).

HRMS: 525.2113 (M+H)

The compound of the following example may be prepared essentially as described in EXAMPLE 522.

| Example | Compound | Data |
|---|---|---|
| 523 | 3-(6-(2-(piperidin-1-yl)acetyl)-6,7-dihydro-6H-[1,4]diaze-pino[6,7,1-hi]indol-1-yl)-4-(imidazo[1,2-a]pyridin-3-yl)-2,5-dioxopyrrole | MS (ES): m/z = 509 ($M^+$ + 1) |

EXAMPLE 524

3-(8-(cyanomethyl)-[1,5]diazoperhydroonino[8,9,1-hi]indol-1-yl)-4-(imidazo[1,2-a]pyridin-3-yl)-2,5-dioxopyrrole Add bromoacetonitrile (0.1 g, 0.96 mmol) to a solution of 3-([1,5]diazoperhydroonino[8,9,1-hi]indol-1-yl)-4-(imidazo[1,2-a]pyridin-3-yl)-2,5-dioxopyrrole dihydrochloride (0.2 g, 0.48 mol) in methanol (15 mL) and triethylamine (0.49 g, 4.8 mmol). Stir at 60° C. overnight. Dilute the reaction mixture with saturated aqueous sodium bicarbonate, extract into ethyl acetate, and concentrate under reduced pressure. Purify by reverse phase preparatory chromatography, eluting with acetonitrile and water, and freeze-dry the pure fractions to provide the title compound as a red solid (0.050 g, 23%).

MS (ES): m/z=451.2 ($M^+$+1)

The compounds of EXAMPLES 525-541 may be prepared essentially as described in EXAMPLE 524.

| Example | Compound | Data |
|---|---|---|
| 525 | 3-(6-((cyanomethyl)-6,7-dihydro-6H-[1,4]diazepino-[6,7,1-hi]indol-1-yl)-4-(imidazo[1,2-a]pyridin-3-yl)-2,5-dioxopyrrole | MS (ES): m/z = 423.2 (M$^+$ + 1) |
| 526 | 3-(6-((carboxymethyl)-6,7-dihydro-6H-[1,4]diazepino-[6,7,1-hi]indol-1-yl)-4-(imidazo[1,2-a]pyridin-3-yl)-2,5-dioxopyrrole hydrochloride | MS (ES): m/z = 442.2 (M$^+$ + 1) |
| 527 | 3-(6-((morpholin-4-yl)carbonylmethyl)-6,7-dihydro-6H-[1,4]diazepino[6,7,1-hi]indol-1-yl)-4-(benzofur-7-yl)-2,5-dioxopyrrole | MS (ES): m/z = 511.2 (M$^+$ + 1) |
| 528 | 3-(6-((morpholin-4-yl)carbonylmethyl)-5,6,7,8-tetrahydro-6H-[1,4]diazocino[7,8,1-hi]indol-1-yl)-4-(benzofur-7-yl)-2,5-dioxopyrrole | HRMS: m/z = 525.2130 (M + H) |
| 529 | 3-(8-((morpholin-4-yl)carbonylmethyl)-[1,5]diazoper-hydroonino[8,9,1-hi]indol-1-yl)-4-(benzofur-7-yl)-2,5-dioxopyrrole | MS (ES): m/z = 539 (M$^+$ + 1) |
| 530 | 3-(6-(carboxamidomethyl)-6,7-dihydro-6H-[1,4]diaze-pino[6,7,1-hi]indol-1-yl)-4-(5-fluorobenzofur-7-yl)-2,5-dioxopyrrole | MS (ES): m/z = 457.2 (M$^+$ − 1) |
| 531 | 3-(6-(carboxymethyl)-6,7-dihydro-6H-[1,4]diaze-pino[6,7,1-hi]indol-1-yl)-4-(5-fluorobenzofur-7-yl)-2,5-dioxopyrrole | MS (ES): m/z = 460.2 (M$^+$ + 1) |
| 532 | 3-(6-(carboxymethyl)-6,7-dihydro-6H-[1,4]diaze-pino[6,7,1-hi]indol-1-yl)-4-(imidazo[1,2-a]pyridin-3-yl)-2,5-dioxopyrrole hydrochloride | MS (ES): m/z = 442.2 (M$^+$ + 1) |
| 533 | 3-(6-(cyanomethyl)-6,7-dihydro-6H-[1,4]diaze-pino[6,7,1-hi]indol-1-yl)-4-(imidazo[1,2-a]pyridin-3-yl)-2,5-dioxopyrrole | MS (ES): m/z = 423.2 (M$^+$ + 1) |
| 534 | 3-(6-((morpholin-4-yl)carbonylmethyl)-6,7-dihydro-6H-[1,4]diazepino[6,7,1-hi]indol-1-yl)-4-(imidazo[1,2-a]pyridin-3-yl)-2,5-dioxopyrrole | MS (ES): m/z = 511.1 (M$^+$ + 1) |
| 535 | 3-(6-((pyridin-3-yl)methyl)-6,7-dihydro-6H-[1,4]diazepino[6,7,1-hi]indol-1-yl)-4-(imidazo[1,2-a]-pyridin-3-yl)-2,5-dioxopyrrole methanesulfonate | MS (ES): m/z = 475.2 (M$^+$ + 1) |
| 536 | 3-(6-((pyridin-4-yl)methyl)-6,7-dihydro-6H-[1,4]diazepino[6,7,1-hi]indol-1-yl)-4-(imidazo[1,2-a]-pyridin-3-yl)-2,5-dioxopyrrole methanesulfonate | MS (ES): m/z = 475.2 (M$^+$ + 1) |
| 537 | 3-(6-((pyridin-2-yl)methyl)-6,7-dihydro-6H-[1,4]diaze-pino[6,7,1-hi]indol-1-yl)-4-(6-fluoroimidazo[1,2-a]-pyridin-3-yl)-2,5-dioxopyrrole methanesulfonate | MS (ES): m/z = 492.8 (M$^+$ + 1) |
| 538 | 3-(6-((pyridin-2-yl)methyl)-6,7-dihydro-6H-[1,4]diaze-pino[6,7,1-hi]indol-1-yl)-4-(6-methylimidazo[1,2-a]-pyridin-3-yl)-2,5-dioxopyrrole | MS (ES): m/z = 489.0 (M$^+$ + 1) |
| 539 | 3-(6-((methoxycarbonyl)methyl)-6,7-dihydro-6H-[1,4]diazepino[6,7,1-hi]indol-1-yl)-4-(imidazo[1,2-a]-pyridin-3-yl)-2,5-dioxopyrrole hydrochloride | MS (ES): m/z = 456.1 (M$^+$ + 1) |
| 540 | 3-(6-((isopropoxycarbonyl)methyl)-6,7-dihydro-6H-[1,4]diazepino[6,7,1-hi]indol-1-yl)-4-(imidazo[1,2-a]-pyridin-3-yl)-2,5-dioxopyrrole hydrochloride | MS (ES): m/z = 484.2 (M$^+$ + 1) |
| 541 | 3-(6-((diethylaminocarbonyl)methyl)-6,7-dihydro-6H-[1,4]diazepino[6,7,1-hi]indol-1-yl)-4-(imidazo[1,2-a]-pyridin-3-yl)-2,5-dioxopyrrole hydrochloride | MS (ES): m/z = 497.2 (M$^+$ + 1) |

EXAMPLE 542

3-(6-(2,2,3,3,3-pentafluoropropyl)-6,7-dihydro-6H-[1,4]diazepino[6,7,1-hi]indol-1-yl)-4-(imidazo[1,2-a]pyridin-3-yl)-2,5-dioxopyrrole Combine 3-(6,7-dihydro-6H-[1,4]diazepino[6,7,1-hi]indol-1-yl)-4-(imidazo[1,2-a]-pyridin-3-yl)-2,5-dioxopyrrole dihydrochloride (300 mg, 0.714 mmol), 2,2,3,3,3-pentafluoropropyl trifluoroacetate (462 mg, 1.64 mmol), and N,N-diisopropylethylamine (508 mg, 3.94 mmol). Heat in a sealed vial at 85° C. for 16 hours. Dilute with dichloromethane and wash with water. Extract aqueous phase with dichloromethane. Combine organic phases, wash with saturated aqueous sodium chloride, dry over magnesium sulfate, and concentrated under reduced pressure. Subject residue to silica gel chromatography, eluting with dichloromethane containing 0-10% methanol to provide the title compound (96 mg, 28%) as an orange solid.

MS (ES): m/z=516 (M+1).

EXAMPLE 543

3-([1,5]diazoperhydroonino[8,9,1-hi]indol-1-yl)-4-(5-hydroxybenzofur-7-yl)-2,5-dioxopyrrole hydrochloride Mix pyridine hydrochloride (5.4 g, 46.7 mmol) and 3-(8-(tert-butoxycarbonyl)-[1,5]diazoperhydroonino[8,9,1-hi]indol-1-yl)-4-(5-methoxybenzofur-7-yl)-2,5-dioxopyrrole (325 mg, 0.60 mmol). Heat and stir the mixture at 190-200° C. under nitrogen for 40 minutes. Cool to 25° C., dissolve in distilled water, and adjust to pH=7.0 using aqueous 3 molar sodium carbonate. Extract the mixture with ethyl acetate. Combine the organic layers, wash with aqueous saturated sodium chloride, dry over anhydrous sodium sulfate, filter, and concentrate under reduced pressure. Chromatograph on a reverse phase preparative high performance chromatography column, eluting with acetonitrile containing 0.01% hydrochloric acid to obtain the title compound as an orange solid (185 mg, 66%).

HRMS: 428.1610 (M+H)

The compounds of EXAMPLES 544-548 may be prepared essentially as described in EXAMPLE 543.

| Example | Compound | Data |
|---|---|---|
| 544 | 3-([1,5]diazoperhydroonino[8,9,1-hi]indol-1-yl)-4-(4-hydroxybenzofur-7-yl)-2,5-dioxopyrrole hydrochloride | MS (ES): m/z = 428.0 (M$^+$ + 1) |
| 545 | 3-(6,7-dihydro-6H-[1,4]diazepino-[6,7,1-hi]indol-1-yl)-4-(4-hydroxy-benzofur-7-yl)-2,5-dioxopyrrole hydrochloride | HRMS: 400.1317 (M + H) |
| 546 | 3-(6,7-dihydro-6H-[1,4]diazepino-[6,7,1-hi]indol-1-yl)-4-(5-hydroxy-benzofur-7-yl)-2,5-dioxopyrrole hydrochloride | HRMS: 400.1315 (M + H) |
| 547 | 3-(5,6-dihydro-4H-pyrrolo[3,2,1-ij]-quinolin-1-yl)-4-(4-hydroxybenzofur-7-yl)-2,5-dioxopyrrole | HRMS: 385.1201 (M + H) |
| 548 | 3-(5,6-dihydro-4H-pyrrolo[3,2,1-ij]-quinolin-1-yl)-4-(5-hydroxybenzofur-7-yl)-2,5-dioxopyrrole | HRMS: 385.1203 (M + H) |

EXAMPLE 549

3-(5,6-dihydro-4H-pyrrolo[3,2,1-ij]quinolin-1-yl)-4-(4-(3-(diethylamino)propoxy)benzofur-7-yl)-2,5-dioxopyrrole 3-(5,6-dihydro-4H-pyrrolo[3,2,1-ij]quinolin-1-yl)-4-(4-(3-(bromo)propoxy)benzofur-7-yl)-2,5-dioxopyrrole Dissolve 3-(5,6-dihydro-4H-pyrrolo[3,2,1-ij]-quinolin-1-yl)-4-(4-(3-(hydroxy)propoxy)benzofur-7-yl)-2,5-dioxopyrrole (0.1 g, 0.232 mmol) in 10 mL dichloromethane. Add carbon tetrabromide (0.077 g) and triphenylphosphine (0.061 g). Stir for 10 minutes and add another equivalent of both reagents. Stir 10 minutes then dilute with dichloromethane and wash with water followed by saturated aqueous sodium chloride. Dry over magnesium sulfate then filter and concentrate under reduced pressure. Subject residue to silica gel chromatography, eluting with 2% methanol in dichloromethane to provide the desired compound (0.116 g)

MS (ES): m/z=506.2 (M+1)

Amination

Dissolve 3-(5,6-dihydro-4H-pyrrolo[3,2,1-ij]-quinolin-1-yl)-4-(4-(3-(bromo)propoxy)benzofur-7-yl)-2,5-dioxopyrrole (0.058 g, 0.118 mmol) in 1.5 mL 1-methyl-2-pyrrolidinone and add diethylamine (2M in tetrahydrofuran, 0.3 mL) and heat to 60° C. for 16 hours. Partition between ethyl acetate and water and concentrate organic layer. Dissolve the residue in a minimal amount of methanol and load onto an SCX™ Varian column (pretreated with a 5% acetic acid:methanol solution). Wash column with methanol and ethyl acetate, and elute with 2M ammonia in methanol to provide the title compound.

MS (ES): 498.2 (M+1)

The compound of the following example may be prepared essentially as described in EXAMPLE 549.

| Example | Compound | Data |
|---------|----------|------|
| 550 | 3-(6-(tert-butoxycarbonyl)-6,7-dihydro-6H-[1,4]diazepino-[6,7,1-hi]indol-1-yl)-4-(4-(3-(diethyl-amino)propoxy)benzofur-7-yl)-2,5-dioxopyrrole | MS (ES): m/z = 613.4 (M + 1) |

EXAMPLE 551

3-(6-(2-(morpholin-4-yl)acetyl)-6,7-dihydro-6H-[1,4]diazepino-[6,7,1-hi]indol-1-yl)-4-(benzofur-7-yl)-2,5-dioxopyrrole hydrochloride Add bromoacetyl chloride (0.084 g, 0.54 mmol) to a mixture of 3-(6,7-dihydro-6H-[1,4]diazepino-[6,7,1-hi]indol-1-yl)-4-(benzofur-7-yl)-2,5-dioxopyrrole hydrochloride (0.15 g, 0.36 mmol) and triethylamine (0.18 g, 1.78 mmol) in methanol (15 ml). Stir for 3 hours, add morpholine (1 ml), and heat to 50° C. for 1 hour. Dilute with ethyl acetate and wash with saturated aqueous sodium bicarbonate followed by saturated aqueous sodium chloride. Concentrate under reduced pressure and subject the residue to silica gel chromatography. Add 2M HCl in diethyl ether to the reaction mixture and concentrate under reduced pressure to give the title compound as a yellow solid (100 mg, 51%).

MS (ES): m/z=545.2 (M⁻−1)

EXAMPLE 552

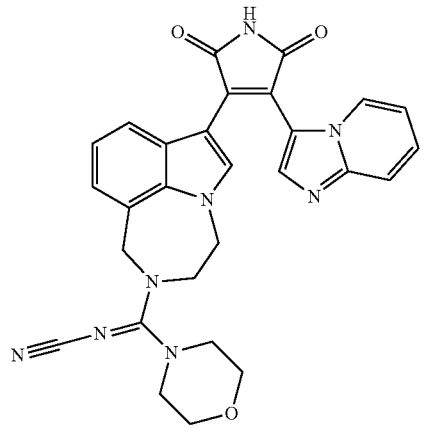

[1-(4-Imidazo[1,2-a]pyridin-3-yl-2,5-dioxo-2,5-dihydro-1H-pyrrol-3-yl)-6,7-dihydro-6H-[1,4]diazepino[6,7,1-hi]indol-6-yl]-[morpholin-4-yl]methylenecyanamide Add diphenyl cyanocarbonimidate (0.26 g, 1.09 mmol) to a solution of 3-(6,7-dihydro-6H-[1,4]diazepino[6,7,1-hi]indol-1-yl)-4-(imidazo[1,2-a]pyridin-3-yl)pyrrole-2,5-dione dihydrochloride and triethyl amine (0.28 g, 2.79 mmol) in isopropanol (20 ml). Reflux for 30 minutes to provide [1-(4-Imidazo[1,2-a]pyridin-3-yl-2,5-dioxo-2,5-dihydro-1H-pyrrol-3-yl)-6,7-dihydro-6H-[1,4]diazepino[6,7,1-hi]indol-6-yl]-[phenoxy]methylene-cyanamide. Add morpholine (0.142 g, 1.64 mmol) and reflux for 6 hours. Cool to room temperature and dilute with saturated aqueous sodium bicarbonate. Extract with ethyl acetate, wash combined organic phase with saturated aqueous sodium chloride and concentrate under reduced pressure. Subject the residue to preparative reversed phase chromatography to provide the title compound as an orange solid.

MS (ES): m/z=528.1 (M⁺+1).

The compound of the following example may be prepared essentially as described in EXAMPLE 552.

| Example | Compound | Data |
|---------|----------|------|
| 553 | [1-(4-Imidazo[1,2-a]pyridin-3-yl-2,5-dioxo-2,5-dihydro-1H-pyrrol-3-yl)-6,7-dihydro-6H-[1,4]diazepino[6,7,1-hi]indol-6-yl]-[piperidin-1-yl]methylenecyanamide | MS (ES): m/z = 519.1 (M + 1) |

EXAMPLE 554

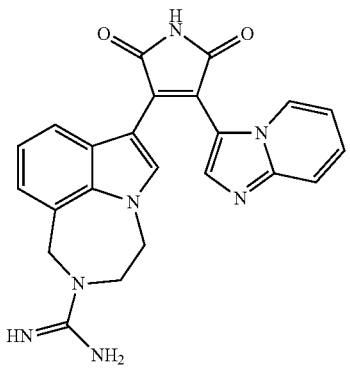

1-(4-Imidazo[1,2-a]pyridin-3-yl-2,5-dioxo-2,5-dihydro-1H-pyrrol-3-yl)-3,4-dihydro-1H-[1,4]diazepino[6,7,1-hi]indole-6-carboxamidine hydrochloride {tert-Butoxycarbonylimino-[7-(4-imidazo[1,2-a]pyridin-3-yl-2,5-dioxopyrrol-3-yl)-6,7-dihydro-1H-[1,4]diazepino[6,7,1-hi]indol-1-yl]methyl}carbamic Acid tert-Butyl Ester Add (tert-butoxycarbonyliminopyrazol-1-ylmethyl)carbamic acid tert-butyl ester (0.25 g, 0.81 mmol) to 3-(6,7-dihydro-6H-[1,4]diazepino[6,7,1-hi]indol-6-yl)-4-(imidazo[1,2-a]pyridin-3-yl)-2,5-dioxopyrrole (0.26 g, 0.67 mmol) in dry dimethylformamide (6.7 mL) and stir at room temperature for 3 days. Partition between ethyl acetate (500 mL) and water (250 mL). Wash the organic phase with saturated aqueous sodium chloride (250 mL), dry over sodium sulfate, and concentrate under reduced pressure. Subject the residue to preparative high performance liquid chromatography (pre-packed silica gel), eluting with 9:1 CH$_2$Cl$_2$/MeOH to afford the desired compound as a thick red oil.

Deprotection

Add 5.86% HCl/dioxane (50 mL) to {tert-Butoxycarbonylimino-[7-(4-imidazo[1,2-a]pyridin-3-yl-2,5-dioxopyrrol-3-yl)-6,7-dihydro-1H-[1,4]diazepino[6,7,1-hi]indol-1-yl]methyl}carbamic Acid tert-Butyl Ester (0.26 g, 0.42 mmol) in 1,4-dioxane (10 mL) and stir at room temperature overnight. Concentrate under reduced pressure. Add diethyl ether and concentrate under reduced pressure. Add diethyl ether (25 mL) an stir for 1 hour. Filter the slurry and wash the filter cake with diethyl ether (25 mL) to provide the title compound (0.16 g, 73%) as an orange-red solid.

HRMS: m/z=426.1712 (M$^+$+1).

EXAMPLE 555

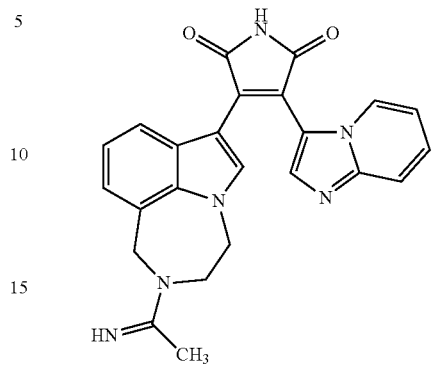

3-(6-(1-iminoeth-1-yl)-6,7-dihydro-6H-[1,4]diazepino[6,7,1-hi]indol-6-yl)-4-(imidazo[1,2-a]pyridin-3-yl)-2,5-dioxopyrrole hydrochloride Add methyl acetimidate hydrochloride (0.072 g, 0.66 mol) and potassium carbonate (0.18 g, 1.3 mmol) to 3-(6,7-dihydro-6H-[1,4]diazepino[6,7,1-hi]indol-6-yl)-4-(imidazo[1,2-a]pyridin-3-yl)-2,5-dioxopyrrole (0.25 g, 0.66 mmol) in dry dimethylformamide (6.6 mL) cooled in an ice bath. Stir at 0° C. for 25 minutes and then at room temperature for 3 days. Add methyl acetimidate hydrochloride (0.072 g, 0.66 mmol) and potassium carbonate (0.18 g, 1.3 mmol). Heat at 50° C. overnight. Cool to room temperature and concentrate under reduced pressure. Subject the residue to chromatography (Varian Mega Bond Elut SCX column), eluting with a gradient: MeOH-2M NH$_3$/MeOH). Subject to reverse-phase HPLC and prepare the HCl salt to provide the title compound (0.042 g, 14%).

HRMS: m/z=425.1722 (M$^+$+1).

EXAMPLE 556

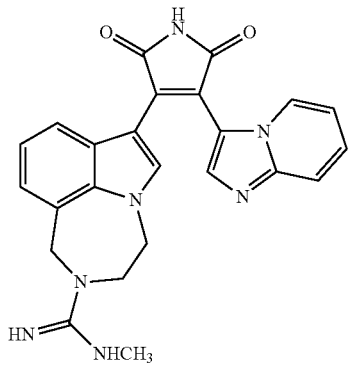

N-[methyl]-1-(4-Imidazo[1,2-a]pyridin-3-yl-2,5-dioxo-2,5-dihydro-1H-pyrrol-3-yl)-3,4-dihydro-1H-[1,4]diazepino[6,7,1-hi]indole-6-carboxamidine dihydrochloride Add sodium hydride (137.7 mg, 3.44 mmol, 60% dispersion in mineral oil) to 1,3-bis-(tert-butoxycarbonyl)-2-thiopseudourea (1.0 g, 3.44 mmol) in dimethylformamide and stir 1 hour. Add iodomethane (0.235 mL, 3.78 mmol) and stir at ambient temperature 18 hours. Pour over ice and partition between ethyl acetate (200 mL) and saturated aqueous sodium chloride (100 mL). Dry over sodium sulfate and concentrate under reduced pressure. Subject residue to chromatography, eluting with Hexanes/ethyl acetate (8:2) to provide 1.0 g of a yellow oil. Add 3-(6,7-dihydro-6H-[1,4]diazepino[6,7,1-hi]indol-6-yl)-4-(imidazo[1,2-a]pyridin-3-yl)-2,5-dioxopyrrole (300 mg, 0.78 mmol) to the yellow oil (238 mg, 0.78 mmol) in dimethylformamide (8.0 mL) and stir 4 days at ambient temperature. Heat to 100° C. for 2 hours, cool, and partition between ethyl acetate (100 mL) and water (100 mL). Dry over sodium sulfate and concentrate under reduced pressure. Subject the residue to chromatography, eluting with dichloromethane/methanol (9:1) to provide 130 mg (26%) of the BOC-protected intermediate as a pale orange solid. Add anhydrous 4 M HCl/dioxane (20 mL) to the BOC-protected intermediate (120 mg, 0.187 mmol) in p-dioxane (20 mL) and stir at ambient temperature 18 hours. Added diethyl ether (50 mL) and filter to provide the title compound (95 mg, 99%) as an orange solid.

MS (ES): m/z=513.8 ($M^+ +1$).

EXAMPLE 557

3-(6-(5-amino-1,2,4-triazol-3-yl)-6,7-dihydro-6H-[1,4]diazepino[6,7,1-hi]indol-1-yl)-4-(imidazo[1,2-a]pyridin-3-yl)pyrrole-2,5-dione Add hydrazine hydrate to a solution of [1-(4-Imidazo[1,2-a]pyridin-3-yl-2,5-dioxo-2,5-dihydro-1H-pyrrol-3-yl)-6,7-dihydro-6H-[1,4]diazepino[6,7,1-hi]indol-6-yl]-[phenoxy]methylene-cyanamide and triethyl amine (0.28 g, 2.79 mmol) in methanol (15 ml). Stir for 20 minutes. Dilute with saturated aqueous sodium bicarbonate and extract with 4:1 ethyl acetate:n-butanol (4×50 ml). Concentrate the combined organic phases under reduced pressure and subject the residue to preparative reversed phase chromatography to provide the title compound (0.075 g) as a maroon solid.

MS (ES): m/z=466.1 ($M^+ +1$).

EXAMPLE 558

3-(6-(pyridin-2-yl)-6,7-dihydro-6H-[1,4]diazepino[6,7,1-hi]indol-1-yl)-4-(imidazo[1,2-a]pyridin-3-yl)pyrrole-2,5-dione Heat a mixture of 3-(6,7-dihydro-6H-[1,4]diazepino[6,7,1-hi]indol-1-yl)-4-(imidazo[1,2-a]pyridin-3-yl)pyrrole-2,5-dione dihydrochloride (0.10 g, 0.22 mmol), triethylamine (0.1 ml, 0.73 mmol), and 2-fluoropyridine (1 ml, 10.29 mmol) in a microwave reactor at 160° C. for 5 minutes at 300 Watts. Dilute with ethyl acetate, wash with saturated aqueous sodium bicarbonate, and concentrate under reduced pressure. Subject the residue to silica gel chromatography to provide the title compound (0.025 g, 24%) as a red solid.

MS (ES): m/z=461.2 ($M^+ +1$).

The compound of the following example may be prepared essentially as described in EXAMPLE 558.

| Example | Compound | Data |
|---|---|---|
| 559 | 3-(6-(pyridin-2-yl)-6,7-dihydro-6H-[1,4]diazepino-[6,7,1-hi]indol-1-yl)-4-(6-methylimidazo[1,2-a]pyridin-3-yl)-pyrrole-2,5-dione | MS (ES): m/z = 474.8 ($M^+$ + 1) |

EXAMPLE 560

3-(6-(pyrimidin-2-yl)-6,7-dihydro-6H-[1,4]diazepino[6,7,1-hi]indol-1-yl)-4-(imidazo[1,2-a]pyridin-3-yl)pyrrole-2,5-dione Add 2-chloropyrimidine (0.24 g, 2.07 mmol) to a solution of 3-(6,7-dihydro-6H-[1,4]diazepino[6,7,1-hi]indol-1-yl)-4-(imidazo[1,2-a]pyridin-3-yl)pyrrole-2,5-dione dihydrochloride (0.90 g, 1.97 mmol) and triethylamine (1.0 ml) in n-butanol (50 ml). Reflux for 30 hours and distill solvent to about 15-20 ml volume. Filter the resulting suspension and wash the solid with large amounts of methanol to give the title compound (0.58 g, 1.26 mmol).

MS (ES): m/z=462.2 ($M^+ +1$).

The compounds of EXAMPLES 561-563 may be prepared essentially as described in EXAMPLE 560.

| Example | Compound | Data |
|---|---|---|
| 561 | 3-(6-(benzothiazol-2-yl)-6,7-dihydro-6H-[1,4]diazepino-[6,7,1-hi]indol-1-yl)-4-(imidazo[1,2-a]pyridin-3-yl)-pyrrole-2,5-dione | MS (ES): m/z = 517.1 ($M^+$ + 1) |
| 562 | 3-(9-fluoro-6-(pyrimidin-2-yl)-6,7-dihydro-6H-[1,4]diazepino[6,7,1-hi]indol-1-yl)-4-(7-chloroimidazo-[1,2-a]pyridin-3-yl)pyrrole-2,5-dione | MS (ES): m/z = 513.9 ($M^+$ + 1) |
| 563 | 3-(6-(pyrimidin-2-yl)-6,7-dihydro-6H-[1,4]diazepino-[6,7,1-hi]indol-1-yl)-4-(6-methylimidazo[1,2-a]pyridin-3-yl)pyrrole-2,5-dione | MS (ES): m/z = 476.0 ($M^+$ + 1) |

EXAMPLE 564

Resolution of 3-(7-methyl-6-oxa-4,5-dihydro-3-azabenzo[cd]azulen-1-yl)-4-(imidazo[1,2-a]pyridin-3-yl)-2,5-dioxopyrrole Subject racemic 3-(7-methyl-6-oxa-4,5-dihydro-3-azabenzo[cd]azulen-1-yl)-4-(imidazo[1,2-a]pyridin-3-yl)-2,5-dioxopyrrole to chiral chromatography on a ChiralPak® AD, 8 cm×30 cm column, eluting with 3A ethanol at a flow rate of 350 ml/min.

The first eluting isomer is (+)-3-(7-methyl-6-oxa-4,5-dihydro-3-azabenzo[cd]azulen-1-yl)-4-(imidazo[1,2-a]pyridin-3-yl)-2,5-dioxopyrrole $[\alpha]_{589}$ (DMSO, c=10 mg/ml)=+34.8°

HRMS: m/z=399.1466 (M+H)

The second eluting isomer is (−)-3-(7-methyl-6-oxa-4,5-dihydro-3-azabenzo[cd]azulen-1-yl)-4-(imidazo[1,2-a]pyridin-3-yl)-2,5-dioxopyrrole $[\alpha]_{589}$ (DMSO, c=10 mg/ml)=−28.1°

HRMS: m/z=399.1437 (M+H)

EXAMPLE 565

(+)- and (−)-3-(5-hydroxy-[1,5]diazaperhydroonino[8,9,1-hi]indol-1-yl)-4-(benzofur-7-yl)-2,5-dioxopyrrole

5-hydroxy-8-(tert-butoxycarbonyl)-[1,5]diazaperhydroonino[8,9,1-hi]indole

Dissolve 5,6-dehydro-8-(tert-butoxycarbonyl)-[1,5]diazaperhydroonino[8,9,1-hi]indole (5.7 g, 19 mmol) in tetrahydrofuran (100 mL) at −78° C. Add $BH_3 \cdot THF$ (1.0 M, 200 mL). Stir and warm the mixture to ambient temperature. After 1.5 hours, quench with water dropwise at 0° C. Add hydrogen peroxide (2.2 mL, 30%) and aqueous 0.1 N sodium hydroxide (2.2 mL). Stir for 16 hours. Dilute with ethyl acetate (100 mL). Wash the organic layer with aqueous sodium hydrogen sulfite and chromatograph on flash silica gel (hexane/EtOAc; 3:1 to 0:1) to afford the desired compound (3.5 g) as a solid.

5-(tert-butyldimethylsilyloxy)-8-(tert-butoxycarbonyl)-[1,5]diazaperhydroonino[8,9,1-hi]indole Stir 5-hydroxy-8-(tert-butoxycarbonyl)-[1,5]diazaperhydroonino[8,9,1-hi]indole (3.5 g, 11 mmol), tert-butyldimethylsilyl chloride (3.3 g, 22 mmol), and imidazole (1.9 g, 28 mmol) in N,N-dimethylformamide (10 mL) at ambient temperature for 2 hours. Dilute with ethyl acetate (100 mL). Wash with water, dry over magnesium sulfate, and concentrate under reduced pressure to provide the desired compound (4.9 g).

Methyl 2-(5-(tert-butyldimethylsilyloxy)-8-(tert-butoxycarbonyl)-[1,5]diazaperhydroonino-[8,9,1-hi]indol-1-yl)oxoacetate Beginning with 5-(tert-butyldimethylsilyloxy)-8-(tert-butoxycarbonyl)-[1,5]diazaperhydroonino[8,9,1-hi]indole, the desired compound was prepared essentially as described in Preparation 22. (1.3 g).
MS (ES): m/z=518 ($M^+$+H).

3-(2-(5-(tert-butyldimethylsilyloxy)-8-(tert-butoxycarbonyl)-[1,5]diazaperhydroonino-[8,9,1-hi]indol-1-yl)-4-(benzofur-7-yl)-2,5-dioxopyrrole and 3-(2-(5-(hydroxy)-8-(tert-butoxycarbonyl)-[1,5]diazaperhydroonino-[8,9,1-hi]indol-1-yl)-4-(benzofur-7-yl)-2,5-dioxopyrrole Beginning with methyl 2-(5-(tert-butyldimethylsilyloxy)-8-(tert-butoxycarbonyl)-[1,5]diazaperhydroonino-[8,9,1-hi]indol-1-yl)oxoacetate and 2-(benzofur-7-yl)acetamide, the desired compounds are prepared essentially as described in Preparation 120:
3-(2-(5-(tert-butyldimethylsilyloxy)-8-(tert-butoxycarbonyl)-[1,5]diazaperhydroonino[8,9,1-hi]indol-1-yl)-4-(benzofur-7-yl)-2,5-dioxopyrrole (180 mg)
MS (ES): m/z=642 ($M^+$+H); and
3-(2-(5-(hydroxy)-8-(tert-butoxycarbonyl)-[1,5]diazaperhydroonino-[8,9,1-hi]-indol-1-yl)-4-(benzofur-7-yl)-2,5-dioxopyrrole (280 mg)
MS (ES): m/z=528 ($M^+$+H).
Deprotection
Stir 3-(2-(5-(tert-butyldimethylsilyloxy)-8-(tert-butoxycarbonyl)-[1,5]diazaperhydroonino[8,9,1-hi]indol-1-yl)-4-(benzofur-7-yl)-2,5-dioxopyrrole (180 mg, 0.28 mmol) and trifluoroacetic acid (3 mL) in dichloromethane (3 mL) at ambient temperature for 1 hour. Concentrate under reduced pressure and subject the residue to chiral chromatography (Chiralpak AD column eluting with 60% ethanol/40% heptane/0.2% dimethylethylamine) to provide the title compound isomers.
MS (ES): m/z=428 ($M^+$+H).

EXAMPLE 566

3-(5-oxo-[1,5]diazaperhydroonino[8,9,1-hi]indol-1-yl)-4-(benzofur-7-yl)-2,5-dioxopyrrole Add Dess-Martin periodinane (110 mg, 0.25 mmol) to 3-(2-(5-(hydroxy)-8-(tert-butoxycarbonyl)-[1,5]diazaperhydroonino-[8,9,1-hi]-indol-1-yl)-4-(benzofur-7-yl)-2,5-dioxopyrrole (90 mg, 0.2 mmol) in dichloromethane (10 mL) and stir for 2 hours at ambient temperature. Wash with 0.1 N sodium hydroxide. Dry over magnesium sulfate and concentrate under reduced pressure. Subject the residue to silica gel chromatography, eluting with hexane/EtOAc; 1:1 to 0:1 to provide to 3-(2-(5-oxo-8-(tert-butoxycarbonyl)-[1,5]diazaperhydroonino[8,9,1-hi]-indol-1-yl)-4-(benzofur-7-yl)-2,5-dioxopyrrole (70 mg, 80%). Treat with trifluoroacetic acid (2 mL) in dichloromethane (2 mL) at ambient temperature for 1 hour to provide the title compound.
MS (ES): m/z=426 ($M^+$+H).

EXAMPLE 567

3-(6-((methoxy)thiocarbonyl)-6,7-dihydro-6H-[1,4]diazepino[6,7,1-hi]indol-1-yl)-4-(imidazo[1,2-a]pyridin-3-yl)-2,5-dioxopyrrole Stir 3-(6,7-dihydro-6H-[1,4]diazepino[6,7,1-hi]indol-1-yl)-4-(imidazo[1,2-a]-pyridin-3-yl)-2,5-dioxopyrrole (0.2 g, 0.44 mmol), 1,1-thiocarbonyldiimidazole (95 mg, 0.48 mmol), and triethylamine (0.2 mL) in methanol (10 mL) at ambient temperature for 2 hours. Dilute with ethyl acetate and wash with water. Dry over magnesium sulfate and concentrate under reduced pressure. Subject the residue to silica gel chromatography, eluting with hexane/EtOAc; 1:1 to 0:1 to provide the title compound.
MS (ES): m/z=458 ($M^+$+H).

EXAMPLE 568

3-(6-((morpholin-4-yl)thiocarbonyl)-6,7-dihydro-6H-[1,4]diazepino[6,7,1-hi]indol-1-yl)-4-(imidazo[1,2-a]pyridin-3-yl)-2,5-dioxopyrrole Stir 1,1-thiocarbonyldiimidazole (100 mg, 0.50 mmol) with morpholine (50 mg, 0.56 mmol) in tetrahydrofuran at ambient temperature for 10 minutes. Add 3-(6,7-dihydro-6H-[1,4]diazepino[6,7,1-hi]indol-1-yl)-4-(imidazo[1,2-a]-pyridin-3-yl)-2,5-dioxopyrrole (0.10 g, 0.22 mmol) and triethylamine in methanol (10 mL). Heat and stir at 80° C. for 4 hours. Cool, dilute with dichloromethane, and wash with water. Dry over magnesium sulfate and concentrate under reduced pressure. Subject the residue to silica gel chromatography, eluting with hexane/EtOAc; 1:1 to 0:1 to provide the title compound (40 mg).
MS (ES): m/z=513 ($M^+$+H).

EXAMPLE 569

3-(6-(pyridin-4-yl)-6,7-dihydro-6H-[1,4]diazepino[6,7,1-hi]indol-1-yl)-4-(benzofur-7-yl)-2,5-dioxopyrrole Add 4-chloropyridine hydrochloride (0.036 g, 0.24 mmol) and triethylamine (0.049 g, 0.48 mmol) to 3-(6,7-dihydro-6H-[1,4]diazepino[6,7,1-hi]indol-1-yl)-4-(benzofur-7-yl)-2,5-dioxopyrrole hydrochloride (0.05 g, 0.12 mmol) in 2 mL dimethylformamide. Heat at 100° C. for 60 hours. Cool to room temperature, dilute with water (30 mL) and extract with ethyl acetate (3×15 mL). Combine the organic phases, dry over sodium sulfate, and concentrate under reduced pressure. Subject the residue to silica gel chromatography, eluting with dichloromethane containing 5% methanol and 2N ammonia to provide the title compound (10 mg).
MS (ES): m/z=461 (M$^+$+H).

EXAMPLE 570

3-(7-oxo-6-methyl-6,7-dihydro-6H-[1,4]diazepino-[6,7,1-hi]indol-1-yl)-4-(imidazo[1,2-a]pyridin-3-yl)-2,5-dioxopyrrole hydrochloride The title compound may be prepared essentially as described in EXAMPLE 1.
HRMS: m/z=412.1421 (M$^+$+1)

EXAMPLE 571

3-(6-(3-(cyclopentyl)propion-1-yl)-6,7-dihydro-6H-[6,7,1-hi]indol-1-yl)-4-(imidazo[1,2-a]pyridin-3-yl)-2,5-dioxopyrrole hydrochloride Beginning with 3-(6,7-dihydro-6H-[6,7,1-hi]indol-1-yl)-4-(imidazo[1,2-a]pyridin-3-yl)-2,5-dioxopyrrole hydrochloride, the title compound was prepared essentially as described in EXAMPLE 239.
MS (ES): m/z=494.1 (M$^+$+1)

EXAMPLE 572

3-(6-(2-(morpholin-4-yl)acetyl)-6,7-dihydro-6H-[6,7,1-hi]indol-1-yl)-4-(imidazo[1,2-a]pyridin-3-yl)-2,5-dioxopyrrole Beginning with 3-(6,7-dihydro-6H-[6,7,1-hi]indol-1-yl)-4-(imidazo[1,2-a]pyridin-3-yl)-2,5-dioxopyrrole hydrochloride, the title compound was prepared essentially as described in EXAMPLE 522.
MS (ES): m/z=511 (M$^+$+1)

EXAMPLE 573

3-(6-(2-(thiomorpholin-4-yl)acetyl)-6,7-dihydro-6H-[6,7,1-hi]indol-1-yl)-4-(imidazo[1,2-a]pyridin-3-yl)-2,5-dioxopyrrole Beginning with 3-(6,7-dihydro-6H-[6,7,1-hi]indol-1-yl)-4-(imidazo[1,2-a]pyridin-3-yl)-2,5-dioxopyrrole hydrochloride, the title compound was prepared essentially as described in EXAMPLE 522.
MS (ES): m/z=527 (M$^+$+1)

EXAMPLE 574

3-(6-((2,3,4,5-tetrahydrothiazol-4-yl)carbonyl)-6,7-dihydro-6H-[6,7,1-hi]indol-1-yl)-4-(imidazo[1,2-a]pyridin-3-yl)-2,5-dioxopyrrole dihydrochloride Beginning with 3-(6,7-dihydro-6H-[6,7,1-hi]indol-1-yl)-4-(imidazo[1,2-a]pyridin-3-yl)-2,5-dioxopyrrole hydrochloride, the title compound was prepared essentially as described in EXAMPLE 64.
MS (ES): m/z=499 (M$^+$+1)

EXAMPLE 575

3-(6-(3,3,3-trifluoroprop-1-yl)-6,7-dihydro-6H-[6,7,1-hi]indol-1-yl)-4-(imidazo[1,2-a]pyridin-3-yl)-2,5-dioxopyrrole Beginning with 3-(6,7-dihydro-6H-[6,7,1-hi]indol-1-yl)-4-(imidazo[1,2-a]pyridin-3-yl)-2,5-dioxopyrrole hydrochloride, the title compound was prepared essentially as described in EXAMPLE 157.
MS (ES): m/z=480 (M$^+$+1)

EXAMPLE 576

3-(6-(3,3,3-trifluoroprop-1-yl)-6,7-dihydro-6H[6,7,1-hi]indol-1-yl)-4-(6-methylimidazo[1,2-a]pyridin-3-yl)-2,5-dioxopyrrole Beginning with 3-(6,7-dihydro-6H-[6,7,1-hi]indol-1-yl)-4-(6-methylimidazo[1,2-a]pyridin-3-yl)-2,5-dioxopyrrole hydrochloride, the title compound was prepared essentially as described in EXAMPLE 157.
MS (ES): m/z=494 (M$^+$+1)

EXAMPLE 577

3-(6-((1-methylimidazol-5-yl)methyl)-6,7-dihydro-6H-[6,7,1-hi]indol-1-yl)-4-(imidazo[1,2-a]pyridin-3-yl)-2,5-dioxopyrrole Beginning with 3-(6,7-dihydro-6H-[6,7,1-hi]indol-1-yl)-4-(imidazo[1,2-a]pyridin-3-yl)-2,5-dioxopyrrole hydrochloride, the title compound was prepared essentially as described in EXAMPLE 157.
MS (ES): m/z=478 (M$^+$+1)

EXAMPLE 578

3-(6-(2-(piperidin-1-yl)eth-1-yl)-6,7-dihydro-6H-[6,7,1-hi]indol-1-yl)-4-(imidazo[1,2-a]pyridin-3-yl)-2,5-dioxopyrrole Beginning with 3-(6,7-dihydro-6H-[6,7,1-hi]indol-1-yl)-4-(imidazo[1,2-a]pyridin-3-yl)-2,5-dioxopyrrole hydrochloride, the title compound was prepared essentially as described in EXAMPLE 524.
MS (ES): m/z=495 (M$^+$+1)

EXAMPLE 579

3-(6-(((2-(piperidin-1-yl)eth-1-yl)oxy)carbonyl)-6,7-dihydro-6H-[6,7,1-hi]indol-1-yl)-4-(imidazo[1,2-a]pyridin-3-yl)-2,5-dioxopyrrole Beginning with 3-(6,7-dihydro-6H-[6,7,1-hi]indol-1-yl)-4-(imidazo[1,2-a]pyridin-3-yl)-2,5-dioxopyrrole hydrochloride, the title compound was prepared essentially as described in EXAMPLE 494.

MS (ES): m/z=539 (M$^+$+1)

Kinase Inhibition Assay

The ability of the compounds of the present invention to inhibit the activity of the GSK-3β enzyme is measured according to a standard protocol (FIOL, Carol J., et al., A Secondary Phosphorylation of CREB$^{341}$ at Ser$^{129}$ Is Required for the cAMP-Mediated Control of Gene Expression: A Role for Glycogen Synthase Kinase-3 in the Control of Gene Expression, *J. Biol. Chem.*, 269, 32187-32193 (1994)). Briefly, the catalysis of the reaction:

KRREILSRRP(pS)YR+AT$^{33}$P→KRREIL($^{33}$pS)RRP(pS)YR[measured]+ADP by GSK-3β is measured in a reaction mixture comprised of the following: 50 mM MOPS (4-morpholinepropanesulfonic acid) pH 7.0; 50 μM phosphoCREB peptide; 50 μM ATP; 0.5 μCi ATP[γ-$^{33}$P]; 12.5 mM MgCl$_2$; 0.03% Triton-X; 4% DMSO; and 1 nM recombinant human GSK-3beta. The reaction is initiated by the addition of enzyme. The final reaction volume is 100 μL. The reaction is allowed to proceed for 60 minutes at room temperature and is stopped by the addition of 75 μL of 10% phosphoric acid. To capture KRREIL($^{33}$pS)RRP(pS)YR formed in the reaction and to remove unreacted AT$^{33}$P, 160 μL of the stopped reaction mixture is transferred to a pre-wetted (0.75% phosphoric acid) phosphocellulose microfiltration plate [Millipore Cat.# MAPH NOB 50] and after 90 minutes incubation on the plate, the stopped reaction mixture is passed through the filter using a Titertek Map Extractor. The filter containing the trapped KRREIL($^{33}$pS)RRP(pS)YR is washed with 220 μL of 0.75% phosphoric acid. Filter plates are blotted to remove droplets from the underdrain. The underdrain is removed from the filter and the filter is placed into a clear plate liner (Wallac, Inc.). Added to each well is 100 μL of Microscint 20 (Packard).

After standing at least six hours (preferably overnight), the plates are counted in a Trilux scintillation counter (Wallac, Inc.). The ability of a compound to inhibit GSK-3beta is determined by including various concentrations of the compound in the reaction mixture and comparing the signal produced to the signal produced in a reaction mixture without the compound.

The assay yields the molar concentration of the test compound that produces a 50% inhibition of the GSK-3beta enzyme activity (IC$_{50}$). The lower the value in this test, the more active the test compound is. The exemplified compounds exhibit IC$_{50}$≦0.2 μM.

In the present invention, inhibitors that demonstrate 50% effective concentrations (IC$_{50}$) of about 200 nM or less are preferred. Furthermore, also preferred are those which show 50% effective concentrations of 50 nM or less, more preferably those which show 50% effective concentrations of 20 nM or less, and most preferably those which show 50% effective concentrations of 10 nM or less. It is also preferred, in the practice of the present invention, that the GSK-3 inhibitor achieve plasma exposures >1000 ng*hr/mL. Additionally; those GSK-3 inhibitors exhibiting a low IC$_{50}$ value, such as below 10 nm, and plasma exposures <1000 ng*hr/mL represent a further preferred embodiment of the present invention.

Glycogen Synthesis Assay

The glycogen synthesis assay measures the increase in the production of glycogen both in the absence and in the presence of insulin in the cells. This test is done according to standard protocols. (Berger, J. and Hayes, N. S., *Anal. Biochem.*, 261, 159-163 (1998)). Briefly, 3T3-L1 adipocytes are plated and differentiated in a 96-well plate at 25,000 cells/well. The plate is serum-starved overnight. The serum-starvation media is removed just prior to assay, and the plate is washed with 100 μl/well Krebs-Ringer-Hepes buffer (KRBH). The KRBH is removed and 50 μl of compound (twice the amount of the final concentration) is added to the assay plate. Next, 50 μl of $^{14}$C-labeled glucose is added to the assay plate at 0.1 μCi/well. The plate is then incubated at 37° C. for 2 hours.

The plate is washed with 100 μL/well of PBS, and the cells are lysed with 75 μl/well of 1N NaOH. The plate is heated at 70° C. for 20 minutes. An aliquot (50 μl) of the supernatant is transferred from the assay plate to a Millipore FC filter plate containing 120 μl/well of ice-cold ethanol. The plate is allowed to stand for 2 hours at 4° C. to facilitate precipitation. The ethanol is removed from the filter plate via a vacuum manifold, and the plate is washed with 100 uL/well of ice-cold 70% ethanol. The plate was allowed to dry overnight, and 75 μl/well of Microscint-20 was added to the filter plate. The plate was then counted on a Packard Topcount. The compound of Example 121 was tested in this assay and increased glycogen synthesis by 3.7-fold at 0.1 μM in the absence of insulin, and increased glycogen synthesis by 6.4-fold at 0.1 μM in the presence of insulin.

Glucose Lowering Assay

The glucose lowering assay is an in vivo test that measures the effect of the test compound on blood glucose and triglycerides relative to insulin. (ELDAR-FINKLEMAN, H., et al., Expression and Characterization of Glycogen Synthase Kinase-3 Mutants and Their Effect on Glycogen Synthase Activity in Intact Cells, *Proc. Nat. Acad. Sci*, 93, 10228-10233 (1996)). Briefly, ZDF rats (Charles River, Inc.) at six weeks of age are housed individually with free access to food and water. Rats are dosed with drug once daily by oral gavage, with the compound prepared as a suspension in 1% caboxymethylcellusolve/0.25% Tween 80 (CMC-Tween). Vehicle controls are dosed with CMC-Tween only. The duration of study varied according to the protocol used, with acute dosing studies lasting one day and dose escalation studies lasting seven days. Body weights and food consumption measurements are also performed once a week for seven-day studies. For measurement of blood glucose and triglycerides, blood samples of 600 μl are collected by the tail snip method. (The tail snip for blood sampling is as follows: 1-2 mm of the tail is snipped with a sharp blade. After collection of blood, a scab forms at the site of wound. This scab is removed and the tail is gently massaged for other subsequent bleedings.) Glucose and triglyceride determinations are performed on a Hitachi 912 metabolic analyzer, with a kit utilizing the Trinder method. On termination of study, specific tissues (e.g., heart, pancreas, adipose tissues, and liver) are excised to evaluate the effect of these drugs on their metabolic functions. The compound of Example 121 was tested in this assay and lowered glucose by 56% at a dose of 10 mg/kg.

Ex Vivo Brain Assay

The ex vivo brain assay assesses the GSK-3β kinase activity of the test compound in brain cortex tissue according to standard protocols (Wang, et al., *Anal. Biochem.*, 220, 397-402 (1994)).

The ex vivo GSK-3β kinase activity of a compound is assayed following oral dosing of 2 to 3 month old PDAPP or CD-1 mice. After a 20 mg/kg, 24-hour dose, followed by an additional three-hour dose, brain cortex tissue is dissected and homogenized in freshly prepared lysis buffer (10 mM $K_2HPO_4$ pH 7.2, 1 mM EDTA, 5 mM EGTA, 10 mM $MgCl_2$, 50 mM β-Glycerophosphate, 1 mM $Na_3VO_4$, 2 mM DTT, 1 μM Microcystin, COMPLETE protease inhibitor tablet, no detergent). Following a thirty-minute incubation on ice, cortex homogenate samples are centrifuged (100,000 G) for 30 minutes at 4° C. (Ahmed, N. N., et al., *Oncogene*, 8, 1957 (1983)). The total protein concentration of homogenate is determined using the BCA method (Pierce). GSK-3β activity in cytosolic homogenate from vehicle- and compound-treated mice is then assayed. The kinase reaction occurs in a 50 μl total volume containing 20 mM MOPS pH 7.4, 25 mM β-glycerol phosphate, 5 mM EGTA, 1 mM $NA_3VO_4$, 1 mM DTT, 15 mM $MgCl_2$, 100 μM cold ATP, 200 μM CREB peptide, 10 μL cytosolic cortex brain homogenate, and 5 μCi γ-$^{33}$P-ATP. The reactions are incubated for thirty minutes at 30° C. using a Costar round-96 polypropylene plate. Reactions are then stopped with the addition of 10% $H_3PO_4$ and transferred to a Millipore MAPH-NOB 96-well phosphocellulose plate. Next, the reaction is incubated at room temperature for 1.5 hours, filtered and washed with 320 μl 0.75% $H_3PO_4$, and filtered and washed with 160 μl $H_3PO_4$ at the same concentration using a vacuum manifold. The filter plate is then placed in a carrier plate, and 100 μl of Microscint 20 is added to each well. The plate is sealed with sealing tape and incubated overnight at room temperature. The following day, the filter plate is read for $^{33}$P on Top Count (Packard). Finally, CPM is normalized to CPM perm of total protein. The compound of Example 121 was tested in this assay and inhibited kinase activity by 30% at a dose of 20 mg/kg.

Beta-Catenin Protection Assay

The beta-catenin assay is the fold induction over basal beta-catenin and is performed according to standard protocols (Hedgepeth, C. M., *Dev. Biol.*, 185, 82-91 (1997); Chen, G., et al., *J. Neurochem.*, 72, 1327-1330 (1999); Hong, M., et al., *J. Biol. Chem.*, 272, 25326-25332 (1997)).

The human familial Alzheimer's disease (FAD) presenilin-1 AG04160C lymphoblast cell line (Coriell Cell Repository, Camden, N.J.) is maintained as a suspension culture in RPMI 1640 (with L-Glutamine) supplemented with 10% fetal bovine serum and 1% penicillin-streptomycin in an atmosphere of 37° C. and 5% $CO_2$. The AG04160C FAD lymphoblast cells are seeded in T-25 cm$^2$ flasks at 2.5 to 5.0×10$^5$ cells/ml in a total volume of 10 ml. Following 16-18 hours of growth, cells are treated with compound at concentrations of 0.1 μM, 1.0 μM, and 10 μM, and are incubated for an additional 24 hours. At the completion of the 24-hour incubation, cells are harvested, washed with PBS, and lysed in freshly prepared lysis buffer (10 mM $K_2HPO_4$ pH 7.2, 1 mM EDTA, 5 mM EGTA, 10 mM $MgCl_2$, 50 mM β-Glycerophosphate, 1 mM $Na_3VO_4$, 2 mM DTT, 1 μM Microcystin, 1 mM PMSF, 10 μg/ml leupeptin, 1 pepstatin, 1 μg/ml aprotinin, 1% Triton X-100). After a thirty-minute incubation on ice, cells are centrifuged (14,000 rpm) for 30 minutes at 4° C., and resulting supernatants are used as whole cell lysates. The total protein concentration in whole cell lysate samples is determined using the BCA method (Pierce). Next, 15 μg of sample is loaded on a 10% Bis-Tris NuPage gel and transferred to a pure nitrocellulose membrane followed by β-catenin immunoblot analysis using a (3-catenin specific antibody (Transduction Labs). The β-catenin accumulation/stability is then quantified following densitometry analysis of protein bands (Kodak Digital Science). Final results are reported as fold induction over basal β-catenin. The compound of Example 121 was tested in this assay and induced a 9.8-fold induction of β-catenin at 0.1 μM.

Bone Deposition

Vehicle or test compound in vehicle (1% Carboxymethylcellulose sodium, 0.25% Polysorbate 80, and 0.05% Dow Corning Antifoam 1510-US in purified water) is administered orally by gavage to female Fischer 344 rats daily for 4 days with three rats in each dosage group. The rats are delivered for necropsy and sections of formalin-fixed, paraffin-embedded bone are examined microscopically to evaluate osteoblast proliferation and deposition of osteoid.

The compounds in the following tables were tested essentially as described above and hypertrophy and proliferation of osteoblasts along surfaces of medullary trabecula and the cortical periosteum accompanied by production of osteoid was observed.

| Compound (Example #) | 10 mg/kg | 50 mg/kg | 150 mg/kg | 200 mg/kg |
|---|---|---|---|---|
| 264 | Not tested | + | Not tested | Not tested |
| 252 | Not tested | + | Not tested | Not tested |
| 321 | Not tested | + | Not tested | Not tested |
| 334 | Not tested | + | Not tested | Not tested |
| 365 | − | + | Not tested | Not tested |
| 351 | Not tested | + | Not tested | Not tested |
| 427 | Not tested | + | Not tested | Not tested |
| 560 | Not tested | + | + | Not tested |
| 472 | Not tested | − | Not tested | + |

"+" = hypertrophy and proliferation of osteoblasts with production of osteoid observed
"−" = hypertrophy and proliferation of osteoblasts with production of osteoid not observed at this dose
"Not tested" = compound not tested at this dose The compound of Example 365 was tested again essentially as described above at 0, 3, 10, and 30 mg/kg with four rats at each dosage level for 21 days. The vertebra and the femur were submitted for analysis of bone mineral density (BMD), bone mineral content (BMC), and cross sectional area following 21 days of daily dosing with the compound of Example 365. The results from this analysis indicate a significant increase in BMD and BMC relative to control ($p<0.05$) without a significant change in cross sectional area in both vertebra and femur. Osteoblast proliferation occurred early followed by deposition of new bone by Day 21, but osteoblast proliferation and trabecular hypertrophy were confined to rats given 30 mg/kg of the compound of Example 365 in this study.

These data illustrate that short-term exposure to GSK-3 inhibitors stimulates deposition of new and functional bone.

Ovariectomized Rat Assay

Six-month-old virgin Sprague-Dawley rats are maintained on a 12-hour light, 12-hour dark cycle at 22° C. with ad libitum access to food (TD89222 with 0.5% calcium and 0.4% phosphate, Teklad, Madison, Wis.) and water. Bilateral or sham ovariectomies are performed on the rats and they are allowed to lose bone for 1 month. When the rats are 7 months old, sham and ovariectomized (Ovx) controls (7 animals per group) are orally administered vehicle (1% carboxymethyl cellulose/0.25% Tween 80) and a second group of 7 Ovx animals is orally administered the test compound in vehicle. Dosing is done once a day for 2 months. At the end of 2 months, rats are euthanized using $CO_2$ anesthesia and left femur and vertebra are removed, cleaned of soft tissue and stored in 50% ethanol/saline. Bones are analyzed by QCT as described previously (Sato M., Comparative x-ray densitometry of bones from ovariectomized rats. *Bone* 17:157 S-162S (1995); Sato M., Kim J., Short L. L., Slemenda C. W, Bryant H. U., Longitudinal and cross-sectional analysis of raloxifene effects on tibiae from ovariectomized aged rats. *J Pharmacol Exp Ther* 272:1252-1259 (1995)).

Ovariectomy reduced vertebral bone mineral density (BMD) by 18% and femoral midshaft BMD by 5.1%. Oral administration of the compound of Example 252 at 3 mg/kg increased both vertebral BMD and femoral midshaft BMD back to sham control levels ($P<0.05$ compared to Ovx control). Thus, the compound of Example 252 was active in restoring lost bone both at trabecular and cortical bone sites.

Oral administration of the compounds of the present invention is preferred. However, oral administration is not the only route or even the only preferred route. For example, transdermal administration may be very desirable for patients who are forgetful or petulant about taking oral medicine, and the intravenous route may be preferred as a matter of convenience or to avoid potential complications related to oral administration. Compounds of Formula I may also be administered by the percutaneous, intramuscular, intranasal or intrarectal route in particular circumstances. The route of administration may be varied in any way, limited by the physical properties of the drugs, the convenience of the patient and the caregiver, and other relevant circumstances (*Remington's Pharmaceutical Sciences,* 18th Edition, Mack Publishing Co. (1990)).

The pharmaceutical compositions are prepared in a manner well known in the pharmaceutical art. The carrier or excipient may be a solid, semi-solid, or liquid material that can serve as a vehicle or medium for the active ingredient. Suitable carriers or excipients are well known in the art. The pharmaceutical composition may be adapted for oral, inhalation, parenteral, or topical use and may be administered to the patient in the form of tablets, capsules, aerosols, inhalants, suppositories, solutions, suspensions, or the like.

The compounds of the present invention may be administered orally, for example, with an inert diluent or capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the present invention, the active ingredient, but may be varied depending upon the particular form and may conveniently be between 4% to about 70% of the weight of the unit. The amount of the compound present in compositions is such that a suitable dosage will be obtained. Preferred compositions and preparations of the present invention may be determined by methods well known to the skilled artisan.

The tablets, pills, capsules, troches, and the like may also contain one or more of the following adjuvants: binders such as povidone, hydroxypropyl cellulose, microcrystalline cellulose, or gelatin; excipients or diluents such as: starch, lactose, microcrystalline cellulose or dicalcium phosphate, disintegrating agents such as: croscarmellose, crospovidone, sodium starch glycolate, corn starch and the like; lubricants such as: magnesium stearate, steric acid, talc or hydrogenated vegetable oil; glidants such as colloidal silicon dioxide; wetting agents such as: sodium lauryl sulfate and polysorbate 80; and sweetening agents such as: sucrose, aspartame or saccharin may be added or a flavoring agent such as: peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials that modify the physical form of the dosage unit, for example, as coatings. Thus, tablets or pills may be coated with sugar, hydroxypropyl methylcellulose, polymethacrylates, or other coating agents. Syrups may contain, in addition to the present compounds, sucrose as a sweetening agent and certain preservatives, dyes and colorings and flavors. Materials used in preparing these various compositions should be pharmaceutically pure and non-toxic in the amounts used.

The compounds of Formula I are generally effective over a wide dosage range. For example, dosages per day normally fall within the range of about 0.0001 to about 30 mg/kg of body weight. In some instances dosage levels below the lower limit of the aforesaid range may be more than adequate, while in other cases still larger doses may be employed without causing any harmful side effect, and therefore the above dosage range is not intended to limit the scope of the invention in any way. It will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms.

We claim:

1. A compound of Formula I:

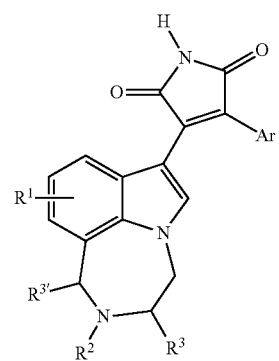

where:
  $R^1$ is hydrogen, halo, or $C_1$-$C_4$ alkyl;
  $R^2$ is hydrogen, —($C_1$-$C_4$ alkylene)-$R^5$, $C_5$-$C_7$ cycloalkyl, tetrahydropyran-4-yl, pyridinyl, pyrimidinyl, triazolyl optionally substituted with amino, benzothiazol-2-yl, —C(S)-(morpholin-4-yl or $C_1$-$C_4$ alkoxy), —C($NR^{16}$) $R^{17}$, —C(O)$R^6$, —$CO_2R^7$, —CO($NR^8R^9$), —$SO_2$ ($NR^8R^9$), —$SO_2$($C_1$-$C_4$ alkyl), or an amino acid residue;
  $R^3$ and $R^{3'}$ are independently selected from the group consisting of hydrogen and $C_1$-$C_4$ alkyl provided that only one of $R^3$ and $R^{3'}$ may be $C_1$-$C_4$ alkyl;
  $R^5$ is hydrogen, pentahaloethyl or trihalomethyl, cyano, hydroxy, $C_1$-$C_4$ alkoxy optionally substituted with $C_1$-$C_4$ alkoxy, $C_3$-$C_6$ cycloalkyl, phenyl optionally substituted with up to three substituents independently selected from the group consisting of halo and $C_1$-$C_4$ alkoxy, pyridinyl, imidazolyl optionally substituted on a nitrogen atom with $C_3$-$C_6$ cycloalkyl, morpholin-4-yl, pyrrolidin-1-yl, —$CO_2H$, —$CO(C_1$-$C_4$ alkoxy), —CO($NR^8R^9$), —$NR^8R^9$ or -(morpholin-4-yl)carbonyl;

$R^6$ is hydrogen, $C_1$-$C_{10}$ alkyl optionally substituted with up to three halo substituents, 1-amino-2-methoxyeth-1-yl, $C_3$-$C_6$ cycloalkyl, pyridinyl optionally substituted with $C_1$-$C_4$ alkyl, trifluoromethyl, carboxyl, or ($C_1$-$C_4$ alkoxy)carbonyl, pyridinyl-N-oxide, pyrazinyl, pyrimidinyl, imidazolyl, morpholin-4-yl optionally substituted with up to two $C_1$-$C_4$ alkyl groups, [1,4]oxazepin-4-yl, azetidin-4-yl, tetrahydropyran-4-yl, 3-methyl-6,7-dihydropyrrolo[1,2-a]imidazol-6-yl, piperazin-4-yl optionally substituted in the 4 position with phenyl or $C_1$-$C_4$ alkyl, pyrrolidin-1-yl, piperidin-1-yl optionally substituted in the 4-position with oxo or geminal dimethyl, piperidin-4-yl optionally substituted in the 1-position with ($C_1$-$C_4$ alkoxy)carbonyl or $C_1$-$C_4$ alkyl, or —($C_1$-$C_4$ alkylene)-$R^{10}$;

$R^7$ is $C_1$-$C_6$ alkyl optionally substituted with halo, 2-methoxyeth-1-yl, —($C_1$-$C_2$ alkylene)-(morpholin-4-yl or pyrrolidin-2-on-1-yl), or phenyl optionally substituted with one or two substituents independently selected from the group consisting of halo, $C_1$-$C_4$ alkyl, $C_1$-$C_4$ alkoxy, and trifluoromethyl;

$R^8$ is hydrogen or $C_1$-$C_6$ alkyl optionally substituted with $C_1$-$C_4$ alkoxy;

$R^9$ is hydrogen or $C_1$-$C_6$ alkyl optionally substituted with $C_1$-$C_4$ alkoxy;

$R^{10}$ is —$OCH_2CH_2OCH_3$, —$NR^{14}R^{15}$, $C_3$-$C_6$ cycloalkyl, morpholin-4-yl, thiomorpholin-4-yl, 1,1-dioxothiomorpholin-4-yl, piperidin-1-yl, pyrrolidin-2-yl optionally substituted at the 1-position with $C_1$-$C_4$ alkyl, or imidazolyl optionally substituted with nitro;

Ar is benzofur-4-yl, benzofur-7-yl, benzothien-4-yl, benzothien-7-yl, 1-($R^{11}$)benzimidazol-4-yl, 1-($R^{11}$)indol-4-yl, indol-7-yl, isoquinolin-5-yl, 2,3-dihydrobenzofur-4-yl, 2,3-dihydrobenzofur-7-yl, 1,3-dihydroisobenzofur-4-yl, 1,3-dihydroisobenzofur-5-yl, benzo[1,3]dioxol-4-yl, benzo[1,3]dioxol-5-yl, 2,3-dihydrobenzo[1,4]dioxin-5-yl, 2,3-dihydrobenzo[1,4]dioxin-6-yl, 2',2'-difluorobenzo[1,3]dioxol-4-yl, or 2',2'-difluorobenzo[1,3]dioxol-5-yl each optionally substituted in the phenyl ring with substituents $R^{12}$ and $R^{13}$, or Ar is a group selected from imidazo[1,2-a]pyridin-3-yl optionally substituted with one or two substituents independently selected from the group consisting of halo, amino, $C_1$-$C_4$ alkyl, $C_1$-$C_4$ alkoxy, benzyloxy, cyano, and trifluoromethyl, 5,6,7,8-tetrahydroimidazo[1,2-c]pyridin-3-yl, imidazo[1,2-c]pyridin-5-yl, imidazo[1,2-c]pyrimidin-3-yl optionally substituted with amino, imidazo[1,2-c]pyrimidin-3-yl, imidazo[1,2-c]pyrazin-3-yl, imidazo[1,2-b]pyridazin-3-yl, imidazo[2,1-b]thiazol-3-yl, thiazolo[3,2-b][1,2,4]triazol-6-yl, furo[3,2-c]pyridin-7-yl optionally substituted with halo or —$NR^{14}R^{15}$, thieno[3,2-b]pyridin-7-yl, pyrazolo[2,3-c]pyridin-3-yl, pyrazolo[1,5-a]pyridin-3-yl, or 4,5,6,7-tetrahydropyrazolo[1,5-c]pyridin-3-yl;

$R^{11}$ is hydrogen, $C_1$-$C_4$ alkyl, or —$(CH_2)_p$-G;
$R^{12}$ is halo, hydroxy, amino, $C_1$-$C_4$ alkoxy, —NHC(O)($C_1$-$C_4$ alkyl), or —O—$(CH_2)_p$-G;
$R^{13}$ is halo;
p is 2, 3, 4, or 5;
G is hydroxy or $NR^{14}R^{15}$;
$R^{14}$ and $R^{15}$ are independently selected from the group consisting of hydrogen and $C_1$-$C_5$ alkyl;
$R^{16}$ is hydrogen or cyano,
$R^{17}$ is —$NR^8R^9$, $C_1$-$C_4$ alkyl, morpholin-4-yl, or piperidin-1-yl; or a pharmaceutically acceptable salt thereof
provided that the compound is not:
3-(9-fluoro-6-((piperidin-1-yl)carbonyl)-6,7-dihydro-6H-[1,4]diazepino-[6,7,1-hi]indol-1-yl)-4-(imidazo[1,2-a]pyridine-3-yl)-2,5-dioxopyrrole;
3-(6-((morpholin-4-yl)carbonyl)-6,7-dihydro-6H-[1,4]diazepino[6,7,1-hi]indol-1-yl)-4-(imidazo[1,2-a]-pyridin-3-yl)-2,5-dioxopyrrole;
3-(6-(N,N-[dimethyl]aminocarbonyl)-6,7-dihydro-6H-[1,4]diazepino[6,7,1-hi]indol-1-yl)-4-(imidazo[1,2-a]pyridin-3-yl)-2,5-dioxopyrrole;
3-(6-(isopropoxycarbonyl)-6,7-dihydro-6H-[1,4]di-azepino[6,7,1-hi]indol-1-yl)-4-(imidazo[1,2-a]pyridin-3-yl)-2,5-dioxopyrrole;
3-(6-(piperidin-1-yl)carbonyl)-6,7-dihydro-6H-[1,4]diazepino[6,7,1-hi]indol-1-yl)-4-(imidazo[1,2-a]pyridin-3-yl)-2,5-dioxopyrrole;
3-((6-(piperidin-1-yl)carbonyl)-6,7-dihydro-6H-[1,4]diazepino[6,7,1-hi]indol-1-yl)-4-(imidazo[1,2-b]pyridazin-3-yl)-2,5-dioxopyrrole;
3-(6-((morpholin-4-yl)carbonyl)-6,7-dihydro-6H-[1,4]-diazepino[6,7,1-hi]indol-1-yl)-4-(4,5,6,7-tetrahydropyrazolo[1,5-a]pyridin-3-yl)-2,5-dioxopyrrole;
3-(6-((pyridin-3-yl)carbonyl)-6,7-dihydro-6H-[1,4]diazepino[6,7,1-hi]indol-1-yl)-4-(imidazo[1,2-a]pyridin-3-yl)-2,5-dioxopyrrole; or
3-(6-(pyrimidin-2-yl)-6,7-dihydro-6H-[1,4]diazepino[6,7,1-hi]indol-1-yl)-4-(imidazo[1,2-a]pyridin-3-yl)pyrrole-2,5-dione.

2. A compound of claim 1, or a pharmaceutically acceptable salt thereof, where Ar is benzofur-4-yl, benzofur-7-yl, or 2,3-dihydrobenzofur-7-yl optionally substituted in the phenyl ring with substituents $R^{12}$ and $R^{13}$.

3. A compound of claim 1, or a pharmaceutically acceptable salt thereof, where Ar is imidazo[1,2-a]pyridin-3-yl optionally substituted with one or two groups independently selected from halo, $C_1$-$C_4$ alkyl, or $C_1$-$C_4$ alkoxy.

4. A compound of claim 1, or a pharmaceutically acceptable salt thereof, where $R^2$ is —C(O)$R^6$.

5. A pharmaceutical composition comprising a compound of claim 1 in combination with a pharmaceutically acceptable carrier, diluent or excipient.

6. A method of treating diabetes in a mammal comprising administering to a mammal in need of such treatment an effective amount of a compound of claim 1.

7. A method of treating Alzheimer's disease in a mammal comprising administering to a mammal in need of such treatment an effective amount of claim 1.

8. A method of stimulating bone deposition in a mammal comprising administering to a mammal in need of such treatment an effective amount of a compound of claim 1.

* * * * *

UNITED STATES PATENT AND TRADEMARK OFFICE
CERTIFICATE OF CORRECTION

PATENT NO. : 8,058,425 B2
APPLICATION NO. : 13/100618
DATED : November 15, 2011
INVENTOR(S) : Thomas Albert Engler et al.

It is certified that error appears in the above-identified patent and that said Letters Patent is hereby corrected as shown below:

Title Page item (57) (Abstract) Line 2: Below "Formula I." delete "I.".

At Column 113, Line 54: In Claim 1, delete "[1,2-c]" and insert -- [1,2-a] --, therefor.

At Column 113, Line 54: In Claim 1, delete "[1,2-c]pyridin" and insert -- [1,2-a]pyridin --, therefor.

At Column 113, Line 55: In Claim 1, delete "[1,2-c]" and insert -- [1,2-a] --, therefor.

At Column 113, Line 56: In Claim 1, delete "[1,2-c]" and insert -- [1,2-a] --, therefor.

At Column 113, Line 60: In Claim 1, delete "[2,3-c]" and insert -- [2,3-a] --, therefor.

At Column 113, Line 62: In Claim 1, delete "[1,5-c]" and insert -- [1,5-a] --, therefor.

At Column 114, Line 24: In Claim 1, delete "3-(6" and insert -- 3-((6 --, therefor.

Signed and Sealed this
Twenty-seventh Day of December, 2011

David J. Kappos
*Director of the United States Patent and Trademark Office*